(12) United States Patent
Ronen et al.

(10) Patent No.: US 8,481,812 B2
(45) Date of Patent: *Jul. 9, 2013

(54) METHODS OF INCREASING ABIOTIC STRESS TOLERANCE AND/OR BIOMASS IN PLANTS GENERATED THEREBY

(75) Inventors: Gil Ronen, Emek Hefer (IL); Ezekiel Golan, Tel-Aviv (IL); Hagai Karchi, Doar-Na Emek Soreq (IL); Rafael Meissner, Rechovot (IL)

(73) Assignee: Evogene Ltd., Rechovot (IL)

( * ) Notice: Subject to any disclaimer, the term of this patent is extended or adjusted under 35 U.S.C. 154(b) by 393 days.

This patent is subject to a terminal disclaimer.

(21) Appl. No.: 12/457,199

(22) Filed: Jun. 3, 2009

(65) Prior Publication Data

US 2009/0260109 A1     Oct. 15, 2009

Related U.S. Application Data

(63) Continuation of application No. 11/284,236, filed on Nov. 22, 2005, now Pat. No. 7,554,007, which is a continuation-in-part of application No. PCT/IL2004/000431, filed on May 20, 2004.

(60) Provisional application No. 60/472,433, filed on May 22, 2003, provisional application No. 60/707,957, filed on Aug. 15, 2005.

(51) Int. Cl.
    *C12N 15/82* (2006.01)
(52) U.S. Cl.
    USPC .......................................... 800/289; 800/290
(58) Field of Classification Search
    None
    See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 4,943,674 A | 7/1990 | Houck et al. |
| 4,945,050 A | 7/1990 | Sanford et al. |
| 5,011,771 A | 4/1991 | Bellet et al. |
| 5,187,267 A | 2/1993 | Comai et al. |
| 5,192,659 A | 3/1993 | Simons |
| 5,268,463 A | 12/1993 | Jefferson |
| 5,272,057 A | 12/1993 | Smulson et al. |
| 5,281,521 A | 1/1994 | Trojanowski et al. |
| 5,296,462 A | 3/1994 | Thomashow |
| 5,316,931 A | 5/1994 | Donson et al. |
| 5,356,816 A | 10/1994 | Thomashow |
| 5,399,680 A | 3/1995 | Zhu et al. |
| 5,464,765 A | 11/1995 | Coffee et al. |
| 5,466,785 A | 11/1995 | De Framond |
| 5,495,070 A | 2/1996 | John |
| 5,504,200 A | 4/1996 | Hall et al. |
| 5,521,708 A | 5/1996 | Beretta |
| 5,569,597 A | 10/1996 | Grimsley et al. |
| 5,597,718 A | 1/1997 | John et al. |
| 5,604,121 A | 2/1997 | Hilder et al. |
| 5,608,142 A | 3/1997 | Barton et al. |
| 5,608,144 A | 3/1997 | Baden et al. |
| 5,608,149 A | 3/1997 | Barry et al. |
| 5,608,152 A | 3/1997 | Kridl et al. |
| 5,620,882 A | 4/1997 | John |
| 5,659,026 A | 8/1997 | Baszczynski et al. |
| 5,693,507 A | 12/1997 | Daniell et al. |
| 5,859,330 A | 1/1999 | Bestwick et al. |
| 5,880,100 A | 3/1999 | Ogiso et al. |
| 5,961,466 A | 10/1999 | Anbar |
| 5,981,834 A | 11/1999 | John et al. |
| 6,080,914 A | 6/2000 | Conner |
| 6,084,153 A | 7/2000 | Good et al. |
| 6,094,198 A | 7/2000 | Shashua |
| 6,167,151 A | 12/2000 | Albeck et al. |
| 6,201,541 B1 | 3/2001 | Shalom et al. |

(Continued)

FOREIGN PATENT DOCUMENTS

| | | |
|---|---|---|
| AU | 2005229157 | 10/2005 |
| AU | 2005234725 | 12/2005 |

(Continued)

OTHER PUBLICATIONS

Whisstock J.C. et al. Prediction of protein function from protein sequence and structure. Q Rev Biophys. Aug. 2003;36(3):307-40. Review.*
Johansson et al. The role of aquaporins in cellular and whole plant water balance. Biochim Biophys Acta. May 1, 2000;1465(1-2):324-42.*
International Preliminary Report on Patentability Dated Dec. 2, 2010 From the International Bureau of WIPO Re. Application No. PCT/IL2009/000508.
Notice of Allowance Dated Oct. 18, 2010 From the US Patent and Trademark Office Re.: U.S. Appl. No. 11/990,386.
Office Action Dated Nov. 11, 2010 From the Israel Patent Office Re. Application No. 206118 and Its Translation Into English.

(Continued)

*Primary Examiner* — Cynthia Collins

(57) ABSTRACT

Provided are methods of increasing the tolerance of a plant to abiotic stresses and/or increasing the biomass and/or increasing the yield of a plant by expressing within the plant an exogenous polynucleotide homologous to SEQ ID NO:13.

17 Claims, 9 Drawing Sheets

(4 of 9 Drawing Sheet(s) Filed in Color)

U.S. PATENT DOCUMENTS

| | | | |
|---|---|---|---|
| 6,313,375 | B1 | 11/2001 | Jung et al. |
| 6,313,376 | B1 | 11/2001 | Jung et al. |
| 6,359,196 | B1 | 3/2002 | Lok et al. |
| 6,392,122 | B1 | 5/2002 | Clendennen et al. |
| 6,403,862 | B1 | 6/2002 | Jiao et al. |
| 6,442,419 | B1 | 8/2002 | Chu et al. |
| 6,472,588 | B1 | 10/2002 | Haigler et al. |
| 6,670,528 | B1 | 12/2003 | Shinozaki et al. |
| 6,701,081 | B1 | 3/2004 | Dwyer et al. |
| 6,720,477 | B2 | 4/2004 | Da Costa e Silva et al. |
| 6,765,607 | B2 | 7/2004 | Hirama et al. |
| 6,801,257 | B2 | 10/2004 | Segev et al. |
| 6,850,862 | B1 | 2/2005 | Chidichimo et al. |
| 6,965,690 | B2 | 11/2005 | Matsumoto |
| 7,072,504 | B2 | 7/2006 | Miyano et al. |
| 7,292,719 | B2 | 11/2007 | Arnon |
| 7,554,007 | B2 * | 6/2009 | Ronen et al. ............... 800/290 |
| 7,812,218 | B2 | 10/2010 | Ronen et al. |
| 7,910,800 | B2 | 3/2011 | Karchi et al. |
| 8,049,069 | B2 | 11/2011 | Wu et al. |
| 8,168,857 | B2 | 5/2012 | Ayal et al. |
| 2001/0046316 | A1 | 11/2001 | Miyano et al. |
| 2002/0046419 | A1 | 4/2002 | Choo et al. |
| 2002/0049999 | A1 | 4/2002 | Allen et al. |
| 2002/0148007 | A1 | 10/2002 | Jiao et al. |
| 2002/0160378 | A1 | 10/2002 | Harper et al. |
| 2002/0170088 | A1 | 11/2002 | Wilkins |
| 2003/0005485 | A1 | 1/2003 | Ohlrogge et al. |
| 2003/0074697 | A1 | 4/2003 | Allen et al. |
| 2003/0084485 | A1 | 5/2003 | Zhu et al. |
| 2003/0162294 | A1 | 8/2003 | Verbruggen |
| 2003/0163839 | A1 | 8/2003 | Helentjaris et al. |
| 2003/0233670 | A1 | 12/2003 | Edgerton et al. |
| 2004/0006794 | A1 | 1/2004 | Wilkins |
| 2004/0031072 | A1 | 2/2004 | La Rosa et al. |
| 2004/0034888 | A1 | 2/2004 | Liu et al. |
| 2004/0123343 | A1 | 6/2004 | La Rosa et al. |
| 2004/0172684 | A1 | 9/2004 | Kovalic et al. |
| 2004/0181830 | A1 | 9/2004 | Kovalic et al. |
| 2004/0236225 | A1 | 11/2004 | Murphy et al. |
| 2005/0096515 | A1 | 5/2005 | Geng |
| 2005/0108791 | A1 | 5/2005 | Edgerton |
| 2006/0048240 | A1 | 3/2006 | Alexandrov et al. |
| 2006/0101543 | A1 | 5/2006 | Somerville et al. |
| 2006/0107345 | A1 | 5/2006 | Alexandrov et al. |
| 2006/0123505 | A1 | 6/2006 | Kikuchi et al. |
| 2006/0123516 | A1 | 6/2006 | Ronen et al. |
| 2006/0137043 | A1 | 6/2006 | Puzio et al. |
| 2006/0150283 | A1 | 7/2006 | Alexandrov et al. |
| 2006/0168684 | A1 | 7/2006 | Renz et al. |
| 2006/0174373 | A1 | 8/2006 | Gipmans et al. |
| 2006/0179511 | A1 | 8/2006 | Chomet et al. |
| 2006/0183137 | A1 | 8/2006 | Harper et al. |
| 2006/0195943 | A1 | 8/2006 | Feldmann et al. |
| 2006/0206961 | A1 | 9/2006 | Cirpus et al. |
| 2006/0260002 | A1 | 11/2006 | Ronen et al. |
| 2006/0288451 | A1 | 12/2006 | Val et al. |
| 2007/0006345 | A1 | 1/2007 | Alexandrov et al. |
| 2007/0006346 | A1 | 1/2007 | Alexandrov et al. |
| 2007/0044171 | A1 | 2/2007 | Kovalic et al. |
| 2007/0044172 | A1 | 2/2007 | Schneeberger et al. |
| 2007/0061916 | A1 | 3/2007 | Kovalic et al. |
| 2007/0124833 | A1 | 5/2007 | Abad et al. |
| 2007/0169219 | A1 | 7/2007 | Nadzan et al. |
| 2007/0214517 | A1 | 9/2007 | Alexandrov et al. |
| 2007/0261130 | A1 | 11/2007 | Lightner et al. |
| 2008/0076179 | A1 | 3/2008 | Hartel et al. |
| 2008/0148432 | A1 | 6/2008 | Abad |
| 2008/0196120 | A1 | 8/2008 | Wu et al. |
| 2008/0301839 | A1 | 12/2008 | Ravanello |
| 2009/0089898 | A1 | 4/2009 | Karchi et al. |
| 2009/0093620 | A1 | 4/2009 | Kovalic et al. |
| 2009/0126042 | A1 | 5/2009 | Ronen et al. |
| 2009/0260109 | A1 | 10/2009 | Ronen et al. |
| 2009/0293154 | A1 | 11/2009 | Yelin et al. |
| 2010/0319088 | A1 | 12/2010 | Ronen et al. |
| 2011/0080674 | A1 | 4/2011 | Durand |
| 2012/0060234 | A1 | 3/2012 | Emmanuel et al. |
| 2012/0180164 | A1 | 7/2012 | Ayal et al. |
| 2012/0297504 | A1 | 11/2012 | Granevitze et al. |

FOREIGN PATENT DOCUMENTS

| | | |
|---|---|---|
| DE | 10150918 | 5/2003 |
| EP | 0834566 | 4/1998 |
| EP | 0905242 | 3/1999 |
| EP | 1033405 | 9/2000 |
| EP | 1225231 | 7/2002 |
| EP | 1945021 | 7/2008 |
| GB | 2358752 | 8/2001 |
| JP | 2005-052114 | 3/2005 |
| JP | 2005-185101 | 7/2005 |
| RU | 2350653 | 3/2009 |
| WO | WO 93/06710 | 4/1993 |
| WO | WO 93/07278 | 4/1993 |
| WO | WO 94/17194 | 8/1994 |
| WO | WO 95/08914 | 4/1995 |
| WO | WO 96/26639 | 9/1996 |
| WO | WO 96/40924 | 12/1996 |
| WO | WO 01/17333 | 3/2001 |
| WO | WO 01/40250 | 6/2001 |
| WO | WO 02/16655 | 2/2002 |
| WO | WO 02/45485 | 6/2002 |
| WO | WO 02/079403 | 10/2002 |
| WO | WO 02/090557 | 11/2002 |
| WO | WO 03/020025 | 3/2003 |
| WO | WO 03/087313 | 10/2003 |
| WO | WO 03/098186 | 11/2003 |
| WO | WO 2004/053055 | 6/2004 |
| WO | WO 2004/058963 | 7/2004 |
| WO | WO 2004/081173 | 9/2004 |
| WO | WO 2004/092367 | 10/2004 |
| WO | WO 2004/104162 | 12/2004 |
| WO | WO 2004/111183 | 12/2004 |
| WO | WO 2005/095614 | 10/2005 |
| WO | WO 2005/108422 | 11/2005 |
| WO | WO 2005/121364 | 12/2005 |
| WO | WO 2006/003658 | 1/2006 |
| WO | WO 2006/138012 | 12/2006 |
| WO | WO 2007/020638 | 2/2007 |
| WO | WO 2007/049275 | 5/2007 |
| WO | WO 2008/069878 | 6/2008 |
| WO | WO 2008/075364 | 6/2008 |
| WO | WO 2008/122980 | 10/2008 |
| WO | WO 2009/013750 | 1/2009 |
| WO | WO 2009/083958 | 7/2009 |
| WO | WO 2009/083973 | 7/2009 |
| WO | WO 2009/083974 | 7/2009 |
| WO | WO 2009/118721 | 10/2009 |
| WO | WO 2009/141824 | 11/2009 |
| WO | WO 2010/020941 | 2/2010 |
| WO | WO 2010/049897 | 5/2010 |
| WO | WO 2010/076756 | 7/2010 |
| WO | WO 2010/100595 | 9/2010 |
| WO | WO 2011/080674 | 7/2011 |
| WO | WO 2011/135527 | 11/2011 |
| WO | WO 2012/028993 | 3/2012 |
| WO | WO 2012/150598 | 11/2012 |

OTHER PUBLICATIONS

Official Action Dated Nov. 23, 2010 From the US Patent and Trademark Office Re. U.S. Appl. No. 12/083,978.
Response Dated Dec. 5, 2010 to Office Action of Aug. 4, 2010 From the Israel Patent Office Re.: Application No. 172135.
Response Dated Dec. 12, 2010 to Examiner's Report of Dec. 17, 2009 From the Australian Patent Office Re.: Application No. 2005252469.
Response Dated Dec. 14, 2010 to Examination Report of Sep. 22, 2010 From the Instituto Mexicano de la Propriedad Industrial Re. Application No. MX/a/2008/005280.
Response Dated Sep. 14, 2010 to Official Action of Aug. 18, 2010 From the US Patent and Trademark Office Re. U.S. Appl. No. 12/083,978.
Response Dated Oct. 24, 2010 to Office Action of Sep. 2, 2010 From the ROSPATENT, Federal State Institution, Federal Institute for Industrial Property of the Federal Service for Intellectual Property, Patents and Trademarks of the Russian Federation Re. Application No. 2008120395.
Summary of Office Action Dated Sep. 2, 2010 From the ROSPATENT, Federal State Institution, Federal Institute for Industrial Property of the Federal Service for Intellectual Property, Patents and Trademarks of the Russian Federation Re. Application No. 2008120395.
Translation of Office Action Dated Oct. 19, 2010 From the State Intellectual Property Office of the People's Republic of China Re. Application No. 200680038391.X.
Wang et al. "Control of Plant Trichome Development by a Cotton Fiber MYB Gene", The Plant Cell, 16: 2323-2334, Sep. 2004.
Wang et al. "Control of Plant Trichome Development by a Cotton Fiber MYB Gene", The Plant Cell, 16: 2323-2334, Sep. 2004. GenEmbl Database, Accession No. AY641990.
Decision on Granting a Patent for Invention Dated Dec. 7, 2010 From the ROSPATENT, Federal State Institution, Federal Institute for Industrial Property of the Federal Service for Intellectual Property, Patents and Trademarks of the Russian Federation Re. Application No. 2008120395 and Its Translation Into English.
Examiner's Report Dated Jan. 13, 2011 From the Australian Patent Office Re.: Application No. 2005252469.
Response Dated Jan. 19, 2011 to Supplementary European Search Report and the European Search Opinion of Jul. 1, 2010 From the European Patent Office Re. Application No. 07849616.3.
Blewitt et al. "Gossypium Hirsutum Strain Acala Maxxa BURP Domain-Containing Protein (BNL1924) mRNA, Complete CDS", GenBank Nucleotide, GenBank Accession No. AY343972, Aug. 16, 2003.
Li et al. "Isolation of Genes Preferntially Expressed in Cotton Fibers by cDNA Filter Arrays and RT-PCR", Plant Science, 163: 1113-1120, 2002. & GenBank Nucleotide "Gossypium Hirstutum Dehydration-Iduced Protein RD22-Like Protein (RDL0 mRNA, Complete CDS", GenBank Accession No. AY072821, Dec. 4, 2002.
Office Action Dated Feb. 3, 2011 From the Israel Patent Office Re.: Application No. 172135 and Its Translation Into English.
Official Action Dated Feb. 15, 2011 From the US Patent and Trademark Office Re. U.S. Appl. No. 12/448,359.
International Preliminary Report on Patentability Dated Mar. 3, 2011 From the International Bureau of WIPO Re.: Application No. PCT/IB2009/053633.
International Search Report and the Written Opinion Dated Jun. 2, 2010 From the International Searching Authority Re. Application No. PCT/IB09/53633.
Invitation to Pay Additional Fees Dated Mar. 2, 2010 From the International Searching Authority Re.: Application No. PCT/IB09/53633.
Communication Pursuant to Article 94(3) EPC Dated Mar. 8, 2011 From the European Patent Office Re.: Application No. 06809784.9.
Communication Pursuant to Article 94(3) EPC Dated Mar. 14, 2011 From the European Patent Office Re. Application No. 07849616.3.
Response Dated Feb. 9, 2011 to Communication Pursuant to Article 94(3) EPC of Nov. 19, 2010 From the European Patent Office Re.: Application No. 06809784.9.
Response Dated Feb. 14, 2011 to Supplementary European Search Report and the European Search Opinion of Jul. 29, 2010 From the European Patent Office Re. Application No. 08776651.5.
Response Dated Mar. 14, 2011 to Official Action of Feb. 15, 2011 From the US Patent and Trademark Office Re. U.S. Appl. No. 12/448,359.
Communciation Pursuant to Rules 70(2) and 70a(2) EPC Dated Aug. 30, 2011 From the European Patent Office Re. Application No. 08738191.9.
Response Dated Feb. 23, 2011 to Communication Pursuant to Rule 70(2) EPC and Reference to Rule 39(1) EPC of Sep. 13, 2010 From the European Patent Office Re.: Application No. 09163033.5.
Response Dated Feb. 24, 2011 to Communciation Pursuant to Rules 70(2) and 70a(2) EPC of Aug. 30, 2011 From the European Patent Office Re. Application No. 08738191.9.
Examiner's Report Dated Mar. 31, 2011 From the Australian Government, IP Australia Re. : Application No. 2005252469.

Invitation to Pay Additional Fees Dated Dec. 18, 2008 From the International Searching Authority Re.: Application No. PCT/IL08/01024.
International Preliminary Report on Patentability Dated Feb. 4, 2010 From the International Bureau of WIPO Re.: Application No. PCT/IL2008/001024.
International Search Report Dated Mar. 4, 2009 From the International Searching Authority Re.: Application No. PCT/IL08/01024.
Office Action Dated Jan. 31, 2010 From the Israel Patent Office Re.: Application No. 172135 and Its Translation Into English.
Response Dated Jan. 7, 2010 to Communication Pursuant to Article 94(3) EPC of Sep. 9, 2009 From the European Patent Office Re.: Application No. 04734072.4.
Response Dated Feb. 22, 2010 to Official Action of Oct. 22, 2009 From the US Patent and Trademark Office Re.: U.S. Appl. No. 11/990,386.
Supplementary European Search Report and the European Search Opinion Dated Feb. 1, 2010 From the European Patent Office Re.: Application No. 06766224.7.
Written Opinion Dated Mar. 4, 2009 From the International Searching Authority Re.: Application No. PCT/IL08/01024.
Nuccio et al. "Metabolic Engineering of Plants for Osmotic Stress Resistance", Current Opinion in Plant Biology, XP002216348, 2(2): 128-134, Apr. 1, 1999.
Communication Pursuant to Article 94(3) EPC Dated Dec. 8, 2008 From the European Patent Office Re.: Application No. 04734072.4.
International Preliminary Report on Patentability Dated Dec. 8, 2005 From the International Bureau of WIPO Re.: Application No. PCT/IL2004/000431.
Communication Pursuant to Article 94(3) EPC Dated Sep. 9, 2009 From the European Patent Office Re.: Application No. 04734072.4.
Examination Report Dated Nov. 13, 2007 From the Government of India, Patent Office Re.: Application No. 3482/CHENP/2005.
International Preliminary Report on Patentability Dated Jan. 22, 2009 From the International Bureau of WIPO Re.: Application No. PCT/IL2006/000947.
International Search Report Dated Nov. 4, 2005 From the International Searching Authority Re.: Application No. PCT/IL04/00431.
International Search Report Dated Aug. 27, 2008 From the International Searching Authority Re.: Application No. PCT/IL06/00947.
Office Action Dated Jan. 9, 2009 From the State Intellectual Property Office of the People's Republic of China Re.: Application No. 200480020597.0.
Office Action Dated Apr. 27, 2009 From the Israeli Patent Office Re.: Application No. 172135 and Its Translation Into English.
Office Letter Dated Jul. 7, 2008 From the Government of India, Patent Office Re.: Application No. 3482/CHENP/2005.
Official Action Dated May 15, 2009 From the US Patent and Trademark Office Re.: U.S. Appl. No. 11/990,386.
Official Action Dated Oct. 18, 2007 From the US Patent and Trademark Office Re.: U.S. Appl. No. 11/284,236.
Official Action Dated Oct. 22, 2009 From the US Patent and Trademark Office Re.: U.S. Appl. No. 11/990,386.
Official Action Dated Jul. 28, 2008 From the US Patent and Trademark Office Re.: U.S. Appl. No. 11/284,236.
Supplementary European Search Report Dated Oct. 31, 2007 From the European Patent Office Re.: Application No. 04734072.4.
Supplementary Partial European Search Report Dated Aug. 30, 2007 From the European Patent Office Re.: Application No. 04734072.4.
Translation of the Office Action Dated Jan. 9, 2009 From the State Intellectual Property Office Re.: Application No. 2004800200597.0.
Written Opinion Dated Nov. 4, 2005 From the International Searching Authority Re.: Application No. PCT/Il04/00431.
Written Opinion Dated Aug. 27, 2008 From the International Searching Authority Re.: Application No. PCT/IL06/00947.
Alcala et al. "Generation of ESTs From Tomato Fruit Tissue", Database GenBank on STIC, National Center for Biotechnology Information, Accession No. AW932839, 2001.
Brandle et al. "Perspectives on the Production of Recombinant Proteins in Plants", AgBiotechNet, 3(ABN 070): 1-4, 2001. Abstract.
Guo et al. "Protein Tolerance to Random Amino Acid Change", Proceedings of the National Academy of Sciences USA, 101(25): 9205-9210, 2004.

Hill et al. "Functional Analysis of Conserved Histidines in ADP-Glucose Pyrophosphorylase From *Escherichia coli*", Biochemical and Biophysical Research Communications, 244(2): 573-577, 1998.
In et al. "Panax Gingseng mRNA for Cytoplasmic Ribosomal Protein S13, Complete Cds", Database EMBL [Online], Retrieved From EBI Accession No. EMBL, Database Accession No. AB043974, 2000.
Kim et al. "Molecular Cloning of Low-Temperature-Inducible Ribosomal Proteins From Soybean", Journal of Experimental Botany, 55(399): 1153-1155, 2004.
Ngo et al. "Computational Complexity, Protein Structure Prediction, and the Levinthal Paradox", The Protein Folding Problem and Tertiary Structure Prediction, p. 433, 492-495, 1994.
Park et al. "Glycine Max Ribosomal Protein S13 (RPS13) mRNA, Complete Cds", Database EMBL [Online], Retreieved From EBI Accession No. EMBL, Database Accession No. AY453393, 2004.
Sáez-Vásquez et al. "Accumulation and Nuclear Targeting of BnC24, A Brassica Napus Ribosomal Protein Corresponding to a mRNA Accumulating in Response to Cold Treatment", Plant Science, 156(1): 35-46, 2000.
Smart et al. "MIP Genes Are Down-Regulated Under Drought Stress in Nicotiana Glauca", Plant and Cell Physiology, 42(7): 686-693, 2001. Referenc to Database Entry AF290618 on p. 686, p. 692, 1-h col., § 2.
Smart et al. "Nicotiana Glauca Putative Delta TIP (MIP2) mRNA, Complete Cds", Database EMBL [Online], Retrieved From EBI Accession No. EMBL: Af290618, Database Accession No. AF290618, 2001.
Tamura et al. "Osmotic Stress Tolerance of Transgenic Tobacco Expressing a Gene Encoding a Membrane-Located Receptor-Like Protein From Tobacco Plants", Plant Physiology, 131(2): 454-462, 2003.
Tanaka et al. "Enhanced Tolerance Against Salt-Stress and Freezing-Stress of *Escherichia coli* Cells Expressing Algal BBC1 Gene", Current Microbiology, 42(3): 173-177, 2001.
Thornton et al. "From Structure to Function: Approaches and Limitations", Nature Structural Biology. Structural Genomic Supplement, Nov. 2000, p. 991-994.
Van der Hoeven et al. "EST301294 Tomato Root During/After Fruit Set, Cornell University Lycopersicon Esculentum cDNA Clone cLEX1K11 Similar to Vernicia Fordii Aquaporin, mRNA Sequence", Database EMBL [Online], Retrieved From EBI Accession No. EMBL: AW218814, Database Accession No. AW218814. Abstract, 1999.
Van der Hoeven et al. "EST301295 Tomato Root During/After Fruit Set, Cornell University Lycopersicon Esculentum cDNA Clone cLEX1K11 Similar to Vernicia Fordii Aquaporin, mRNA Sequence", Database EMBL [Online], Retrieved From EBI Accession No. EMBL: AW218815, Database Accession No. AW218815. Abstract, 1999.
Van der Hoeven et al. "EST428934 Tomato Nutrient Deficient Roots Lycopersicon Esculentum cDNA Clone cLEW26B2 5' Sequence, mRNA Sequence", Database EMBL, Retrieved From EBI Accession No. EMBL, Database Accession No. BF098413, 2000.
Wells "Additivity of Mutational Effects in Proteins", Biochemistry, 29 (37): 8509-8517, 1990.
Response Dated Mar. 8, 2011 to Examiner's Report of Jan. 13, 2011 From the Australian Government, IP Australia Re.: Application No. 2005252469.
Response Dated Mar. 9, 2011 to Office Action of Nov. 11, 2010 From the Israel Patent Office Re. Application No. 206118.
Response Dated Mar. 23, 2011 to Official Action of Nov. 23, 2010 From the US Patent and Trademark Office Re. U.S. Appl. No. 12/083,978.
Response Dated Mar. 24, 2011 to Examination Report of Nov. 3, 2010 From the Government of India, Patent Office Re.: Application No. 158/CHENP/2007.
International Preliminary Report on Patentability Dated Jan. 22, 2009 From the International Bureau of WIPO Re.: Application No. PCT/IL2006/001223.
Invitation to Pay Additional Fees Dated Feb. 7, 2008 From the International Searching Authority Re.: Application No. PCT/IL06/001223.

Communication Pursuant to Article 94(3) EPC Dated Nov. 27, 2009 From the European Patent Office Re.: Application No. 06809784.9.
International Search Report and the Written Opinion Dated Jul. 29, 2008 From the International Searching Authority Re.: Application No. PCT/IL06/001223.
Supplementary European Search Report and the European Search Opinion Dated Sep. 14, 2009 From the European Patent Office Re.: Application No. 06809784.9.
Gardiner et al. "Zea Mays PCO131392 mRNA Sequence", Database EMBL/GenBank/DDBJ, EBI Database Accession No. AY107021, XP002542347, May 28, 2002. 96,5% Identity in 1118 nt Overlap of AY107021 (1118 nt) With SEQ ID No. 68 (1348 nt) of the Present Application, Abstract.
Grover et al. "Understanding Molecular Alphabets of the Plant Abiotic Stress Responses", Current Science, 80(2): 206-216, Jan. 25, 2001.
Liu et al. "Root-Specific Expression of a Western White Pine PR10 Gene Is Mediated by Different Promoter Regions in Transgenic Tobacco", Plant Molecular Biology, 52: 103-120, 2003.
Official Action Dated Apr. 29, 2011 From the US Patent and Trademark Office Re. U.S. Appl. No. 12/448,359.
Response Dated Apr. 21, 2011 to Communication Pursuant to Article 94(3) EPC of Nov. 8, 2010 From the European Patent Office Re.: Application No. 04734072.4.
Supplementary European Search Report and the European Search Opinion Dated May 6, 2011 From the European Patent Office Re. Application No. 09750276.9.
Payne et al. "Heterologous MYB Genes Distinct From GL1 Enhance Trichome Production When Overexpressed in Nicotiana Tabacum", Development, 126: 671-682, 1999.
Sunkar et al. "Small RNAs as Big Players in Plant Abiotic Stress Responses and Nutrient Deprivation", Trends in Plant Science XP022148764, 12(7): 301-309, Jul. 1, 2007.
Communication Pursuant to Rules 70(2) and 70a(2) EPC Dated May 24, 2011 From the European Patent Office Re. Application No. 09750276.9.
Examination Report Dated Apr. 19, 2011 From the Instituto Mexican de la Propriedad Industrial Re. Application No. MX/a/2008/002262 and Its Summary Into English.
Examination Report Dated Feb. 17, 2010 From the Instituto Mexicano de la Propriedad Industrial Re. Application No. PA/a/2005/012565 and Its Summary in English.
Communication Pursuant to Article 94(3) EPC Dated May 12, 2010 From the European Patent Office Re.: Application No. 06766224.7.
Response Dated May 31, 2010 to Office Action of Jan. 31, 2010 From the Israel Patent Office Re.: Application No. 172135.
Requisition by the Examiner Dated Jun. 15, 2011 From the Canadian Intellectual Property Office Re. Application No. 2,526,440.
Communication Pursuant to Article 94(3) EPC Dated Jun. 29, 2011 From the European Patent Office Re. Application No. 08738191.9.
Response Dated Jun. 2, 2011 to Office Action of Feb. 3, 2011 From the Israel Patent Office Re.: Application No. 172135.
Communication Relating to the Results of the Partial International Search Dated Jul. 8, 2009 From the International Searching Authority Re.: Application No. PCT/IL2008/001657.
International Search Report and the Written Opinion Dated Oct. 30, 2009 From the International Searching Authority Re.: Application No. PCT/IL2008/001657.
Fray et al. "Nucleotide Sequence and Expression of a Ripening and Water Stress-Related cDNA From tomato With Homology to the MIP Class of Membrane Channel Proteins", Plant Molecular Biology [Online], XP009117320, 24(3): 539-543, 1994. Figs.1, 2. & Database UniProt, REcName: Full=Probable Aquaporin PIP-Type pTOM75; AltName: Full=Ripening-Associated Membrane Protein; Short=RAMP, Oct. 1, 1994.
Hachez et al. "Modulating the Expression of Aquaporin Genes in Planta: A Key to Understand Their Physiological Functions?", Biochimica et Biophysica Acta, XP005655605, 1758(8): 1142-1156, Aug. 1, 2006. p. 1151, col. 1, § 2—p. 1153, col. 1, § 1, Table 1.
Kirkness et al. "Lycopersicon Esculentum Clone 133453R, mRNA Sequence", Database EMBL [Online], XP002529190, Retrieved From EBI Accession No. EMBL:BT014251, Database Accession No. BT014251, May 12, 2004.

Maurel "Plant Aquaporins: Novel Functions and Regulation Properties", FEBS Letters, XP022078418, 581(12): 2227-2236, May 25, 2007. p. 2230, col. 2, Last §—p. 2231, col. 1, § 2, Fig.1.
Wu et al. "SubName: Full=Major intrinsic Protein", Database UniProt [Online], XP002529191, Retrieved From EBI Accession No. UNIPROT:AOFI89, Database Accession No. AOFI89, Nov. 28, 2006.
Examiner's Report Dated Dec. 20, 2011 From the Australian Government, IP Australia Re. Application No. 2005234725.
Examiner's Report Dated Jun. 24, 2011 From the Australian Government, IP Australia Re. Application No. 2006281018.
Examiner's Report Dated Jun. 30, 2011 From the Australian Government, IP Australia Re. Application No. 2006307457.
Office Action Dated Jun. 19, 2011 From the Israel Patent Office Re. Application No. 199391 and Its Translation Into English.
Response Dated Jun. 9, 2011 to Examiner's Report of Dec. 20, 2011 From the Australian Government, IP Australia Re. Application No. 2005234725.
International Preliminary Report on Patentability Dated Jul. 8, 2010 From the International Bureau of WIPO Re.: Application No. PCT/IL2008/001657.
Office Action Dated Jun. 17, 2010 From the Israel Patent Office Re. Application No. 190918 and Its Translation Into English.
Response Dated Jun. 29, 2010 to Examination Report of Feb. 17, 2010 From the Instituto Mexicano de la Propriedad Industrial Re. Application No. PA/a/2005/012565.
European Search Report and the European Search Opinion Dated Jun. 14, 2011 From the European Patent Office Re. Application No. 11154193.4.
European Search Report and the European Search Opinion Dated Jun. 21, 2011 From the European Patent Office Re. Application No. 11154213.0.
Office Action Dated Jun. 20, 2011 From the Israel Patent Office Re. Application No. 190918 and Its Translation Into English.
Partial European Search Report Dated Jul. 12, 2011 From the European Patent Office Re. Application No. 10194223.3.
Response Dated Jun. 15, 2011 to Examiner's Report of Mar. 31, 2011 From the Australian Government, IP Australia Re.: Application No. 2005252469.
Li et al. "Gossypium Hirsutum Dehydration-Induced Protein RD22-Like Protein (RDL) mRNA, Complete CDS", EBI Accession No. EMBL:AY072821, XP002639385, Database Accession No. AY072821, Dec. 4, 2002. Compound.
Purnelle et al. "Arabidopsis Thaliana DNA Chromosome 3, BAC Clone F3C22", Database EMBL [Online], XP002640829, Retrieved From EBI Accession No. EMBL:AL353912, Database Accession No. AL 353912, Apr. 27, 2000. Compound.
Wing et al. "GA_Eb0026P18f Gossypium Arboreum 7-10 Dpa Fiber Library Gossypium Arboreum cDNA Clone GA_Eb0026P18f, mRNA Sequence", Database EMBL [Online], XP002640830, Retrieved From EBI Accession No. EMBL:BF277249, Database Accession No. BF277249, Nov. 20, 2000.
Yamada et al. "Arabidopsis Thaliana Unknown Proein (At3g51610) mRNA, Complete CDS", Database EMBL [Online], XP002640828, Retrieved Fom EBI Accession No. EMBL:AY034915, Database Accession No. AY034915, Jun. 13, 2001. Compound.
Official Action Dated Jul. 8, 2011 From the US Patent and Trademark Office Re. U.S. Appl. No. 12/083,978.
Response Dated Jun. 17, 2011 to Examiner's Report of Mar. 31, 2011 From the Australian Government, IP Australia Re.: Application No. 2005252469.
Supplementary European Search Report and the European Search Opinion Dated Jul. 29, 2010 From the European Patent Office Re. Application No. 08776651.5.
Invitation to Pay Additional Fees Dated Aug. 23, 2005 From the International Search Authority Re. Application No. PCT/IL2004/000431.
Official Action Dated Aug. 18, 2010 From the US Patent and Trademark Office Re. U.S. Appl. No. 12/083,978.
Office Action Dated Aug. 4, 2010 From the Israel Patent Office Re.: Application No. 172135 and Its Translation Into English.
Response Dated Sep. 13, 2010 to Office Action Dated May 13, 2010 From the Israel Patent Office Re. Application No. 180022.

Communication Pursuant to Article 94(3) EPC Dated Feb. 13, 2009 From the European Patent Office Re.: Application No. 05750089.4.
European Search Report and the European Search Opinion Dated Aug. 9, 2010 From the European Patent Office Re.: Application No. 09163033.5.
Examiner's Report Dated Dec. 17, 2009 From the Australian Patent Office Re.: Application No. 2005252469.
International Preliminary Report on Patentability Dated Jan. 14, 2010 From the International Bureau of WIPO Re.: Application No. PCT/IL2008/000489.
International Preliminary Report on Patentability Dated Jan. 21, 2010 From the International Bureau of WIPO Re.: Application No. PCT/IL2007/001590.
International Preliminary Report on Patentability Dated Mar. 29, 2007 From the International Bureau of WIPO Re.: Application No. PCT/IL2005/000627.
International Preliminary Report on Patentability Dated Jan. 30, 2007 From the International Bureau of WIPO Re.: Application No. PCT/IL05/00627.
International Search Report and the Written Opinion Dated Nov. 24, 2008 From the International Searching Authority Re.: Application No. PCT/IL08/00489.
International Search Report Dated Jul. 2, 2009 From the International Searching Authority Re.: Application No. PCT/IL07/01590.
International Search Report Dated Jan. 3, 2007 From the International Searching Authority Re.: Application No. PCT/IL2005/000627.
Invitation to Pay Additional Fees Dated Sep. 8, 2006 From the International Searching Authority Re.: Application No. PCT/IL05/00627.
Notice of Allowance Dated Apr. 16, 2010 From the US Patent and Trademark Office Re.: U.S. Appl. No. 11/629,411.
Office Action Dated May 13, 2010 From the Israel Patent Office Re. Application No. 180022 and Its Translation Into English.
Office Action Dated Jan. 22, 2010 From the State Intellectual Property Office of the People's Republic of China Re.: Application No. 200580027481.4 and Its Translation Into English.
Official Action Dated May 1, 2009 From the US Patent and Trademark Office Re.: U.S. Appl. No. 11/629,411.
Official Action Dated Sep. 2, 2009 From the US Patent and Trademark Office Re.: U.S. Appl. No. 11/629,411.
Official Action Dated Jun. 8, 2010 From the US Patent and Trademark Office Re.: U.S. Appl. No. 11/629,411.
Partial European Search Report Dated Apr. 19, 2010 From the European Patent Office Re.: Application No. 09163033.5.
Response Dated Jan. 4, 2010 to Official Action of Sep. 2, 2009 From the US Patent and Trademark Office Re.: U.S. Appl. No. 11/629,411.
Response Dated May 17, 2010 to Office Action of Jan. 22, 2010 From the State Intellectual Property Office of the People's Republic of China Re.: Application No. 200580027481.4.
Supplementary European Search Report and the European Search Opinion Dated Jul. 1, 2010 From the European Patent Office Re. Application No. 07849616.3.
Supplementary European Search Report and the European Search Opinion Dated Aug. 11, 2010 From the European Patent Office Re. Application No. 08738191.9.
Supplementary European Search Report Dated Apr. 23, 2008 From the European Patent Office Re.: Application No. 05750089.4.
Translation of Notice of Payment of the Restoration Fee for Unity of Invention Dated Mar. 20, 2009 From the State Intellectual Property Office of the People's Republic of China Re.: Application No. 200580027481.4.
Written Opinion Dated Jul. 2, 2009 From the International Searching Authority Re.: Application No. PCT/IL07/01590.
Written Opinion Dated Jan. 3, 2007 From the International Searching Authority Re.: Application No. PCT/IL2005/000627.
Blewitt et al. "BNLGHi10083 Six-Day Cotton Fiber Gossypium Hirsutum cDNA 5' Similar to (AC004521) Unknown Protein [Arabidopsis Thaliana], mRNA Sequence", XP002576188, Retrieved Fron EBI Accession No. EMBL:AI728187, Database Accession No. AI728187, Jun. 12, 1999. Sequence.
Blewitt et al. "BNLGHi8081 Six-Day Cotton Fiber Gossypium Hirsutum cDNA 5' Similar to (AC004521) Unknown Protein [Arabidopsis Thalian], mRNA Sequence", XP002576189, Retrieved From EBI Accesion No. EMBL:AI730835, Database Accession No. AI730835, Jun. 12, 1999. Sequence.

Blewitt et al. "BNLGHi8396 Six-Day Cotton Fiber Gossypium Hirsutum cDNA 5' Similar to (AC004521) Unknown Protein [Arabidopsis Thaliana], mRNA Sequence", XP002576190, Retrieved From EBI Accession No. EMBL:AI27553, Database Accession No. AI27553, Jun. 12, 1999. Sequence.

Bowie et al. "Deciphering the Message in Protein Sequences: Tolerance to Amino Acid Substitutions", Science, 247(4948): 1306-1310, Mar. 16, 1990.

Cheuk et al. "Arabidopsis Thaliana At2g46960/F14M4.21 mRNA, Complete CDS", Database EMBL [Online], XP002593835, Retrieved From EBI Accession No. EMBL:AY091688, Database Accession No. AY091688, Apr. 14, 2002.

François et al. "Overexpression of the VvLTP1 Gene Interferes With Somatic Embryo Development in Grapevine", Functional Plant Biology, 35(5): 394-402, 2008.

Ji et al. "Gossypium Hirsutum Expansin mRNA, Complete CDs", XP002474936, Retrieved From EBI Accession No. EMBL:AY189969, Database Accession No. AY189969.

Ji et al. "Isolation and Analyses of Genes Preferentially Expressed During Early Cotton Fiber Development by Subtractive PCR and cDNA Array", Nucleic Acids Research, XP002474935, 31(10): 2534-2543, May 15, 2003.

Kim et al. "Arabidopsis Thaliana At2g46960/F14M4.21 mRNA, Complete CDS", Database EMBL [Online], XP002593834, Retrieved From EBI Accession No. EMBL:AF367329, Database Accession No. AF367329, Apr. 12, 2001.

Kirubakaran et al. "Characterization of a New Antifungal Lipid Transfer Protein From Wheat", Plant Physiology and Biochemistry, 46: 918-927, 2008.

McConnell et al. "Role of Phabulosa and Phavoluta in Determining Radial Patterning in Shoots", Nature, 411(6338): 709-713, Jun. 7, 2001.

Merriam-Webster "Exogenous Definition", Merrian-Webster On-Line Dictionary, 2010.

NCBI "Protein Sequence (588 Letters)", NCBI BLAST Basic Local Alignment Search Tool, 3 P., Retrieved From the Internet on Nov. 24, 2009.

Orford et al. "Specific Expression of an Expansin Gene During Elongation of Cotton Fibres", Biochimica et Biophysica Acta, XP000866032, 1398(3): 342-346, Jul. 9, 1998. Abstract, 8343, Fig.1.

Orzaez et al. "Agroinjection of Tomato Fruits. A Tool for Rapid Functional Analysis of Transgenes Directly in Fruit", Plant Physiology, 140: 3-11, 2006.

Udall et al. "A Global Assembly of Cotton ESTs", Genome Research, 16(3): 441-450, 2006.

Wallace et al. "Oligonucleotide Probes for the Screening of Recombinant DNA Libraries", Methods in Enzymology, XP002957829, 152: 432-442, Jan. 1, 1987.

Wing et al. "An Integrated Analysis of the Genetics, Devlopment, and Evolution of Cotton Fiber", NBCI GenBank Accession No. BE052336, 2000.

Wing et al. "GA_Eb0023E09f Gossypium Arboreum 7-10 Dpa Fiber Library Gossypium Arboreum cDNA Clone GA_Eb0023F09f, mRNA Sequence", XP002576191, Retrieved From EBI Accession No. EMBL:BF275177, Database Accession No. BF275177, Nov. 20, 2000. Sequence.

Communication Pursuant to Rule 70(2) EPC and Reference to Rule 39(1) EPC Dated Sep. 13, 2010 From the European Patent Office Re.: Application No. 09163033.5.

Response Dated Sep. 21, 2010 to Notice of Allowance of Apr. 16, 2010 From the US Patent and Trademark Office Re.: U.S. Appl. No. 11/629,411.

Response Dated Oct. 12, 2010 to Communication Pursuant to Article 94(3) EPC of May 12, 2010 From the European Patent Office Re.: Application No. 06766224.7.

Response Dated Oct. 14, 2010 to Office Action of Jun. 17, 2010 From the Israel Patent Office Re. Application No. 190918.

Gardiner et al. "Zea Mays PCO131392 mRNA Sequence", Database EMBL/GenBank/DDBJ, EBI Database Accession No. AY107021, XP002542347, May 28, 2002. 96,5% Identity in 1118 nt Overlap of AY107021 (1118 nt) With SEQ ID No. 68 (1348 nt) of the Present Application, Abstract.

Keskin et al. "A New, Structurally Nonredundant, Diverse Data Set of Protein-Protein Interfaces and Its Implications", Protein Science, 13: 1043-1055, 2004.

Communication Pursuant to Article 94(3) EPC Dated Nov. 8, 2010 From the European Patent Office Re.: Application No. 04734072.4.

Communication Pursuant to Article 94(3) EPC Dated Nov. 19, 2010 From the European Patent Office Re.: Application No. 06809784.9.

Examination Report Dated Nov. 3, 2010 From the Government of India, Patent Office Re.: Application No. 158/CHENP/2007.

Examination Report Dated Sep. 22, 2010 From the Instituto Mexican de la Propriedad Industrial Re. Application No. MX/a/2008/005280 and Its Summary Into English.

International Search Report and the Written Opinion Dated Feb. 17, 2010 From the International Searching Authority Re.: Application No. PCT/IL09/00508.

Invitation to Pay Additional Fees Dated Nov. 19, 2009 From the International Searching Authority Re.: Application No. PCT/IL09/00508.

Office Action Dated Oct. 18, 2010 From the Israel Patent Office Re. Application No. 180022 and Its Translation Into English.

Yamada e tal. "Arabidopsis Thaliana Clone RAFL14-87-A16 (R20399) Unknown Protein (At1g60770) mRNA, Complete Cds", GenBank Accession No. BT002876, Retrieved From the internet, Jan. 21, 2010.

International Search Report and the Written Opinion Dated Aug. 22, 2011 From the International Searching Authority Re: Application No. PCT/IB2010/56023.

Good et al. "Can Less Yield More? Is Reducing Nutrient Input Into the Environment Compatible With Maintaining Crop Production?", Trends in Plant Science, 9(12): 597-605, Dec. 2004.

Good et al. "Engineering Nitrogen Use Efficiency With Alanine Aminotransferase", Canadian Journal of Botany, 85: 252-262, 2007.

Yanagisawa et al. "Metabolic Engineering With Dof1 Transcription Factor in Plants: Improved Nitrogen Assimilation and Growth Under Low-Nitrogen Conditions", Proc. Natl. Acad. Sci USA, PNAS, 101(20): 7833-7838, May 18, 2004.

Examiner's Report Dated Mar. 15, 2012 From the Australian Government, IP Australia Re. Application No. 2011239323.

Communication Pursuant to Rule 69 EPC—Reminder Concerning Payment of the Designation Fee (Art. 79(2) EPC) and of the Examination Fee (Art. 94(1) EPC)—and Invitation Pursuant to Rule 70a(1) EPC Dated Jul. 18, 2011 From the European Patent Office Re. Application No. 11154193.4.

Communication Pursuant to Rule 69 EPC—Reminder Concerning Payment of the Designation Fee (Art. 79(2) EPC) and of the Examination Fee (Art. 94(1) EPC)—and Invitation Pursuant to Rule 70a(1) EPC Dated Jul. 25, 2011 From the European Patent Office Re. Application No. 11154213.0.

Examiner's Report Dated Jul. 21, 2011 From the Australian Government, IP Australia Re. Application No. 2005234725.

Response Dated Jul. 3, 2011 to Examination Report of Apr. 19, 2011 From the Instituto Mexicano de la Propriedad Industrial Re. Application No. MX/a/2008/002262 and Its Summary Into English.

Response Dated Jul. 25, 2011 to Examiner's Report of Jul. 21, 2011 From the Australian Government, IP Australia Re. Application No. 2005234725.

Advisory Action Before the Filing of an Appeal Brief Dated Aug. 5, 2011 From the US Patent and Trademark Office Re. U.S. Appl. No. 12/083,978.

Invitation to Pay Additional Fees Dated Aug. 18, 2011 From the International Searching Authority Re.: Application No. PCT/IL08/00489.

Katavic et al. "Utility of the Arabidopsis FAE1 and Yeast SLC1-1 Genes for Improvement in Erucic Acid and Oil Content in Rapeseed", Biochemical Society Transaction, 28(6): 935-937, Dec. 2000.

International Preliminary Report on Patentability Dated Sep. 15, 2011 From the International Bureau of WIPO Re. Application No. PCT/IB2010/050871.

European Search Report and the European Search Opinion Dated Oct. 6, 2011 From the European Patent Office Re. Application No. 11172514.9.
Response Dated Oct. 3, 2011 to Examiner's Report of Jun. 24, 2011 From the Australian Government, IP Australia Re. Application No. 2006281018.
Response Dated Oct. 4, 2011 to Official Action of Jul. 8, 2011 From the US Patent and Trademark Office Re. U.S. Appl. No. 12/083,978.
Taliercio et al. "GH_TMIRS_129_Gl0_F Cooton Normalized Library dT Primed Gossypium Hirsutum cDNA, mRNA Sequence", EMBL-Bank, XP002659970, Retrieved From EBI Accession No. EM_EST:DW508992, Database Accession No. DW508992.
Taliercio et al. "GH_TMIRS_129_G10_R Cotton Normalized Library dT Primed Gossypium Hirsutum cDNA, mRNA Sequence", EMBL-Bank, XP002659971, Retrieved From EBI Accession No. EM_EST:DW508993, Database Accession No. DW508993.
Office Action Dated Sep. 22, 2011 From the Israeli Patent Office Re. Application No. 201242 and Its Translation Into English.
Response Dated Oct. 17, 2011 to Requisition by the Examiner of Jun. 15, 2011 From the Canadian Intellectual Property Office Re. Application No. 2,526,440.
Chames et al. "Direct Selection of a Human Antibody Fragment Directed Against the Tumor T-Cell Epitope HLA-Al-MAGE-Al From a Nonimmunized Phage-Fab Library", Proc. Natl. Acad. Sci. USA, PNAS, XP002967292, 97(14): 7969-7974, Jul. 5, 2000.
European Search Report and the European Search Opinion Dated Nov. 2, 2011 From the European Patent Office Re. Application No. 10194223.3.
Examiner's Report Dated Oct. 19, 2011 From the Australian Government, IP Australia Re. Application No. 2006281018.
Examiner's Report Dated Oct. 28, 2011 From the Australian Government, IP Australia Re. Application No. 2006307457.
International Search Report and the Written Opinion Dated Oct. 31, 2011 From the International Searching Authority Re.: Application No. PCT/IL08/00489.
Response Dated Oct. 19, 2011 to Official Action of Apr. 29, 2011 From the US Patent and Trademark Office Re. U.S. Appl. No. 12/448,359.
Response Dated Oct. 27, 2011 to Communication Pursuant to Article 94(3) EPC of Jun. 29, 2011 From the European Patent Office Re. Application No. 08738191.9.
Response Dated Oct. 27, 2011 to Office Action of Jul. 1, 2011 From the State Intellectual Property Office of the People's Republic of China Re. Application No. 200880017707.6.
Response Dated Oct. 27, 2011 to Supplementary European Search Report and the European Search Opinion of May 6, 2011 From the European Patent Office Re. Application No. 09750276.9.
Response Dated Oct. 31, 2011 to Notification of the First Office Action of Jun. 30, 2011 From the State Intellectual Property Office of the People's Republic of China Re. Application No. 200680047610.0.
Kandel et al. "Cloning, Functional Expression, and Characterization of CYP709C1, the First Sub-Terminal Hydroxylase of Long Chain Fatty Acid in Plants", Journal of Biological Chemistry, JBC, 280(43): 35881-35889, Oct. 28, 2005. p. 35887, col. 1, Para 2.
International Preliminary Report on Patentability Dated Dec. 1, 2011 From the International Bureau of WIPO Re. Application No. PCT/IL2008/000489.
Lin et al. "Arabidopsis Thaliana Chromosome III BAC F7O18 Genomic Sequence, Complete Sequence", GenBank Accession No. AC011437, Oct. 30, 2002.
Communication Pursuant to Rules 70(2) and 70a(2) EPC and Reference to Rule 39(1) EPC Dated Dec. 5, 2011 From the European Patent Office Re. Application No. 10194223.3.
Communication Pursuant to Rules 70(2) and 70a(2) EPC and Reference to Rule 39(1) EPC Dated Nov. 7, 2011 From the European Patent Office Re. Application No. 11172514.9.
Examiner's Report Dated Jan. 10, 2012 From the Australian Government, IP Australia Re. Application No. 2005234725.
Official Action Dated Dec. 21, 2011 From the US Patent and Trademark Office Re. U.S. Appl. No. 12/810,855.

Response Dated Jan. 10, 2012 to European Search Report and the European Search Opinion of Jun. 14, 2011 From the European Patent Office Re. Application No. 11154193.4.
Aharon et al. "Overexpression of a Plasma Membrane Aquaporin in Transgenic Tobacco Improves Plant Vigor Under Favorable Growth Conditions But Not Under Drought or Salt Stress", The Plant Cell, 15: 439-447, Feb. 2003.
Davletova et al. "The Zinc-Finger Protein Zatl 2 Plays a Central Role in Reactive Oxygen and Abiotic Stress Signaling in Arabidopsis", Plant Physiology, 139: 847-856, Oct. 2005.
Friedberg "Automated Protein Function Prediction—The Genomic Challenge", Briefings in Bioinformatics, 7(3): 225-242, 2006.
International Search Report and the Written Opinion Dated Sep. 7, 2010 From the International Searching Authority Re. Application No. PCT/IB10/50871.
Invitation to Pay Additional Fees Dated Jun. 9, 2011 From the International Searching Authority Re. Application No. PCT/IB10/56023.
Apse et al. "Engineering Salt Tolerance in Plants", Current Opinion in Biotechnology, 13: 146-150, 2002.
Gaxiola et al. "Drought- and Salt-Tolerant Plants Result From Overexpression of the AVP1 H+-Pump", Proc. Natl. Acad. Sci. USA, PNAS, 98(20): 11444-11449, Sep. 25, 2001.
Gowik et al. "cis-Regulatory Elements for Mesophyll-Specific Gene Expression in the C4 Plant Flaveria trinervia, the Promoter of the C4 Phosphoenolpyruvate Carboxylase Gene", The Plant Cell, 16: 1077-1090, 2004.
Hattori et al. "An Acetohydroxy Acid Synthase Mutant Reveals a Single Site Involved in Multiple Herbicide Resistance", Molecular and General Genetics, 246: 419-425, 1995. Abstract!
Holmström et al. "Drought Tolerance in Tobacco", Nature, 379: 683-684, 1996. Abstract!
Jiao et al.
Katavic et al. "Utility of the Arabidopsis FAE1 and Yeast SLC1-1 Genes for Improvements in Erucic Acid and Oil Content in Rapeseed", Biochemical Society Transactions, 28: 935-7, 2000. Abstract!
Pilon-Smits et al. "Improved Performance of Transgenic Fructan-Accumulating Tobacco under Drought Stress", Plant Physiology, 107: 125-130, 1995.
Quesada et al. "Genetic Architecture of NaCl Tolerance in Arabidopsis", Plant Physiology, 130: 951-963, 2002. Abstract!
Saijo et al. "Over-Expression of a Single Ca 2+-Dependent Protein Kinase Confers Both Cold and Salt/Drought Tolerance on Rice Plants", The Plant Journal 23(3): 319-327, 2000.
Skriver et al. "Cis-Acting DNA Elements Responsive to Gibberellin and Its Antagonist Abscisic Acid", Proceedings of the National Academy of Sciences USA 88: 7266-7270, 1991.
Tarczynski et al. "Stress Protection of Transgenic Tobacco by Production of the Osmolyte Mannitol", Science, 259: 508-510, 1993. Abstract!
van Haaren et al. "A Functional Map of the Fruit-Specific Promoter of the Tomato 2A11 Gene", Plant Molecular Biology, 21: 625-640, 1993. Abstract!
Vigcolas et al. "Increasing Seed Oil Content in Oil-Seed Rape (Brassica Napus L.) by Over-Expression of a Yeast Glycerol-3-Phosphate Dehydrogenase Under the Control of a Seed-Specific Promoter", Plant Biotechnology Journal, 5 Issue: 431-441, 2007. Abstract!
Wang et al. "The Soybean Dof-Type Transcription Factor Genes, GmDof4 and GmDof11, Enhance Lipid Content in the Seeds of Transgenic Arabidopsis Plants", The Plant Journal, 52: 716-729, 2007. Abstract!
Xu et al. "Expression of a Late Embryogenesis Abundant Protein Gene, HVAl, From Barley Confers Tolerance to Water Deficit and Salt Stress in Transgenic Rice", Plant Physiology, 110: 249-257, 1996.
Yanagisawa et al. "Diversity and Similarity Among Recognition Sequences of Dof Transcription Factors", The Plant Journal, 17(2): 209-214, 1999.
Zabrouskov et al. "Oxidative Metabolism and the Physiological Age of Seed Potatoes Are Affected by Increased Alpha-Linolenate Content", Physiologia Plantarum, 116: 172-185, 2002.
Official Action Dated Sep. 19, 2011 From the US Patent and Trademark Office Re. U.S. Appl. No. 12/810,855.

Response Dated Sep. 25, 2011 to Examiner's Report of Jun. 30, 2011 From the Australian Government, IP Australia Re. Application No. 2006307457.
Official Action Dated Apr. 10, 2012 From the US Patent and Trademark Office Re. U.S. Appl. No. 12/669,975.
Examiner's Report Dated Jan. 13, 2012 From the Australian Government, IP Australia Re. Application No. 2011239323.
Supplementary European Search Report and the European Search Opinion Dated Jan. 2, 2012 From the European Patent Office Re. Application No. 09807983.3.
Translation of Decision of Rejection Dated Dec. 9, 2011 From the State Intellectual Property Office of the People's Republic of China Re.: Application No. 200580027481.4.
Adachi et al. "Oryza Sativa Japonica Group cDNA Clone:J023021L06, Full Insert Sequence", Database EMBASE [Online], XP002665608, Retrieved From EBI, Database Accession No. AK099270, Jul. 19, 2003.
Feng et al. "Probable Cinnamyl Alcohol Dehydrogenase 6", Darabase UniProt [Online], XP002665609, Retrieved From EBI, Database Accession No. Q7XWU3, Mar. 1, 2004.
Translation of Office Action Dated Jan. 4, 2012 From the State Intellectual Property Office of the People's Republic of China Re. Application No. 200880109464.9.
Translation of Office Action Dated Jan. 17, 2012 From the State Intellectual Property Office of the People's Republic of China Re. Application No. 201110104274.1.
Translation of Office Action Dated Dec. 31, 2011 From the State Intellectual Property Office of the People's Republic of China Re. Application No. 200910217137.1.
Examination Report Dated Aug. 1, 2011 From the Government of India, Patent Office Re.: Application No. 158/CHENP/2007.
Examination Report Dated May 25, 2011 From the Government of India, Patent Office Re.: Application No. 158/CHENP/2007.
Examiner's Report Dated Aug. 1, 2011 From the Australian Government, IP Australia Re. Application No. 2005234725.
Response Dated Jul. 6, 2011 to Examiner's Report of Dec. 20, 2010 From the Australian Government, IP Australia Re. Application No. 2005234725.
Response Dated Jul. 20, 2011 to Examination Report of May 25, 2011 From the Government of India, Patent Office Re.: Application No. 158/CHENP/2007.
Translation of Notification of the First Office Action Dated Jun. 30, 2011 From the State Intellectual Property Office of the People's Republic of China Re. Application No. 200680047610.0.
Van der Hoeven et al. "EST312975 Tomato Root During/After Fruit Set, Cornell University Solanum Lycopersicum cDNA Clone cLEX14020 5-, mRNA Sequence", GenBank, GenBank Accession No. AW622177.1.
Communication Pursuant to Article 94(3) EPC Dated Jan. 12, 2011 From the European Patent Office Re. Application No. 08867385.0.
Communication Pursuant to Article 94(3) EPC Dated Dec. 21, 2010 From the European Patent Office Re. Application No. 08866783.7.
International Preliminary Report on Patentability Dated Oct. 7, 2010 From the International Bureau of WIPO Re. Application No. PCT/IL2008/001684.
International Preliminary Report on Patentability Dated Jul. 15, 2010 From the International Bureau of WIPO Re. Application No. PCT/IL2008/001683.
International Preliminary Report on Patentability Dated Jul. 15, 2010 From the International Bureau of WIPO Re. Application No. PCT/IL2008/001685.
International Search Report Dated Jun. 2, 2009 From the International Searching Authority Re.: Application No. PCT/IL2008/001683.
International Search Report Dated Apr. 14, 2009 From the International Searching Authority Re.: Application No. PCT/IL2008/001684.
International Search Report Dated May 18, 2009 From International Searching Authority Re.: Application No. PCT/IL2008/001685.
Response Dated Aug. 11, 2011 to Examination Report of Aug. 1, 2011 From the Government of India, Patent Office Re.: Application No. 158/CHENP/2007.

Response Dated Jul. 12, 2011 to Communication Pursuant to Article 94(3) EPC of Jan. 12, 2011 From the European Patent Office Re. Application No. 08867385.0.
Response Dated Jun. 21, 2011 to Communication Pursuant to Article 94(3) EPC of Dec. 21, 2010 From the European Patent Office Re. Application No. 08866783.7.
Translation of Office Action Dated Jul. 1, 2011 From the State Intellectual Property Office of the People's Republic of China Re. Application No. 200880017707.6.
Translation of Office Action Dated Jun. 22, 2011 From the State Intellectual Property Office of the People's Republic of China Re. Application No. 200880127685.9.
Written Opinion Dated Jun. 2, 2009 From the International Searching Authority Re.: Application No. PCT/IL2008/001683.
Written Opinion Dated Apr. 14, 2009 From the International Searching Authority Re.: Application No. PCT/IL2008/001684.
Written Opinion Dated May 18, 2009 From the International Searching Authority Re.: Application No. PCT/IL2008/001685.
Agostini et al. "Evaluation of Feature-Based Registration in Dynamic Infrared Imaging for Breast Cancer Diagnosis", Proceedings of the 28th IEEE EMBS (Engineering in Medicine and Biology) Annual International Conference, New York City, USA, Aug. 30-Sep. 3, 2006, XP031235634, p. 953-956, Aug. 30, 2006. p. 953, § 2, 3.
Aksenov et al. "3D Thermography for Quantification of Heat Generation Resulting From Inflammation", Proceedings of the 8th 3D Modelling Symposium, Paris, France, XP))2523191, 11 P., 2003.
Bichinho et al. "A Computer Tool for the Fusion and Visualization of Thermal and Magnetic Resonance Images", Journal of Digital Imaging, XP002527797, 22(5): 527-534, Oct. 2009. p. 3, col. 1, Line 5—col. 2, Line 6, Fig.1.
Deng et al. "Enhancement of Thermal Diagnostics on Tumors Underneath the Skin by Induced Evaporation", Proceedings of the 2005 27th Annual International Conference of the Engineering in Medicine and Biology Society, Shanghai, China, Sep. 1-4, 2005, IEEE-EMBS 2005, XP002519610, 7: 7525-7528, 2005. Passage Bridging p. 7526 and p. 7527, Abstract, Figs.4, 5.
Deng et al. "Mathematical Modeling of Temperature Mapping Over Skin Surface and Its Implementation in Thermal Disease Diagnostics", Computers in Biology and Medicine, XP002523192, 34(6): 495-521, Sep. 2004. Abstract, p. 497.
Kaczmack et al. "Optical Excitation Methods in Active Dynamic Thermography in Medical Diagnostics", Proceedings of the SPIE—The International Society for Optical Engineering SPIE, XP002519609, 5566(1): 120-126, 2004. p. 121, Last §, p. 123, First §, Fig.3.
Lipari et al. "Advanced Infrared Image Processing for Breast Cancer Risk Assessment", Proceedings of the 19th Annual International Conference of the IEEE/EMBS Engineering in Medicine and Biology Society, Chicago, IL, USA, Oct. 30-Nov. 2, 1997, XP010325780, 2: 673-676, Oct. 30, 1997. Abstract, Sections II, III, Fig.3.
Moderhak et al. "Problems of 3D Breast Imaging", Gdansk University of Technology, Department of Biomedical Engineering, 2 P.
Tan et al. "A Novel Cognitive Interpretation of Breast Cancer Thermography With Complementary Learning Fuzzy Neural Memory Structure", Expert Systems With Applications, XP005919120, 33(3): 652-666, Mar. 13, 2007. Abstract, p. 658-659, Section 4, Fig.5.
Yanagisawa et al. "Metabolic Engineering With Dofl Transcription Factor in Plants: Improved Nitrogen Assimilation and Growth Under Low-Nitrogen Conditions", Proc. Natl. Acad. Sci. USA, PNAS, 101(20): 7833-7838, May 18, 2004.
Response Dated Oct. 18, 2011 to Official Action of Sep. 19, 2011 From the US Patent and Trademark Office Re. U.S. Appl. No. 12/810,855.
Communication Pursuant to Rule 55 EPC Dated Mar. 16, 2012 From the European Patent Office Re. Application No. 11190921.4.
Restriction Official Action Dated Apr. 11, 2012 From the US Patent and Trademark Office Re. U.S. Appl. No. 12/834,106.
Communication Pursuant to Article 94(3) EPC Dated Feb. 14, 2012 From the European Patent Office Re.: Application No. 04734072.4.
Requisition by the Examiner Dated Feb. 2, 2012 From the Canadian Intellectual Property Office Re. Application No. 2,570,195.

International Search Report and the Written Opinion Dated Dec. 6, 2011 From the International Searching Authority Re. Application No. PCT/IB2011/051843.
Notice of Allowance Dated Dec. 5, 2011 From the US Patent and Trademark Office Re. U.S. Appl. No. 12/448,359.
Response Dated Dec. 15, 2011 to Examiner's Report of Aug. 1, 2011 From the Australian Government, IP Australia Re. Application No. 2005234725.
Translation of Notification of the Office Action Dated Dec. 1, 2011 From the State Intellectual Property Office of the People's Republic of China Re. Application No. 200680047610.0.
Communication Pursuant to Article 94(3) EPC Dated Apr. 3, 2012 From the European Patent Office Re.: Application No. 06766224.7.
Applicant-Initiated Interview Summary Dated Aug. 6, 2012 From the US Patent and Trademark Office Re. U.S. Appl. No. 12/669,975.
Communication Pursuant to Article 93(3) EPC Dated Jun. 15, 2012 From the European Patent Office Re. Application No. 11154193.4.
Communication Pursuant to Article 94(3) EPC Dated Jul. 4, 2012 From the European Patent Office Re. Application No. 10194223.3.
Communication Pursuant to Article 94(3) EPC DAted Jul. 13, 2012 From the European Patent Office Re. Application No. 11172514.9.
Communication Pursuant to Article 94(3) EPC Dated Jun. 21, 2012 From the European Patent Office Re. Application No. 11154213.0.
Communication Pursuant to Rules 70(2) and 70a(2) EPC Dated Jul. 24, 2012 From the European Patent Office Re. Application No. 10748403.2.
Communication Under Rule 71(3) EPC Dated Jun. 5, 2012 From the European Patent Office Re.: Application No. 06809784.9.
Examination Report Dated Jun. 6, 2012 From the Federal Service of Intellectual Property, Federal State Budget Institute, Federal Institute of Industrial Property of the Russian Federation Re. Application No. 2011113420 and Its Translation Into English.
Examination Report Dated Jun. 11, 2012 From the Instituto Mexican de la Propicdad Industrial Re. Application No. MX/a/2011/007294 and Its Translation Into English.
International Preliminary Report on Patentability Dated Jul. 12, 2012 From the International Bureau of WIPO Re. Application No. PCT/IB2010/056023.
International Search Report and the Written Opinion Dated Aug. 6, 2012 From the International Searching Authority Re. Application No. PCT/IB11/53697.
Office Action Dated Jun. 25, 2012 From the State Intellectual Property Office of the People's Republic of China Re.: Application No. 200880109464.9 and Its Translation Into English.
Official Action Dated Jun. 13, 2012 From the US Patent and Trademark Office Re. U.S. Appl. No. 12/594,853.
Official Action Dated Jul. 17, 2012 From the US Patent and Trademark Office Re. U.S. Appl. No. 12/834,106.
Official Action Dated Jun. 19, 2012 From the US Patent and Trademark Office Re. U.S. Appl. No. 13/450,547.
Supplementary European Search Report and the European Search Opinion Dated Jul. 6, 2012 From the European Patent Office Re. Application No. 10748403.2.
Bernhardt et al. "The bHLH Genes GLABRA3 (GL3) and Enhancer of GLABRA3 (EGL3) Specify Epidermal Cell Fate in the Arabidopsis Root", Development, 130(26): 6431-6439, 2003.
Daniell et al. "Solanum Bulbocastanum Chloroplast, Complete Genome", GenBank NCBI, Accession No. NC_007943, Mar. 26, 2010. p. 1, Source, p. 10-11, Nucleotides 46590-47195, Gene 'RPS4'.
Ishikawa et al. JP 2005-185101: Full Length cDNA of Plant and the Use Thereof, Database EMBL [Online], XP002678022, Retrieved From EBI Accession No. EM_PAT:HV067703, Database Accession No. HV067703, Jul. 15, 2011. Sequence.
Kano-Murakami et al. "A Rice Homeotic Gene, OSH1, Causes Unusual Phenotypes in Transgenic Tobacco", FEBS Letters, 334(3): 365-368, Nov. 1993.
Kikuchi et al. "Rice cDNA-Encoded Protein SEQ ID No. 31047", Database Geneseq [Online], XP002678021, Retrieved From EBI Accession No. GSP:AQD37188, Database Accession No. AGD37188, Jun. 12, 2008. Shows 100% Identity to Present SEG ID No. 246 (Protein) and Corresponding Polynucleotide Shows 100% Identity to SEQ ID No. 7 Over 458 Nucleotides. Abstract.
La Rosa et al. "Oryza Sativa Amino Acid Sequence SEQ ID No. 133688", Database Geneseq [Online], XP002678023, Retrieved From EBI Accession No. GSP:ANM19687, Database Accession No. ANM19687, Dec. 28, 2007. 100% Identity to Present SEQ IFD No. 246, Corresponding Polynucleotide Has 99,6% Identity to Present SEQ ID No. 7 Over 488 Nucleotides. Abstract, Sequence.
La Rosa et al. "Oryza Sativa Nucleotide Sequence SEQ ID No. 31205", Database Geneseq [Online], XO002678024, Retrieved From EBI Accession No. GSN:ANL17203, Database Accession No. ANL17203, Dec. 28, 2007. Sequence.
Payne et al. "GL3 Encodes a bHLH Protein That Regulates Trichome Development in Arabidopsis Through Interaction With GL1 and TTG1", Genetics, 156: 1349-1362, Nov. 2000.
Communication Pursuant to Article 94(3) EPC Dated Oct. 23, 2012 From the European Patent Office Re. Application No. 11154193.4.
Communication Pursuant to Article 94(3) EPC Dated Oct. 23, 2012 From the European Patent Office Re. Application No. 11154213.0.
Communication Under Rule 71(3) EPC Dated Nov. 19, 2012 From the European Patent Office Re. Application No. 08738191.9.
Examination Report Dated Oct. 15, 2012 From the Instituto Mexicano de la Propiedad Industrial Re. Application No. MX/a/2009/006660 and Its Translation Into English.
Invitation to Pay Additional Fees Dated Oct. 17, 2012 From the International Searching Authority Re. Application No. PCT/IL2012/050154.
Notice of Allowance Dated Nov. 19, 2012 From the US Patent and Trademark Office Re. U.S. Appl. No. 13/450,547.
Patent Examination Report Dated Dec. 12, 2012 From the Australian Government, IP Australia Re. Application No. 2008236316.
Requisition by the Examiner Dated Oct. 3, 2012 From the Canadian Intellectual Property Office Re. Application No. 2,526,440.
Restriction Official Action Dated Nov. 13, 2012 From the US Patent and Trademark Office Re. U.S. Appl. No. 12/992,902.
Translation of Notice of Paying Restoration Fee for Unity of Invention Dated Oct. 29, 2012 From the State Intellectual Property Office of the People's Republic of China Re. Application No. 200880127757.X.
Alcala et al. "EST543159 Tomato Callus Solanum Lycopersicum cDNA Clone cLEC80A19 5-end, mRNA Sequence", GenBank: BI923254.1, GenBank Accession No. BI923254, Oct. 17, 2001.
Backhaus et al. "Nucleotide Sequence of a cDNA for a P2 60S Acidic Ribosomal Protein From Parthenium Argentatum", Plant Physiology, 106: 395, 1994.
Del Pozo et al. "F-Box Proteins and Protein Degradation: An Emerging Theme in Cellular Regulation", Plant Molecular Biology, 44(2): 123-128, Sep. 2000.
Harwood "Plant Fatty Acid Synthesis", The AOCS Lipid Library, 11 P., Apr. 12, 2010.
Communication Pursuant to Rules 70(2) and 70a(2) EPC Dated Aug. 30, 2010 From the European Patent Office Re. Application No. 08738191.9.
Examiner's Report Dated Dec. 20, 2010 From the Australian Government, IP Australia Re. Application No. 2005234725.

* cited by examiner

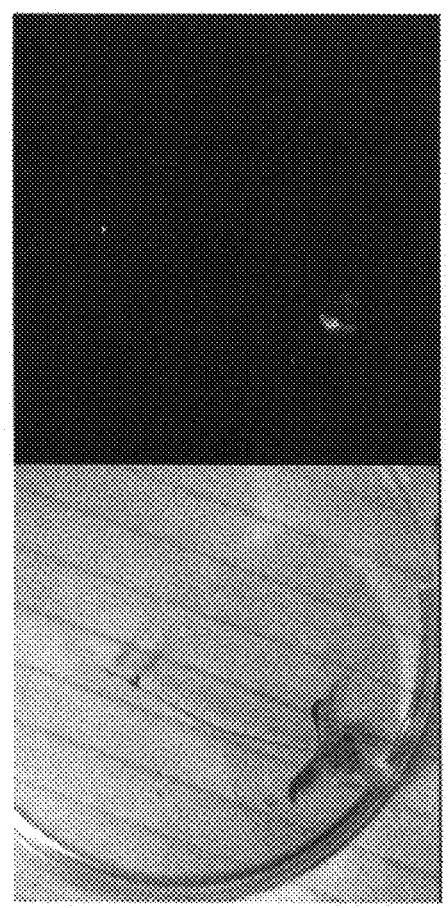
Fig. 3A
Fig. 3B
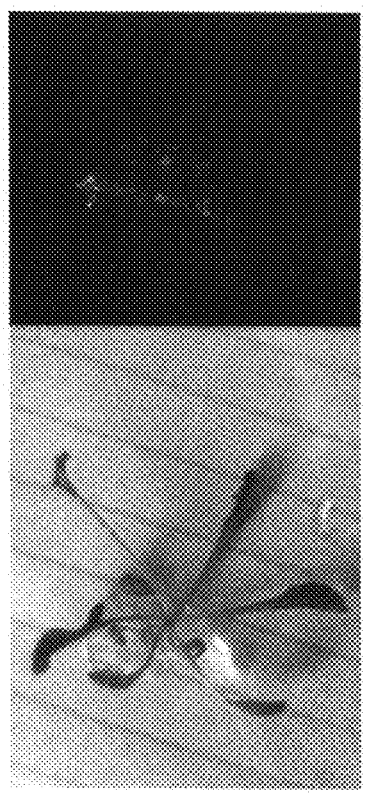
Fig. 3C
Fig. 3D

METHODS OF INCREASING ABIOTIC STRESS TOLERANCE AND/OR BIOMASS IN PLANTS GENERATED THEREBY

RELATED APPLICATIONS

This application is a continuation of U.S. patent application Ser. No. 11/284,236 filed on Nov. 22, 2005, which is a continuation-in-part (CIP) of PCT Patent Application No. PCT/IL2004/000431 filed on May 20, 2004, which claims the benefit of priority from U.S. Provisional Patent Application No. 60/472,433 filed on May 22, 2003.

U.S. patent application Ser. No. 11/284,236 also claims the benefit of priority from U.S. Provisional Patent Application No. 60/707,957 filed on Aug. 15, 2005.

The contents of the above applications are incorporated herein by reference.

FIELD AND BACKGROUND OF THE INVENTION

The present invention relates to methods of increasing abiotic stress tolerance and/or biomass in plants and, more particularly, to plants expressing exogenous abiotic stress-tolerance genes.

Abiotic stress (also referred to as "environmental stress") conditions such as salinity, drought, flood, suboptimal temperature and toxic chemical pollution, cause substantial damage to agricultural plants. Most plants have evolved strategies to protect themselves against these conditions. However, if the severity and duration of the stress conditions are too great, the effects on plant development, growth and yield of most crop plants are profound. Furthermore, most crop plants are very susceptible to abiotic stress (ABS) and thus necessitate optimal growth conditions for commercial crop yields. Continuous exposure to stress causes major alterations in plant metabolism which ultimately lead to cell death and consequently yields losses. Thus, despite extensive research and the use of sophisticated and intensive crop-protection measures, losses due to abiotic stress conditions remain in the billions of dollars annually (1,2).

Developing stress-tolerant plants is a strategy that has the potential to solve or mediate at least some of these problems. However, traditional plant breeding strategies used to develop new lines of plants that exhibit tolerance to ABS are relatively inefficient since they are tedious, time consuming and of unpredictable outcome. Furthermore, limited germplasm resources for stress tolerance and incompatibility in crosses between distantly related plant species represent significant problems encountered in conventional breeding. Additionally, the cellular processes leading to ABS tolerance are complex in nature and involve multiple mechanisms of cellular adaptation and numerous metabolic pathways (4-7).

Genetic engineering efforts, aimed at conferring abiotic stress tolerance to transgenic crops, have been described in the prior art. Studies by Apse and Blumwald (Curr Opin Biotechnol. 13:146-150, 2002), Quesada et al. (Plant Physiol. 130:951-963, 2002), Holmström et al. (Nature 379: 683-684, 1996), Xu et al. (Plant Physiol 110: 249-257, 1996), Pilon-Smits and Ebskamp (Plant Physiol 107: 125-130, 1995) and Tarczynski et al. (Science 259: 508-510, 1993) have all attempted at generating stress tolerant plants.

In addition, several U.S. patents and patent applications also describe polynucleotides associated with stress tolerance and their use in generating stress tolerant plants. U.S. Pat. Nos. 5,296,462 and 5,356,816 describe transforming plants with polynucleotides encoding proteins involved in cold adaptation in *Arabidopsis thaliana*, to thereby promote cold tolerance in the transformed plants.

U.S. Pat. No. 6,670,528 describes transforming plants with polynucleotides encoding polypeptides binding to stress responsive elements, to thereby promote tolerance of the transformed plants to abiotic stress.

U.S. Pat. No. 6,720,477 describes transforming plants with a polynucleotide encoding a signal transduction stress-related protein, capable of increasing tolerance of the transformed plants to abiotic stress.

U.S. application Ser. Nos. 09/938,842 and 10/342,224 describe abiotic stress-related genes and their use to confer upon plants tolerance to abiotic stress.

U.S. application Ser. No. 10/231,035 describes overexpressing a molybdenum cofactor sulfurase in plants to thereby increase their tolerance to abiotic stress.

Although the above described studies were at least partially successful in generating stress tolerant plants, there remains a need for stress tolerant genes which can be utilized to generate plants tolerant of a wide range of abiotic stress conditions.

While reducing the present invention to practice, the present inventors have identified through bioinformatic and laboratory studies several novel abiotic stress-tolerance genes, which can be utilized to increase tolerance to abiotic stress and/or biomass in plants.

SUMMARY OF THE INVENTION

According to one aspect of the present invention there is provided a method of increasing tolerance of a plant to an abiotic stress. The method includes expressing within the plant an exogenous polynucleotide at least 90% homologous to a polynucleotide selected from the group consisting of SEQ ID NOs: 1-18, 93-98 and 247-252.

According to an additional aspect of the present invention there is provided a method of increasing tolerance of a plant to an abiotic stress. The method includes expressing within the plant an exogenous polynpeptide including an amino acid sequence selected from the group consisting of SEQ ID NOs: 39-92 and 105-230.

According to another aspect of the present invention there is provided a method of increasing biomass and/or yield of a plant. The method includes expressing within the plant an exogenous polynucleotide at least 90% homologous to a polynucleotide selected from the group consisting of SEQ ID NOs: 1-18, 93-98 and 247-252.

According to still additional aspect of the present invention there is provided a method of increasing biomass and/or yield of a plant. The method includes expressing within the plant an exogenous polypeptide including an amino acid sequence selected from the group consisting of SEQ ID NOs: 39-92 and 105-230.

According to yet another aspect of the present invention there is provided a plant cell comprising an exogenous polynucleotide at least 90% homologous to a polynucleotide selected from the group consisting of SEQ ID NOs: 1-18, 93-98 and 247-252.

According to yet another aspect of the present invention there is provided a plant cell comprising an exogenous polynucleotide encoding a polypeptide including an amino acid sequence selected from the group consisting of SEQ ID NOs: 39-92 and 105-230.

According to still another aspect of the present invention there is provided a nucleic acid construct, including a polynucleotide at least 90% homologous to a nucleotide sequence selected from the group consisting of SEQ ID NOs: 1-18, 93-98 and 247-252 and a promoter capable of directing transcription of the polynucleotide in a host cell.

According to another aspect of the present invention there is provided a nucleic acid construct, including a polynucleotide encoding a polypeptide comprising an amino acid sequence selected from the group consisting of SEQ ID NOs: 39-92 and 105-230 and a promoter capable of directing transcription of the polynucleotide in a host cell.

According to further yet another aspect of the present invention there is provided an isolated polypeptide, including an amino acid sequence at least 90% homologous to the amino acid sequence encoded by a polynucleotide selected from the group consisting of SEQ ID NOs: 1-18, 93-98 and 247-252.

According to an additional aspect of the present invention there is provided an isolated polypeptide including an amino acid sequence selected from the group consisting of SEQ ID NOs: 39-92 and 105-230.

According to further features in preferred embodiments of the invention described below, the expressing is effected by (i) transforming a cell of the plant with the exogenous polynucleotide; (ii) generating a mature plant from the cell; and (iii) cultivating the mature plant under conditions suitable for expressing the exogenous polynucleotide within the mature plant.

According to still further features in the described preferred embodiments the transforming is effected by introducing to the plant cell a nucleic acid construct including the exogenous polynucleotide and at least one promoter capable of directing transcription of the exogenous polynucleotide in the plant cell.

According to still further features in the described preferred embodiments the at least one promoter is a constitutive promoter.

According to still further features in the described preferred embodiments the constitutive promoter is CaMV 35S promoter.

According to still further features in the described preferred embodiments the Q constitutive promoter is At6669 promoter.

According to still further features in the described preferred embodiments the at least one promoter is an inducible promoter.

According to still further features in the described preferred embodiments the inducible promoter is an abiotic stress inducible promoter.

According to still further features in the described preferred embodiments the at least one promoter is a tissue-specific promoter.

According to still further features in the described preferred embodiments the expressing is effected by infecting the plant with a virus including the exogenous polynucleotide.

According to still further features in the described preferred embodiments the virus is an avirulent virus.

According to still further features in the described preferred embodiments the abiotic stress is selected from the group consisting of salinity, water deprivation, low temperature, high temperature, heavy metal toxicity, anaerobiosis, nutrient deficiency, nutrient excess, atmospheric pollution and UV irradiation.

According to still further features in the described preferred embodiments the plant is a dicotyledonous plant.

According to still further features in the described preferred embodiments the plant is a monocotyledonous plant.

According to still further features in the described preferred embodiments the plant cell forms a part of a plant.

The present invention successfully addresses the shortcomings of the presently known configurations by providing methods of utilizing novel abiotic stress-tolerance genes to increase plants tolerance to abiotic stress and/or biomass and/or commercial yield.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIGS. 3A-D are photographs illustrating a $T_2$ transgenic *Arabidopsis thaliana* mature plant at flowering stage, expressing exogenous luciferase transgene from the At6669 promoter. The same plant is shown in FIGS. 3A and 3B and a second plant is shown in FIGS. 3C and 3D. FIGS. 3A and 3C are photographs taken under normal light conditions and FIGS. 3B and 3D are photographs taken in the dark. Strong illumination indicative of luciferase expression is observed in the flower and root tissues;

FIG. 8A is a photograph of a tomato plant over-expressing ABST_1, SEQ ID NO. 1 (right; 28) compared to its isogenic line that does not carry the gene (left; 29). FIG. 8B is a photograph of roots from a tomato plant over-expressing ABST_1, SEQ I.D. NO. 1 (right; 28) compared to its isogenic line that does not carry the gene (left; 29). FIG. 8C is a photograph of tomato plant canopies of a plant over-expressing ABST_36, SEQ I.D. NO. 13 (right; 30) compared to a control plant (left; 31). FIG. 8D is a photograph of total fruits of a tomato plant over-expressing ABST_36, SEQ I.D. NO. 13 (right; 30) compared to a control plant (left; 31); FIG. 9A illustrates the relative expression of ABST_36 gene in Evoline 2 tomato leaves following salt induction compared to its expression in leaves of the Evoline 1 variety. FIG. 9B illustrates the relative expression of ABST_36 gene in Evoline 2 tomato roots following salt induction compared to its expression in roots of the Evoline 1 variety. FIG. 9C illustrates the relative expression of ABST_37 gene in Evoline 2 tomato leaves following salt induction compared to its expression in leaves of the Evoline 1 variety.

DESCRIPTION OF THE PREFERRED EMBODIMENTS

Figure 1:
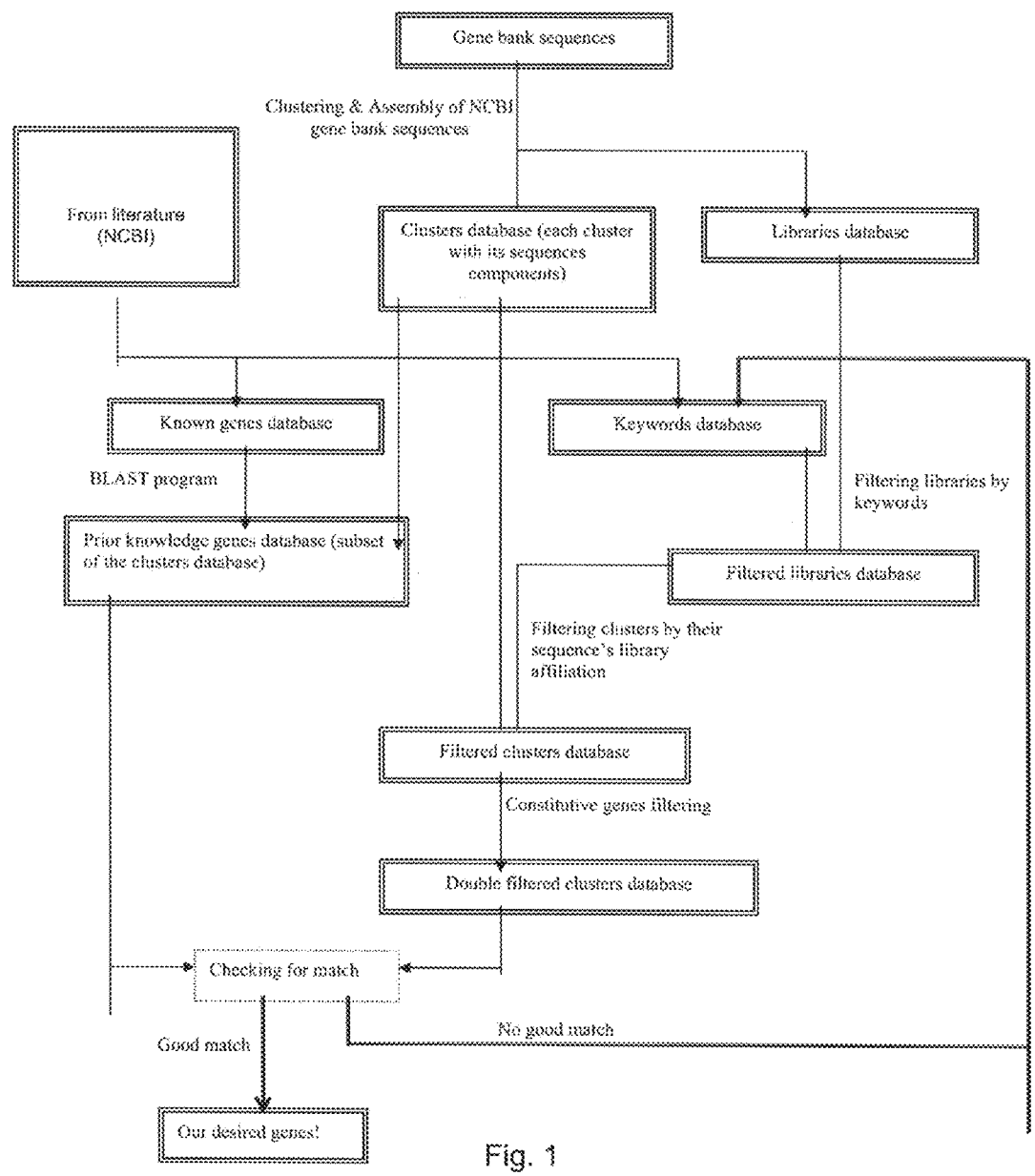
FIG. 1 is a flow chart illustrating a process of identifying putative plant stress-tolerance genes from nucleic-acid sequence databases.

The present invention is of methods of increasing plants tolerance to abiotic stress and/or biomass by utilizing novel abiotic stress tolerance genes and of plants exhibiting increased tolerance to stress conditions and/or increased capacity to accumulate biomass.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

While reducing the present invention to practice, the present inventors while employing bioinformatic techniques, identified polynucleotide sequences which encode putative abiotic-stress tolerance (ABST) proteins (Examples 1 and 11). Selected sequences were isolated (Examples 3 and 12), cloned into expression vectors (Example 4 and 13) and introduced into *Arabidopsis thaliana* plants (Example 8) and tomato plants (Example 10). These plants, which were grown under salinity stress conditions, or under normal conditions, exhibited significantly higher biomass as compared with similar plants not carrying the exogenous ABST genes (Examples 9 and 10).

Thus, according to one aspect of the present invention, there is provided a method of increasing tolerance of a plant to an abiotic stress and/or plant biomass. The method includes expressing within the plant an exogenous polynucleotide at least 70% homologous, preferably at least 80% homologous, more preferably at least 85% homologous, most preferably at least 90% homologous to a polynucleotide selected from the group consisting of SEQ ID NOs: 1-18, 93-98 and 247-252. Alternatively, the exogenous polynucleotide of the present invention encodes a polypeptide having an amino acid sequence selected from the group consisting of SEQ ID NOs: 39-92 and 105-230.

As demonstrated in Example 8 herein below, introduction of SEQ ID NOs: 1, 4, 9, 13 and 14 into *Arabidopsis thaliana* plants increased plant tolerance to abiotic stress, such as a salinity stress as measured by an increase in fresh weight, dry weight, and/or seed weight. Transgenic tomato plants showed an increase in fresh canopy weight, dry weight, root weight, seed weight and increase in total fruit yield during abiotic stress, such as salinity or drought stress following introduction of these polynucleotide sequences as demonstrated in Example 10.

The nucleic acid sequences of the present invention may be altered, to further improve expression levels for example, by optimizing the nucleic acid sequence in accordance with the preferred codon usage for a particular plant cell type which is selected for the expression of the polypeptides of the present invention.

Construction of synthetic genes by altering the codon usage is described in for example PCT Patent Application WO 93/07278.

Alternatively, ortholog sequences in a particular plant may be identified (e.g. by bioinformatics techniques) as described in Example 10. Following qualification, these may be used to direct the expression of the polypeptides of the present invention in a particular plant species. Since this may increase the probability of gene silencing, it may be preferable to optimize the nucleic acid sequence in accordance with the preferred codon usage as described above.

The phrase "abiotic stress" used herein refers to any adverse effect on metabolism, growth, reproduction and/or viability of a plant. Accordingly, abiotic stress can be induced by suboptimal environmental growth conditions such as, for example, salinity, water deprivation, flooding, low or high temperature, heavy metal toxicity, anaerobiosis, nutrient deficiency, atmospheric pollution or UV irradiation.

The phrase "abiotic stress tolerance" as used herein refers to the ability of a plant to endure an abiotic stress without suffering a substantial alteration in metabolism, growth, productivity and/or viability.

The polynucleotides of the present invention may enhance abiotic stress tolerance by any mechanism. The polynucleotides may enhance abiotic stress tolerance by encoding for polypeptides which increase the amount of water available to the plant. For example, SEQ ID NO: 13 encodes a polypeptide that enhances symplastic water transport. Alternatively the polynucleotides may enhance abiotic stress tolerance by encoding for polypeptides which are involved in enhancing the expression of other proteins involved in abiotic stress tolerance. For example, SEQ ID NO: 1 encodes a cytoplasmic ribosomal protein and SEQ ID NO: 14 is a transcription factor.

A suitable plant for use with the method of the present invention can be any monocotyledonous or dicotyledonous plant including, but not limited to, maize, wheat, barely, rye, oat, rice, soybean, peanut, pea, lentil and alfalfa, cotton, rapeseed, canola, pepper, sunflower, potato, tobacco, tomato, eggplant, eucalyptus, a tree, an ornamental plant, a perennial grass and a forage crop.

As used herein, the term "exogenous polynucleotide" refers to a nucleic acid sequence which is not naturally expressed within the plant but which, when introduced into the plant either in a stable or transient manner, produces at least one polypeptide product.

Expressing the exogenous polynucleotide of the present invention within the plant can be effected by transforming one or more cells of the plant with the exogenous polynucleotide, followed by generating a mature plant from the transformed cells and cultivating the mature plant under conditions suitable for expressing the exogenous polynucleotide within the mature plant.

Preferably, the transformation is effected by introducing to the plant cell a nucleic acid construct which includes the exogenous polynucleotide of the present invention and at least one promoter capable of directing transcription of the exogenous polynucleotide in the plant cell. Further details of suitable transformation approaches are provided hereinbelow.

As used herein, the term "promoter" refers to a region of DNA which lies upstream of the transcriptional initiation site of a gene to which RNA polymerase binds to initiate transcription of RNA. The promoter controls where (e.g., which portion of a plant, which organ within an animal, etc.) and/or when (e.g., which stage or condition in the lifetime of an organism) the gene is expressed.

Any suitable promoter sequence can be used by the nucleic acid construct of the present invention. Preferably the promoter is a constitutive promoter, a tissue-specific, or an abiotic stress-inducible promoter.

Suitable constitutive promoters include, for example, CaMV 35S promoter (SEQ ID NO: 19; Odell et al., Nature 313:810-812, 1985); *Arabidopsis* At6669 promoter (SEQ ID NO: 20); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Suitable tissue-specific promoters include, but not limited to, leaf-specific promoters such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993.

Suitable abiotic stress-inducible promoters include, but not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11: 1285-1295, 1997) and maize Ivr2 gene promoter (Pelleschi et. al., Plant Mol. Biol. 39:373-380, 1999); and heat-inducible promoters such as heat tomato hsp80-promoter from tomato (U.S. Pat. No. 5,187,267).

The nucleic acid construct of the present invention preferably further includes an appropriate selectable marker and/or an origin of replication. Preferably, the nucleic acid construct utilized is a shuttle vector, which can propagate both in *E. coli* (wherein the construct comprises an appropriate selectable marker and origin of replication) and be compatible for propagation in cells. The construct according to the present invention can be, for example, a plasmid, a bacmid, a phagemid, a cosmid, a phage, a virus or an artificial chromosome.

The nucleic acid construct of the present invention can be utilized to stably or transiently transform plant cells. In stable transformation, the exogenous polynucleotide of the present invention is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338:274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S., and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988)

p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Preferably, mature transformed plants generated as described above are further selected for abiotic stress tolerance. Accordingly, transformed and non-transformed (wild type) plants are exposed to an abiotic stress condition, such as water depravation, suboptimal temperature, nutrient deficiency, or preferably a salt stress condition. Salt stress can be effected in many ways such as, for example, by irrigating the plants with a hyperosmotic solution, by cultivating the plants hydroponically in a hyperosmotic growth solution (e.g., Hoagland solution), or by culturing the plants in a hyperosmotic growth medium (e.g., MS medium). Since different plants vary considerably in their tolerance to salinity, the salt concentration in the irrigation water, growth solution, or growth medium is preferably adjusted according to the specific characteristics of the specific plant cultivar or variety, so as to inflict a mild or moderate effect on the physiology and/or morphology of the plants (for guidelines as to appropriate concentration see, Bernstein and Kafkafi, Root Growth Under Salinity Stress In: Plant Roots, The Hidden Half 3rd ed. Waisel Y, Eshel A and Kafkafi U. (editors) Marcel Dekker Inc., New York, 2002, and reference therein). Following exposure to the stress condition the plants are frequently monitored until substantial physiological and/or morphological effects appear in wild type plants. Subsequently, transformed plants not exhibiting substantial physiological and/or morphological effects, or exhibiting higher biomass than wild-type plants, are identified as abiotic stress tolerant plants.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Preferably, the virus of the present invention is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous polynucleotide sequences such as those included in the construct of the present invention is demonstrated by the above references as well as in U.S. Pat. No. 5,316,931.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since abiotic stress tolerance in plants can involve multiple genes acting additively or in synergy (see, for example, in Quesda et al., Plant Physiol. 130:951-063, 2002), the present invention also envisages expressing a plurality of exogenous polynucleotides in a single host plant to thereby achieve superior abiotic stress tolerance.

Expressing a plurality of exogenous polynucleotides in a single host plant can be effected by co-introducing multiple nucleic acid constructs, each including a different exogenous polynucleotide, into a single plant cell. The transformed cell can than be regenerated into a mature plant using the methods described hereinabove.

Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic message including all the different exogenous polynucleotide sequences. To enable co-translation of the different polypeptides encoded by the polycistronic message, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence.

The plant cell transformed with the construct including a plurality of different exogenous polynucleotides, can be regenerated into a mature plant, using the methods described hereinabove.

Alternatively, expressing a plurality of exogenous polynucleotides in a single host plant can be effected by introducing different nucleic acid constructs, including different exogenous polynucleotides, into a plurality of plants. The regenerated transformed plants can then be cross-bred and resultant progeny selected for superior abiotic stress tolerance and/or biomass traits, using conventional plant breeding techniques.

Hence, the present application provides methods of utilizing novel abiotic stress-tolerance genes to increase tolerance to abiotic stress and/or biomass and/or yield in a wide range of economical plants, safely and cost effectively.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Identifying Putative Abiotic Stress Tolerance Genes

Putative abiotic stress-tolerance (ABST) genes were selected from NCBI databases of tomato expressed sequence tags (ESTs) and cDNAs. The database sequences were clustered and assembled using the LEADS™ software (Compugen). Clustering resulted in more than 20,000 clusters, each representing a different gene. An expression profile summary was compiled for each cluster by pooling all keywords included in the sequence records comprising the cluster. The clusters were then screened to include polynucleotides originating from libraries identified by keywords relating to ABST. The selected clusters were further filtered to exclude any cluster which included more than 100 ESTs per cluster and/or any cluster in which less than 50% of the sequences were annotated by ABST-related keywords.

Prior art ABST plant genes were identified from the publications of Quesada et al. (Plant Physiol. 130:951-963, 2002); Apse and Blumwald (Curr Opin Biotechnol. 13:146-150, 2002); Rontein et al. (Metab Eng 4:49-56, 2002); and references therein. Known plant ABST genes were aligned with the clustered tomato nucleic-acid sequences using the BLAST program. The tomato sequences having an e-score value lower than 5 were identified as ABST orthologes. Additional prior art tomato ABST genes were identified by searching the clustered tomato sequence records using the keywords "root", "crown gall", "nutrient", "callus", "disease", "pathogen", "elicitor" and "pseudomonas".

Finally, all identified prior art ABST genes were matched (by sequence alignment using the BLAST software) with the output set of tomato gene clusters, selected as described above. Consequently, about 40% of the genes selected in the output set of clusters which matched with prior art ABST genes proved to be known ABST genes, indicating that the remaining genes of the selected clusters are potentially capable of increasing abiotic stress tolerance in plants.

The selected polynucleotide sequences (Table 1A), were analyzed for presence of ORFs using Vector NTI suite (InforMax, U.K.) version 6 (Hasting Software, Inc: World Wide Web (dot) Generunner (dot) com/). ORFs identified in each of these polynucleotide sequences were compared to Genbank database sequences, using Blast (World Wide Web (dot) ncbi (dot) nlm (dot) nih (dot) gov/BLAST/); the ORF displaying the highest homology to a GenBank sequence or sequences, was mapped in order to identify an ATG start codon. The position of the ATG start codon of this ORF was then compared with that of the identified polynucleotide sequence in order to verify that each of the eighteen sequences described herein includes a full length ORF and an ATG start codon (thus qualifying as a "putative ABST gene").

TABLE 1A

Putative ABST genes

| ABST No. | SEQ ID No. |
|---|---|
| 1 | 1 |
| 3 | 2 |
| 5 | 3 |
| 6 | 4 |
| 10 | 5 |
| 11 | 6 |
| 12 | 7 |
| 19 | 8 |
| 22 | 9 |
| 24 | 10 |
| 26 | 11 |
| 27 | 12 |
| 36 | 13 |
| 37 | 14 |
| 39_T0 | 15 |
| 39_T1 | 16 |
| 49_T0 | 17 |
| 49_T1 | 18 |

ABST polypeptide homologues were identified from the NCBI databases using BLAST software (Table 1B).

TABLE 1B

ABST homologues

| ABST Putative Gene SEQ ID No. | ABST Polypeptide Homologue NCBI Accession No. | ABST Polypeptide Homologue SEQ ID No. | Protein Homology (%) |
|---|---|---|---|
| 1 | BAA96366 | 39 | 98 |
| 1 | AAS47510 | 40 | 98 |
| 1 | NP_567151 | 41 | 97 |
| 1 | NP_567104 | 42 | 96 |
| 1 | AAK55664 | 43 | 96 |
| 1 | P46298 | 44 | 97 |
| 1 | T01338 | 45 | 96 |
| 1 | T47888 | 46 | 95 |
| 1 | BAD09465 | 47 | 92 |
| 1 | Q05761 | 48 | 91 |
| 1 | BAD09464 | 49 | 88 |
| 1 | CAA79496 | 50 | 84 |
| 1 | EAJ94592 | 51 | 85 |
| 4 | NP_188036 | 52 | 76 |
| 4 | NP_035977 | 53 | 70 |
| 4 | XP_342608 | 54 | 69 |
| 4 | T09295 | 55 | 60 |
| 4 | NP_564717 | 56 | 59 |
| 4 | AAM63624 | 57 | 59 |
| 9 | P37707 | 58 | 93 |
| 9 | CAD37200 | 59 | 81 |
| 9 | CAA04664 | 60 | 78 |
| 9 | AAM64572 | 61 | 77 |
| 9 | NP_189345 | 62 | 77 |
| 9 | NP_974979 | 63 | 60 |
| 13 | AAC49992 | 64 | 88 |
| 13 | T10804 | 65 | 87 |
| 13 | AAL38357 | 66 | 87 |
| 13 | NP_188245 | 67 | 87 |
| 13 | NP_193465 | 68 | 87 |
| 13 | AAG44945 | 69 | 86 |
| 13 | T07819 | 70 | 86 |
| 13 | T12632 | 71 | 86 |
| 13 | CAC39073 | 72 | 86 |
| 13 | T01648 | 73 | 86 |
| 13 | AAF90121 | 74 | 86 |
| 13 | S48116 | 75 | 86 |
| 13 | AAO86710 | 76 | 86 |
| 13 | T14002 | 77 | 85 |
| 13 | T14001 | 78 | 85 |
| 13 | T48886 | 79 | 85 |
| 13 | T14314 | 80 | 85 |
| 13 | P33560 | 81 | 85 |
| 13 | P21653 | 82 | 85 |
| 13 | T14000 | 83 | 85 |
| 13 | T48884 | 84 | 85 |
| 13 | P24422 | 85 | 85 |
| 13 | AAB53329 | 86 | 85 |
| 14 | NP_200279 | 87 | 67 |
| 14 | AAM64276 | 88 | 67 |
| 14 | AAO72577 | 89 | 66 |
| 14 | NP_175518 | 90 | 64 |
| 14 | BAC78588 | 91 | 64 |
| 14 | BAD03011 | 92 | 62 |

Five of these genes were selected as having the most potential of being putative ABS tolerance genes on the basis of digital expression profiles (i.e. known to be up-regulated under different stress conditions) as listed in Tables 2-6, and homologies to public protein sequences and domains through multi sequence alignment searches. Also, only genes with low and medium expression levels were included.

The five genes are listed together with their functions in Table 1C below.

TABLE 1C

Selected Putative ABST genes

| Gene name | AC number, | Length of CDS bps | Protein length aa | Protein domain Similarities | Go classification |
|---|---|---|---|---|---|
| ABST_1 SEQ ID NO: 1 | BG123819/ TC153989 | 833 | 151 | Ribosomal protein S13 | RNA binding, morphogenesis, protein biosynthesis in cytosol |
| ABST_6 SEQ ID NO: 4 | BG627487/ TC162949 | 1242 | 163 | DnaJ domain | Chaperone activity, protein folding |
| ABST_22 SEQ ID NO: 9 | BG127611/ TC154372 | 1518 | 311 | Asparagine-rich region profile | Unknown |

TABLE 1C-continued

Selected Putative ABST genes

| Gene name | AC number, | Length of CDS bps | Protein length aa | Protein domain Similarities | Go classification |
|---|---|---|---|---|---|
| ABST_36 SEQ ID NO: 13 | AA824892/ TC154006 | 1466 | 249 | Major intrinsic protein | Water channel, endomembrane activity |
| ABST_37 SEQ ID NO: 14 | AW220029/ TC156100 | 1245 | 244 | Helix-loop-helix DNA-binding domain | DNA binding, transcription factor activity |

Digital expression, also known as electronic northern blot, is a tool for virtually displaying the expression profile of query genes based on the EST sequences forming the cluster. The tool can provide the expression profile of a cluster in terms of plant anatomy (in what tissues/organs is the gene expressed), developmental stage (the developmental stages at which a gene can be found) and profile of treatment (provides the physiological conditions under which a gene is expressed such as drought, cold, pathogen infection, etc). Given a random distribution of ESTs in the different clusters, the digital expression provides a probability value that describes the probability of a cluster having a total of N ESTs to contain X ESTs from a certain collection of libraries. For the probability calculations, various considerations are taken: a) the number of ESTs in the cluster, b) the number of ESTs of the implicated and related libraries, c) the overall number of ESTs available representing the species. Thereby clusters with low probability values are highly enriched with ESTs from the group of libraries of interest indicating a specialized expression.

The digital expression profile for ABST_1 (SEQ ID NO:1) is summarized below in Table 2.

TABLE 2

Change in expression of ABST_1 due to exposure to various treatments

| Keyword | ESTs in Gene | ESTs in Production | Expected ESTs | Fold | p-value |
|---|---|---|---|---|---|
| hormone treatment | 3 | 23195 | 7.14655 | 0.419783 | 0.978926 |
| Elicitors and pathogens mix | 1 | 14540 | 4.47988 | 0.22322 | 0.990341 |
| Mix of elicitors | 2 | 8655 | 2.66667 | 0.749999 | 0.751616 |
| nutrient deficiencies | 1 | 3258 | 1.00381 | 0.9962 | 0.636393 |
| —N, —P, —K, —Fe, —Al | 1 | 3258 | 1.00381 | 0.9962 | 0.636393 |
| pathogen | 13 | 30639 | 9.4401 | 1.3771 | 0.141666 |
| Agrobacterium tumefaciens C58 | 4 | 5107 | 1.5735 | 2.5421 | 0.0728454 |

TABLE 2-continued

Change in expression of ABST_1 due to exposure to various treatments

| Keyword | ESTs in Gene | ESTs in Production | Expected ESTs | Fold | p-value |
|---|---|---|---|---|---|
| CONTROL Ralstonia s. | 1 | 419 | 1 | 1 | 0.12124 |
| Elicitors and pathogens mix | 1 | 14540 | 4.47988 | 0.22322 | 0.990341 |

The digital expression profile for ABST_6 (SEQ ID NO:4) is summarized below in Table 3.

TABLE 3

Change in expression of ABST_6 due to exposure to various treatments

| Keyword | ESTs in Gene | ESTs in Production | Expected ESTs | Fold | p-value |
|---|---|---|---|---|---|
| hormone treatment | 3 | 23195 | 2.59875 | 1.1544 | 0.489866 |
| Mix of elicitors | 3 | 8655 | 1 | 3 | 0.0509528 |
| pathogen | 2 | 30639 | 3.43276 | 0.582621 | 0.876812 |
| pseudomonas syringae | 2 | 10177 | 1.14022 | 1.75405 | 0.316866 |

The digital expression profile for ABST_22 (SEQ ID NO:9) is summarized below in Table 4.

TABLE 4

Change in expression of ABST_22 due to exposure to various treatments

| Keyword | ESTs in Gene | ESTs in Production | Expected ESTs | Fold | p-value |
|---|---|---|---|---|---|
| hormone treatment | 2 | 23195 | 5.7389 | 0.348499 | 0.982893 |
| Mix of elicitors | 2 | 8655 | 2.14142 | 0.933961 | 0.636873 |
| nutrient deficiencies | 3 | 3258 | 1 | 3 | 0.0469483 |
| —N, —P, —K, —Fe, —Al | 3 | 3258 | 1 | 3 | 0.0469483 |
| pathogen | 6 | 30639 | 7.58069 | 0.791485 | 0.788347 |
| Agrobacterium tumefaciens C58 | 2 | 5107 | 1.26357 | 1.58282 | 0.361357 |

The digital expression profile for ABST_36 (SEQ ID NO: 13) is summarized below in Table 5.

TABLE 5

Change in expression of ABST_36 due to exposure to various treatments

| Keyword | ESTs in Gene | ESTs in Production | Expected ESTs | Fold | p-value |
|---|---|---|---|---|---|
| heavy metals | 1 | 741 | 1 | 1 | 0.307469 |
| 0.2 mM CdCl2 | 1 | 476 | 1 | 1 | 0.210111 |
| hormone treatment | 12 | 23195 | 11.4778 | 1.0455 | 0.480794 |
| Elicitors and pathogens mix | 4 | 14540 | 7.19496 | 0.555945 | 0.934556 |
| Mix of elicitors | 8 | 8655 | 4.28283 | 1.86792 | 0.0656842 |
| nutrient deficiencies | 9 | 3258 | 1.61219 | 5.58248 | 3.76416E−05 |
| —N, —P, —K, —Fe, —Al | 9 | 3258 | 1.61219 | 5.58248 | 3.76416E−05 |
| pathogen | 17 | 30639 | 15.1614 | 1.12127 | 0.344706 |
| *Agrobacterium tumefaciens* C58 | 3 | 5107 | 2.52714 | 1.18711 | 0.464783 |
| Elicitors and pathogens mix | 4 | 14540 | 7.19496 | 0.555945 | 0.934556 |
| *pseudomonas syringae* | 10 | 10177 | 5.03598 | 1.98571 | 0.0295878 |

The digital expression profile for ABST_37 (SEQ ID NO: 14) is summarized below in Table 6.

TABLE 6

Change in expression of ABST_37 due to exposure to various treatments

| Keyword | ESTs in Gene | ESTs in Production | Expected ESTs | Fold | p-value |
|---|---|---|---|---|---|
| hormone treatment | 1 | 23195 | 1 | 1 | 0.643514 |
| Mix of elicitors | 1 | 8655 | 1 | 1 | 0.31009 |
| nutrient deficiencies | 3 | 3258 | 1 | 3 | 0.000275679 |
| —N, —P, —K, —Fe, —Al | 3 | 3258 | 1 | 3 | 0.000275679 |

Example 2

In-situ Validation/Expression Studies

The five genes listed in Table 1C were validated in situ as putative ABST genes by analyzing their expression profile in tomato plants under favorable, salt and drought stress conditions.

The expression studies were carried out on three tomato lines—sensitive tomato variety (Evoline 1), processing tomato line with moderate tolerance to salt (Evoline 3, also referred to herein as M82) and drought and high salt tolerant tomato line (Evoline 2). All lines were tested for several seasons for their levels of tolerance to salt and other soil stresses such as drought. All lines are commercially available from Evogene, Rehovot, Israel.

Methods

Salt Induction:

Salt stress induction was performed by introducing the roots of 14 days old tomato seedlings, of different tomato homozygote varieties, into a water bath which contained a solution of Hogland (comprising $KNO_3$-8 mM, $MgSO_4$-1 mM, $KH_2PO_4$-1 mM, and microelements, all dissolved in water, at pH 6.5), and 300 mM NaCl. Plants were placed on a floating tray, such that only the roots were dipped in the solution. Plants were grown in salt solution for 5 weeks during which the degree of tolerance to the salt stress was measured, by comparing plant development and biomass. The experiment was performed in 3 sequential seasons and with 5 repeats for each line in each experiment. The experiments identified 3 tomato lines showing consistent level of either weak (Evoline1), moderate (Evoline3), or high (Evoline2) level of tolerance. During the last experiment RNA samples from leaves and roots from Evoline1 and Evoline3 were taken 5, 9, 72, 240 hours after introducing the plants to salt solution.

Drought Induction:

Levels of tolerance to drought induction were tested on Evoline, Evoline2, and Evoline3 tomato plants. The plants were grown in CYG Germination Pouches, (Mega International, MN, USA), from germination until 4 true leaf stage in a regular nutrient solution. Drought conditions were applied by adding polyethylene glycol-PEG to the growth solution to a final concentration of 15%. RNA samples from leaves and roots were taken at time 0, 0.5 h, 3 h, 6 h and 48 h following drought induction. RNA expression level was measured by using quantitative RT PCR.

Results

Figure 2:
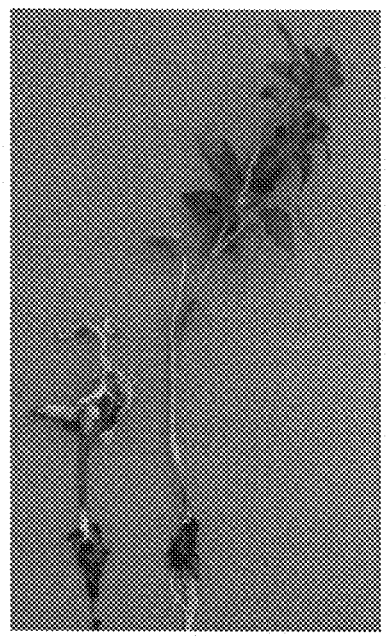
FIG. 2 is a photograph of tomato seedling of a sensitive line (Evoline 1, Evogene, Rehovot, Israel) as seen on the left and a tolerant line (Evoline 2, Evogene, Rehovot, Israel) as seen on the right following 4 week growth under water irrigation containing 300 mM NaCl. Evoline 1 was proved for several seasons as being a relatively salt-sensitive line. Evoline 2 was proved for several seasons as being a highly salt-tolerant line.

As illustrated in FIG. 2, seedlings of the sensitive line (Evoline 1) were much smaller with far fewer leaves than seedlings of the tolerant line (Evoline 2) following four weeks growth under water irrigation containing 300 mM NaCl.

Tables 7-9 below summarise the up-regulation change in gene expression in response to various stress conditions (e.g. drought and salt) of polynucleotides of the present invention in tomato plants as calculated by quantitative RT-PCR.

TABLE 7

Relative expression of the ABST genes following salt induction compared to their expression at time 0 (T0) in leaves and roots of a tomato tolerant line (Evoline 2 = highly tolerant line)

| Time after induction (hours) | Organ | ABST_1 | ABST_6 | ABST_19 | ABST_22 | ABST_27 | ABST_36 | ABST_37 |
|---|---|---|---|---|---|---|---|---|
| 0 | leaves | 1.00 | 1.00 | 1.00 | 1.00 | 1.00 | 1.00 | 1.00 |
| 5 | leaves | 1.32 | 0.56 | 1.19 | 1.33 | 1.61 | 1.97 | 1.63 |
| 9 | leaves | 1.54 | 0.48 | 0.99 | 1.51 | 1.50 | 1.17 | 1.76 |
| 72 | leaves | 1.26 | 0.30 | 1.13 | 1.75 | 1.22 | 0.57 | 3.60 |
| 240 | leaves | 0.54 | 1.89 | 1.22 | 0.62 | 0.46 | 0.74 | 8.05 |
| 0 | roots | 1.00 | 1.00 | 1.00 | 1.00 | 1.00 | 1.00 | 1.00 |
| 5 | roots | 0.89 | 1.23 | 0.89 | 1.09 | 0.66 | 0.57 | 1.20 |
| 9 | roots | 0.72 | 1.03 | 1.01 | 0.78 | 0.69 | 0.42 | 0.83 |
| 72 | roots | 0.81 | 2.06 | 1.24 | 1.38 | 0.97 | 0.29 | 1.15 |
| 240 | roots | 0.50 | 7.91 | 1.70 | 0.66 | 0.57 | 0.10 | 4.77 |

TABLE 8

Relative expression of the ABST genes following salt induction compared to their expression in leaves and roots of tomato sensitive variety (Evoline 1 = salt sensitive line)

| Time after induction (hours) | Organ | ABST_1 | ABST_6 | ABST_19 | ABST_22 | ABST_27 | ABST_36 | ABST_37 |
|---|---|---|---|---|---|---|---|---|
| 0 | leaves | 1.00 | 1.00 | 1.00 | 1.00 | 1.00 | 1.00 | 1.00 |
| 5 | leaves | 1.60 | 0.00 | 1.10 | 1.18 | 1.58 | 1.18 | 0.00 |
| 9 | leaves | 0.88 | 0.34 | 1.14 | 0.83 | 1.80 | 0.58 | 0.83 |
| 72 | leaves | 0.70 | 0.20 | 1.21 | 0.81 | 0.95 | 0.40 | 1.71 |
| 240 | leaves | 0.44 | 2.25 | 1.56 | 0.69 | 0.56 | 0.23 | 7.63 |
| 0 | roots | 1.00 | 1.00 | 1.00 | 1.00 | 1.00 | 1.00 | 1.00 |
| 5 | roots | 0.96 | 1.56 | 1.05 | 1.01 | 1.25 | 0.84 | 0.81 |
| 9 | roots | 0.84 | 1.10 | 1.08 | 0.58 | 1.09 | 0.46 | 0.47 |
| 72 | roots | 0.83 | 1.31 | 1.43 | 1.00 | 1.41 | 0.24 | 0.44 |
| 240 | roots | 0.59 | 9.13 | 2.03 | 0.77 | 1.00 | 0.07 | 1.77 |

TABLE 9

Relative expression of the ABST genes following drought induction compared to their expression in T0 in leaves and roots of seedlings of processing tomato variety (Evoline 3 = moderate salt tolerant line-M82)

| Time after induction (h) | Organ | ABST_1 | ABST_6 | ABST_19 | ABST_22 | ABST_27 | ABST_36 | ABST_37 |
|---|---|---|---|---|---|---|---|---|
| 0 | Roots | 1.00 | 1.00 | 1.00 | 1.00 | 1.00 | 1.00 | 1.00 |
| 0.5 | Roots | 0.62 | 0.24 | 0.94 | 0.58 | 0.81 | 0.40 | 0.51 |
| 3 | Roots | 0.40 | 0.21 | 0.77 | 0.40 | 0.54 | 0.25 | 0.26 |
| 6 | Roots | 0.58 | 0.13 | 1.15 | 0.36 | 0.82 | 0.24 | 0.29 |
| 48 | Roots | 0.72 | 0.15 | 1.19 | 1.43 | 3.05 | 0.49 | 1.30 |
| 0 | Leaves | 1.00 | 1.00 | 1.00 | 1.00 | 1.00 | 1.00 | 1.00 |
| 0.5 | Leaves | 2.21 | 2.84 | 0.86 | 2.49 | 1.37 | 1.18 | 0.75 |
| 3 | Leaves | 2.24 | 3.83 | 1.40 | 2.97 | 0.84 | 2.55 | 0.81 |
| 6 | Leaves | 3.29 | 4.99 | 1.68 | 6.47 | 6.18 | 2.08 | 1.91 |
| 48 | Leaves | 2.70 | 4.99 | 1.20 | 8.80 | 3.60 | 0.46 | 1.88 |

As seen from tables 7-9, ABST 1, 6, 22, 27, 36 and 37 all showed induction of expression under different stress conditions. The changes in gene expression as a response to various stresses could be classified into two main categories—immediate up-regulation e.g. ABST_36 and ABST_1 (from 30 minutes to 6 hours following induction) and delayed up-regulation e.g. ABST_37 and ABST_6 (24 to 240 hours following induction).

The expression profile of most the genes was also affected by the genotype of the plants (highly tolerant line vs. sensitive line) and the specific stress the plants were exposed to (i.e. salt or PEG). Three genes showed changes in expression in leaves only (ABST_1, 22, 36). Only ABST 6 and 37 showed up-regulation of expression in both leaves and roots.

Significant changes were not detected in the expression of the ABST_19 as a response to salt or drought stress.

Table 10 below summarises the main expression modes of the ABST genes of the present invention under salt and osmotic stress.

TABLE 10

Expression modes of the ABST genes of the present invention under salt and osmotic stresses

| Gene name/ time range | Salt stress (100 mM NaCl) Evoline 1 | Osmotic stress Evoline 2 Leaf | Evoline 3 | Salt stress (100 mM NaCl) Evoline 1 | Evoline 2 Root | Osmotic stress (10% PEG) Evoline 3 |
|---|---|---|---|---|---|---|
| ABST_1 Early response | Up × 1.5 | Up × 1.5 | Up × 3 | Stable | Stable | Down × 2 |
| ABST_1 Early response | Down × 2 | Down × 2 | Stable | Down × 2 | Down × 2 | Stable |
| ABST_6 Early response | Down × 3 | Down × 2 | Up × 5 | Stable | Stable | Down × 7 |
| ABST_6 Late response | Up × 2 | Up × 2 | Up × 5 | Up × 9 | Up × 8 | Down × 7 |
| ABST_22 Early response | Stable | Up × 1.5 | Up × 6 | Stable | Stable | Down × 3 |
| ABST_22 Late response | Stable | Stable | Up × 8 | Stable | Stable | Stable |
| ABST_36 Early response | Stable | Up × 2 | Up × 2 | Down × 2 | Down × 2 | Down × 5 |
| ABST_36 Late response | Down × 5 | Stable | Down × 2 | Down × 5 | Down × 3 | Down × 2 |
| ABST_37 Early response | Stable | Up × 2 | Stable | Down × 2 | Stable | Down × 3 |
| ABST_37 Late response | Up × 8 | Up × 8 | Up × 2 | Up × 1.5 | Up × 5 | Stable |

Evoline 1: has low salt tolerance
Evoline 2: has high salt tolerance
Evoline 3: has moderate salt tolerance
Early response: 0.5 hours to 9 hours from induction
Late response: 48 hours to 240 hours from induction Example 3

Isolation of ABS Tolerance Genes of the Present Invention

RNA was extracted from 4 week-old tomato root and leaf tissues using Tri Reagent (Molecular Research Center, Inc), following the protocol provided by the manufacturer (World Wide Web (dot) Mrcgene (dot) com/tri (dot) htm). Complementary DNA molecules were produced from the extracted mRNA using M-MuLV reverse-transcriptase (RT) enzyme (Roche) and T16NN DNA primer, according to the manufacturer's instructions. The cDNA sequences set forth in SEQ ID NOs: 1, 4, 8-9 and 12-14, were amplified by PCR using the primers described in Table 11 below, with PFU proof reading DNA polymerase enzyme (Promega-World Wide Web (dot) Promega (dot) com/pnotes/68/7381_07/7381_07 (dot) html), following the protocol provided by the manufacturer. Additional restriction endonuclease sites were added to the 5' prime end of each primer to facilitate cloning of the ABS tolerance genes of the present invention in binary vectors.

TABLE 11

PCR primers used for amplifying ABS tolerance (ABST) genes of the present invention

| ABST gene SEQ ID No | Forward Primer SEQ ID No | Reverse Primer SEQ ID No | upstream restriction site | downstream restriction site |
|---|---|---|---|---|
| 1 | 21 | 22 | BamH1 | SacI |
| 4 | 23 | 24 | BamH1 | SacI |
| 8 | 25 | 26 | BamH1 | SacI |
| 9 | 27 | 28 | XbaI | SmaI |
| 12 | 29 | 30 | BamH1 | SacI |
| 13 | 31 | 32 | BamH1 | SacI |
| 14 | 33 | 34 | BamH1 | SmaI |

Example 4

Cloning the ABST Genes of the Present Invention

The resulting PCR blunt ended products were purified using PCR Purification Kit (Qiagen, Germany), digested with the appropriate restriction enzymes (Roche) and then inserted into the binary plasmid vector pPI. The plasmid pPI was constructed by inserting a synthetic poly-(A) signal sequence, originating from pGL3 basic plasmid vector (Promega, Acc No U47295; bp 4658-4811) into the HindIII restriction site of the binary vector pBI101.3 (Clontech, Acc. No. U12640).

The resulting pPI plasmid was digested with restriction enzymes (BamHI and SacI; MBI Fermentas) and purified using PCR Purification Kit (Qiagen, Germany). The open pPI construct was then ligated with each of the seven PCR products described hereinabove. The ligation was effected using a ligation mixture containing T4 DNA ligase enzyme (Roche) and was performed according to the manufacturer's instructions.

The pPI constructs harboring ABST genes of the present invention were introduced to *E. coli* DH5 competent cells by electroporation, using a MicroPulser electroporator (Biorad), 0.2 cm cuvettes (Biorad) and EC-2 electroporation program (Biorad). The treated cells were cultured in LB liquid medium at 37° C. for 1 hr, then plated over LB agar supplemented with kanamycin (50 mg/L; Sigma) and incubated at 37° C. for 16 hrs. Colonies which developed on the selective medium were analyzed by PCR using the primers set forth in SEQ ID NOs: 35-36, which were designed to span the inserted sequence in the pPI plasmid. The resulting PCR products were separated on 1.5% agarose gels and the DNA fragment having the predicted size were isolated and sequenced using the ABI 377 sequencer (Amersham Biosciences Inc) in order to verify that the correct DNA sequences were properly introduced to the *E. coli* cells.

Example 5

Generating Binary Vectors Comprising ABST Genes of the Present Invention and Plant Promoters Operably Linked Thereto Generating binary vectors comprising the Cauliflower Mosaic Virus 35S promoter: The Cauliflower Mosaic Virus 35S promoter sequence (set forth in SEQ ID NO: 19) was inserted upstream of the ABST genes of the present invention in each of the pPI constructs described above. The promoter was isolated from the pBI121 plasmid (Clontech, Accession No. AF485783) using the restriction endonucleases HindIII and BamHI (Roche). The isolated promoter was ligated into the pPI constructs digested with the same enzymes. Altogether, seven pPI constructs were generated, each comprising the CaMV 35S promoter positioned upstream of the ABST genes of the present invention having a sequence set forth in SEQ ID NO: 1,4,8,9,12,13 or 14.

Generating Binary Vectors Comprising the At6669 Promoter:

The At6669 promoter sequence (set forth in SEQ ID NO: 20) was inserted upstream of the ABST genes of the present invention in each of the pPI binary constructs described above. The promoter was isolated from *Arabidopsis thaliana* var Col0 genomic DNA by PCR amplification using the primers set forth in SEQ ID NOs: 37-38. The PCR product was purified (Qiagen, Germany) and digested with the restriction endonucleases HindIII and BamHI (Roche). The resulting promoter sequence was introduced into the open binary constructs digested with the same enzymes. Altogether, seven pPI constructs were generated, each comprising the At6669 promoter positioned upstream of the ABST genes of the present invention having a sequence set forth in SEQ ID NO: 1,4,8, 9,12,13 or 14.

Example 6

Confirming At6669 Promoter Activity in Transgenic *Arabidopsis thaliana*

The capacity of At-6669 promoter to regulate transcription of genes carried by the pPI vector in plants was tested. Accordingly, the promoter At6669 was inserted into the pPI binary vector upstream of a Luciferase reporter gene. The binary vector was introduced to *Arabidopsis thaliana* plants using the procedure as described in Example 6 below. Mature transformed $T_2$ *Arabidopsis* plants were assayed for bio-illumination in a darkroom using an ultra-low light detection camera (Princeton Instruments Inc., USA) using the procedure described by Meissner et al. (Plant J. 22:265, 2000). Illumination indicating positive Luciferase activity was observed in the flower and root meristem tissues of transformed plants (FIGS. 3A-D).

To study the regulation mode of the promoter under stress conditions, the 6669 promoter and 35S promoter were both fused to the *Arabidopsis* Rab7 gene. Rab7 expression under the 6669 promoter gave significantly higher salt and osmotic tolerance performance compared to 35S in *Arabidopsis*, as determined by vegetative growth.

Figure 4:
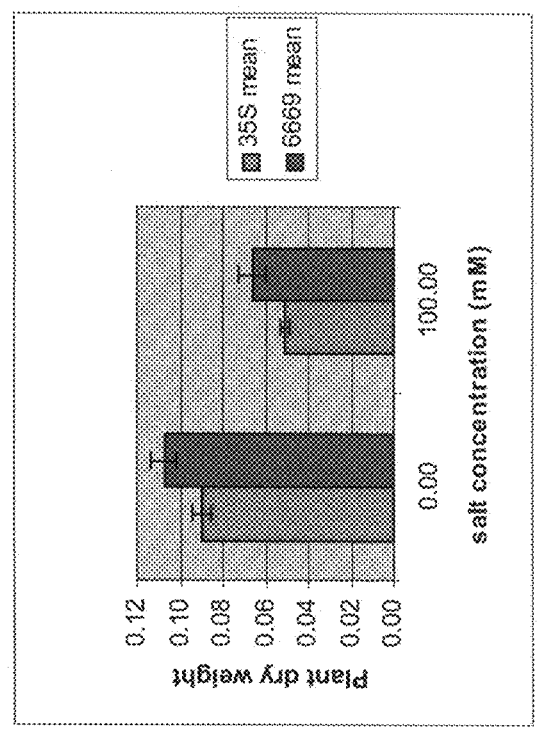
FIG. 4 is a bar graph illustrating the mean plant dry weight of transgenic $T_2$ *A. thaliana* plants grown under salinity stress conditions (irrigated with 100 mM NaCl solution), as compared with similar plants grown under normal conditions (irrigated with water only). The plants were transformed with putative stress tolerance genes of the present invention (ABST_1, 6, 19, 22, 27, 36, 37) and the effect of the promoters (35S vs. 6669) on biomass was examined.

The promoter was further validated by comparing tolerance level of *Arabidopsis* plants containing the ABST genes of the present invention under the regulation of 6669 and under the regulation of 35S promoter (FIG. 4). The plants were transformed with seven ABST genes of the present invention (ABST_1, 6, 19, 22, 27, 36, 37) as described in Example 8. As illustrated in FIG. 4, the plant dry weight increased following transformation of the ABST genes under the 6669 promoter to a greater extent than following transformation of the ABST genes under the 35S promoter both under normal and stress (100 mM salt) conditions.

Example 7

Transforming *Agrobacterium tumefaciens* Cells with Binary Vectors Harboring ABST Genes of the Present Invention Each of the binary vectors described in Example 5 above were used to transform *Agrobacterium* cells. Two additional binary constructs, having the Luciferase reporter gene replacing an ABST gene (positioned downstream of the 35S or At6669 promoter), were used as negative controls.

The binary vectors were introduced to *Agrobacterium tumefaciens* GV301, or LB4404 competent cells (about $10^9$ cells/mL) by electroporation. The electroporation was effected by using a MicroPulser electroporator (Biorad), 0.2 cm cuvettes (Biorad) and EC-2 electroporation program (Biorad). The treated cells were cultured in LB liquid medium at 28° C. for 3 hr, then plated over LB agar supplemented with gentamycin (50 mg/L; for *Agrobacterium* strains GV301) or streptomycin (300 mg/L; for *Agrobacterium* strain LB4404) and kanamycin (50 mg/L) at 28° C. for 48 hrs. *Abrobacterium* colonies which developed on the selective media were analyzed by PCR using the primers set forth in SEQ ID NOs: 35-36, which were designed to span the inserted sequence in the pPI plasmid. The resulting PCR products were isolated and sequenced as described in Example 5 above, to verify that the correct ABST sequences were properly introduced to the *Agrobacterium* cells.

Example 8

**Transformation of *Arabidopsis thaliana* Plants with ABST Genes of the Present Invention**

*Arabidopsis thaliana* Columbia plants ($T_0$ plants) were transformed using the Floral Dip procedure described by Clough and Bent (10) and by Desfeux et al. (11), with minor modifications. Briefly, $T_0$ Plants were sown in 250 ml pots filled with wet peat-based growth mix. The pots were covered with aluminum foil and a plastic dome, kept at 4° C. for 3-4 days, then uncovered and incubated in a growth chamber at 18-24° C. under 16/8 hr light/dark cycles. The To plants were ready for transformation six days before anthesis.

Single colonies of *Agrobacterium* carrying the binary constructs, generated as described in Example 6 above, were cultured in LB medium supplemented with kanamycin (50 mg/L) and gentamycin (50 mg/L). The cultures were incubated at 28° C. for 48 hrs under vigorous shaking and then centrifuged at 4000 rpm for 5 minutes. The pellets comprising *Agrobacterium* cells were re-suspended in a transformation medium containing half-strength (2.15 g/L) Murashig-Skoog (Duchefa); 0.044 µM benzylamino purine (Sigma); 112 µg/L B5 Gambourg vitamins (Sigma); 5% sucrose; and 0.2 ml/L Silwet L-77 (OSI Specialists, CT) in double-distilled water, at a pH of 5.7.

Transformation of $T_0$ plants was effected by inverting each plant into an *Agrobacterium* suspension, such that the above ground plant tissue was submerged for 3-5 seconds. Each inoculated $T_0$ plant was immediately placed in a plastic tray, then covered with a clear plastic dome to maintain humidity and was kept in the dark at room temperature for 18 hrs, to facilitate infection and transformation. Transformed (transgenic) plants were then uncovered and transferred to a greenhouse for recovery and maturation. The transgenic $T_0$ plants were grown in the greenhouse for 3-5 weeks until siliques were brown and dry. Seeds were harvested from plants and kept at room temperature until sowing.

For generating $T_1$ and $T_2$ transgenic plants harboring the genes, seeds collected from transgenic $T_0$ plants were surface-sterilized by soaking in 70% ethanol for 1 minute, followed by soaking in 5% sodium hypochloride and 0.05% triton for 5 minutes. The surface-sterilized seeds were thoroughly washed in sterile distilled water then placed on culture plates containing half-strength Murashig-Skoog (Duchefa); 2% sucrose; 0.8% plant agar; 50 mM kanamycin; and 200 mM carbenicylin (Duchefa). The culture plates were incubated at 4° C. for 48 hours then transferred to a growth room at 25° C. for an additional week of incubation. Vital $T_1$ *Arabidopsis* plants were transferred to a fresh culture plates for another week of incubation. Following incubation, the $T_1$ plants were removed from culture plates and planted in growth mix contained in 250 ml pots. The transgenic plants were allowed to grow in a greenhouse to maturity. Seeds harvested from $T_1$ plants were cultured and grown to maturity as $T_2$ plants under the same conditions as used for culturing and growing the $T_1$ plants.

Example 9

Evaluating Growth of Transgenic Plants Cultivated Under Abiotic Stress Conditions Methods

$T_1$ or $T_2$ transgenic plants generated as described above were individually transplanted into pots containing a growth mixture of peat and vermiculite (volume ratio 3:2, respectively). The pots were covered for a 24 hr period for hardening, then placed in the greenhouse in random order and irrigated with tap water (provided from the pots' bottom every 3-5 days) for seven days. Thereafter, half of the plants were irrigated with a salt solution (100 mM NaCl and 5 mM $CaCl_2$) to induce salinity stress (stress conditions). The other half was irrigated with tap water throughout (normal conditions). All plants were grown in the greenhouse at 100% RH for 28 days and then harvested (the above ground tissue).

Vigor Measurement:

Fresh and dry mass were measured as a function of plant vigor. Dry mass was measured immediately following drying in an oven at 50° C. for seven days.

Figure 5:
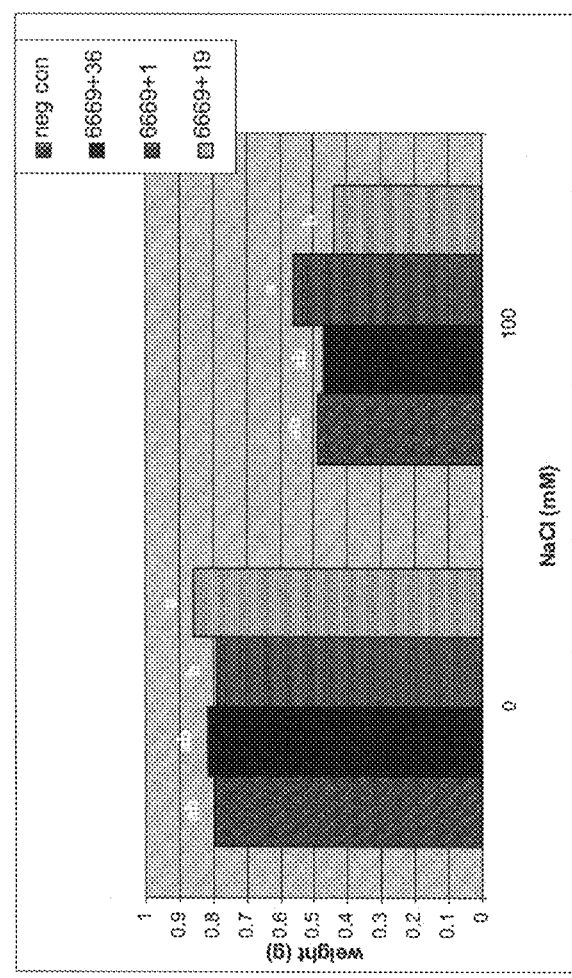
FIG. 5 illustrates the mean fresh weight of transgenic $T_1$ *A. thaliana* plants grown under normal and stress conditions (irrigated with 0 or 100 M NaCl solution, respectively). The plants were transformed with putative stress tolerance genes, or with a luciferase reporter gene (control), positioned under the transcriptional control of the At6669 promoter. Means followed by the same letter are not significantly different according to a one way ANOVA T-Test.

Results:

Fresh Weight:

No significant differences in plant fresh weights were observed between the $T_1$ plants transformed with 3 different ABST genes and plants transformed with the Luciferase reporter gene, grown either under normal or stress conditions (FIG. 5 and Table 12 below). Yet, $T_1$ plants transformed with SEQ ID NO: 1 positioned under the regulatory control of the At6669 promoter maintained 71% of their fresh weight when exposed to stress conditions, while the control plants (carrying Luciferase gene positioned under the regulatory control of the AT6669 promoter) maintained only 61% of their fresh weight under similar stress conditions.

TABLE 12

Fresh weight of $T_1$ transgenic *Arabidopsis* plants irrigated with water or salt solution

| Transgene (SEQ ID NO) | Promoter | N Rows[1] | Irrigation solution (mM NaCl) | Mean (g) | Std Error |
|---|---|---|---|---|---|
| Luciferase | At6669 | 2 | 0 | 0.7925 | 0.0275 |
| Luciferase | At6669 | 2 | 100 | 0.485 | 0.045 |
| 13 | At6669 | 8 | 0 | 0.81625 | 0.020305 |
| 13 | At6669 | 8 | 100 | 0.4725 | 0.029246 |
| 1 | At6669 | 8 | 0 | 0.7875 | 0.026032 |
| 1 | At6669 | 8 | 100 | 0.55875 | 0.044699 |
| 8 | At6669 | 8 | 0 | 0.8575 | 0.023088 |
| 8 | At6669 | 8 | 100 | 0.440625 | 0.011198 |

[1] N Rows represent number of independent transformation event plants measured. For each transgene, 3-5 independent transformation events with 1-3 plants per a single transformation event were used.

Figures 6A, 6B:
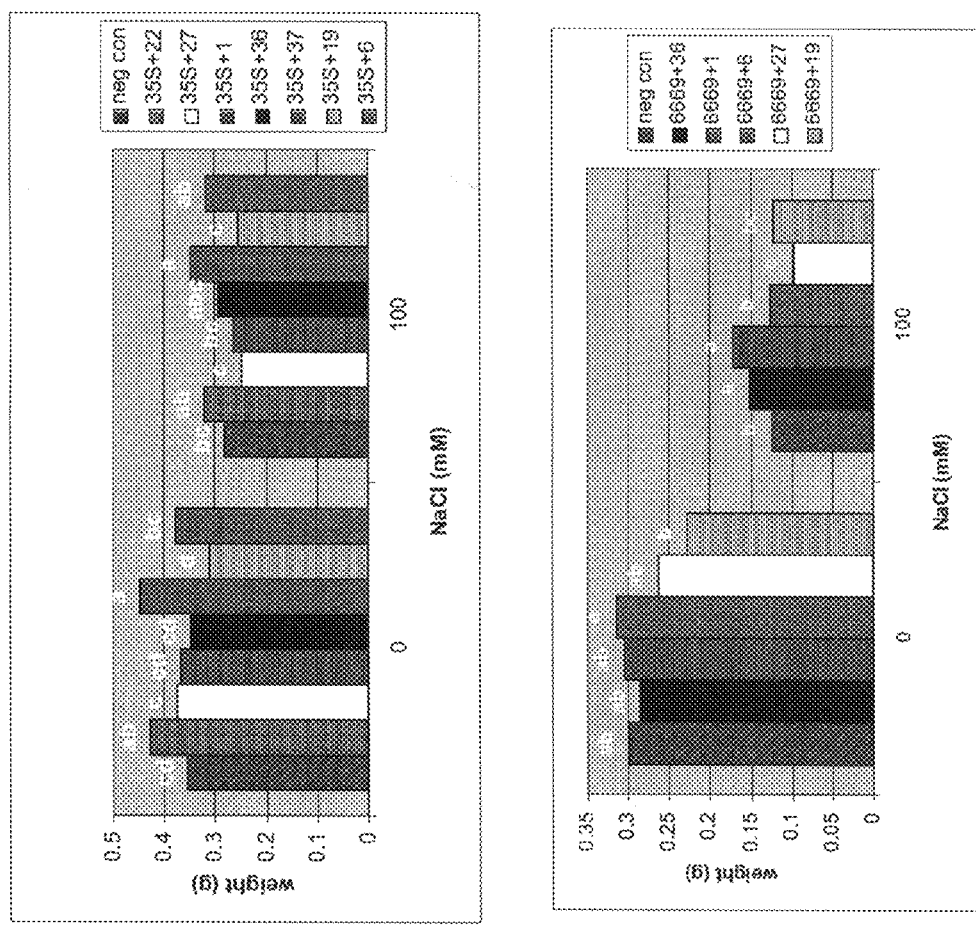
FIG. 6A illustrates the mean fresh weight of $T_2$ *A. thaliana* plants grown under normal or stress conditions (irrigated with 0 or 100 M NaCl solution, respectively). The plants were transformed with the putative stress tolerance genes of the present invention, or with luciferase reporter gene (control), positioned under the transcriptional control of the 35S promoter. Means followed by the same letter are not significantly different according to a one way ANOVA T-Test.
FIG. 6B illustrates the mean fresh weight of $T_2$ *A. thaliana* plants grown under normal or stress conditions (irrigated with 0 or 100 M NaCl solution, respectively). The plants were transformed with the putative stress tolerance genes of the present invention, or with luciferase reporter gene (control), positioned under the transcriptional control of the At6669 promoter. Means followed by the same letter are not significantly different according to a one way ANOVA T-Test.

$T_2$ plants transformed with SEQ ID NOs: 7 or 14 positioned under the regulatory control of the 35S promoter accumulated significantly higher biomass than control plants, regardless of growth conditions. As shown in FIG. 6A and Table 13 below, the mean fresh weight of plants transformed with SEQ ID NOs: 7 and 14, grown under stress conditions, were 15% and 24%, respectively, higher than the mean fresh weight control plants grown under similar stress conditions. Similarly, the mean fresh weight of plants transformed with SEQ ID NOs: 7 or 14, grown under normal conditions, were 21% and 27%, respectively, higher than the mean fresh weight control plants grown under similar normal conditions.

Similar phenomenon was observed with $T_2$ plants transformed with SEQ ID NO: 4 positioned under the regulatory control of the 35S promoter. Accordingly, as shown in FIG. 6A and Table 13 below, the mean fresh weight of plants transformed with SEQ ID NO: 4 was 14% and 7% was higher than the mean fresh weight of control plants grown under stress and normal conditions, respectively. Similarly, $T_2$ plants transformed with SEQ ID NO: 4 positioned under the regulatory control of the At6669 promoter exhibited 1.3 and 5% higher biomass than control plants grown under stress and normal conditions, respectively (Table 14). However, these differences were not found statistically different under the experimental conditions.

TABLE 13

Fresh weight of T₂ transgenic *Arabidopsis* plants irrigated with water or salt solution

| Transgene (SEQ ID NO) | Promoter | N Rows | Irrigation solution (mM NaCl) | Mean (g) | Std Error |
|---|---|---|---|---|---|
| Luciferase | CaMV-35S | 11 | 0 | 0.352727 | 0.011208 |
| Luciferase | CaMV-35S | 11 | 100 | 0.280909 | 0.010484 |
| 9 | CaMV-35S | 11 | 0 | 0.426364 | 0.019599 |
| 9 | CaMV-35S | 11 | 100 | 0.322727 | 0.027306 |
| 12 | CaMV-35S | 11 | 0 | 0.374545 | 0.015746 |
| 12 | CaMV-35S | 11 | 100 | 0.249091 | 0.020647 |
| 1 | CaMV-35S | 8 | 0 | 0.36625 | 0.034171 |
| 1 | CaMV-35S | 8 | 100 | 0.265 | 0.031225 |
| 13 | CaMV-35S | 11 | 0 | 0.349091 | 0.013515 |
| 13 | CaMV-35S | 11 | 100 | 0.293636 | 0.019921 |
| 14 | CaMV-35S | 11 | 0 | 0.446364 | 0.025558 |
| 14 | CaMV-35S | 11 | 100 | 0.348182 | 0.023772 |
| 8 | CaMV-35S | 11 | 0 | 0.310909 | 0.015223 |
| 8 | CaMV-35S | 11 | 100 | 0.253636 | 0.01539 |
| 4 | CaMV-35S | 11 | 0 | 0.379091 | 0.010992 |
| 4 | CaMV-35S | 11 | 100 | 0.318182 | 0.013336 |

¹N Rows represent number of independent transformation event plants measured. For each transgene, 3-5 independent transformation events with 1-3 plants per a single transformation event were used.

T₂ plants transformed with SEQ ID NOs: 1 and 13 positioned under the regulatory control of the At6669 promoter and grown under stress conditions, exhibited significantly higher biomass than control plants grown under similar stress conditions. The mean fresh weight of T₂ plants transformed with SEQ ID NOs: 1 and 13 positioned under the regulatory control of the At6669 promoter, and grown under stress conditions, were 37% and 21%, respectively, higher than the mean fresh weight control plants grown under similar stress conditions (FIG. 6B and Table 14 below). No significant increase in biomass over control was observed when these transgenic plants (carrying SEQ ID NOs: 1 and 13 regulated under At6669 promoter) where grown under normal conditions.

The results illustrate that the isolated ABST genes of the present invention, set forth in SEQ ID NOs: 1 and 13, are capable of increasing plant tolerance to abiotic stress, such as a salinity stress. In addition, the isolated ABST genes of the present invention as set forth in SEQ ID NOs: 7, 14 (and possibly also 4), are capable of substantially promoting biomass in plants grown under stress, as well as under normal conditions.

Dry Mass:

Table 15 summarises the results the dry mass of T1 plants grown under 100 mM NaCl.

TABLE 14

Fresh weight of T₂ transgenic *Arabidopsis* plants irrigated with water or salt solution

| Transgene (SEQ ID NO) | Promoter | N Rows | Irrigation solution (mM NaCl) | Mean (g) | Std Error |
|---|---|---|---|---|---|
| Luciferase | At6669 | 6 | 0 | 0.3 | 0.010328 |
| Luciferase | At6669 | 6 | 100 | 0.125 | 0.009916 |
| 13 | At6669 | 6 | 0 | 0.286667 | 0.024449 |
| 13 | At6669 | 6 | 100 | 0.151667 | 0.007032 |
| 1 | At6669 | 6 | 0 | 0.305 | 0.03423 |
| 1 | At6669 | 6 | 100 | 0.171667 | 0.012225 |
| 4 | At6669 | 6 | 0 | 0.315 | 0.049983 |
| 4 | At6669 | 6 | 100 | 0.126667 | 0.005578 |
| 12 | At6669 | 6 | 0 | 0.263333 | 0.012824 |
| 12 | At6669 | 6 | 100 | 0.098333 | 0.007923 |
| 8 | At6669 | 6 | 0 | 0.228333 | 0.020235 |
| 8 | At6669 | 6 | 100 | 0.121667 | 0.004014 |

¹N Rows represent number of independent transformation event plants measured. For each transgene, 3-5 independent transformation events with 1-3 plants per a single transformation event were used.

TABLE 15

Dry mass of T1 plants grown under 100 mM Nacl

| Gene name | Mean (g) | Std Error | Relative dry mass compared to control (%) |
|---|---|---|---|
| Pver + 6669 (negative control) | 0.05635 | 0.00674 | 100 |
| Rab7 positive control) | 0.0656 | 0.00674 | 117.1428571 |
| ABST_1 | 0.074417 | 0.00389 | 132.8875 |
| ABST_19 | 0.054567 | 0.00389 | 97.44107143 |
| ABST_36 | 0.059117 | 0.00389 | 105.5660714 |

Table 16 summarises the results of the absolute and relative dry mass of the of the T2 transgenic lines overexpressing the ABST genes under regular growth conditions.

TABLE 16

Summary of absolute (g) and relative dry mass (relative to negative control %) of the T2 transgenic lines overexpressing the ABST genes under regular growth conditions

| Gene name | T2 plants overexpressing the ABST gene under the 35S promoter | | | T2 plants overexpressing the ABST gene under the 6669 promoter | | |
|---|---|---|---|---|---|---|
| | Mean dry mass (g) | Std Error | Relative expression % | Mean dry mass (g) | Std Error | Relative expression % |
| Negative control | 0.048666667 | 0.006557 | 100 | 0.0391 | 0.006154 | 100 |
| ABST_1 | 0.056416667 | 0.007331 | 117.534722 | 0.05790333 | 0.006251 | 148.4700854 |
| ABST_6 | 0.052666667 | 0.006557 | 109.722222 | 0.0561 | 0.006154 | 143.8461538 |
| ABST_19 | 0.0432 | 0.006557 | 90 | 0.03553333 | 0.006251 | 91.11111103 |
| ABST_22 | 0.066 | 0.006557 | 137.5 | ND | ND | ND |
| ABST_36 | 0.049333333 | 0.006557 | 102.777778 | 0.0484 | 0.006154 | 124.1025641 |
| ABST_37 | 0.0632 | 0.006557 | 131.666667 | ND | ND | ND |

As summarized in Table 16 above, transgenic $T_2$ *Arabidopsis* plants over-expressing ABST genes of the present invention as set forth in SEQ ID NOs: 1 (ABST_1) and 4 (ABST_6) showed significant elevation of dry mass both under the 35S promoter and the 6669 promoter (ABST_1: 18%, 49% respectively, ABST_6: 10%, 44% respectively). SEQ ID NO: 13 (ABST_36) over-expression caused elevation in dry mass only under the regulation of 6669 promoter (24%). ABST_22 and 37 over-expression (SEQ ID NOs: 9 and 14 respectively), under the regulation of the 35S promoter, caused more than a 40% increase in the dry mass of the transgenic lines.

The results showed that all five tested genes improve vegetative growth development under favorable conditions. ABST_1 and 6 improve plant vigor in both regulation modes (6669 and 35S promoters).

The specific gene-promoter combination has a significant effect on dry mass elevation.

Figure 7:
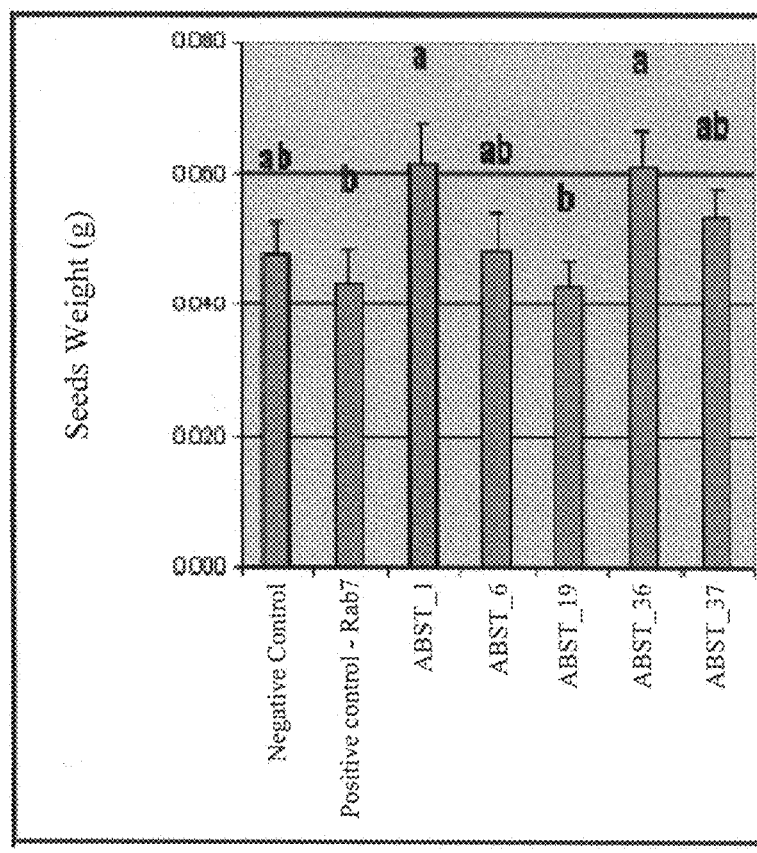
FIG. 7 illustrates the total seed weight from $T_2$ *A. thaliana* plants over-expressing the ABST genes of the present invention regulated by the 6669 promoter grown under regular conditions. Means followed by the same letter are not significantly different according to a one way ANOVA T-Test.
Figure 8B:
FIGS. 8A-D are photographs depicting control and transgenic tomato plants (of the genetic background of Evoline 3) of the present invention illustrating the increase in yield following over-expression of the putative ABST genes of the present invention.
Figure 8D:
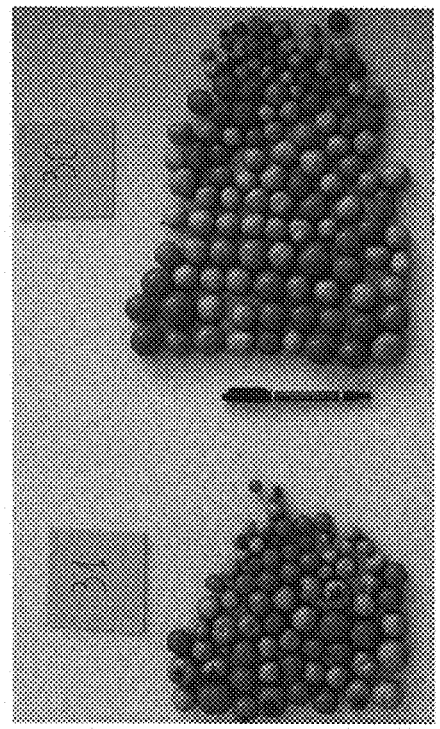
Figure 8A:
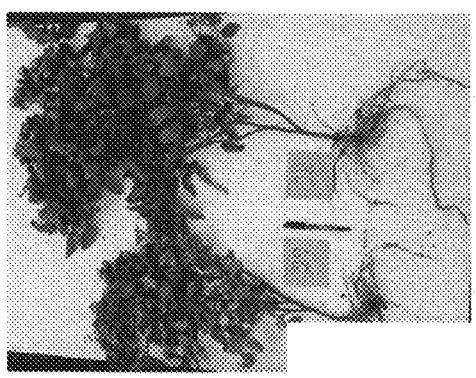
Figure 8C:
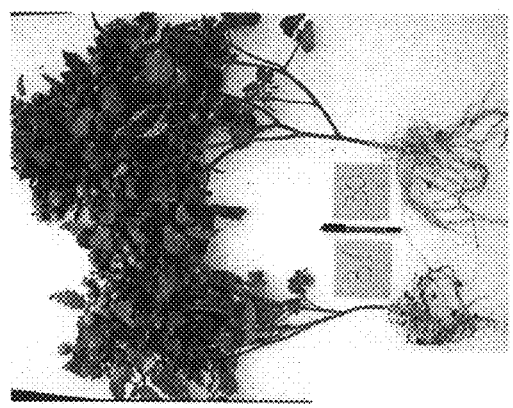

To further examine if elevation in plant vigor has a direct effect on total seed weight, $T_2$ plant seeds (grown under regular conditions) over-expressing ABST 1, (SEQ ID NO: 1) 6 (SEQ ID NO: 4), 36 (SEQ ID NO: 13) and 37 (SEQ ID NO: 14) under the 6669 promoter were weighed. The seeds from plants over-expressing ABST_1 and 36 weighed 50% more compared to control lines as illustrated in FIG. 7 and Table 17 below.

TABLE 17

Average seed weight of arabidopsis lines over-expressing ABST genes 1, 6, 19, 36, 37 under the 6669 promoter

| Level | Least Sq Mean | Level of significance* | Level of significance* | Std Error |
|---|---|---|---|---|
| ABST_1 | 0.062 | A | | 0.006 |
| ABST_36 | 0.061 | A | | 0.005 |
| ABST_37 | 0.053 | A | B | 0.004 |
| ABST_6 | 0.048 | A | B | 0.006 |
| Negative control | 0.048 | A | B | 0.005 |
| Positive control-Rab7 | 0.043 | | B | 0.005 |
| ABST_19 | 0.043 | | B | 0.004 |

*Levels not connected by same letter are significantly different

The effect of over-expression of ABST genes in plants subjected to salt stress on dry mass was tested using the same plant populations grown under continuous irrigation of saline water.

As summarized in Table 18 below, ABST_6 and 36 (SEQ ID NOs: 4 and 13 respectively) increased the plant dry mass under both the 35S and 6669 promoters (ABST_6: 25%, 16% respectively; ABST_36: 15%, 33% respectively). Plants over-expressing ABST_1 (SEQ ID NO: 1) showed higher dry mass only under the 6669 promoter (66%). ABST_22 and 37 (SEQ ID NOs: 9 and 14 respectively) were tested only under the 35S promoter and showed a significant increase (>43%) of plant dry mass compared to control line.

TABLE 18

Summary of absolute (g) and relative dry mass (relativ to negative control %) of the T2 transgenic lines overexpressing the ABST genes under salt stress conditions

| Gene name | T2 plants overexpressing the ABST gene under the 35S promoter | | | T2 plants overexpressing the ABST gene under the 6669 promoter | | |
|---|---|---|---|---|---|---|
| | Mean dry mass (g) | Std Error | Relative expression compare to control (%) | Mean dry mass (g) | Std Error | Relative expression compare to control (%) |
| Negative control | 0.041 | 0.005 | 100.000 | 0.019 | 0.002 | 100.000 |
| ABST_1 | 0.035 | 0.006 | 93.280 | 0.032 | 0.002 | 166.035 |
| ABST_6 | 0.052 | 0.005 | 124.750 | 0.022 | 0.001 | 114.480 |
| ABST_19 | 0.040 | 0.005 | 102.273 | 0.017 | 0.002 | 87.753 |
| ABST_22 | 0.056 | 0.005 | 142.455 | ND | ND | ND |

TABLE 18-continued

Summary of absolute (g) and relative dry mass (relativ to negative control %) of the T2 transgenic lines overexpressing the ABST genes under salt stress conditions

| Gene name | T2 plants overexpressing the ABST gene under the 35S promoter | | | T2 plants overexpressing the ABST gene under the 6669 promoter | | |
|---|---|---|---|---|---|---|
| | Mean dry mass (g) | Std Error | Relative expression compare to control (%) | Mean dry mass (g) | Std Error | Relative expression compare to control (%) |
| ABST_36 | 0.049 | 0.005 | 115.910 | 0.027 | 0.002 | 132.576 |
| ABST_37 | 0.059 | 0.005 | 143.068 | ND | ND | ND |

ND = not determined

Table 19 below summarizes the results of all the dry mass and seed measurements that were performed on the transgenic *arabidopsis* over-expressing the ABST genes. (calculated as percentage compare negative control).

TABLE 19

Dry Mass and seed measurements

| Growth conditions | Measurement/Gene name | ABST_1 | ABST_6 | ABST_22 | ABST_36 | ABST_37 |
|---|---|---|---|---|---|---|
| Favorable conditions | Increase (%) of dry mass of plant over expressing ABST genes under 35S promoter | 18 | 10 | 38 | 0 | 32 |
| Favorable conditions | Increase (%) of dry mass of plant over expressing ABST genes under 6669 promoter | 49 | 44 | ND | 24 | ND |
| Favorable conditions | Increase of seeds weight in plants over expressing ABST genes under 6669 regulation | 28 | 0 | ND | 27 | 11 |
| Salt stress conditions | Increase of dry mass of plant over expressing ABST genes under 6669 regulation | 66 | 14 | ND | 33 | ND |
| Salt stress conditions | Increase of dry mass of plant over expressing ABST genes under ABST 35S regulation | 0 | 25 | 42 | 16 | 43 |

Example 10

Evaluating Growth of Transgenic Tomato Plants Cultivated Under Abiotic Stress Conditions The M82 tomato variety strain (Evoline 3) was used to determine whether improvement of plant vigor under stress may be translated into improvement of commercial yield. ABST genes 1, 6 and 36 (SEQ I.D. NOs. 1, 4 and 13 respectively) were transformed under the regulation of the 6669 promoter. As described in Example 9, all three gene combinations showed significant improvement of stress tolerance in *arabidopsis* plants. The genes were introduced into M82 variety by crossing transgenic miniature tomato lines with M82 plants. To represent the variation of the position effect, a pool of pollen from transgenic lines representing 4 different insertion events from each one of the genes were used as the male parent. The F1 hybrids were used for further evaluation.

The segregating F1 populations were divided into two isogenic populations, i.e. plants over-expressing the ABST genes of the present invention and plants that were not transformed to over-express ABST genes (NT) from the same populations used as negative controls. During the first three weeks, all the plants were grown in a nursery under regular conditions. Following this period the plants were transplanted into a commercial greenhouse under two different treatments. The first group of plants was grown under favorable conditions while the second group was grown under continuous irrigation of saline water (180 mM NaCl). Each transgenic line was compared to a NT plant derived from the same F1 population. The plants were evaluated for their plant and fruit performance at a stage where the percentage of red fruit was on average 80%.

Results:

The plants over-expressing ABST genes showed improved vigor and larger root systems than the NT plants. In addition, the plants over-expressing ABST genes showed improved yield under salt stress conditions.

Specifically, plants over-expressing ABST genes showed an elevation in the fresh weight of both canopies and roots. The populations expressing ABST_1, 6 and 36 showed elevations of 165%, 162%, 206% respectively in canopy fresh weight compared to NT populations (Table 20) and higher root weight of 162%, 168% and 121% respectively compared to NT plants.

TABLE 20

Summary of absolute (g) and relative fresh mass (relative to negative control %) of the canopies of M82 tomato T2 transgenic lines overexpressing the ABST genes under saline water irrigation M82 tomato T2 plants overexpressing the ABST gene under the 6669 promoter

| Gene name | Mean canopies fresh weight | Std Error | Level of significancy* | Relative increase compare to control (%) |
|---|---|---|---|---|
| [MT] × [M82]_T (transgenic negative control) Plasmid backbone only) | 142.780 | 26.375 | c | 99.986 |
| [ABST_1] × [M82] | 235.780 | 32.302 | ab | 165.112 |
| [ABST_6] × [M82] | 231.280 | 45.682 | abc | 161.961 |
| [ABST_36] × [M82] | 294.168 | 52.263 | a | 206.000 |

*Levels not connected by same letter are significantly different)

To further prove that this elevation in weight was due to accumulation of biomass and not only due to water accumulation, the dry mass of both the canopies and roots was measured. The dry mass of the canopies increased by 156%, 145% and 161% in the lines expressing ABST_1, 6, 36 respectively compared to the corresponding NT lines. Similar effects were observed in the roots of these lines. Roots of the plants over-expressing ABST genes contained 40% (as summarized in Table 21 below) more dry matter than roots of the NT control plants (ABST_1-168%,6-159% and 36-140%).

TABLE 21

Summary of absolute (g) and relative dry mass (relative to negative control %) of the roots of M82 tomato T2 transgenic lines overexpressing the ABST genes under saline water irrigation M82 tomato T2 plants overexpressing the ABST gene under the 6669 promoter

| Gene name | Mean root dry weight (g) | Std Error | Level of significancy* | Relative increase compare to control (%) |
|---|---|---|---|---|
| [MT] × [M82]_T (transgenic negative control) | 2.073 | 0.310 | b | 100.000 |
| [ABST_1] × [M82] | 3.700 | 0.379 | a | 168.182 |
| [ABST_6] × [M82] | 3.500 | 0.424 | a | 159.091 |
| [ABST_36] × [M82] | 3.067 | 0.693 | ab | 139.394 |

*Levels not connected by same letter are significantly different)

Only transgenic plants over expressing ABST_36 had a lower root/shoot mass ratio than control plants (Table 22 below). This lower ratio (0.067 compared to more than 0.08 in control plants) is the result of a nearly 50% increase in shoot fresh weight rather than a major decrease in root fresh weight. This finding suggests that under stress growth conditions, the ABST_36 over-expressing plants require a relatively lower root mass to support shoot growth and development.

TABLE 22

Ratio between root to shoot mass in control plants and three transgenic lines over expressing ABST_1, 6, 36

| Gene name | Ratio dry weight roots per canopy |
|---|---|
| [MT] × [M82] Non-transgenic negative control | 0.086287522 |
| [ABST_1] × [M82] | 0.083090052 |
| [ABST_6] × [M82] | 0.085003036 |
| [ABST_36] × [M82] | 0.067 |

Fruit yield was analyzed by measuring the number of fruit clusters, the number of green and red fruits and weight of the green and red fruits in each one of the lines.

Plants over-expressing ABST_36 comprise (37%) significantly more fruit clusters compared to control line suggesting a link between vigor and yield potential as summarized in Table 23 below.

All three tested ABST genes of the present invention improved total fruit yield as illustrated in Table 24. Specifically, ABST_1 increased fruit yield by 137%. ABST_6 increased fruit yield by 151%. ABST_36 increased fruit yield by 191%. The relative large internal variation within populations reflects the variation that exists between different insertion events.

A more detailed analysis of the yield determinants showed that most of the additional yield (50% to 90%) was due to elevation in the weight of green fruit (Table 25). In addition most of the elevation in yield was due to an increase in the number of fruits rather than enlargement of fruit size (Table 26).

The significant difference in the number of green fruits between the lines largely depends on the physiological status of the plants. The control NT plants wilted much earlier while the plants over-expression ABST genes continued to develop for a longer period.

TABLE 23

Average number of fruit clusters in transgenic lines over-expressing the ABST genes and control lines M82 tomato T2 plants overexpressing the ABST gene under the 6669 promoter

| Gene name | Mean number of clusters | Std Error | Level of significant | Relative per control (%) |
|---|---|---|---|---|
| [MT] × [M82]_T (Transgenic negative control) | 18.586 | 1.493 | b | 100.000 |
| [ABST_1] × [M82] | 19.402 | 1.829 | ab | 104.874 |
| [ABST_6] × [M82] | 22.533 | 2.586 | ab | 121.799 |
| [ABST_36] × [M82] | 25.467 | 2.876 | a | 137.660 |

TABLE 24

Total fruit yield in transgenic lines over-expressing the ABST genes and control lines M82 tomato T2 plants overexpressing the ABST gene under the 6669 promoter

| Gene name | Mean of total fruits weight (g) | Std Error | Level of significant | Relative per control (%) |
|---|---|---|---|---|
| [MT] × [M82]_T (Transgenic negative control) | 431.974 | 61.573 | c | 100.000 |
| [ABST_1] × [M82] | 592.724 | 71.693 | bc | 137.104 |
| [ABST_6] × [M82] | 652.338 | 101.389 | bc | 148.869 |
| [ABST_36] × [M82] | 825.934 | 115.330 | b | 187.029 |

TABLE 25

Green fruit weight of transgenic lines over-expressing the ABST genes and control lines (gram)

M82 tomato T2 plants overexpressing the ABST gene under the 6669 promoter

| Gene name | Mean of green fruits weight (g) | Std Error | Level of significant | Relative per control (%) |
|---|---|---|---|---|
| [MT] × [M82]_T (Transgenic negative control) | 145.401 | 47.168 | c | 100.000 |
| [ABST_1] × [M82] | 221.722 | 55.219 | bc | 152.491 |
| [ABST_6] × [M82] | 256.431 | 78.091 | bc | 176.362 |
| [ABST_36] × [M82] | 421.925 | 87.206 | b | 290.182 |

TABLE 26

Average number of the green fruits that were produced in the transgenic lines over-expressing the ABST genes and control lines M82 tomato T2 plants overexpressing the ABST gene under the 6669 promoter

| Gene name | Mean of number of green fruits | Std Error | Level of significant | Relative per control (%) |
|---|---|---|---|---|
| [MT] × [M82]_T (Transgenic negative control) | 26.127 | 6.173 | bc | 100.000 |
| [ABST_1] × [M82] | 41.666 | 7.146 | ab | 160.254 |
| [ABST_6] × [M82] | 41.047 | 10.106 | ab | 157.875 |
| [ABST_36] × [M82] | 58.703 | 11.756 | a | 225.780 |

FIGS. 8A-D depict control and transgenic plants of the present invention illustrating the increase in yield following over-expression of the ABST genes of the present invention.

Comparison between lines expressing ABST_1, 6, 36 under favorable conditions to control lines under favorable conditions did not show any significant changes in the vigor of the vegetative parts or in the fruit yield. The following parameters were tested: fresh and dry weight of the roots and canopies, green fruit weight, red fruit weight and the average green and red fruit diameter. In all these parameters no differences were detected.

Table 27 below summarizes the results on crop yield following over-expression of ABST in tomato plants.

TABLE 27

Comparison of plant and fruit performances between transgenic and control plants grown under favorable and salt stress conditions (irrigation of 180 Mm NaCl)

| | Control (Water) | ABST_1 (Water) | ABST_6 (Water) | ABST_36 (Water) | Control (180 mM NaCl) | ABST_1 (180 mM NaCl) | ABST_6 (180 mM NaCl) | ABST_36 (180 mM NaCl) |
|---|---|---|---|---|---|---|---|---|
| Canopy fresh weight | ND | ND | ND | ND | 143 c | 236 ab | 231 ab | 295 a |
| Root fresh weight | 84 a | 74 a | 72 a | 87 a | 16 c | 27 a | 28 a | 20 ab |
| Number of fruits per plant | 195 a | 185 a | 186 a | 171 a | 66 c | 90 bc | 87 bc | 104 b |
| Total Fruit weight per plant | 2750 a | 2845 a | 2846 a | 2501 a | 432 c | 593 bc | 652 bc | 826 b |

Tomato plants that were crossed between transgenic miniature tomatos and the M82 line (line 3) were also grown under both salt stress and favorable conditions. The salt stress was carried out by continuous irrigation of saline water containing 180 mM NaCl.

The miniature populations expressing ABST_1 and 22 showed the highest improvement in salt tolerance compare to the control line based on plant and root mass and yield performance. The dry mass of the transgenic lines expressing ABST_1, 22 was increased by 300% and 257,% respectively. ABST_36 improved both shoot mass and yield by about 30% as compared to control plants. The lines expressing ABST_1 and 22 showed the highest yield performance (165% and 140% respectively) compared to control population.

Figure 9B:
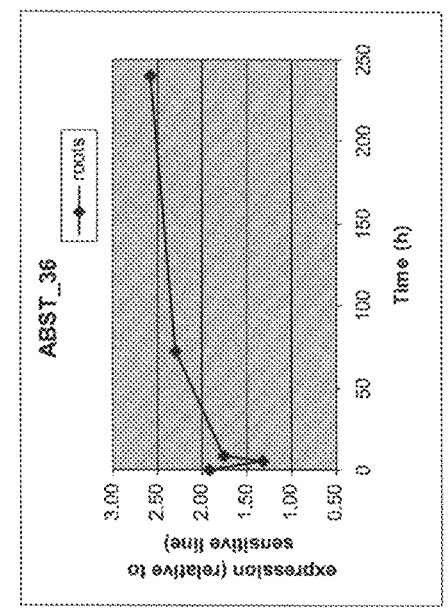
FIGS. 9A-C are line graphs illustrating the relative expression of putative ABST genes in stress tolerant tomato leaves (Evoline 2) versus stress sensitive tomato leaves (Evoline 1).
Figure 9A:
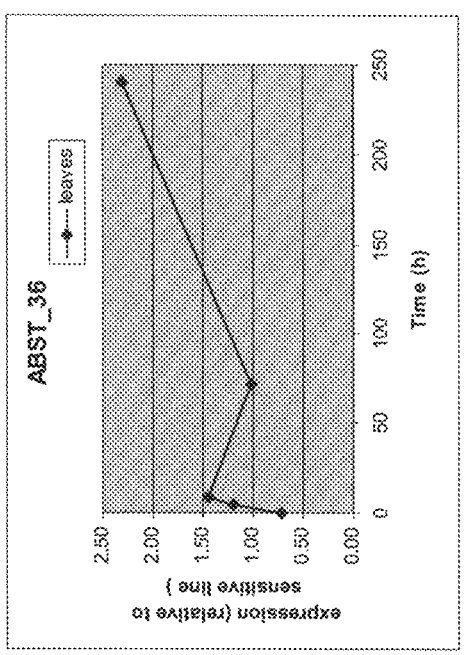
Figure 9C:
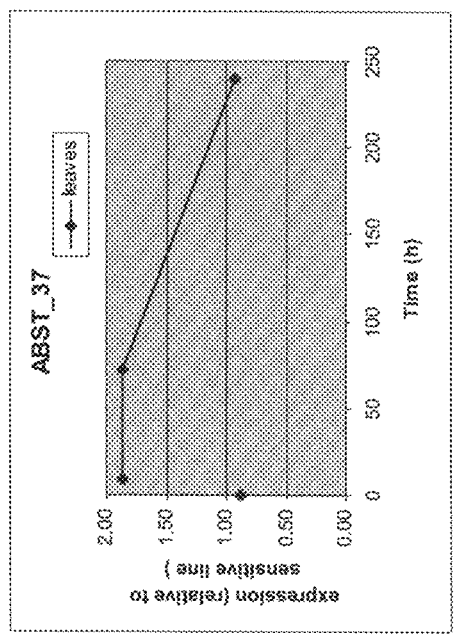

ABST 36 and 37 were also over-expressed in a line 2 tolerant tomato plant (Y361) and its expression was compared to that in a line 1 sensitive tomato plant (Shirly). As illustrated in FIGS. 9A-C, ABST_36 expression was higher in the tolerant plants in both roots and leaves. ABST_37 was up-regulated in leaves of both tolerant and sensitive lines. However in the tolerant line (line 2) the expression was up-regulated in leaves much faster than in leaves of sensitive line (line 1). Up-regulation in roots occurred only in the tolerant lines (line 2).

Hence, the results from Examples 1-10, clearly indicate that the abiotic stress tolerance genes of the present invention described herein can be readily isolated and utilized to substantially increase tolerance to abiotic stress and/or biomass in plants.

Example 11

Identifying Putative Abiotic Stress-Tolerance Genes from Monocots

Monocot ortholog sequences for the 5 putative ABST tomato genes (SEQ I.D. NOs. 1,4,9,13 and 14) were sought. Monocot genomic databases namely NCBI (Hypertext Transfer Protocol://World Wide Web (dot) ncbi (dot) nlm (dot)nih (dot)gov/) and TIGR (Hypertext Transfer Protocol://World Wide. Web (dot) tigr (dot) org/) databases of Maize, *Sorghum* and Barley were initially screened. The expressed sequence tags (ESTs) and cDNA sequences were clustered and assembled using the LEADS™ software (Compugen) and compared to the TIGR (http://www.tigr.org/) databases of the above monocots. Overall, clustering of 372,000 maize ESTs resulted in 41,990 clusters among them 19,870 singletons. In *Sorghum*, about 190,000 ESTs were clustered into 39,000 clusters while in barley 370,500 ESTs generated 50,000 different clusters each representing a different gene. A digital expression profile summary was compiled for each cluster according to all keywords included in the sequence records comprising the cluster.

Yet, while comparing the monocot sequences to the tomato ABST genes, sequence homology levels differed dramatically, ranging from 45% to 88%. Moreover, the in-silico expression profile of the monocot genes did not always fit the profile of a gene involved in ABS tolerance.

In an attempt to identify the best orthologues for the tomato ABST genes various additional factors were analyzed. First, the sequences of the 5 tomato ABST genes (SEQ ID NO: 1, 4, 9, 13 and 14) and their deduced polypeptide sequences (SEQ ID NOs: 236-240) were compared to all monocot putative proteins, encoded by DNA sequences of gene clusters mentioned above. The comparison was performed on the protein level looking for identity higher than 45% along the entire protein sequences. Table 28 shows the best homologous genes and their identity level to the tomato ABST proteins. Next, these monocot proteins originating from different monocot species (barley, sorghum and maize) were screened based on their expression pattern during the development of several monocot species. This screening was based on digital expression of the genes, as described above. The genes were selected based on three criteria: genes with higher expression in roots, roots and leaves and or induce expression by treatments representing soil stress conditions (drought, salinity, soil deficiencies). The increase of expression was only counted in cases where the increase was greater than 2 fold (relative to the random EST distribution) with significance probability lower than 0.05. Table 29 summarizes the expression profile of the genes in different organ or tissues and the treatments that set off significant elevation in their expression level.

TABLE 28

The level of homology between the tomato ABST genes and their homologs from monocots

| Tomato gene SEQ ID NO | TIGR Name/Acc No of Homologous gene | Plant origin | Level of homology (e value) | % Identity (Percenrtage from the entire protein sequence) |
|---|---|---|---|---|
| 1 | TC104838 | *Sorghum* | 2E-70 | 88% |
|  | SEQ ID NO: 93 |  |  |  |
|  | TC103857 | *Sorghum* | 2E-70 | 88% |
|  | TC258871 | Maize | 1E-69 | 86% |
|  | TC139195 | Barley | 5E-69 | 86% |
| 4 | TC94284 | *Sorghum* | 3E-43 | 45% |
|  | SEQ ID NO: 94 |  |  |  |
|  | TC132394 | Barley | 6E-40 | 44% |
| 9 | TC93449 | *Sorghum* | 1E-99 | 58% |
|  | SEQ ID NO: 95 |  |  |  |
|  | TC146720 | Barley | 3E-99 | 58% |
| 13 | TC92953 | *Sorghum* | 7E-59 | 47% |
|  | SEQ ID NO: 96 |  |  |  |
|  | TC91426 | *Sorghum* | 4E-98 | 74% |
|  | SEQ ID NO: 97 |  |  |  |
|  | TC91474 | *Sorghum* | 5E-98 | 72% |
|  | TC263205 | Maize | 2E-97 | 74% |
| 14 | TC103772 | *Sorghum* | 1E-52 | 49% |
|  | SEQ ID NO: 98 |  |  |  |
|  | TC148356 | Barley | 1E-54 | 46% |
|  | TC260731 | Maize | 1E-54 | 46% |

TABLE 29

The expression profile of ABST homologous in silico genes as represented by statistical analysis of their EST distribution

| Name of Homologous gene | Plant species | Organs/tissues with the highest gene expression | Fold increase (All results are singnificant in P value >0.05) | Treatments that induce th expression level | Fold increase (all results are singnificant in P value >0.05) |
|---|---|---|---|---|---|
| TC104838 SEQ ID NO: 93 | Sorghum | Pollen preanthesis stage | 3 | Ethylene, drought | 2 |
| TC103857 | Sorghum | Diverse expression | 2 | None* | None* |
| TC258871 | Maize | Diverse expression, preferentially in cell lignification region of leaves | 2 | None* | None* |
| TC139195 | Barley | In various grain tissues | 2-3.5 | None | None |
| TC94284 SEQ ID NO: 94 | Sorghum | Leaves, roots during fruit loading | 4.5 2 | Drought, nitrogen deficiencies, soil acidity | 4 2 2 |
| TC132394 | Barley | Leaves, coleoptile mainly during fruit development | 2.5 3 | None | None |
| TC93449 SEQ ID NO: 95 | Sorghum | Flowers ovary | 3 | Salinity stress | 4 |
| TC146720 | Barley | Seeds preferentially in the embryo and scutellum during ripening | 2 | Cold stress, Fusarium infection | 3 3.5 |
| TC92953 SEQ ID NO: 96 | Sorghum | Leaves during fruit loading | 2 | Drought, Nitrogen-deficiency, salinity (150 Mm) | 4 4 2.5 |
| TC91426 SEQ ID NO: 97 | Sorghum | Young roots | 12 | Ethylene, etiolation, soil acidity | 4 3 12 |
| TC91474 | Sorghum | Entire seedling | 2 | Etiolation | 16 |
| TC263205 | Maize | Primary root system in seedling stage | 3 | Drought | 2 |
| TC103772 SEQ ID NO: 98 | Sorghum | Young roots | 2 | Drought, soil acidity | 2 2 |
| TC148356 | Barley | Callus, leaves in the vetatative stage | 4, 2 | Infection by Blumeria graminis | 2 |
| TC260731 | Maize | Root preferntialy primary roots | 2.5 | None | None |

None* - None of the treatments with significant elevation in digital expression could be considered as soil stress treatment A combination of the above screening as described in Table 28 and in Table 29 revealed the final list of six monocot genes that are predicted to be the most related to the tomato ABST genes (SEQ ID NOs. 93, 94, 95, 96, 97 and 98).

Another type of sequence alignment for finding putative orthologous sequences from barley, rice, maize and sorghum, using the tomato ABST genes as involved the use of an evology system. Digital expression analysis was performed on these genes allowing for the identification of other putative monocot orthologs. The results were corroborated by phylogenetic analysis which studies the relationships between the tomato ABST genes and the putative monocot orthologs.

The Evology system is a method for constructing ortholog groups across multiple eukaryotic taxa, using the Markov cluster algorithm to group putative orthologs and paralogs. The method coherent with the groups identified by EGO (Hypertext Transfer Protocol://World Wide Web (dot) tigr (dot) org/tdb/tgi/ego/index (dot) shtml) but improved the identification of "recent paralogs" since EGO is easily misled by the functional redundancy of multiple paralogs and by the absence of true orthologs within incomplete genome data set as in most of the plant species.

The Evologs is a tool for large-scale automated eukaryotic ortholog group identification. To resolve the many-to-many orthologous relationships inherent in comparisons across multiple genomes, Evologs applied the Markov Cluster algorithm (Hypertext Transfer Protocol://micans (dot) org/mcl/), which is based on probability and graph flow theory and allows simultaneous classification of global relationships in a similarity space. MCL simulates random walks on a graph using Markov matrices to determine the transition probabilities among nodes of the graph. The MCL algorithm has previously been exploited for clustering a large set of protein sequences, where it was found to be very fast and reliable in dealing with complicated domain structures. Evologs generates clusters of at least two proteins, where each cluster consists of orthologs or paralogs from at least one species.

The putative orthologs were obtained using three levels of stringency. The first group with the lowest level (p value<=1e-20 and identity>=50%), the second group with moderate level of stringency (p value<=1e-42 and identity>=50%) and the third group with the highest stringency include p value<=1e-70 and identity>=70%.

1. Eight genes were identified as putative orthologs for ABST_1. This group was defined using the highest stringency parameters (highest cutoff—level 3).
2. Nine monocot genes were identified as ABST_6 putative orthologs. These genes were found only after filtering under the lowest stringency alignment (level 1) parameters. This reduces the probability of finding a real monocot ortholog.
3. Eight monocot genes were identified as ABST_22 putative orthologs. These genes were found by using the highest stringency parameters (highest cutoff—level 3).
4. Twenty three putative ortholog genes were found for ABST_36 (Table 2). This group was found by using the highest stringency parameters (the highest cutoff—level 3).
5. Fourteen putative orthologs for ABST_37 were found only after reducing the alignment parameters to the second stringency level. However since the genes are transcription factors more accurate comparison should be done on their binding domains.

These genes were subjected to digital expression analysis. Genes that were identified as being up-regulated under stress conditions underwent phylogenetic analysis. The phylogenetic trees showed similar distances between tomato, *Arabidopsis* and monocots supporting the claim that conservation in function in *Arabidopsis* and tomato strongly indicates conservation in function in monocot (data not shown).

A final list of ten candidate monocot ortholog genes was drawn up, as detailed in Table 30 below.

TABLE 30

List of ten candidate monocot orthologues as revealed by evolog analysis, phylogenetic analysis and digital expression analysis

| Tomato gene SEQ ID NO: | TIGR Name/ Acc No of Homologous gene | Plant origin | % Identity (Percentage from the entire protein sequence) |
|---|---|---|---|
| 1 | TC104838 SEQ ID NO: 93 | *Sorghum* | 88% |
| 4 | TC94284 SEQ ID NO: 94 | *Sorghum* | 45% |
| 9 | TC93449 SEQ ID NO: 95 | *Sorghum* | 58% |
|  | TC102291 SEQ ID NO: 241 | *Sorghum* | 54% |
| 13 | TC131030 SEQ ID NO: 242* | Barley | 72% |
|  | AF057183 SEQ ID NO: 245 | maize | 70% |
|  | TC249365 SEQ ID NO: 244 | maize | 70% |
|  | TC249366 SEQ ID NO: 243 | maize | 70% |
|  | TC263205 SEQ ID NO: 246 | Maize | 74% |
| 14 | TC103772 SEQ ID NO: 98 | *Sorghum* | 49% |

*SEQ ID NO: 242 is identical to SEQ ID NO: 74

The digital expression profile for TC104838 (SEQ ID NO:93) is listed in Tables 31-33 herein below.

TABLE 31

Expression of TC104838 in different anatomical regions of the plant

| Keyword | ESTs in Gene | ESTs in Production | Expected ESTs | Fold | p-value |
|---|---|---|---|---|---|
| flower | 3 | 26937 | 1.11986 | 2.6789 | 0.0865946 |
| pollen | 3 | 8840 | 1 | 3 | 0.00431486 |
| leaf | 1 | 17487 | 1 | 1 | 0.535872 |
| seedling | 2 | 95402 | 3.96618 | 0.504263 | 0.970844 |

TABLE 32

Expression of TC104838 during development

| Keyword | ESTs in Gene | ESTs in Production | Expected ESTs | Fold | p-value |
|---|---|---|---|---|---|
| flowering | 4 | 32705 | 1.35966 | 2.94192 | 0.0301425 |
| 8-14 days pre-anthesis | 3 | 8840 | 1 | 3 | 0.00431486 |
| post-flowering | 1 | 5768 | 1 | 1 | 0.216515 |
| germination | 2 | 104379 | 4.33939 | 0.460895 | 0.985772 |
| 1.5 week | 2 | 47911 | 1.99182 | 1.00411 | 0.636908 |
| vegetative | 1 | 21465 | 1 | 1 | 0.615042 |
| 5 weeks old | 1 | 9746 | 1 | 1 | 0.34123 |

TABLE 33

Expression of TC104838 under various treatments

| Keyword | ESTs in Gene | ESTs in Production | Expected ESTs | Fold | p-value |
|---|---|---|---|---|---|
| drought | 2 | 18855 | 1 | 2 | 0.180136 |
| drought stress after flowering | 1 | 5768 | 1 | 1 | 0.216515 |
| drought stress, 7, 8 days after water witheld | 1 | 9746 | 1 | 1 | 0.34123 |
| hormone treatment | 2 | 26047 | 1.08286 | 1.84696 | 0.29656 |
| ethylene-induced with ACC, 27 and 72 hours after induction | 2 | 6261 | 1 | 2 | 0.0256292 |

The digital expression profile for TC94284 (SEQ ID NO:94) is listed in Tables 34-36 herein below.

TABLE 34

Expression of TC94284 in different anatomical regions of the plant

| Keyword | ESTs in Gene | ESTs in Production | Expected ESTs | Fold | p-value |
|---|---|---|---|---|---|
| leaf | 5 | 17487 | 1.14242 | 4.37668 | 0.0032544 |
| seedling | 6 | 95402 | 6.23257 | 0.962684 | 0.675068 |
| leaf | 2 | 19738 | 1.28947 | 1.55102 | 0.375678 |
| root | 2 | 7258 | 1 | 2 | 0.078916 |

TABLE 35

Expression of TC94284 during development

| Keyword | ESTs in Gene | ESTs in Production | Expected ESTs | Fold | p-value |
|---|---|---|---|---|---|
| flowering | 4 | 32705 | 2.1366 | 1.87213 | 0.148602 |
| post-flowering | 4 | 5768 | 1 | 4 | 0.000374052 |
| germination | 6 | 104379 | 6.81904 | 0.87989 | 0.795559 |
| 1.5 week | 2 | 47911 | 3.13001 | 0.638976 | 0.864874 |
| 2 weeks old | 4 | 27953 | 1.82616 | 2.19039 | 0.094453 |
| vegetative | 1 | 21465 | 1.4023 | 0.713114 | 0.7769 |
| 4 weeks old | 1 | 8221 | 1 | 1 | 0.423423 |

TABLE 36

Expression of TC94284 under various treatments

| Keyword | ESTs in Gene | ESTs in Production | Expected ESTs | Fold | p-value |
|---|---|---|---|---|---|
| drought | 4 | 18855 | 1.23179 | 3.24731 | 0.0271328 |
| drought stress after flowering | 4 | 5768 | 1 | 4 | 0.000374052 |
| nutrient deficiencies | 2 | 9927 | 1 | 2 | 0.134282 |
| Nitrogen deficient | 2 | 3313 | 1 | 2 | 0.0189181 |
| pathogen | 3 | 17272 | 1.12837 | 2.6587 | 0.0951298 |

The digital expression profile for TC93449 (SEQ ID NO:95) is listed in Tables 37-39 herein below.

TABLE 37

Expression of TC93449 in different anatomical regions of the plant

| Keyword | ESTs in Gene | ESTs in Production | Expected ESTs | Fold | p-value |
|---|---|---|---|---|---|
| callus | 2 | 9585 | 1.36622 | 1.46389 | 0.40017 |
| cell suspension | 2 | 9585 | 1.36622 | 1.46389 | 0.40017 |
| flower | 6 | 26937 | 3.83953 | 1.56269 | 0.17419 |
| ovary | 4 | 9434 | 1.3447 | 2.97465 | 0.0426186 |
| leaf | 3 | 17487 | 2.49255 | 1.20359 | 0.461176 |
| seedling | 13 | 95402 | 13.5983 | 0.955999 | 0.676721 |
| leaf | 1 | 19738 | 2.8134 | 0.355442 | 0.949846 |
| root + leaf | 5 | 19261 | 2.74541 | 1.82122 | 0.131853 |
| callus | 2 | 9585 | 1.36622 | 1.46389 | 0.40017 |

TABLE 38

Expression of TC93449 during development

| Keyword | ESTs in Gene | ESTs in Production | Expected ESTs | Fold | p-value |
|---|---|---|---|---|---|
| flowering | 7 | 32705 | 4.66168 | 1.5016 | 0.169309 |
| 8 weeks old (immature) | 4 | 9434 | 1.3447 | 2.97465 | 0.0426186 |
| post-flowering | 1 | 5768 | 1 | 1 | 0.56683 |
| pre-anthesis | 2 | 8663 | 1.2348 | 1.6197 | 0.352104 |
| germination | 13 | 104379 | 14.8779 | 0.873779 | 0.841438 |
| 1 week | 1 | 19538 | 2.78489 | 0.35908 | 0.948201 |
| 1.5 week | 11 | 47911 | 6.8291 | 1.61075 | 0.0526309 |
| 2 weeks old | 1 | 27953 | 3.98435 | 0.250982 | 0.987187 |
| vegetative | 2 | 21465 | 3.05956 | 0.653688 | 0.82924 |
| 4 weeks old | 2 | 8221 | 1.1718 | 1.70678 | 0.328675 |

TABLE 39

Expression of TC93449 under various treatments

| Keyword | ESTs in Gene | ESTs in Production | Expected ESTs | Fold | p-value |
|---|---|---|---|---|---|
| drought | 1 | 18855 | 2.68754 | 0.372087 | 0.942184 |
| drought stress after flowering | 1 | 5768 | 1 | 1 | 0.56683 |
| heat stress | 1 | 8875 | 1.26502 | 0.790502 | 0.727378 |
| 4 and 24 hours at 40-42° C. | 1 | 8875 | 1.26502 | 0.790502 | 0.727378 |
| hormone treatment | 6 | 26047 | 3.71267 | 1.61609 | 0.155303 |
| ethylene-induced with ACC, 27 and 72 hours after induction | 4 | 6261 | 1 | 4 | 0.0111844 |
| Salicylic acid-treated | 2 | 4793 | 1 | 2 | 0.148347 |
| nutrient deficiencies | 1 | 9927 | 1.41497 | 0.70673 | 0.767414 |
| Iron deficient | 1 | 3353 | 1 | 1 | 0.382937 |
| pathogen | 3 | 17272 | 2.4619 | 1.21857 | 0.452792 |
| Resistant plants, 48 h after *Colletotrichum graminicola* innoculation (fungi) | 1 | 9051 | 1.29011 | 0.775131 | 0.734507 |
| Susceptible plants, 48 h after *Colletotrichum graminicola* innoculation (fungi) | 2 | 8221 | 1.1718 | 1.70678 | 0.328675 |
| salinity | 4 | 6080 | 1 | 4 | 0.010119 |
| 150 mM NaCl for 3, 6, 12 and 24 hr | 4 | 6080 | 1 | 4 | 0.010119 |

The digital expression profile for TC102291 (SEQ ID NO: 241 and 247) is listed in Tables 40-42 herein below.

TABLE 40

Expression of TC102291 in different anatomical regions of the plant

| Keyword | ESTs in Gene | ESTs in Production | Expected ESTs | Fold | p-value |
|---|---|---|---|---|---|
| callus | 4 | 9585 | 1.48007 | 2.70257 | 0.0576229 |
| cell suspension | 4 | 9585 | 1.48007 | 2.70257 | 0.0576229 |
| leaf | 5 | 17487 | 2.70026 | 1.85167 | 0.126138 |
| seedling | 14 | 95402 | 14.7315 | 0.950342 | 0.688991 |
| leaf | 2 | 19738 | 3.04785 | 0.6562 | 0.825957 |
| root + leaf | 9 | 19261 | 2.97419 | 3.02603 | 0.00168405 |

TABLE 41

Expression of TC102291 during development

| Keyword | ESTs in Gene | ESTs in Production | Expected ESTs | Fold | p-value |
|---|---|---|---|---|---|
| flowering | 3 | 32705 | 5.05016 | 0.594041 | 0.904756 |
| post-flowering | 3 | 5768 | 1 | 3 | 0.0581305 |
| germination | 14 | 104379 | 16.1177 | 0.868609 | 0.854646 |
| 1 week | 2 | 19538 | 3.01697 | 0.662917 | 0.821366 |
| 1.5 week | 4 | 47911 | 7.3982 | 0.540672 | 0.962528 |

TABLE 41-continued

Expression of TC102291 during development

| Keyword | ESTs in Gene | ESTs in Production | Expected ESTs | Fold | p-value |
|---|---|---|---|---|---|
| 2 weeks old | 8 | 27953 | 4.31637 | 1.85341 | 0.0543811 |
| vegetative | 5 | 21465 | 3.31453 | 1.50851 | 0.230885 |
| 5 weeks old | 3 | 9746 | 1.50493 | 1.99344 | 0.188518 |
| pre-flowering | 2 | 3341 | 1 | 2 | 0.0935317 |

TABLE 42

Expression of TC102291 under various treatments

| Keyword | ESTs in Gene | ESTs in Production | Expected ESTs | Fold | p-value |
|---|---|---|---|---|---|
| drought | 8 | 18855 | 2.9115 | 2.74772 | 0.00599968 |
| drought stress after flowering | 3 | 5768 | 1 | 3 | 0.0581305 |
| drought stress before flowering | 2 | 3341 | 1 | 2 | 0.0935317 |
| drought stress, 7, 8 days after water withheld | 3 | 9746 | 1.50493 | 1.99344 | 0.188518 |
| heat stress | 1 | 8875 | 1.37044 | 0.729694 | 0.755364 |
| 4 and 24 hours at 40-42° C. | 1 | 8875 | 1.37044 | 0.729694 | 0.755364 |
| hormone treatment | 6 | 26047 | 4.02206 | 1.49177 | 0.204473 |
| Abscisic acid-treated | 5 | 4306 | 1 | 5 | 0.000458231 |
| ethylene-induced with ACC, 27 and 72 hours after induction | 1 | 6261 | 1 | 1 | 0.626674 |
| light response | 1 | 18685 | 2.88525 | 0.34659 | 0.953042 |
| etiolated | 1 | 10663 | 1.64653 | 0.607337 | 0.817519 |
| nutrient deficiencies | 1 | 9927 | 1.53288 | 0.652366 | 0.794035 |
| Nitrogen deficient | 1 | 3313 | 1 | 1 | 0.403524 |
| pathogen | 2 | 17272 | 2.66706 | 0.749889 | 0.761847 |
| Resistant plants, 48 h after *Colletotrichum graminicola* innoculation (fungi) | 2 | 9051 | 1.39761 | 1.43101 | 0.411127 |
| salinity | 3 | 6080 | 1 | 3 | 0.0659796 |
| 150 mM NaCl for 3, 6, 12 and 24 hr | 3 | 6080 | 1 | 3 | 0.0659796 |

The digital expression profile for TC131030 (SEQ ID NO:242 and 248) is listed in Tables 43-45 herein below.

TABLE 43

Expression of TC131030 in different anatomical regions of the plant

| Keyword | ESTs in Gene | ESTs in Production | Expected ESTs | Fold | p-value |
|---|---|---|---|---|---|
| root | 5 | 16560 | 1 | 5 | 1.48052E-06 |
| seedling | 1 | 57039 | 1 | 1 | 0.662622 |
| root | 1 | 1988 | 1 | 1 | 0.0341428 |
| shoot | 1 | 8317 | 1 | 1 | 0.136442 |

TABLE 44

Expression of TC131030 during development

| Keyword | ESTs in Gene | ESTs in Production | Expected ESTs | Fold | p-value |
|---|---|---|---|---|---|
| germination | 1 | 92778 | 1.61655 | 0.6186 | 0.847952 |
| 5-8 days | 1 | 29670 | 1 | 1 | 0.417607 |
| seedling | 5 | 33561 | 1 | 5 | 4.84613E-05 |
| 3 weeks old | 5 | 21898 | 1 | 5 | 5.90628E-06 |

TABLE 45

Expression of TC131030 under various treatments

| Keyword | ESTs in Gene | ESTs in Production | Expected ESTs | Fold | p-value |
|---|---|---|---|---|---|
| drought | 3 | 8410 | 1 | 3 | 0.00027555 |
| drought stressed | 2 | 4939 | 1 | 2 | 0.00296904 |
| drought stressed (6 and 10 h on moist paper in light) | 1 | 1496 | 1 | 1 | 0.0257848 |
| light response | 2 | 6815 | 1 | 2 | 0.00557109 |
| etiolated | 1 | 4697 | 1 | 1 | 0.0791 |
| Low light | 1 | 888 | 1 | 1 | 0.0153731 |
| waterlogged | 1 | 2259 | 1 | 1 | 0.0387209 |
| waterlogged | 1 | 2259 | 1 | 1 | 0.0387209 |

The digital expression profile for TC249366 (SEQ ID NO:243 and 251) is listed in Tables 46-48 herein below.

TABLE 46

Expression of TC249366 in different anatomical regions of the plant

| Keyword | ESTs in Gene | ESTs in Production | Expected ESTs | Fold | p-value |
|---|---|---|---|---|---|
| root | 26 | 36059 | 2.69511 | 9.6471 | 2.22045E-15 |
| primary root system | 26 | 33886 | 2.5327 | 10.2657 | 0 |

TABLE 47

Expression of TC249366 during development

| Keyword | ESTs in Gene | ESTs in Production | Expected ESTs | Fold | p-value |
|---|---|---|---|---|---|
| germination | 26 | 74869 | 5.59584 | 4.64631 | 7.54952E-15 |
| young seedling | 26 | 34586 | 2.58502 | 10.058 | 0 |

TABLE 48

Expression of TC249366 under various treatments

| Keyword | ESTs in Gene | ESTs in Production | Expected ESTs | Fold | p-value |
|---|---|---|---|---|---|
| drought | 21 | 21216 | 1.58572 | 13.2432 | 7.77156E-16 |
| CONTROL well watered 0 h | 8 | 5966 | 1 | 8 | 1.00075E-08 |
| water stress 48 h | 2 | 6113 | 1 | 2 | 0.0761554 |

TABLE 48-continued

Expression of TC249366 under various treatments

| Keyword | ESTs in Gene | ESTs in Production | Expected ESTs | Fold | p-value |
|---|---|---|---|---|---|
| water stress 5 h | 7 | 6417 | 1 | 7 | 3.8251E−07 |
| water stress 5 h and 48 h, Subtracted library | 4 | 2720 | 1 | 4 | 4.97583E−05 |

The digital expression profile for TC249365 (SEQ ID NO:244 and 250) is listed in Tables 49-51 herein below.

TABLE 49

Expression of TC249365 in different anatomical regions of the plant

| Keyword | ESTs in Gene | ESTs in Production | Expected ESTs | Fold | p-value |
|---|---|---|---|---|---|
| flower | 11 | 89278 | 11.7349 | 0.937375 | 0.649792 |
| seedling + female flower | 8 | 9012 | 1.18456 | 6.75357 | 2.20576E−05 |
| silk | 3 | 1536 | 1 | 3 | 0.001119 |
| leaf | 3 | 35689 | 4.69104 | 0.639517 | 0.859653 |
| mix | 19 | 90046 | 11.8359 | 1.60529 | 0.0168681 |
| root | 11 | 36059 | 4.73968 | 2.32083 | 0.00638112 |
| primary root system | 11 | 33886 | 4.45405 | 2.46966 | 0.00399824 |
| seedling | 12 | 32466 | 4.26741 | 2.81201 | 0.000841861 |
| seedling + female flower | 8 | 9012 | 1.18456 | 6.75357 | 2.20576E−05 |
| shoot | 4 | 16152 | 2.12306 | 1.88408 | 0.162096 |

TABLE 50

Expression of TC249365 during development

| Keyword | ESTs in Gene | ESTs in Production | Expected ESTs | Fold | p-value |
|---|---|---|---|---|---|
| flowering | 11 | 89278 | 11.7349 | 0.937375 | 0.649792 |
| developed seedling + silking | 8 | 9012 | 1.18456 | 6.75357 | 2.20576E−05 |
| silking | 3 | 2160 | 1 | 3 | 0.00293981 |
| germination | 26 | 74869 | 9.84095 | 2.64202 | 3.92859E−07 |
| developed seedling | 9 | 31271 | 4.11033 | 2.1896 | 0.0196511 |
| developed seedling + silking | 8 | 9012 | 1.18456 | 6.75357 | 2.20576E−05 |
| young seedling | 9 | 34586 | 4.54606 | 1.97974 | 0.034885 |
| mix | 19 | 70970 | 9.32846 | 2.03678 | 0.00110629 |

TABLE 51

Expression of TC249365 under various treatments

| Keyword | ESTs in Gene | ESTs in Production | Expected ESTs | Fold | p-value |
|---|---|---|---|---|---|
| drought | 7 | 21216 | 2.78868 | 2.51015 | 0.0204171 |
| CONTROL well watered 0 h | 1 | 5966 | 1 | 1 | 0.546304 |
| water stress 48 h | 1 | 6113 | 1 | 1 | 0.555122 |
| water stress 5 h | 5 | 6417 | 1 | 5 | 0.00154268 |
| mix | 3 | 36475 | 4.79436 | 0.625736 | 0.869757 |
| pathogen | 3 | 2260 | 1 | 3 | 0.00333671 |
| Fusarium, 6 h post infection | 3 | 667 | 1 | 3 | 9.9034E−05 |
| salinity | 4 | 3579 | 1 | 4 | 0.00127889 |
| 150 mM NaCl 24 h | 4 | 3579 | 1 | 4 | 0.00127889 |

The digital expression profile for AF057183 (SEQ ID NO:245 and 249) is listed in Tables 52-54 herein below.

TABLE 52

Expression of AF057183 in different anatomical regions of the plant

| Keyword | ESTs in Gene | ESTs in Production | Expected ESTs | Fold | p-value |
|---|---|---|---|---|---|
| flower | 15 | 83646 | 25.2528 | 0.593995 | 0.994869 |
| pollen | 1 | 11265 | 3.40091 | 0.294039 | 0.968401 |
| seedling + female flower | 9 | 8119 | 2.45113 | 3.67178 | 0.000831679 |
| silk | 5 | 1651 | 1 | 5 | 0.000156853 |
| leaf | 3 | 34159 | 10.3126 | 0.290906 | 0.998479 |
| mix | 31 | 88820 | 26.8148 | 1.15608 | 0.205053 |
| root | 46 | 35521 | 10.7238 | 4.28952 | 3.55271E−15 |
| primary root system | 46 | 33407 | 10.0856 | 4.56097 | 4.88498E−15 |
| seedling | 13 | 29180 | 8.80945 | 1.47569 | 0.10175 |
| seedling + female flower | 9 | 8119 | 2.45113 | 3.67178 | 0.000831679 |
| shoot | 4 | 14803 | 4.46903 | 0.895049 | 0.65764 |

TABLE 53

Expression of AF057183 during development

| Keyword | ESTs in Gene | ESTs in Production | Expected ESTs | Fold | p-value |
|---|---|---|---|---|---|
| flowering | 15 | 83646 | 25.2528 | 0.593995 | 0.994869 |
| developed seedling + silking | 9 | 8119 | 2.45113 | 3.67178 | 0.000831679 |
| silking | 5 | 2284 | 1 | 5 | 0.000684783 |
| tasseling | 1 | 17200 | 5.19269 | 0.192579 | 0.995102 |
| germination | 62 | 70016 | 21.1379 | 2.93313 | 0 |
| developed seedling | 13 | 28013 | 8.45713 | 1.53716 | 0.0800076 |
| developed seedling + silking | 9 | 8119 | 2.45113 | 3.67178 | 0.000831679 |
| young seedling | 40 | 33884 | 10.2296 | 3.91023 | 1.82077E−14 |
| mix | 30 | 66869 | 20.1878 | 1.48605 | 0.0138371 |

TABLE 54

Expression of AF057183 under various treatments

| Keyword | ESTs in Gene | ESTs in Production | Expected ESTs | Fold | p-value |
|---|---|---|---|---|---|
| drought | 33 | 21241 | 6.41266 | 5.14607 | 1.42109E−14 |
| CONTROL well watered 0 h | 11 | 5813 | 1.75495 | 6.268 | 1.69797E−06 |
| water stress 48 h | 3 | 6130 | 1.85065 | 1.62105 | 0.282624 |
| water stress 5 h | 13 | 6304 | 1.90318 | 6.83067 | 6.879E−08 |
| water stress 5 h and 48 h, Subtracted library | 6 | 2825 | 1 | 6 | 0.000233093 |
| mix | 6 | 30831 | 9.30789 | 0.644614 | 0.91149 |
| pathogen | 5 | 2415 | 1 | 5 | 0.000877511 |
| *Fusarium*, 6 h post infection | 4 | 710 | 1 | 4 | 7.00937E−05 |
| *Fusarium*, 72 h post infection | 1 | 251 | 1 | 1 | 0.0730116 |
| salinity | 8 | 3603 | 1.08775 | 7.35465 | 1.52409E−05 |
| 150 mM NaCl 24 h | 8 | 3603 | 1.08775 | 7.35465 | 1.52409E−05 |

The digital expression profile for TC263205 (SEQ ID NO:246 and 252) is listed in Tables 55-57 herein below.

TABLE 55

Expression of TC263205 in different anatomical regions of the plant

| Keyword | ESTs in Gene | ESTs in Production | Expected ESTs | Fold | p-value |
|---|---|---|---|---|---|
| flower | 1 | 89278 | 2.53106 | 0.395092 | 0.943664 |
| seedling + female flower | 1 | 9012 | 1 | 1 | 0.227799 |
| mix | 3 | 90046 | 2.55283 | 1.17517 | 0.488081 |
| root | 3 | 36059 | 1.02228 | 2.93461 | 0.075106 |
| primary root system | 3 | 33886 | 1 | 3 | 0.0645285 |
| seedling | 1 | 32466 | 1 | 1 | 0.617579 |
| seedling + female flower | 1 | 9012 | 1 | 1 | 0.227799 |

TABLE 56

Expression of TC263205 during development

| Keyword | ESTs in Gene | ESTs in Production | Expected ESTs | Fold | p-value |
|---|---|---|---|---|---|
| flowering | 1 | 89278 | 2.53106 | 0.395092 | flowering |
| developed seedling + silking | 1 | 9012 | 1 | 1 | developed seedling + silking |
| germination | 4 | 74869 | 2.12256 | 1.88452 | germination |
| developed seedling + silking | 1 | 9012 | 1 | 1 | developed seedling + silking |
| young seedling | 3 | 34586 | 1 | 3 | young seedling |
| mix | 3 | 70970 | 2.01202 | 1.49104 | mix |

TABLE 57

Expression of TC263205 under various treatments

| Keyword | ESTs in Gene | ESTs in Production | Expected ESTs | Fold | p-value |
|---|---|---|---|---|---|
| drought | 3 | 21216 | 1 | 3 | 0.0193621 |
| water stress 5 h | 1 | 6417 | 1 | 1 | 0.167604 |
| water stress 5 h and 48 h, Subtracted library | 2 | 2720 | 1 | 2 | 0.00259071 |

The digital expression profile for TC103772 (SEQ ID NO:98) is listed in Tables 58-60 herein below.

TABLE 58

Expression of TC103772 in different anatomical regions of the plant

| Keyword | ESTs in Gene | ESTs in Production | Expected ESTs | Fold | p-value |
|---|---|---|---|---|---|
| leaf | 2 | 17487 | 1.24628 | 1.60478 | 0.358705 |
| seedling | 10 | 95402 | 6.79917 | 1.47077 | 0.053411 |
| leaf | 2 | 19738 | 1.4067 | 1.42177 | 0.419124 |
| leaf + root | 2 | 9479 | 1 | 2 | 0.143927 |
| root | 2 | 7258 | 1 | 2 | 0.092071 |

TABLE 59

Expression of TC103772 during development

| Keyword | ESTs in Gene | ESTs in Production | Expected ESTs | Fold | p-value |
|---|---|---|---|---|---|
| flowering | 2 | 32705 | 2.33084 | 0.858059 | 0.708441 |
| post-flowering | 2 | 5768 | 1 | 2 | 0.0616601 |
| germination | 10 | 104379 | 7.43895 | 1.34428 | 0.106822 |
| 1.5 week | 5 | 47911 | 3.41455 | 1.46432 | 0.236642 |
| 2 weeks old | 5 | 27953 | 1.99217 | 2.50982 | 0.0357911 |

TABLE 60

Expression of TC103772 under various treatments

| Keyword | ESTs in Gene | ESTs in Production | Expected ESTs | Fold | p-value |
|---|---|---|---|---|---|
| drought | 2 | 18855 | 1.34377 | 1.48835 | 0.395639 |
| drought stress after flowering | 2 | 5768 | 1 | 2 | 0.0616601 |
| light response | 3 | 18685 | 1.33166 | 2.25284 | 0.140391 |
| CONTROL for etiolated | 3 | 8022 | 1 | 3 | 0.0172009 |
| nutrient deficiencies | 1 | 9927 | 1 | 1 | 0.517716 |
| Iron deficient | 1 | 3353 | 1 | 1 | 0.214459 |
| oxidative stress | 2 | 9479 | 1 | 2 | 0.143927 |
| 3 12 and 27 h with hydrogen peroxide and Paraquat | 2 | 9479 | 1 | 2 | 0.143927 |
| pathogen | 2 | 17272 | 1.23095 | 1.62476 | 0.352853 |
| Resistant plants, 48 h after *Colletotrichum graminicola* innoculation (fungi) | 2 | 9051 | 1 | 2 | 0.133444 |
| soil acidity | 2 | 7258 | 1 | 2 | 0.092071 |
| acid and alkaline stress | 2 | 7258 | 1 | 2 | 0.092071 |

Selected polynucleotide sequences (SEQ ID NOs: 93-98) were analyzed for presence of ORFs using Vector NTI suite (InforMax, U.K.) version 6 (Hasting Software, Inc: World Wide Web (dot) generunner (dot) com/). ORFs identified in each of these polynucleotide sequences were compared to Genbank database sequences, using Blast (World Wide Web (dot) ncbi (dot) nlm (dot) nih (dot)gov/BLAST/); the ORF displaying the highest homology to a GenBank sequence or sequences, was mapped in order to identify an ATG start codon. The position of the ATG start codon of this ORF was then compared with that of the identified polynucleotide sequence in order to verify that each of the five sequences described herein includes a full length ORF and an ATG start codon (thus qualifies as a "putative monocot ABST gene").

Polypeptides with significant homology to monocot ABST genes (SEQ ID NOs: 93-98) have been identified from the NCBI databases using BLAST software (Table 61).

TABLE 61

ABST homologs

| Monocot ABST Putative Gene SEQ ID NO. | ABST Polypeptide Homologue, encoded by TIGR Acession No | Source Organism | ABST Polypeptide Homologue SEQ ID NO: | Homology in Polypeptide sequence (%) |
|---|---|---|---|---|
| 93 | TC270110 | Zea mays | 105 | 100 |
| 93 | TC56855 | Saccharum officinarum | 106 | 100 |
| 93 | TC104838 | sorghum | 107 | 100 |
| 93 | TC57929 | Saccharum officinarum | 108 | 98 |
| 93 | TC103857 | sorghum | 109 | 98 |
| 93 | TC262554 | Oryza sativa | 110 | 98 |
| 93 | TC258871 | Zea mays | 111 | 97 |
| 93 | TC139195 | Hordeum vulgare | 112 | 96 |
| 93 | TC262556 | Oryza sativa | 113 | 95 |
| 93 | TC232174 | Triticum aestivum | 114 | 95 |
| 93 | TC232139 | Triticum aestivum | 115 | 95 |
| 93 | TC139194 | Hordeum vulgare | 116 | 95 |
| 93 | CA486561 | Triticum aestivum | 117 | 100 |
| 93 | TC258873 | Zea mays | 118 | 100 |
| 93 | CA187014 | Saccharum officinarum | 119 | 90 |
| 93 | TC233455 | Triticum aestivum | 120 | 96 |
| 93 | CF063450 | Zea mays | 121 | 98 |
| 93 | CA617041 | Triticum aestivum | 122 | 100 |
| 94 | TC94284 | sorghum | 123 | 100 |
| 94 | TC49791 | Saccharum officinarum | 124 | 95 |
| 95 | TC93449 | sorghum | 125 | 100 |
| 95 | TC49718 | Saccharum officinarum | 126 | 95 |
| 95 | TC49720 | Saccharum officinarum | 127 | 96 |
| 96 | TC92953 | sorghum | 128 | 100 |
| 96 | TC66617 | Saccharum officinarum | 129 | 90 |
| 96 | TC273860 | Zea mays | 130 | 91 |
| 96 | TC253191 | Zea mays | 131 | 90 |
| 98 | TC103772 | sorghum | 132 | 100 |
| 98 | TC272084 | Zea mays | 133 | 92 |
| 98 | TC60928 | Saccharum officinarum | 134 | 94 |
| 93 | TC5422 | canola | 135 | 88 |
| 93 | TC904 | canola | 136 | 88 |
| 93 | TC121774 | Solanum tuberosum | 137 | 88 |
| 93 | TC40342 | Gossypium | 138 | 88 |
| 93 | TC40115 | Gossypium | 139 | 88 |
| 93 | TC155918 | Lycopersicon esculentum | 140 | 88 |
| 93 | TC154398 | Lycopersicon esculentum | 141 | 88 |
| 93 | TC154397 | Lycopersicon esculentum | 142 | 88 |
| 93 | TC153989 | Lycopersicon esculentum | 143 | 88 |
| 93 | TC120511 | Solanum tuberosum | 144 | 88 |
| 93 | TC113582 | Solanum tuberosum | 145 | 88 |
| 93 | TC112701 | Solanum tuberosum | 146 | 88 |
| 93 | TC111912 | Solanum tuberosum | 147 | 88 |
| 93 | TC4674 | Capsicum annum | 148 | 88 |
| 93 | TC270923 | arabidopsis | *149 | 87 |
| 93 | CD823817 | canola | 150 | 86 |
| 93 | TC526 | canola | 151 | 86 |
| 93 | TC525 | canola | 152 | 86 |
| 93 | BG442528 | Gossypium | 153 | 87 |
| 93 | TC33702 | Gossypium | 154 | 87 |
| 93 | TC32714 | Gossypium | 155 | 87 |
| 93 | TC270782 | arabidopsis | **156 | 87 |
| 93 | TC225449 | Glycine max | ***157 | 87 |
| 93 | TC5255 | Capsicum annum | 158 | 88 |
| 93 | TC28221 | populus | 159 | 84 |
| 93 | TC108140 | medicago | 160 | 85 |

TABLE 61-continued

ABST homologs

| Monocot ABST Putative Gene SEQ ID NO. | ABST Polypeptide Homologue, encoded by TIGR Acession No | Source Organism | ABST Polypeptide Homologue SEQ ID NO: | Homology in Polypeptide sequence (%) |
|---|---|---|---|---|
| 93 | TC28222 | populus | 161 | 84 |
| 93 | TC94402 | medicago | 162 | 84 |
| 93 | TC28223 | populus | 163 | 83 |
| 93 | TC102506 | medicago | 164 | 85 |
| 93 | TC132070 | Hordeum vulgare | 165 | 79 |
| 93 | TC251944 | Triticum aestivum | 166 | 77 |
| 93 | NP890576 | Oryza sativa | 167 | 76 |
| 93 | TC280376 | Oryza sativa | 168 | 73 |
| 93 | CN009841 | Triticum aestivum | 169 | 75 |
| 93 | BI948270 | Hordeum vulgare | 170 | 75 |
| 93 | TC259334 | arabidopsis | 171 | 75 |
| 93 | BQ767154 | Hordeum vulgare | 172 | 73 |
| 93 | TC60345 | Saccharum officinarum | 173 | 73 |
| 93 | TC138474 | Hordeum vulgare | 174 | 85 |
| 93 | TC41472 | populus | 175 | 72 |
| 93 | BJ458177 | Hordeum vulgare | 176 | 72 |
| 93 | CB674176 | Oryza sativa | 177 | 82 |
| 93 | TC216405 | Glycine max | 178 | 88 |
| 93 | AJ777371 | populus | 179 | 70 |
| 93 | CV019213 | tobacco | 180 | 85 |
| 93 | CK215690 | Triticum aestivum | 181 | 80 |
| 93 | CD830784 | canola | 182 | 85 |
| 93 | CA624722 | Triticum aestivum | 183 | 85 |
| 93 | TC32906 | populus | 184 | 76 |
| 93 | CR285127 | Oryza sativa | 185 | 89 |
| 93 | TC251945 | Triticum aestivum | 186 | 72 |
| 94 | TC274823 | Oryza sativa | 187 | 77 |
| 94 | TC132394 | Hordeum vulgare | 188 | 75 |
| 94 | TC267180 | Triticum aestivum | 189 | 77 |
| 94 | TC261921 | Zea mays | 190 | 87 |
| 94 | TC267181 | Triticum aestivum | 191 | 74 |
| 94 | TC261922 | Zea mays | 192 | 81 |
| 94 | TC267182 | Triticum aestivum | 193 | 73 |
| 95 | TC249531 | Zea mays | 194 | 86 |
| 95 | TC232170 | Triticum aestivum | 195 | 85 |
| 95 | TC146720 | Hordeum vulgare | 196 | 85 |
| 95 | TC249329 | Oryza sativa | 197 | 84 |
| 95 | TC249532 | Zea mays | 198 | 88 |
| 95 | TC232150 | Triticum aestivum | 199 | 85 |
| 95 | TC249330 | Oryza sativa | 200 | 76 |
| 95 | CB672603 | Oryza sativa | 201 | 71 |
| 95 | TC32440 | Gossypium | 202 | 81 |
| 95 | TC119105 | Solanum tuberosum | 203 | 72 |
| 96 | TC247999 | Triticum aestivum | 204 | 78 |
| 96 | TC247359 | Triticum aestivum | 205 | 77 |
| 96 | TC132566 | Hordeum vulgare | 206 | 77 |
| 96 | TC248676 | Triticum aestivum | 207 | 74 |
| 96 | TC249667 | Oryza sativa | 208 | 77 |
| 96 | TC66618 | Saccharum officinarum | 209 | 88 |
| 97 | TC253495 | Oryza sativa | 214 | 90 |
| 97 | TC224823 | Glycine max | 215 | 75 |
| 97 | TC234990 | Triticum aestivum | 216 | 74 |
| 97 | TC266178 | Triticum aestivum | 217 | 73 |
| 97 | TC119051 | Solanum tuberosum | 218 | 83 |
| 97 | TC56409 | Saccharum officinarum | 219 | 75 |
| 97 | TC35873 | Populus | 220 | 80 |
| 97 | TC119052 | Solanum tuberosum | 221 | 82 |
| 97 | TC204518 | Glycine max | 222 | 85 |
| 97 | TC112169 | Solanum tuberosum | 223 | 84 |
| 97 | TC254696 | Zea mays | 224 | 79 |
| 97 | TC254696 | Zea mays | 225 | 82 |
| 97 | TC248906 | Oryza sativa | 226 | 77 |
| 97 | TC154007 | Lycopersicon esculentum | 227 | 82 |
| 97 | TC6466 | Capsicum annuum | 228 | 74 |
| 97 | TC131227 | Hordeum vulgare | 229 | 74 |
| 97 | TC27564 | Gossypium | 230 | 71 |
| 98 | TC275473 | Oryza sativa | 210 | 78 |

TABLE 61-continued

ABST homologs

| Monocot ABST Putative Gene SEQ ID NO. | ABST Polypeptide Homologue, encoded by TIGR Acession No | Source Organism | ABST Polypeptide Homologue SEQ ID NO: | Homology in Polypeptide sequence (%) |
|---|---|---|---|---|
| 98 | TC267485 | Triticum aestivum | 211 | 77 |
| 98 | TC148621 | Hordeum vulgare | 212 | 76 |
| 98 | TC275474 | Oryza sativa | 213 | 85 |

*SEQ ID NO: 149 is identical to SEQ ID NO: 41
**SEQ ID NO: 156 is identical to SEQ ID NO: 42
***SEQ ID NO: 157 is identical to SEQ ID NO: 40

Example 12

Generating Putative Monocot ABST Genes

DNA sequences of six putative Monocot ABST genes were synthesized by GeneArt (Hypertext Transfer Protocol://World Wide Web (dot) geneart (dot) com/). Synthetic DNA was designed in silico, based on the encoded amino-acid sequences of the Monocot ABST genes (SEQ ID NOs: 99, 100, 101, 102, 103 and 104), and by using plant-based codon-usage. The synthetic sequences and the plant native orthologues were compared. At least 1 mutation per 20 nucleotide base pairs was added to avoid possible silencing, when overexpressing the gene in favorable monocot species, such as maize. The planned sequences were bordered with the following restriction enzymes sites polylinker—SaIII, XbaI, BamHI, SmaI at the 5' end and SacI at the 3' end. The sequences were cloned in double strand, PCR Script plasmid (GeneArt).

Example 13

Cloning the Putative ABST Genes

The PCR Script plasmids harboring the synthetic, monocot-based ABST genes were digested with the restriction endonucleases XbaI and SacI (Roche), purified using PCR Purification Kit (Qiagen, Germany), and inserted via DNA ligation using T4 DNA ligase enzyme (Roche) and according to the manufacturer's instructions, into pKG(NOSter), (SEQ ID NO: 233) and pKG(35S+NOSter), (SEQ ID NO: 234), plant expression vector plasmids, also digested with XbaI and SacI (Roche) and purified. pKG plasmid is based on the PCR Script backbone (GeneArt), with several changes in the polylinker site to facilitate cloning a gene of interest downstream to a promoter and upstream to a terminator, suitable for expression in plant cells. Moreover, the inserted gene, together with the promoter and the terminator could be easily moved to a binary vector.

The resulting pKG(NOSter) and pKG(35S+NOSter) harboring putative Monocot ABST genes were introduced into E. coli DH5 competent cells by electroporation, using a MicroPulser electroporator (Biorad), 0.2 cm cuvettes (Biorad) and EC-2 electroporation program (Biorad). The treated cells were cultured in LB liquid medium at 37° C. for 1 hour, plated over LB agar supplemented with ampicillin (100 mg/L; Duchefa) and incubated at 37° C. for 16 hrs. Colonies that developed on the selective medium were analyzed by PCR using the primers of SEQ ID NO: 231 and SEQ ID NO: 232, which were designed to span the inserted sequence in the pKG plasmids. The resulting PCR products were separated on 1% agarose gels and from the colonies having the DNA fragment of the predicted size, a plasmid was isolated using miniprep Plasmid Kit (Qiagen) and sequenced using the ABI 377 sequencer (Amersham Biosciences Inc) in order to verify that the correct DNA sequences were properly introduced to the E. coli cells.

Positive pKG(NOSter) plasmids harboring putative Monocot ABST genes were digested with the restriction enzymes HindIII and SalI (Roche), purified using PCR Purification Kit (Qiagen, Germany), and then ligated (as described above) with At6669 promoter sequence (set forth in SEQ ID NO: 20) digested from pPI+At6669 plasmid with the same enzymes and purified. The resulting plasmids were introduced into E. coli DH5 competent cells by electroporation, the treated cells were cultured in LB liquid medium at 37° C. for 1 hr, subsequently plated over LB agar supplemented with ampicillin (100 mg/L; Duchefa) and incubated at 37° C. for 16 hours. Colonies grown on the selective medium were analyzed by PCR using the primers SEQ ID NO: 235 and SEQ ID NO: 232. Positive plasmids were identified isolated and sequenced as described above.

The plasmid pPI was constructed by inserting a synthetic poly-(A) signal sequence, originating from pGL3 basic plasmid vector (Promega, Acc No U47295; bp 4658-4811) into the HindIII restriction site of the binary vector pBI101.3 (Clontech, Acc. No. U12640).

The At6669 promoter was isolated from Arabidopsis thaliana var Col0 genomic DNA by PCR amplification using the primers set forth in SEQ ID NOs: 37 and 38. The PCR product is purified (Qiagen, Germany) and digested with the restriction endonucleases HindIII and SalI (Roche). The resulting promoter sequence was introduced into the open binary pPI vector digested with the same enzymes, to produce pPI+At6669 plasmid.

Example 14

Generating Binary Vectors Comprising Putative Monocot ABST Genes and Plant Promoters Operably Linked Thereto Generating binary vectors comprising the Cauliflower Mosaic Virus 35S promoter: The five pKG(35S+NOSter) constructs harboring putative Monocot ABST genes (SEQ ID Nos: 93, 94, 95, 96, 97 and 98) were digested with HindIII and EcoRI (Roche) restriction endonucleases in order to excise expression cassettes and ligated to pPI plasmid digested with the same endonucleases and purified (as described above). Altogether, five pPI constructs were generated, each comprising putative Monocot ABST gene having a sequence set forth in SEQ ID NOs: 93, 94, 95, 96, 97 and 98 positioned downstream to the Cauliflower Mosaic Virus 35S promoter and upstream to the Nopaline Synthase (NOS) terminator, which was originated from the digestion of pBI101.3 (Clontech, Acc. No. U12640), using the restriction sites SacI and EcoRI.

Generating Binary Vectors Comprising the At6669 Promoter:

The five pKG(At6669+NOSter) constructs harboring putative Monocot ABST genes downstream to At6669 promoter sequence (set forth in SEQ ID NO: 20), and upstream to the Nopaline Synthase (NOS) terminator, were digested with HindIII and EcoRI (Roche) in order to excise expression cassettes and ligated into pPI plasmid which was digested with the same restriction endonucleases and purified (as described above). Altogether, five pPI constructs were generated, each comprising the At6669 promoter positioned upstream of a putative Monocot ABST gene having a sequence set forth in SEQ ID NOs: 93, 94, 95, 96, 97 and 98.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent or patent application or sequence identified by their accession number was specifically and individually indicated to be incorporated herein by reference. In addition, citation or identification of any reference in this application shall not be construed as an admission that such reference is available as prior art to the present invention.

REFERENCES CITED (Additional References are Cited Hereinabove)

1. World Wide Web (dot) fao (dot) org/ag/agl/agll/spush/degrad (dot) htm.
2. World Wide Web (dot) fao (dot) org/ag/agl/aglw/water-management/introduc (dot) stm
3. McCue K F, Hanson A D (1990).Drought and salt tolerance: towards understanding and application. Trends Biotechnol 8: 358-362.
4. Flowers T J, Yeo Ar (1995). Breeding for salinity resistance in crop plants: where next? Aust J Plant Physiol 22:875-884.
5. Nguyen B D, Brar D S, Bui B C, Nguyen T V, Pham L N, Nguyen H T (2003). Identification and mapping of the QTL for aluminum tolerance introgressed from the new source, ORYZA RUFIPOGON Griff., into indica rice (*Oryza sativa* L.). Theor Appl Genet. 106:583-93.
6. Sanchez A C, Subudhi P K, Rosenow D T, Nguyen H T (2002). Mapping QTLs associated with drought resistance in sorghum (*Sorghum bicolor* L. Moench). Plant Mol. Biol. 48:713-26.
7. Quesada V, Garcia-Martinez S, Piqueras P, Ponce M R, Micol J L (2002). Genetic architecture of NaCl tolerance in *Arabidopsis*. Plant Physiol. 130:951-963.
8. Apse M P, Blumwald E (2002). Engineering salt tolerance in plants. Curr Opin Biotechnol. 13:146-150.
9. Rontein D, Basset G, Hanson A D (2002). Metabolic engineering of osmoprotectant accumulation in plants. Metab Eng 4:49-56
10. Clough S J, Bent A F (1998). Floral dip: a simplified method for *Agrobacterium*-mediated transformation of *Arabidopsis thaliana*. Plant J 16:735-43.
11. Desfeux C, Clough S J, Bent A F (2000). Female reproductive tissues are the primary target of *Agrobacterium*-mediated transformation by the *Arabidopsis* floral-dip method. Plant Physiol 123:895-904.

What is claimed is:

1. A method of increasing tolerance of a plant to an abiotic stress, comprising transforming a cell of the plant with a nucleic acid construct which comprises an exogenous polynucleotide encoding a polypeptide at least 90% homologous to the amino acid sequence encoded by SEQ ID NO:13 and at least one promoter capable of directing transcription of said exogenous polynucleotide in said cell of the plant, and growing a plant having increased tolerance to an abiotic stress as compared to a control plant.

2. The method of claim 1, wherein said polypeptide is at least 95% homologous to the amino acid sequence encoded by SEQ ID NO:13.

3. The method of claim 1, further comprising growing the plant under the abiotic stress.

4. The method of claim 1, wherein the plant is a dicotyledonous plant.

5. The method of claim 1, wherein the plant is a monocotyledonous plant.

6. A method of increasing biomass and/or yield of a plant, comprising transforming a cell of the plant with a nucleic acid construct which comprises an exogenous polynucleotide encoding a polypeptide at least 90% homologous to the amino acid sequence encoded by SEQ ID NO:13 and at least one promoter capable of directing transcription of said exogenous polynucleotide in said cell of the plant, and growing a plant having increased biomass and/or yield as compared to a control plant.

7. The method of claim 6, wherein said polypeptide is at least 95% homologous to the amino acid sequence encoded by SEQ ID NO:13.

8. The method of claim 6, wherein the plant is a dicotyledonous plant.

9. The method of claim 6, wherein the plant is a monocotyledonous.

10. The method of claim 1, wherein said polypeptide is selected from the group consisting of SEQ ID NOs: 65, 70, 71, 78, 66, 67, 69, 79, 80, 81, 77, 82, 84, 86, 85, 242, 74, 72, 103, 83, 246, 73, 76, 68, 243, 245, 244, 217, 216, and 215.

11. The method of claim 1, wherein said polypeptide is selected from the group consisting of SEQ ID NOs: 65, 70, 71, 78, 66, 67, 69, 79, 80, 81, 77, 82, 84, 86, 85, 242, 74, and 72.

12. The method of claim 6, wherein said polypeptide is selected from the group consisting of SEQ ID NOs: 65, 70, 71, 78, 66, 67, 69, 79, 80, 81, 77, 82, 84, 86, 85, 242, 74, 72, 103, 83, 246, 73, 76, 68, 243, 245, 244, 217, 216, and 215.

13. The method of claim 6, wherein said polypeptide is selected from the group consisting of SEQ ID NOs: 65, 70, 71, 78, 66, 67, 69, 79, 80, 81, 77, 82, 84, 86, 85, 242, 74, and 72.

14. The method of claim 1, wherein said polynucleotide is selected from the group consisting of SEQ ID NOs: 252, 97, 248, 251, 250 and 249.

15. The method of claim 1, wherein said polynucleotide is selected from the group consisting of SEQ ID NOs: 97, 248, 251, and 250.

16. The method of claim 6, wherein said polynucleotide is selected from the group consisting of SEQ ID NOs: 252, 97, 248, 251, 250 and 249.

17. The method of claim 6, wherein said polynucleotide is selected from the group consisting of SEQ ID NOs: 97, 248, 251, and 250.

\* \* \* \* \*

SEQUENCE LISTING

<160> NUMBER OF SEQ ID NOS: 252

<210> SEQ ID NO 1
<211> LENGTH: 456
<212> TYPE: DNA
<213> ORGANISM: Lycopersicon esculentum

<400> SEQUENCE: 1

```
atgggtcgta tgcacagtcg tggtaagggt atttcagctt ctgctctccc ttacaagaga      60
actcctccta gttggctcaa gatctctgct ccagatgttg aggacaacat ctgcaagttc     120
gctaagaaag gattgacccc ttcacagatt ggtgtgattc ttcgtgattc tcatggaatt     180
gcacaagtga agagtgttac tggtagcaag atcttgcgta tcctcaaggc acatgggctt     240
gcacctgaga ttccagagga tttgtaccac ctgattaaga aggctgttgc cattaggaag     300
catttggaga ggaacaggaa ggataaggat tctaagttcc gtttgatttt ggtggagagc     360
aggattcatc gccttgctcg ttattacaag aaaacaaaaa agctcccacc tgtctggaaa     420
tacgaatcta ccactgctag cacacttgtg gcatag                               456
```

```
<210> SEQ ID NO 2
<211> LENGTH: 1386
<212> TYPE: DNA
<213> ORGANISM: Lycopersicon esculentum

<400> SEQUENCE: 2
atggctattc ctcttcaatt ctctagtata tccactcgca cagatctctc cttgccggag    60
actagaactt tcaggttacc gaaacctttc tccgtcatca gatgctccgc cggcgaacct   120
gttccttcct cgtcggctac tgctgagtca gagttcgatg ctaaggtttt ccggaagaat   180
ctgaccagaa gtgctaatta caatcgtaaa ggttttggac acaaagaagc tactcttgaa   240
ctcatgaatc gcgaatatac cagtgatatc atcaagaaat tgaaggagaa tgaatttgag   300
tatacatggg gaaacgtaac cgtaaaaactt gcagagtcct atggtttctg ttgggggtt   360 gagcgtgcag ttcagattgc ttatgaagcg aggaaacagt ttccaacaga gaggatttgg   420
ataactaatg aaattattca acccccact gtgaataaga ggctagagga tatggatgtt   480
aagaacattc cacttgagga agggaagaaa aactttgatg ttgttgacaa ggatgatgtt   540
gtggttttgc ctgcttttgg ggctgctgtt gatgaaatgt tggttttgag tgataaaaac   600
gtacaaattg ttgatacaac ctgcccgtgg gtgactaagg tttggaacac ggttgaaaag   660
cacaagaagg gagaatatac ctccattatc catggtaaat atgctcatga ggaaactgtt   720
gcgactgcat cctttgctgg gaaatacatc attgtgaaga acatggcaga ggcaacttat   780
gtctgtgatt atattcttgg aggtaaaactt gatggttcta gctcaaccaa agaggcattt   840
atgcagaaat ttaaatatgc agtttctgaa gggtttgatc cggatgttga ccttgtaaaa   900
gctggtattg caaaccaaac aactatgttg aagggagaaa cagaagatat tgggaagttg   960
gtcgagagga ccatgatgca aaatatgggg gtggaaaatg ttaacaacca cttcgtaagt  1020
ttcaacacta tatgcgatgc cacacaagag cgtcaagatg caatgtataa gctggttgag  1080
caaaagctgg atcttatgtt agtgattggt ggctggaact caagtaacac ttcacatcta  1140
caggagattg cagaggaacg tggaattccc tcatactgga ttgacagtga acagagagta  1200
ggtcctggaa acaaaataag ttacaagtta atgcatggtg agttggttga aaagagaac   1260 ttcttaccgg agggtcctat tacagttggg gtgacatctg gtgcatccac ccccgataag  1320
gttgttgaag atgtccttat caaggtgttt gatatcaagc gcgaggaagc cttacaattg  1380
gcctaa                                                             1386

<210> SEQ ID NO 3
<211> LENGTH: 2418
<212> TYPE: DNA
<213> ORGANISM: Lycopersicon esculentum

<400> SEQUENCE: 3
atggctcaac gtgttctaac tcgtgttcac agtcttcgtg aacgtcttga tgctactttg    60
gatgctcatc gcaatgaaat tttgctctttt ctttcaagga tcgaaagcca cgggaaaggg   120
atcttgaaac ctcaccagct actggctgag tttgaatcaa ttcagaaaga agacaaagac   180
aaactgaatg atcatgcctt tgaagaagtc ctgaaatcca ctcaggaagc aattgttttg   240
cccccatggg ttgcacttgc tattcgtttg aggcccggtg tgtgggaata tgtccgtgtg   300
aatgttaatg ctcttagtgt tgaggagctg actgtgcctg agttttttgca attcaaggaa   360 gaacttgtta acggaacttc cagtgataac tttgttcttg aattggattt tgagcccttc   420
actgcatcat ttccaaaacc aaccctcacg aaatcaattg gaaatggagt tgaattcctc   480
```

-continued

```
aacaggcacc tctctgctaa aatgttccat gacaaggaaa gcatgacccc tcttctcgag    540
tttcttcgag ttcaccacta caatggaaag tcaatgatgc tgaatgatag aattcagaat    600
ttgtatactc tccaaaaagt cctgaggaag gccgaggaat acctcaccac cctttcgcca    660
gaaacttcat actcctcatt tgagcacaag ttccaagaaa ttggcttgga gagaggttgg    720
ggtgacaccg cagagcgtgt tctagagatg atctgcatgc tcctggatct ccttgaggct    780
cctgactcat gtactcttga gaagttcctt agtagaattc ctatggtttt caatgtagtt    840
atactttcac ctcatggata tttcgcccag gaaaatgtct tgggttaccc cgacactggt    900
ggtcaggttg tctatatttt ggatcaagtt cctgccttgg agcgtgagat gctcaagcgc    960
ataaaggagc aaggacttga tatcaaaccg cgtattctta ttgttactcg gcttctccct   1020
gatgcagttg gtaccacttg tggtcagcga ctcgagaagg tatttggaac tgagcattca   1080
catattctta gggtccccct taggactgaa aagggcattg ttcgcaaatg gatctctcgt   1140
tttgaagtct ggccatacat ggagactttc attgaggatg tggggaaaga ataaccgca    1200 gaactgcaag ctaagccaga tcttattatt ggaaactata gtgagggaaa ccttgcagcc   1260
tccttgttgg ctcacaagtt aggtgtaaca cagtgcacca ttgctcatgc attggagaaa   1320
accaaatatc ctgattctga catttacttg aacaaatttg acgagaaata ccacttctca   1380
gctcagttca cagctgatct tatagcaatg aatcatactg atttcattat caccagcacc   1440
ttccaggaga tagcaggaag caaggacact gttggacagt atgagagcca catggccttc   1500
acaatgcctg gattgtatag agttgttcat ggcattgatg tgttcgaccc caaattcaac   1560
attgtgtcac caggagctga tgtgaatctc tatttcccat actccgaaaa ggaaaagaga   1620
ttgacaactt ttcaccctga aattgaagac ttgctgttta gcgatgttga gaacgaagaa   1680
cacctgtgtg tgttgaagga caggaataag cccatcatat tcaccatggc aagattggac   1740
cgagtgaaga acttaactgg acttgtcgag tggtatgcta agaatccacg actaagggag   1800
ttggttaacc ttgtagtggt tggtggagac cgaagaaagg aatccaaaga cttggaagag   1860
caggcagaga tgaagaagat gtatgaactt ataaagactc acaatttgaa tggccagttc   1920
cgatggattt cttcccagat gaaccgcgtg aggaatgggg aactctacag gtacattgct   1980
gacacaaggg gagctttcgt gcagcctgca ttctacgagg ctttcggtct gactgttgtt   2040
gaggccatga gctgcggttt gcctacattt gcaactaatc aaggtggtcc agctgagatc   2100
atcgttcatg gaaagtctgg tttccaaatt gatccatacc atggcgagca ggctgctgat   2160
ctcctcgctg agttcttcga gaatgtaag gtagacccct tcacattggga agccatttcc   2220 aagggtggcc ttaagcgtat acaggagaag tacacatggc aaatctactc cgaccggctg   2280
ttgacactag ctgctgtttta cgggttctgg aagcacgttt ccaagcttga tcgtcttgaa   2340
attcgtcgtt atcttgagat gttttacgct ctcaaattcc gcaagctggc tgaacttgtc   2400
ccattggctg ttgagtaa                                                 2418
```

<210> SEQ ID NO 4
<211> LENGTH: 522
<212> TYPE: DNA
<213> ORGANISM: Lycopersicon esculentum

<400> SEQUENCE: 4

```
atggaagaca aaagcaatga ttattatgca gttttggggt tgaagaagga atgcactgac    60
acagaactta ggaatgccta taagaagctt gcactgaaat ggcacccaga tcgctgttca   120
gcatcgggga atttgaagtt tgtagatgaa gcaaagaagc aatttcaggc aattcaagaa   180
```

| | |
|---|---|
| gcatattctg tgttatcgga tgcaaacaaa aagttttttgt acgatgtagg agtttatgac | 240 |
| tctggtgatg atgacgacga aaatggcatg ggtgatttcc tgaatgaaat ggcagctatg | 300 |
| atgagccaaa ataagtccaa tgaaaatcag ggagaagaaa cctttgagga attgcaggat | 360 |
| atgtttaatg aaatgttcaa cagtgataat ggaacgtttt cttcttcttc ttcttcttct | 420 |
| tcttcttctt ggactggaac tccttcaatg tgctctacta catcatctac atcttcaagt | 480 |
| gagactttt taacctttcc ccaacaagag aagttcaggt ga | 522 |

<210> SEQ ID NO 5
<211> LENGTH: 1434
<212> TYPE: DNA
<213> ORGANISM: Lycopersicon esculentum

<400> SEQUENCE: 5

| | |
|---|---|
| atggctactg ctactactct ctctcctgct gatgctgaaa agctcaacaa cctcaaatct | 60 |
| gccgtcgccg gtctaaatca atcagtgaa atgagaaat ctggatttat taaccttgtc | 120 |
| ggtcgctatc taagtggtga agcacaacac attgactgga gtaagatcca gacgccaact | 180 |
| gatgaagttg tggtgcctta tgacaagtta gcacctcttt ctgaagatcc cgcggaaact | 240 |
| aagaagcttt tggacaaact tgttgtcctg aagctcaatg gaggcttggg aacaacaatg | 300 |
| ggatgcacgg gtcccaaatc agttattgaa gttcgtaatg gtttgacatt ccttgacttg | 360 |
| attgtcaagc aaaattgagg cactcaatgcc aagttcggat gcagtgttcc cctgcttttg | 420 |
| atgaattcgt tcaacaccca cgatgataca ctgaagattg ttgaaaaata tgcaaactca | 480 |
| aacattgata ttcatacatt caatcagagc cagtaccctc gcctggttac tgaagacttt | 540 |
| gccccacttc catgcaaagg caattccgga aagatggat ggtacccctcc aggtcatggt | 600 |
| gatgttttcc cttctttgat gaatagtgga agcttgatg cactactagc aaagggcaag | 660 |
| gaatatgtct ttgttgcaaa ctctgataat ttgggcgcca ttgttgattt gaaaatctta | 720 |
| aatcatttga tcctaaacaa aaatgagtac tgcatggagg ttactcccaa aactttagct | 780 |
| gatgtcaaag gtggcacctt aatctcatat gaaggaaaag tacagctatt ggaaatagca | 840 |
| caagtccctg atgaacatgt caatgaattc aagtcaattg aaaaattcaa aattttcaac | 900 |
| accaacaact tgtgggtgag tcttagtgct attaaaagac ttgtagaagc agatgcactc | 960 |
| aagatggaga ttattcccaa cccaaaggaa gtagacggag ttaaagttct caacttgaa | 1020 |
| actgctgccg tgctgcgat taagttttttc gaccgggcaa ttggtgctaa tgttcctcga | 1080 |
| tctcgtttcc ttcccgtgaa agcaacttca gatttgctcc ttgttcagtc tgatctttac | 1140 |
| accttgactg atgagggcta tgtcatccga aacccggcca ggtctaatcc gtccaaccca | 1200 |
| tccatcgagt taggacctga attcaagaag gtggccaact tcttaggccg tttcaagtcc | 1260 |
| attcccagca tcattgatct aggtagcttg aaggtgaccg tgatgtatg gtttggatct | 1320 |
| agcgttaccc taaaggggaa agtgactgtt gcagccaaat ccggagtgaa gctagaaatt | 1380 |
| ccagatggtg ctgtgattgc aaacaaggac atcaatggac ctgaggatat atag | 1434 |

<210> SEQ ID NO 6
<211> LENGTH: 1485
<212> TYPE: DNA
<213> ORGANISM: Lycopersicon esculentum

<400> SEQUENCE: 6

| | |
|---|---|
| atggcaaaga gtggcatttt ggtaattgtt tcagctcttg ttgttcttgc agtttgtggt | 60 |
| gttttttgctg aggagaacga atatgtgttg actttggacc attctaaccct cactgagact | 120 |

-continued

```
gttgctaagc acaacttcat tgttgttgaa ttctatgcac cttggtgtgg acactgtaag      180
agtcttgctc ctgagtatga aaagctgcc tcagagctga gtagtcatga ccctccaatt      240
gttctagcta agtatgatgc aaatgatgaa gccaatagag aactttcaaa acagtacgag      300
atccagggtt tcccaactat taagatattg agagatggga gaaagaaagt tcaagactat      360
aacggtcctc gtgaagcagc tggtattgta tcctacttga gaaacaagt gggtcctgca      420 tctgctgaaa tcaagtcgaa ggaagatgcc acaaacctta ttgatgagaa agtatctttt    480
gttgttggta tatttccaga cccctccgga gagaaattcg agaactattt aacgctagct    540
gaaaaactgc gaggcgagtt cgattttgct cacactgttg atgctaaaca cctccctcgg    600
ggtggaccag tcaacaagcc cactcttcgt cttctaaagc catttgatga actctttgtt    660
gattttgagg actttgatgt cgatgcaatg gagaagttca tctcagaatc tagtattcct    720
gttgttacta ttttttgacaa tgacccaaac aaccatcctt atgttaacaa gttcttcgaa    780
ggcaccaacg ccaaggcatt gctatttgtg aactttagct ctgaatttga tgctttaag    840 tccaagtaca acgatgttgc tgtgatttac aaaggggatg gggtgagctt tctcttgggt    900
gatgttgagg ctggtcaagg tgcttttgag tacttcggac tgaagccgga acaggcacct    960
gtgatcatca taatggacgc tgatgaacaa agtatattta aggaccatgt ggaacctgat    1020
gccattgctg cttacttgaa ggattacaag gaaggaaaac tgaagccaca tgtgaagtca    1080
gagcccatcc ctgaagtcaa tgacgaacct gttaaggtgg ttgttaggga taccctccag    1140
gatatggttt acaaatcggg aaaaaatgtg ctgttagagt ctatgcacc ttggtgtggc      1200 cactgcaaga gtctggctcc aattttggat gaagtggctg tatcatttga aagcgatcct    1260
gatgttctca ttgcaaaact ggacgcaacc gcaaatgatc tcccgaaagg tgactttgat    1320
gttcagggat tccctactat gtacttcaga tccgcctctg gtaacttgtc acagtacaat    1380
ggtgagagaa caaagaggc tatcatcgaa ttcatcgaga gaatcgtgg caagcctgct      1440 cagtcagact ctgccaaagt cgattcagca aaggatgaac tttag                      1485

<210> SEQ ID NO 7
<211> LENGTH: 250
<212> TYPE: DNA
<213> ORGANISM: Lycopersicon esculentum

<400> SEQUENCE: 7
atgccgggtg cgctcgcatg gcaggtcaca aaacctaata agatgcgat ttttgtgttc      60 ggaggggaga tggtacgggg ttttttgccc gactctcctc tctgtgtctg tctttggcct    120
cctttctttt ctagaactgt ctgcaagatc tattcagata aacgtctcat caaatttggc    180
gttaatgtcc ccgaacgatg gtttcgatat ccgcaaagtt atagcagcgc tctacctttt    240
caatggatag                                                              250

<210> SEQ ID NO 8
<211> LENGTH: 717
<212> TYPE: DNA
<213> ORGANISM: Lycopersicon esculentum

<400> SEQUENCE: 8
atgaattctc agatttgcag atctgctaca agagcagcta agtcactcct ttctgcttca    60
tctaagcaga cttctcgtgc ttttcagga ggacgagcag cagctgcagc agccacagtt      120
tcattgagag gagtggtgcc ttctctagcc tcatatggca ggaatgaatc tggaaatgca    180
tctagagctt ggatttctgg tgtgcttgcc cttcctgcag cagcttacat gctccaggag    240
```

| | |
|---|---|
| caagaagcac atgctgccga gatggagcgc acctttattg ccatcaagcc agatggagta | 300 |
| cagagaggcc tgatttcaga aatcgtatca cggtttgagc gcaagggctt caagctggtt | 360 |
| gcaatcaaag ttgtgattcc ttccaaggaa tttgcaaaga agcactatca tgacttgagt | 420 |
| gagcgaccat tctttaacgg cttgtgcgac ttccttagct ctggccctgt cttagcaatg | 480 |
| gtttgggaag gtgaaggtgt aatcagatat ggaaggaagc ttatcggagc caccgatcca | 540 |
| cagaaatctg aacctggaac catcagaggc gatttagctg ttgtagtagg aaggaacatc | 600 |
| atccatggca gcgatggccc cgagaccgca aaggatgaga tcaacctatg gtttaaacca | 660 |
| gaggagttgg ttaattacac cagcaactct gagaagtggc tatatggtga taactaa | 717 |

<210> SEQ ID NO 9
<211> LENGTH: 897
<212> TYPE: DNA
<213> ORGANISM: Lycopersicon esculentum

<400> SEQUENCE: 9

| | |
|---|---|
| atggagaata tgcagagcta ttggcaattt ggcgacgagc ttcgaggaca atcaaaagcc | 60 |
| tcagaggatc ataaatggtc aacagctgct ataaaattat ctgaacagat gaagtacaaa | 120 |
| ggtgaacgta ggaataacct tgacctttca aagagctctg ctgaaattag gcccaggggt | 180 |
| aatcatatgt ttcaggaaga taacaagtgg aaagcctta acttcaatat gttaaatttg | 240 |
| gaaagcaaga tgactgaaaa tatgagcaag aatcgcatta tggatagcat tttcaatgca | 300 |
| aatccagttt atcttaagcc caattttaac agcttgggaa attcatcttt aagcaagttc | 360 |
| aatgctagca actataccaa ggaacctagc aagaataaca ataacaacgt tgagagcaca | 420 |
| aatggaaata ctccgttgca caaaggtttt aagactctgc ctgctgctga aacactgccg | 480 |
| aagaatgagg ttcttggtgg atatatattt gtttgtaaca atgacacaat gcaggaagac | 540 |
| ctaaagcgcc tgctctttgg ccttcctcct agatacagag attccgtgag gcaataaca | 600 |
| ccagggttgc ccttgttcct atataattac actactcacc agttgcatgg tatctttgag | 660 |
| gcatcgagtt ttggaggttc caacattgat ccaactgcct gggaggataa aaagtgtaaa | 720 |
| ggagagtcaa ggttccctgc tcaggtgagg atccgtgtcc ggaaagtctg taatcctttg | 780 |
| gaggaagatg ctttcagacc agttttacat cattatgatg ccccaagtt ccgtctggag | 840 |
| ctctccattc ctgagacttt ggacttacta gatctctgtg aaaaagccgg tgtgtag | 897 |

<210> SEQ ID NO 10
<211> LENGTH: 489
<212> TYPE: DNA
<213> ORGANISM: Lycopersicon esculentum

<400> SEQUENCE: 10

| | |
|---|---|
| atgtcacacc ccaccgcagc tccgctatca ggaccacgcc tctcacaacc ctcgtcgtcg | 60 |
| gcgatgtctc ccttgtacaa acagaaatct tggtcaccgg acacgtttcg cgacgaggcg | 120 |
| tggcagcggc ggaagggtac ccacggaagc tgcctcaaac ggcggagcaa gagcgttacc | 180 |
| gatgaggact tgatgagat taaggcctgt atcgaattag ggtttggatt tgattcgcca | 240 |
| gaaatggatc agcgattgtc tgatactttt ccggcgtatg acctgttta cgccgtgaat | 300 |
| aaacaataca ccgacactct ttcaaagact tcctctgtat catcggtcat ctccaattgc | 360 |
| gagtcaaccc ttcctcccgt cagtccccac accattgtct ttccaggaga taatccacag | 420 |
| gcagtgaaga caaggttgcg gcaatgggca caggtggttg cgtgtgtggt gcgtcaatct | 480 |
| tcgtattaa | 489 |

<210> SEQ ID NO 11
<211> LENGTH: 489
<212> TYPE: DNA
<213> ORGANISM: Lycopersicon esculentum

<400> SEQUENCE: 11

| | | | | | | |
|---|---|---|---|---|---|---|
| atgtcacacc | ccaccgcagc | tccgctatca | ggaccacgcc | tctcacaacc | ctcgtcgtcg | 60 |
| gcgatgtctc | ccttgtacaa | acagaaatct | tggtcaccgg | acacgtttcg | cgacgaggcg | 120 |
| tggcagcggc | ggaagggtac | ccacggaagc | tgcctcaaac | ggcggagcaa | gagcgttacc | 180 |
| gatgaggact | tgatgagat | taaggcctgt | atcgaattag | ggtttggatt | tgattcgcca | 240 |
| gaaatggatc | agcgattgtc | tgatactttt | ccggcgtatg | acctgtttta | cgccgtgaat | 300 |
| aaacaataca | ccgacactct | ttcaaagact | tcctctgtat | catcggtcat | ctccaattgc | 360 |
| gagtcaaccc | ttcctcccgt | cagtccccac | accattgtct | ttccaggaga | taatccacag | 420 |
| gcagtgaaga | caaggttgcg | gcaatgggca | caggtggttg | cgtgtgtggt | gcgtcaatct | 480 |
| tcgtattaa | | | | | | 489 |

<210> SEQ ID NO 12
<211> LENGTH: 606
<212> TYPE: DNA
<213> ORGANISM: Lycopersicon esculentum

<400> SEQUENCE: 12

| | | | | | | |
|---|---|---|---|---|---|---|
| atgggatact | ggaaagcaaa | ggttcttcca | aagatcaagc | agatctttga | taaaaatgga | 60 |
| cccaagaaaa | ctgctgctgc | tgaggcatgc | aagactttg | atcaagctaa | ggaggaatat | 120 |
| agcaaggagt | ttgaagagaa | gaagactgag | cttcaaccca | agttgttga | aatttatgaa | 180 |
| gctgctgcag | ttgagatcaa | gagcttagtg | aaggaaccaa | agggtgcagg | gctgaagaaa | 240 |
| aactcagatg | gggttcagaa | attccttgat | gaccttgtca | agattgaatt | tccgggatca | 300 |
| aaagctgtta | gcgaagcaag | ttcaaacttt | gggccttcct | atgtatcggg | cccaattatt | 360 |
| tttgtgttcg | aaaaagtttc | cactttcata | gtcacagaag | ataagaagga | agaggaaccc | 420 |
| gcggctgctg | atgacgtgca | tgcaccagcc | gccacgtcaa | ctgaagaggt | ggaggtgaag | 480 |
| gtgaaggaga | aggagaagga | gatagttatt | gagtctggag | aaccaaacaa | ggaagaagca | 540 |
| cctgctactg | ttgttgctga | cgtggcacct | gcaactaagg | tggaagaagc | accaaaggtg | 600 |
| gtttaa | | | | | | 606 |

<210> SEQ ID NO 13
<211> LENGTH: 750
<212> TYPE: DNA
<213> ORGANISM: Lycopersicon esculentum

<400> SEQUENCE: 13

| | | | | | | |
|---|---|---|---|---|---|---|
| atggctggcg | gctagctat | tggaagtttt | agtgattcat | tcagcgttgt | ctctcttaag | 60 |
| tcctatcttg | ccgaattcat | ctccacactc | atctttgtct | tcgccggagt | tggttccgcc | 120 |
| attgcttacg | gcaagttgac | aacaaatgct | gcacttgatc | cggctgggct | tgtagctatt | 180 |
| gcagtttgcc | atggatttgc | tctattcgta | gccgtttcga | tttccgctaa | catctccggt | 240 |
| ggtcatgtta | accctgcggt | cacctgtgga | ttaaccttcg | gcggacatat | tacctttatc | 300 |
| actggctcct | tctacatgct | tgctcaactt | accggcgccg | ctgtagcttg | cttcctcctc | 360 |
| aaattcgtca | ccggaggatg | tgctattcca | acccatggag | tgggagctgg | tgtgagcata | 420 |
| ctagaaggac | tcgtgatgga | aataataatc | acatttggtt | tagtttatac | tgtgttcgca | 480 |

```
accgccgctg acccgaagaa gggttcattg ggcacaattg caccgattgc aattggtctc      540
attgttggag ctaatatttt ggctgccgga ccattctccg gtggatcaat gaacccagct      600
cgttcatttg gacctgcaat ggttagtggt aactttgagg gtttctggat ctactggatt      660
ggtccattag ttggtggtag tttggctggt cttatttaca caaatgtgtt catgacacaa      720
gaacatgctc ctttatccaa tgagttctaa                                       750
```

<210> SEQ ID NO 14
<211> LENGTH: 735
<212> TYPE: DNA
<213> ORGANISM: Lycopersicon esculentum
<400> SEQUENCE: 14

```
atggaggtcg attctagtgg gaatcctaat tggttatttg attatgagtt gatgacggat       60
attacttctg ctgcatctgt taccgtcgct gagtttcagt ctccggctac tattgatttc      120
agctggcctg ctcaaacgat ctatgcttct tctaatctca ttactgaaac agattacaca      180
tttgcggatt cagaagttag caaggaggca agctcacgaa agcggttaaa aagtgaatgt      240
tgcagctctc cgagatctaa ggcatgcaga gagaaattgc ggaggacag actgaatgag       300 aggttcctcg cattgagctc tgtccttgat cctggaaggc accaaaaaac tgagaaagtt      360
gcaattctaa gtgatgctca aaggatgctg attgagctgc gaactgaaac ccagaagctg      420
aaggagtcaa atgaggagct gcaagagaag ataaagaac ttaaggcaga agaatgag         480 ctccgagatg aaaagcaaag gctaaaggaa gaaaaggata atttggagca gcaggttaaa      540
agcttagctt ctaaagcagg atttctctcc catccttctg ccatgggagc tgcatttact      600
gcacaaggac aagttgctgc aggcaacaaa ttgatgcctt tcattggtta tcccagygty      660
gcgatgtggc rattcatgca acctgctgtt gttgacacat ctcaagatca tgtgctccgt      720
cctccagttg cttaa                                                       735
```

<210> SEQ ID NO 15
<211> LENGTH: 645
<212> TYPE: DNA
<213> ORGANISM: Lycopersicon esculentum
<400> SEQUENCE: 15

```
cccttcaaac ctaaaaaaaa gagaaaatca acaaaaaaaa tgggagcttg tgcaacgaag       60
ccaaaggatt tgaaaggaga tgcaccggaa accgcaccgg aaaatgttcc ggcgactgaa      120
atcgccacca aggatgcggc ggaagtagcc gtcgccgcca aggatgtggt ggttgtggcg      180
gaagtagaag tgaaaaagga aattgaggcc gatgctgctg ctgcagatga cgacgatgct      240
gaaaaacgcc gatctctatc taacttgttc aaagagaacg aagaatgtaa ggggtcagag      300
caagtaaacg aggaggcatc caagatcaca ccatcagaag ctaagccaga agaagttgag      360
aaggttgttg atgctcctgt aacttcagag atagaaaaag cactagaagt ggcctcaatt      420
actgctgagg ctcccaaggt ggagccttcc gaggagaaga agatagatga agtgaaatca      480
gaacctaaga ctcctgctga agagaaagta gaggaagcaa accggcagt agagactcct       540 gcagagaaga aaatagaaga ggcaccagtt gctccaactc acgtggagac gaaagccgaa      600
gatgctccaa aggtaactgt agtagaagaa aagaagtcga gctag                      645
```

<210> SEQ ID NO 16
<211> LENGTH: 630
<212> TYPE: DNA
<213> ORGANISM: Lycopersicon esculentum -continued

```
<400> SEQUENCE: 16
cccttcaaac ctaaaaaaaa gagaaaatca acaaaaaaaa tgggagcttg tgcaacgaag      60
ccaaaggatt tgaaaggaga tgcaccggaa accgcaccgg aaaatgttcc ggcgactgaa     120
atcgccacca aggatgcggc ggaagtagcc gtcgccgcca aggatgtggt ggttgtggcg     180
gaagtagaag tgaaaaagga aattgaggcc gatgctgctg ctgcagatga cgacgatgct     240
gaaaaacgcc gatctctatc taacttgttc aaagagaacg aagaatgtaa ggggtcagag     300
caagtaaacg aggaggcatc caagatcaca ccatcagaag ctaagccaga agaagttgag     360
aaggttgttg atgctcctgt aacttcagag atagaaaaag cactagaagt ggcctcaatt     420
actgctgagg ctcccaaggt ggagccttcc gaggagaaga agatagatga agtgaaatca     480
gaacctaaga ctcctgctga agaaaagta gaggaagcaa aaccggcagt agagactcct      540
gcagagaaga aaatagaaga ggcaccagtt gctccaactc acgtggagac gaaagccgaa     600
gattgcatgg tgaaaaacgc gtggaaatga                                      630

<210> SEQ ID NO 17
<211> LENGTH: 216
<212> TYPE: DNA
<213> ORGANISM: Lycopersicon esculentum

<400> SEQUENCE: 17
atggagataa catgtgcact tgtctgtgag atcttactag caatcttgct tcctcctctt      60 ggtgttttgcc ttcgcaatgg ttgctgcact gtggagttct tgatttgctt ggtattgacc    120
atattgggct atgttcctgg aattatctat gctctctatg caatcctctt tgttgaacgt    180
gaaccaagaa gggattatta tgacactctt gcttga                              216

<210> SEQ ID NO 18
<211> LENGTH: 216
<212> TYPE: DNA
<213> ORGANISM: Lycopersicon esculentum

<400> SEQUENCE: 18
atggactcaa gatgtgcaat tctgtgtgaa gttttactag caatcttgct tcctcctctt      60 ggtgttttgcc ttcgcaatgg ttgctgcact gtggagttct tgatttgctt ggtattgacc   120
atattgggct atgttcctgg aattatctat gctctttatg caatcctctg tattcaaagt    180
gaaccacact accatcatta ccattctctt gcttga                              216

<210> SEQ ID NO 19
<211> LENGTH: 877
<212> TYPE: DNA
<213> ORGANISM: Cauliflower mosaic virus

<400> SEQUENCE: 19
aagcttgcat gcctgcaggt ccccagatta gccttttcaa tttcagaaag aatgctaacc      60
cacagatggt tagagaggct tacgcagcag gtctcatcaa gacgatctac ccgagcaata    120
atctccagga aatcaaatac cttcccaaga aggttaaaga tgcagtcaaa agattcagga    180
ctaactgcat caagaacaca gagaaagata tatttctcaa gatcagaagt actattccag    240
tatggacgat tcaaggcttg cttcacaaac caaggcaagt aatagagatt ggagtctcta    300
aaaaggtagt tcccactgaa tcaaaggcca tggagtcaaa gattcaaata gaggacctaa    360
cagaactcgc cgtaaagact ggcgaacagt tcatacagag tctcttacga ctcaatgaca    420
agaagaaaat cttcgtcaac atggtggagc acgacacact tgtctactcc aaaaatatca    480
```

| | |
|---|---|
| aagatacagt ctcagaagac caaagggcaa ttgagacttt tcaacaaagg gtaatatccg | 540 |
| gaaacctcct cggattccat tgcccagcta tctgtcactt tattgtgaag atagtggaaa | 600 |
| aggaaggtgg ctcctacaaa tgccatcatt gcgataaagg aaaggccatc gttgaagatg | 660 |
| cctctgccga cagtggtccc aaagatggac ccccacccac gaggagcatc gtggaaaaag | 720 |
| aagacgttcc aaccacgtct tcaaagcaag tggattgatg tgatatctcc actgacgtaa | 780 |
| gggatgacgc acaatcccac tatccttcgc aagacccttc ctctatataa ggaagttcat | 840 |
| ttcatttgga gagaacacgg gggactctag aggatcc | 877 |

<210> SEQ ID NO 20
<211> LENGTH: 2322
<212> TYPE: DNA
<213> ORGANISM: Arabidopsis thaliana

<400> SEQUENCE: 20

| | |
|---|---|
| aagctttaag ctccaagccc acatctatgc acttcaacat atctttttct agatgagttg | 60 |
| gtaaaagtag aaaaagatat gatgatttta aatttgtttc tatttatatg tgttcatcga | 120 |
| aacttcattt tttttagttt taatagagag tttatatgac ttttaaaaat tgatttaaaa | 180 |
| ctgtgtcaaa aattaaaagg acaataaaaa atttgcatac aaccgaaaat acttatattt | 240 |
| agacaagaaa aataatact tgtgatgctg attttatttt attatatatc atgaatcatg | 300 |
| atcatccaat tttccggata agccaaagtc aaaatgatgg gttccccta atcttttatg | 360 |
| ctgagaaata gatgtatatt cttagatagt aatataaaat tggggttaaag aatgatgatt | 420 |
| cgattatagc ctcaactaga agatacgtgt agtgcaggtg tgtagttaac tggtggtagt | 480 |
| ggcagacaac cagattagga gttaaataaa gcctttagat ttgagagatt gaaatattcg | 540 |
| attggaaacct ttctagattt ttacagccat ctaaaattag atgcagatca cctactacca | 600 |
| ttcaaaatg aacaaaataa tttcatttac attttcctag cataagatat aataataaaa | 660 |
| tagtgctcat tttaattact ttttctaaat attttcgtta ttttaaattt tgcttgtcta | 720 |
| tactctacag ctcatttaat aacggaaaca aaaataattg cagggatacg gatgggtagc | 780 |
| tttcaaaact tacatcatct tctgtttctt gagatcaact attttggag ctttgtctca | 840 |
| atcgtaccaa aggataatgg tcctacctcc ttttgcattc ttaactttat cttctctact | 900 |
| tatttctttt ttgggatttt tggggtatt atttttatctt ttgtagatat acacattgat | 960 |
| ttactacaaa cgtatactac tatccatctt caactcttcg gaatatgatt tcgaaaaaac | 1020 |
| tatgaagatt aacgggtatc ttaaacatgt taagatacac cggacaattt tcatttagaa | 1080 |
| gaattgatat gcaattaaca ataaatagtt gatgatcttt tagttttgaa gatgtgcgtt | 1140 |
| aagacttaag cgtgtggtaa caaggtggga ctcgggcaac gcaaagcctt gtagagtcca | 1200 |
| cttgctcaac ttgtctttct tttatctctt ttccaagtct caagattcaa tgaactccgt | 1260 |
| gtaacacaaa cacgcccata gatgagctca ttttggtat ttccaatatt gccactccat | 1320 |
| gataatatca tctagggatg gggttcattt attttgaaat ctcaacaaat ctcgtcgatt | 1380 |
| ctaacacaca tgattgattt gtttacttac ttgaaagttg caactatct gggattaaaa | 1440 |
| tttatctttt tctactgcta gctagaagca tctatatatg ttagcctaat acgtggaaga | 1500 |
| tgtcattgct aataatggct aaagatgtgt attaattttt cttctttttt ccttgaattt | 1560 |
| ttgttctttg acataaacta tgctgtcaaa atgtgtagaa tcttttaca taaatcattc | 1620 |
| cctgttacac actaaaaggt tcacaacgga cgattgtatt ggacttccag atcataaacc | 1680 |
| atgcaaaact gaaaaccaca agaataatta gttctaactt tagaacgttc gtacgtgttt | 1740 |

-continued

```
catgttcaaa aagcgtcaat tataaaagtt gggaaattac ttttgagttt tgacatttct   1800
aaggacagtc aaatatgaca acattgggat gcaacttacc ttgtattaac ttattttgtt   1860
ataaaaccat atattacata ttttaaaggg ttgataaata atcaaatata ccaaaacata   1920
gcttttcaat atatttgtaa aacacgtttg gtctactagc taattatgag aacatttgtt   1980
caatgcatga ttatctagta tctactagtg gattatgaaa attagatatt ttcattgcat   2040
gattatcttc catatatagt gataacatca aaagaatcta caccaattat tgcattttt    2100 cattatataa taagcactaa actgtaaaat tatattcagc cacccaaacc atgacaaatc   2160
accttaaagg cttaaacaca taacagccat tacgagtcac aggtaagggt ataatagtaa   2220
agaatcaatc tatataatat acgacccacc ctttctcatt ctttctggag agtaacatcg   2280
agacaaagaa gaaaaactaa aaaagagaac cccaaaggat cc                      2322
```

<210> SEQ ID NO 21
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 21
gggaaggatc catgggtcgt atgcacagtc g                              31

<210> SEQ ID NO 22
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 22
cgacggagct cctatgccac aagtgtgcta gc                             32

<210> SEQ ID NO 23
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 23
gggaaggatc cggtggtatt gaagttatgg aagac                          35

<210> SEQ ID NO 24
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 24
gctgcgagct cctaatgctt ccgtccactc                                30

<210> SEQ ID NO 25
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 25
gggaaggatc catgaattct cagatttgca gatc                           34

```
<210> SEQ ID NO 26
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 26
gaggagagct cttagttatc accatatagc cacttc                          36

<210> SEQ ID NO 27
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 27
gggaatctag acaacatgga gaatatgcag agc                             33

<210> SEQ ID NO 28
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 28
agaagcccgg gcacatagca cctacacacc g                               31

<210> SEQ ID NO 29
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 29
gggaaggatc cgatgggata ctggaaagca aag                             33

<210> SEQ ID NO 30
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 30
agccggagct cttaaaccac ctttggtgct tc                              32

<210> SEQ ID NO 31
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 31
gggaaggatc caaatggctg gcggcgtag                                  29

<210> SEQ ID NO 32
<211> LENGTH: 34
<212> TYPE: DNA
<213> ORGANISM: Artificial sequence
<220> FEATURE:
<223> OTHER INFORMATION: Single strand DNA oligonucleotide
```

-continued

```
<400> SEQUENCE: 32
agaaggagct ctagaactca ttggataaag gagc                                34

<210> SEQ ID NO 33
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 33
gggaaggatc catggaggtc gattctagtg gg                                  32

<210> SEQ ID NO 34
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 34
agaagcccgg gttaagcaac tggaggacgg ag                                  32

<210> SEQ ID NO 35
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 35
ggtggctcct acaaatgcca tc                                             22

<210> SEQ ID NO 36
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 36
aagttgggta acgccagggt                                                20

<210> SEQ ID NO 37
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 37
tagtttggtc agatgggaaa cg                                             22

<210> SEQ ID NO 38
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 38
aaatattgga tcctttgggg ttctc                                          25

<210> SEQ ID NO 39
<211> LENGTH: 151
<212> TYPE: PRT
```

-continued

<213> ORGANISM: Panax ginseng

<400> SEQUENCE: 39

Met Gly Arg Met His Ser Arg Gly Lys Gly Ile Ser Ser Ala Leu
1               5                   10                  15

Pro Tyr Lys Arg Thr Pro Pro Ser Trp Leu Lys Ile Thr Pro Gln Asp
            20                  25                  30

Val Asp Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 40
<211> LENGTH: 151
<212> TYPE: PRT
<213> ORGANISM: Glycine max

<400> SEQUENCE: 40

Met Gly Arg Met His Ser Arg Gly Lys Gly Ile Ser Ser Ser Ala Leu
1               5                   10                  15

Pro Tyr Lys Arg Thr Pro Pro Ser Trp Leu Lys Ile Ser Ser Gln Asp
            20                  25                  30

Val Glu Glu Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Asn
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ser Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 41
<211> LENGTH: 151
<212> TYPE: PRT
<213> ORGANISM: Arabidopsis thaliana

<400> SEQUENCE: 41

```
Met Gly Arg Met His Ser Arg Gly Lys Gly Ile Ser Ala Ser Ala Leu
1               5                   10                  15

Pro Tyr Lys Arg Ser Ser Pro Ser Trp Leu Lys Thr Thr Ser Gln Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
        130                 135                 140

Thr Ala Ser Thr Leu Val Ala
145                 150
```

<210> SEQ ID NO 42
<211> LENGTH: 151
<212> TYPE: PRT
<213> ORGANISM: Arabidopsis thaliana

<400> SEQUENCE: 42

```
Met Gly Arg Met His Ser Arg Gly Lys Gly Ile Ser Ala Ser Ala Leu
1               5                   10                  15

Pro Tyr Lys Arg Ser Ser Pro Ser Trp Leu Lys Thr Thr Pro Gln Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
        130                 135                 140

Thr Ala Ser Thr Leu Val Ala
145                 150
```

<210> SEQ ID NO 43
<211> LENGTH: 151
<212> TYPE: PRT
<213> ORGANISM: Arabidopsis thaliana

<400> SEQUENCE: 43

```
Met Gly Arg Met His Ser Arg Gly Lys Gly Ile Ser Ala Ser Ala Leu
1               5                   10                  15

Pro His Lys Arg Ser Ser Pro Ser Trp Leu Lys Thr Thr Pro Gln Asp
```

```
                20                  25                  30
Val Asp Glu Ser Ile Cys Lys Phe Ala Lys Lys Gly Leu Thr Pro Ser
         35                  40                  45

Gln Ile Gly Val Ile Leu Arg Asp Ser His Gly Ile Pro Gln Val Lys
     50                  55                  60

Ser Val Thr Gly Ser Lys Ile Leu Arg Ile Leu Lys Ala His Gly Leu
 65                  70                  75                  80

Ala Pro Glu Ile Pro Glu Asp Leu Tyr His Leu Ile Lys Lys Ala Val
                 85                  90                  95

Ala Ile Arg Lys His Leu Glu Arg Asn Arg Lys Asp Lys Asp Ser Lys
             100                 105                 110

Phe Arg Leu Ile Leu Val Glu Ser Arg Ile His Arg Leu Ala Arg Tyr
         115                 120                 125

Tyr Lys Lys Thr Lys Lys Leu Pro Pro Val Trp Lys Tyr Glu Ser Thr
     130                 135                 140

Thr Ala Ser Thr Leu Val Ala
 145                 150

<210> SEQ ID NO 44
<211> LENGTH: 151
<212> TYPE: PRT
<213> ORGANISM: Pisum sativum

<400> SEQUENCE: 44

Met Gly Arg Leu His Ser Lys Gly Lys Gly Ile Ser Ser Ser Ala Leu
 1                5                  10                  15

Pro Tyr Arg Arg Thr Ala Pro Ser Trp Leu Lys Ile Ser Ser Gln Asp
             20                  25                  30

Val Asp Glu Thr Ile Cys Lys Phe Ala Lys Lys Gly Leu Thr Pro Ser
         35                  40                  45

Gln Ile Gly Val Ile Leu Arg Asp Ser His Gly Ile Ala Gln Val Lys
     50                  55                  60

Ser Val Thr Gly Ser Lys Ile Leu Arg Ile Leu Lys Ala His Gly Leu
 65                  70                  75                  80

Ala Pro Glu Ile Pro Glu Asp Leu Tyr His Leu Ile Lys Lys Ala Val
                 85                  90                  95

Ser Ile Arg Lys His Leu Glu Arg Phe Arg Lys Asp Lys Asp Ser Lys
             100                 105                 110

Phe Arg Leu Ile Leu Val Glu Ser Arg Ile His Arg Leu Ala Arg Tyr
         115                 120                 125

Tyr Lys Lys Thr Lys Lys Leu Pro Pro Val Trp Lys Tyr Glu Ser Thr
     130                 135                 140

Thr Ala Ser Thr Leu Val Ala
 145                 150

<210> SEQ ID NO 45
<211> LENGTH: 150
<212> TYPE: PRT
<213> ORGANISM: Arabidopsis thaliana

<400> SEQUENCE: 45

Met Gly Arg Met His Ser Arg Gly Lys Gly Ile Ser Ala Ser Ala Leu
 1                5                  10                  15

Pro Tyr Lys Arg Ser Ser Pro Ser Trp Leu Lys Thr Thr Ser Gln Asp
             20                  25                  30

Val Asp Glu Ser Ile Cys Lys Phe Ala Lys Lys Gly Leu Thr Pro Ser
         35                  40                  45
```

```
Gln Ile Gly Val Ile Leu Arg Asp Ser His Gly Ile Pro Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
                115                 120                 125

Tyr Lys Lys Thr Lys Lys Leu Pro Pro Val Trp Asn Glu Ser Thr Thr
                130                 135                 140

Ala Ser Thr Leu Val Ala
145                 150

<210> SEQ ID NO 46
<211> LENGTH: 150
<212> TYPE: PRT
<213> ORGANISM: Arabidopsis thaliana

<400> SEQUENCE: 46

Met Gly Arg Met His Ser Arg Gly Lys Gly Ile Ser Ala Ser Ala Leu
1               5                   10                  15

Pro Tyr Lys Arg Ser Ser Pro Ser Trp Leu Lys Thr Thr Pro Gln Asp
                20                  25                  30

Val Asp Glu Ser Ile Cys Lys Phe Ala Lys Lys Gly Leu Thr Pro Ser
                35                  40                  45

Gln Ile Gly Val Ile Leu Arg Asp Ser His Gly Ile Pro Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
                115                 120                 125

Tyr Lys Lys Thr Lys Lys Leu Pro Pro Val Trp Asn Glu Ser Thr Thr
                130                 135                 140

Ala Ser Thr Leu Val Ala
145                 150

<210> SEQ ID NO 47
<211> LENGTH: 151
<212> TYPE: PRT
<213> ORGANISM: Oryza sativa

<400> SEQUENCE: 47

Met Gly Arg Met His Ser Arg Gly Lys Gly Ile Ser Ser Ser Ala Leu
1               5                   10                  15

Pro Tyr Lys Arg Thr Pro Pro Ser Trp Leu Lys Thr Ala Ala Ser Asp
                20                  25                  30

Val Glu Glu Met Ile Met Lys Ala Ala Lys Lys Gly Gln Met Pro Ser
                35                  40                  45

Gln Ile Gly Val Val Leu Arg Asp Gln His Gly Ile Pro Leu Val Lys
    50                  55                  60
```

-continued

Ser Val Thr Gly Ser Lys Ile Leu Arg Ile Leu Lys Ala His Gly Leu
 65                  70                  75                  80

Ala Pro Glu Ile Pro Glu Asp Leu Tyr Phe Leu Ile Lys Lys Ala Val
                 85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
            115                 120                 125

Tyr Lys Arg Thr Lys Lys Leu Pro Pro Thr Trp Lys Tyr Glu Ser Thr
        130                 135                 140

Thr Ala Ser Thr Leu Val Ala
145                 150

<210> SEQ ID NO 48
<211> LENGTH: 151
<212> TYPE: PRT
<213> ORGANISM: Zea mays

<400> SEQUENCE: 48

Met Gly Ala Met His Ser Arg Gly Lys Gly Ile Ser Ser Ala Leu
 1               5                  10                  15

Pro Tyr Lys Arg Thr Pro Thr Trp Leu Lys Thr Ala Ala Ser Asp
                 20                  25                  30

Val Glu Glu Met Ile Thr Lys Ala Ala Lys Lys Gly Gln Met Pro Ser
             35                  40                  45

Gln Ile Gly Val Leu Leu Arg Asp Gln His Gly Ile Pro Leu Val Lys
         50                  55                  60

Ser Val Thr Gly Ser Lys Ile Leu Arg Ile Leu Lys Ala His Gly Leu
 65                  70                  75                  80

Ala Pro Glu Ile Pro Glu Asp Leu Tyr Phe Leu Ile Lys Lys Ala Val
                 85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
            115                 120                 125

Tyr Lys Arg Thr Lys Lys Leu Pro Pro Thr Trp Lys Tyr Glu Ser Thr
        130                 135                 140

Thr Ala Ser Thr Leu Val Ala
145                 150

<210> SEQ ID NO 49
<211> LENGTH: 156
<212> TYPE: PRT
<213> ORGANISM: Oryza sativa

<400> SEQUENCE: 49

Met Gly Arg Met His Ser Arg Gly Lys Gly Ile Ser Ser Ala Ile
 1               5                  10                  15

Pro Tyr Lys Arg Thr Pro Ser Trp Val Lys Thr Ala Ala Ala Asp
                 20                  25                  30

Val Glu Glu Met Ile Met Lys Ala Ala Lys Lys Gly Gln Met Pro Ser
             35                  40                  45

Gln Ile Gly Val Val Leu Arg Asp Gln His Gly Ile Pro Leu Val Lys
         50                  55                  60

Ser Val Thr Gly Ser Lys Ile Leu Arg Ile Leu Lys Ala His Gly Leu
 65                  70                  75                  80

Ala Pro Glu Ile Pro Glu Asp Leu Tyr Phe Leu Ile Lys Lys Ala Val

```
                85                  90                  95
Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Arg Thr Lys Lys Leu Pro Pro Thr Trp Lys Thr Thr Tyr Gln
        130                 135                 140

Leu Ser Ala Val Cys Leu Asn Tyr Phe Gln Ala Pro
145                 150                 155

<210> SEQ ID NO 50
<211> LENGTH: 151
<212> TYPE: PRT
<213> ORGANISM: Drosophila melanogaster

<400> SEQUENCE: 50

Met Gly Arg Met His Ala Pro Gly Lys Gly Ile Ser Gln Ser Ala Leu
1               5                   10                  15

Pro Tyr Arg Arg Thr Val Pro Ser Trp Leu Lys Leu Asn Ala Asp Asp
            20                  25                  30

Val Lys Glu Gln Ile Lys Lys Ala Gly Gln Gly Ser Asp Ser Leu
        35                  40                  45

Gln Ile Gly Ile Ile Leu Arg Asp Ser His Gly Val Ala Gln Val Arg
    50                  55                  60

Phe Val Asn Gly Asn Lys Ile Leu Arg Ile Met Lys Ser Val Gly Leu
65                  70                  75                  80

Lys Pro Asp Ile Pro Glu Asp Leu Tyr His Met Ile Lys Lys Ala Val
                85                  90                  95

Ala Ile Arg Lys His Leu Glu Arg Asn Arg Lys Asp Lys Asp Gly Lys
            100                 105                 110

Phe Arg Leu Ile Leu Val Glu Ser Arg Ile His Arg Leu Ala Arg Tyr
            115                 120                 125

Tyr Lys Thr Lys Ser Val Leu Pro Pro Asn Trp Lys Tyr Glu Ser Ser
        130                 135                 140

Thr Ala Ser Ala Leu Val Ala
145                 150

<210> SEQ ID NO 51
<211> LENGTH: 155
<212> TYPE: PRT
<213> ORGANISM: Unknown
<220> FEATURE:
<223> OTHER INFORMATION: environmental sequence

<400> SEQUENCE: 51

Met Gly Arg Met His Thr Pro Gly Lys Gly Met Ser Gly Ser Ala Leu
1               5                   10                  15

Pro Tyr Lys Arg Ser Ala Pro Ser Trp Leu Lys Ile Thr Pro Thr Glu
            20                  25                  30

Val Thr Glu Met Ile Val Lys Met Ala Lys Lys Gly Met Thr Pro Ser
        35                  40                  45

Gln Ile Gly Val Met Leu Arg Asp Asn Gln Gly Ile Ala Gln Val Ser
    50                  55                  60

Thr Val Thr Asn Ser Lys Ile Leu Arg Ile Leu Arg Gly Gln Gly Leu
65                  70                  75                  80

Ala Pro Ser Leu Pro Glu Asp Leu Tyr Cys Leu Ile Lys Lys Ala Val
                85                  90                  95
```

```
Ser Val Arg Lys His Leu Glu Arg Asn Arg Lys Asp Met Asp Ser Lys
                100                 105                 110

Phe Arg Leu Ile Leu Ile Glu Ser Arg Ile His Arg Leu Ala Arg Tyr
            115                 120                 125

Tyr Lys Leu Ala Lys Lys Leu Glu Pro Thr Phe Lys Tyr Asp Ser Ala
        130                 135                 140

Thr Ala Ser Thr Leu Leu Thr Ala Ala Gly Lys
145                 150                 155

<210> SEQ ID NO 52
<211> LENGTH: 230
<212> TYPE: PRT
<213> ORGANISM: Arabidopsis thaliana

<400> SEQUENCE: 52

Met Ala Ser Ser Asn Ser Glu Lys Ile Asn Glu Asn Leu Tyr Ala Val
1               5                   10                  15

Leu Gly Leu Lys Lys Glu Cys Ser Lys Thr Glu Leu Arg Ser Ala Tyr
            20                  25                  30

Lys Lys Leu Ala Leu Arg Trp His Pro Asp Arg Cys Ser Ser Met Glu
        35                  40                  45

Phe Val Glu Glu Ala Lys Lys Lys Phe Gln Ala Ile Gln Glu Ala Tyr
    50                  55                  60

Ser Val Leu Ser Asp Ser Asn Lys Arg Phe Leu Tyr Asp Val Gly Ala
65                  70                  75                  80

Tyr Asn Thr Asp Asp Asp Asp Asp Gln Asn Gly Met Gly Asp Phe Leu
                85                  90                  95

Asn Glu Met Ala Thr Met Met Asn Gln Ser Lys Pro Ser Asp Asn Asn
            100                 105                 110

Thr Gly Asp Ser Phe Glu Gln Leu Gln Asp Leu Phe Asn Glu Met Phe
        115                 120                 125

Gln Gly Asp Ala Ala Ala Phe Pro Ser Ser Ser Cys Ser Thr Ser
    130                 135                 140

Asn Phe Thr Ser Ser Arg Ser Phe Val Phe Asp Thr Asn Ser Gln Arg
145                 150                 155                 160

Ser Ser Ser Phe Ala Thr Ser Ser Met Gly Met Asn Asn Asp Pro Phe
                165                 170                 175

Gly Tyr Asp Pro Arg Ala His Ser Phe Ser Leu Gly Val Asp His Gln
            180                 185                 190

Gln Glu Phe Lys Lys Gly Lys Asn Asn Gly Gly Arg Arg Asn Arg Arg
        195                 200                 205

Lys Asn Asn Val Pro Ser Ala Gly His Glu Thr Ser Ser Ser Asn Asn
    210                 215                 220

Tyr Gly Val Pro Thr Ser
225                 230

<210> SEQ ID NO 53
<211> LENGTH: 242
<212> TYPE: PRT
<213> ORGANISM: Mus musculus

<400> SEQUENCE: 53

Met Val Asp Tyr Tyr Glu Val Leu Gly Val Gln Arg His Ala Ser Pro
1               5                   10                  15

Glu Asp Ile Lys Lys Ala Tyr Arg Lys Gln Ala Leu Lys Trp His Pro
            20                  25                  30

Asp Lys Asn Pro Glu Asn Lys Glu Glu Ala Glu Arg Lys Phe Lys Gln
```

```
                    35                  40                  45
Val Ala Glu Ala Tyr Glu Val Leu Ser Asp Ala Lys Lys Arg Asp Ile
 50                  55                  60

Tyr Asp Lys Tyr Gly Lys Glu Gly Leu Asn Gly Gly Gly Gly Gly Gly
 65                  70                  75                  80

Gly Ile His Phe Asp Ser Pro Phe Glu Phe Gly Thr Phe Arg Asn
                     85                  90                  95

Pro Asp Asp Val Phe Arg Glu Phe Phe Gly Gly Arg Asp Pro Phe Ser
                100                 105                 110

Phe Asp Phe Phe Glu Asp Pro Phe Asp Asp Phe Phe Gly Asn Arg Arg
                115                 120                 125

Gly Pro Arg Gly Asn Arg Ser Arg Gly Ala Ala Pro Phe Phe Ser Thr
                130                 135                 140

Phe Ser Gly Phe Pro Ser Phe Gly Ser Gly Phe Pro Ala Phe Asp Thr
145                 150                 155                 160

Gly Phe Thr Pro Phe Gly Ser Leu Gly His Gly Gly Leu Thr Ser Phe
                165                 170                 175

Ser Ser Thr Ser Phe Gly Gly Ser Gly Met Gly Asn Phe Lys Ser Ile
                180                 185                 190

Ser Thr Ser Thr Lys Ile Val Asn Gly Lys Lys Ile Thr Thr Lys Arg
                195                 200                 205

Ile Val Glu Asn Gly Gln Glu Arg Val Glu Val Glu Glu Asp Gly Gln
                210                 215                 220

Leu Lys Pro Leu Thr Ile Asn Gly Lys Glu His Leu Leu Arg Leu Asp
225                 230                 235                 240

Asn Lys

<210> SEQ ID NO 54
<211> LENGTH: 242
<212> TYPE: PRT
<213> ORGANISM: Rattus norvegicus

<400> SEQUENCE: 54

Met Val Asp Tyr Tyr Glu Val Leu Gly Val Gln Arg His Ala Ser Pro
  1               5                  10                  15

Glu Asp Ile Lys Lys Ala Tyr Arg Lys Gln Ala Leu Lys Trp His Pro
                 20                  25                  30

Asp Lys Asn Pro Glu Asn Lys Glu Glu Ala Glu Arg Lys Phe Lys Gln
                 35                  40                  45

Val Ala Glu Ala Tyr Glu Val Leu Ser Asp Ala Lys Lys Arg Asp Ile
 50                  55                  60

Tyr Asp Lys Tyr Gly Lys Glu Gly Leu Asn Gly Gly Gly Gly Gly Gly
 65                  70                  75                  80

Gly Ser His Phe Asp Ser Pro Phe Glu Phe Gly Phe Thr Phe Arg Asn
                     85                  90                  95

Pro Asp Asp Val Phe Arg Glu Phe Phe Gly Gly Arg Asp Pro Phe Ser
                100                 105                 110

Phe Asp Phe Phe Glu Asp Pro Phe Asp Asp Phe Phe Gly Asn Arg Arg
                115                 120                 125

Gly Pro Arg Gly Ser Arg Ser Arg Gly Ala Ser Phe Phe Ser Ala
                130                 135                 140

Phe Ser Gly Phe Pro Ser Phe Gly Ser Gly Phe Pro Ala Phe Asp Thr
145                 150                 155                 160

Gly Phe Thr Pro Phe Gly Ser Leu Gly His Gly Gly Leu Thr Ser Phe
                165                 170                 175
```

Ser Ser Ala Ser Phe Gly Gly Ser Gly Met Gly Asn Phe Lys Ser Ile
        180                 185                 190

Ser Thr Ser Thr Lys Ile Val Asn Gly Lys Lys Ile Thr Thr Lys Arg
        195                 200                 205

Ile Val Glu Asn Gly Gln Glu Arg Val Glu Val Glu Glu Asp Gly Gln
210                 215                 220

Leu Lys Ser Leu Thr Ile Asn Gly Lys Glu His Leu Leu Arg Leu Asp
225                 230                 235                 240

Asn Lys

<210> SEQ ID NO 55
<211> LENGTH: 158
<212> TYPE: PRT
<213> ORGANISM: Picea glauca

<400> SEQUENCE: 55

Met Glu Thr Thr Phe Tyr Ser Ile Leu Gly Val Asn Lys Asp Ser Ser
1               5                   10                  15

Ser Ala Glu Ile Arg Ser Ala Tyr Arg Lys Leu Ala Met Lys Trp His
        20                  25                  30

Pro Asp Lys Trp Ser Thr Asp Pro Ser Ser Glu Thr Ala Lys Leu
        35                  40                  45

Arg Phe Gln Gln Ile Gln Glu Ala Tyr Ser Val Leu Ser Asp Asp Thr
    50                  55                  60

Lys Arg Ala Leu Tyr Asp Ala Gly Met Tyr Glu Pro Ser Glu Asp Met
65                  70                  75                  80

Asp Ala Phe Cys Asp Phe Leu Asp Glu Leu Ser Ser Leu Ile Ala Thr
                85                  90                  95

Val Lys Val Gln Ser Asn Lys Asp Asp Glu Leu Leu Gln Leu Gln Glu
            100                 105                 110

Met Phe Thr Lys Met Leu Glu Gly Asp Trp Phe Ser Thr Asp Asn Phe
        115                 120                 125

Glu Ala Phe Lys Glu Ile Ser Ser Gln His Ser Asp Asp Lys Pro Glu
    130                 135                 140

Asn Gly Gln Asp His Glu Pro Tyr Gly Ser Val Asp Asp Leu
145                 150                 155

<210> SEQ ID NO 56
<211> LENGTH: 156
<212> TYPE: PRT
<213> ORGANISM: Arabidopsis thaliana

<400> SEQUENCE: 56

Met Ala Cys Glu Gly Gly Gly Ser Asn Val Arg Ser Ser Tyr Tyr Thr
1               5                   10                  15

Ile Leu Gly Ile Arg Lys Asp Ala Ser Val Ser Asp Ile Arg Thr Ala
        20                  25                  30

Tyr Arg Lys Leu Ala Met Lys Trp His Pro Asp Arg Tyr Ala Arg Asn
        35                  40                  45

Pro Gly Val Ala Gly Glu Ala Lys Arg Arg Phe Gln Gln Ile Gln Glu
    50                  55                  60

Ala Tyr Ser Val Leu Asn Asp Glu Asn Lys Arg Ser Tyr Asp Val
65                  70                  75                  80

Gly Leu Tyr Asp Pro His Glu Asp Asp Asp Phe Cys Asp Phe
                85                  90                  95

Met Gln Glu Met Ile Ser Met Met Asn Asn Val Lys Asp Ala Gly Glu

```
                    100                 105                 110
Ser Leu Glu Asp Leu Gln Arg Met Phe Thr Asp Met Val Gly Gly Asp
            115                 120                 125

Gly Val Ser Tyr Asp Cys Asn Asn Pro Lys Gly Asn Lys Arg Pro
        130                 135                 140

Arg Val Asn Ile Ser Arg Ser Ser Ala Ala Met Arg
145                 150                 155

<210> SEQ ID NO 57
<211> LENGTH: 156
<212> TYPE: PRT
<213> ORGANISM: Arabidopsis thaliana

<400> SEQUENCE: 57

Met Ala Cys Glu Gly Gly Gly Ser Asn Val Arg Ser Tyr Tyr Thr
1               5                   10                  15

Val Leu Gly Ile Arg Lys Asp Ala Ser Val Ser Asp Ile Arg Thr Ala
            20                  25                  30

Tyr Arg Lys Leu Ala Met Lys Trp His Pro Asp Arg Tyr Ala Arg Asn
        35                  40                  45

Pro Gly Val Ala Gly Glu Ala Lys Arg Arg Phe Gln Gln Ile Gln Glu
    50                  55                  60

Ala Tyr Ser Val Leu Asn Asp Glu Asn Lys Arg Ser Met Tyr Asp Val
65                  70                  75                  80

Gly Leu Tyr Asp Pro His Glu Asp Asp Asp Asp Phe Cys Asp Phe
                85                  90                  95

Met Gln Glu Met Ile Ser Met Met Asn Asn Val Lys Asp Glu Gly Glu
            100                 105                 110

Ser Leu Glu Asp Leu Gln Arg Met Phe Thr Asp Met Val Gly Gly Asp
        115                 120                 125

Gly Val Ser Tyr Asp Cys Asn Asn Pro Lys Gly Ser Lys Arg Pro
    130                 135                 140

Arg Val Asn Val Ser Arg Ser Ser Ala Ala Met Arg
145                 150                 155

<210> SEQ ID NO 58
<211> LENGTH: 207
<212> TYPE: PRT
<213> ORGANISM: Daucus carota

<400> SEQUENCE: 58

Met Ile Asp Gln Glu Glu Ser Asn Phe Asn Phe Asn Phe Asn Gln Pro
1               5                   10                  15

Gln Gln Pro Gln Gln Gln Gln Phe His Gly Lys Ser Val Lys Lys Asn
            20                  25                  30

Lys Asn Lys Asn Asn Asn Asn Ser Glu Ser Gly Asn Lys Asn Gly
        35                  40                  45

Gly Glu Asn Lys Asn Gly Val Glu Lys Arg Phe Lys Thr Leu Pro Pro
    50                  55                  60

Ala Glu Ser Leu Pro Arg Asn Glu Thr Val Gly Gly Tyr Ile Phe Val
65                  70                  75                  80

Cys Asn Asn Asp Thr Met Gln Glu Asn Leu Lys Arg Gln Leu Phe Gly
                85                  90                  95

Leu Pro Pro Arg Tyr Arg Asp Ser Val Arg Ala Ile Thr Pro Gly Leu
            100                 105                 110

Pro Leu Phe Leu Tyr Asn Tyr Ser Thr His Gln Leu His Gly Val Phe
        115                 120                 125
```

```
Glu Ala Ala Ser Phe Gly Gly Thr Asn Ile Asp Pro Thr Ala Trp Glu
    130                 135                 140

Asp Lys Lys Asn Gln Gly Glu Ser Arg Phe Pro Ala Gln Val Arg Val
145                 150                 155                 160

Met Thr Arg Lys Ile Cys Glu Pro Leu Glu Glu Asp Ser Phe Arg Pro
                165                 170                 175

Ile Leu His His Tyr Asp Gly Pro Lys Phe Arg Leu Glu Leu Asn Ile
            180                 185                 190

Pro Glu Ala Ile Ser Leu Leu Asp Ile Phe Glu Glu Thr Lys Ala
        195                 200                 205
```

<210> SEQ ID NO 59
<211> LENGTH: 213
<212> TYPE: PRT
<213> ORGANISM: Pisum sativum

<400> SEQUENCE: 59

```
Met Asn Lys Asn Ser Leu Arg Asn Gly Val Tyr Asn Met Asn Ala Val
1               5                   10                  15

Tyr Gln Lys Ser Asn Ala Asn Phe Val Gly Asn Met Asn Ser Asn Lys
            20                  25                  30

Tyr Ser Gly Asn Val Gln Leu Asn Lys Asp Pro His Ser Asn Asn Asn
        35                  40                  45

Asn Asn Asn Glu Asn Asn Thr Asn Ala Thr Asp Lys Arg Phe Lys
    50                  55                  60

Thr Leu Pro Ala Ala Glu Thr Leu Pro Arg Asn Glu Val Leu Gly Gly
65                  70                  75                  80

Tyr Ile Phe Val Cys Asn Asn Asp Thr Met Gln Glu Asp Leu Lys Arg
                85                  90                  95

Gln Leu Phe Gly Leu Pro Pro Arg Tyr Arg Asp Ser Val Arg Ala Ile
            100                 105                 110

Thr Pro Gly Leu Pro Leu Phe Leu Tyr Asn Tyr Thr Thr His Gln Leu
        115                 120                 125

His Gly Ile Phe Glu Ala Thr Cys Phe Gly Gly Ser Asn Ile Asp Pro
    130                 135                 140

Thr Ala Trp Glu Asp Lys Lys Cys Lys Gly Glu Ser Arg Phe Pro Ala
145                 150                 155                 160

Gln Val Arg Ile Arg Val Arg Lys Ile Cys Lys Ala Leu Glu Glu Asp
                165                 170                 175

Ser Phe Arg Pro Val Leu His His Tyr Asp Gly Pro Lys Phe Arg Leu
            180                 185                 190

Glu Leu Ser Val Pro Glu Thr Leu Asp Leu Met Asp Leu Cys Glu Gln
        195                 200                 205

Ala Gly Ser Ala Ala
    210
```

<210> SEQ ID NO 60
<211> LENGTH: 305
<212> TYPE: PRT
<213> ORGANISM: Citrus X paradisi

<400> SEQUENCE: 60

```
Met Asp Asn Met His Ser Phe Trp Gln Leu Gly Asp Glu Leu Arg Gly
1               5                   10                  15

Gln Ser Arg Thr Ser Glu Asp Gln Ser Trp Leu Arg Ala Ala Ser Arg
            20                  25                  30
```

```
Leu Ala Glu Gln Thr Arg Phe Lys Gly Glu Arg Met Asn Asn Leu Asp
         35                  40                  45

Leu Ser Lys Gly Met Thr Glu Ile Arg Pro Arg Asp Lys Ile Met Tyr
 50                  55                  60

His Glu Asp Asn Asn Phe Glu Ser Phe Asn Phe Asn Phe Asn Met Met
 65                  70                  75                  80

Asn Leu Asp Asn Lys Val Val Glu Asn Val Thr Lys Ser Ser Leu Arg
                 85                  90                  95

Asn Gly Ile Tyr Asn Met Asn Ala Val Tyr Gln Lys Asn Ser Gly His
                100                 105                 110

Asn Met Gly Asn Leu Met Val Asn Lys Tyr Gly Gly Asn Asn Leu Ser
            115                 120                 125

Val Lys Glu Ala Glu Asn Asn Asn Asn Asn Asn Asn Asn Asn Asn Asp
130                 135                 140

Ser Asn Ala Asn Ser Ala Leu Asp Lys Arg Phe Lys Thr Leu Pro Ala
145                 150                 155                 160

Thr Glu Thr Leu Pro Arg Asn Glu Val Leu Gly Gly Tyr Ile Phe Val
                165                 170                 175

Cys Asn Asn Asp Thr Met Gln Glu Asp Leu Lys Arg Gln Leu Phe Gly
                180                 185                 190

Leu Pro Pro Arg Tyr Arg Asp Ser Val Arg Ala Ile Thr Pro Gly Leu
            195                 200                 205

Pro Leu Phe Leu Tyr Asn Tyr Thr Thr His Gln Leu His Gly Ile Phe
210                 215                 220

Glu Ala Thr Gly Phe Gly Gly Ser Asn Ile Asp Pro Thr Ala Trp Glu
225                 230                 235                 240

Asp Lys Lys Cys Lys Gly Glu Ser Arg Phe Pro Ala Gln Val Arg Ile
                245                 250                 255

Arg Val Arg Lys Leu Cys Lys Ala Leu Glu Glu Asp Ala Phe Arg Pro
            260                 265                 270

Val Leu His His Tyr Asp Gly Pro Lys Phe Arg Leu Glu Leu Ser Val
        275                 280                 285

Pro Glu Thr Leu Asp Leu Met Asp Leu Cys Glu Gln Ala Gly Ser Ala
    290                 295                 300

Ala
305

<210> SEQ ID NO 61
<211> LENGTH: 296
<212> TYPE: PRT
<213> ORGANISM: Arabidopsis thaliana

<400> SEQUENCE: 61

Met Asp Ser Phe Trp Gln Leu Gly Asp Glu Leu Arg Gly Gln Thr Arg
 1               5                  10                  15

Ala Ser Glu Asp His Lys Trp Ser Thr Val Ala Thr Lys Leu Ala Glu
                 20                  25                  30

Gln Thr Arg Met Lys Gly Glu Arg Met Asn Asn Leu Asp Leu Ser Lys
             35                  40                  45

Gly Tyr Thr Glu Phe Arg Pro Ser Glu Lys Phe Ser Phe Gln Glu Asn
 50                  55                  60

Asn Leu Asn Phe Asn Met Leu Asn Leu Asp Gly Lys Phe Gly Glu Ser
 65                  70                  75                  80

Ile Met Gly Lys Thr Ser Met Gln Ser Asn Val Tyr Asn Met Asn Thr
                 85                  90                  95
```

Val Phe Gln Lys Asn Asp Phe Lys Ser Gly Gly Asn Met Lys Val Asn
              100                 105                 110

Lys Tyr Asn Gly Asn Ile Val Ala Asn Lys Glu Met Ser Asn Asn Lys
            115                 120                 125

His Asn Asn Asn Cys Asn Asp Asn Gly Asn Met Asn Leu Ala Val Asp
130                 135                 140

Lys Arg Phe Lys Thr Leu Pro Ala Ser Glu Thr Leu Pro Arg Asn Glu
145                 150                 155                 160

Val Leu Gly Gly Tyr Ile Phe Val Cys Asn Asn Asp Thr Met Gln Glu
                165                 170                 175

Asp Met Lys Arg His Leu Phe Gly Leu Pro Pro Arg Tyr Arg Asp Ser
            180                 185                 190

Val Arg Ala Ile Thr Pro Gly Leu Pro Leu Phe Leu Tyr Asn Tyr Thr
        195                 200                 205

Thr His Gln Leu His Gly Ile Phe Glu Ala Thr Thr Phe Gly Gly Thr
    210                 215                 220

Asn Ile Asp Ala Thr Ala Trp Glu Asp Lys Lys Cys Lys Gly Glu Ser
225                 230                 235                 240

Arg Phe Pro Ala Gln Val Arg Ile Arg Val Arg Lys Ile Cys Lys Ala
                245                 250                 255

Leu Glu Glu Asp Ser Phe Arg Pro Val Leu His His Tyr Asp Gly Pro
            260                 265                 270

Lys Phe Arg Leu Glu Leu Ser Val Pro Glu Thr Leu Asp Leu Leu Asp
        275                 280                 285

Leu Cys Glu Gln Ala Gly Ser Ala
    290                 295

<210> SEQ ID NO 62
<211> LENGTH: 296
<212> TYPE: PRT
<213> ORGANISM: Arabidopsis thaliana

<400> SEQUENCE: 62

Met Asp Ser Phe Trp Gln Leu Gly Asp Glu Leu Arg Gly Gln Thr Arg
1               5                   10                  15

Ala Ser Glu Asp His Lys Trp Ser Thr Val Ala Thr Lys Leu Ala Glu
            20                  25                  30

Gln Thr Arg Met Lys Gly Glu Arg Met Asn Asn Leu Asp Leu Ser Lys
        35                  40                  45

Gly Tyr Thr Glu Phe Arg Pro Ser Glu Lys Phe Ser Phe Gln Glu Asn
    50                  55                  60

Asn Leu Asn Phe Asn Met Leu Asn Leu Asp Gly Lys Phe Gly Glu Ser
65                  70                  75                  80

Ile Met Gly Lys Thr Ser Met Gln Ser Asn Val Tyr Asn Met Asn Thr
                85                  90                  95

Val Phe Gln Lys Asn Asp Phe Lys Ser Gly Gly Asn Met Lys Val Asn
            100                 105                 110

Lys Tyr Asn Gly Asn Val Val Ala Asn Lys Glu Met Ser Asn Asn Lys
        115                 120                 125

His Asn Asn Asn Cys Asn Asp Asn Gly Asn Met Asn Leu Ala Val Asp
    130                 135                 140

Lys Arg Phe Lys Thr Leu Pro Ala Ser Glu Thr Leu Pro Arg Asn Glu
145                 150                 155                 160

Val Leu Gly Gly Tyr Ile Phe Val Cys Asn Asn Asp Thr Met Gln Glu
                165                 170                 175

-continued

```
Asp Met Lys Arg His Leu Phe Gly Leu Pro Arg Tyr Arg Asp Ser
        180                 185                 190

Val Arg Ala Ile Thr Pro Gly Leu Pro Leu Phe Leu Tyr Asn Tyr Thr
            195                 200                 205

Thr His Gln Leu His Gly Ile Phe Glu Ala Thr Thr Phe Gly Gly Thr
    210                 215                 220

Asn Ile Asp Ala Thr Ala Trp Glu Asp Lys Lys Cys Lys Gly Glu Ser
225                 230                 235                 240

Arg Phe Pro Ala Gln Val Arg Ile Arg Val Arg Lys Ile Cys Lys Ala
                245                 250                 255

Leu Glu Glu Asp Ser Phe Arg Pro Val Leu His His Tyr Asp Gly Pro
            260                 265                 270

Lys Phe Arg Leu Glu Leu Ser Val Pro Glu Thr Leu Asp Leu Leu Asp
        275                 280                 285

Leu Cys Glu Gln Ala Gly Ser Ala
        290                 295

<210> SEQ ID NO 63
<211> LENGTH: 742
<212> TYPE: PRT
<213> ORGANISM: Arabidopsis thaliana

<400> SEQUENCE: 63

Met Ala Glu Ala Met Glu Thr Glu Met Asp Phe Ser Asp Gly Glu Gln
1               5                   10                  15

Thr Asn Gly Asn Ser His Val Thr Ala Ser Gln Tyr Phe Ala Pro Pro
            20                  25                  30

Gly Tyr Asn Arg Ser Leu Val Ala Ala Tyr Gly Asn Gly Asn Thr Thr
        35                  40                  45

Ile Gly Leu Glu Lys Gly Ile Glu Arg Arg Leu Asp His His Glu Gln
    50                  55                  60

Leu Pro Gly Tyr Ile Phe Met Cys Asn Gly Arg Thr Lys Thr Asp Cys
65                  70                  75                  80

Tyr Arg Tyr Arg Val Phe Gly Ile Pro Arg Gly Gly Lys Asp Val Val
                85                  90                  95

Glu Ser Ile Lys Pro Gly Met Lys Leu Phe Leu Tyr Asp Phe Glu Lys
            100                 105                 110

Arg Leu Leu Tyr Gly Val Tyr Glu Ala Thr Val Gly Gly Arg Leu Asp
        115                 120                 125

Ile Glu Pro Glu Ala Phe Glu Gly Lys Tyr Pro Ala Gln Val Gly Phe
    130                 135                 140

Arg Ile Val Met Asn Cys Leu Pro Leu Thr Glu Asn Thr Phe Lys Ser
145                 150                 155                 160

Ala Ile Tyr Glu Asn Tyr Lys Gly Ser Lys Phe Lys Gln Glu Leu Ser
                165                 170                 175

Pro His Gln Val Met Ser Leu Leu Ser Leu Phe Arg Ser Phe Thr Ser
            180                 185                 190

Pro Glu Leu Asp Leu Leu Pro His Arg Leu Ala Ser Arg Ala Ser Ala
        195                 200                 205

Pro Arg Thr Leu Ser Phe Glu Glu Arg Phe Ile Ala Ala Thr His Leu
    210                 215                 220

Arg Asn Ala Ser Ser Val Leu Asp Pro Leu Ser Ala Arg His Val Glu
225                 230                 235                 240

Pro Arg Leu Gly Ser Val Met Ala His Gln Pro Val Pro Arg Thr Ser
                245                 250                 255
```

```
Leu Leu Gln His Ser Tyr Phe Arg Gln Asp Asp Tyr Thr Thr Pro Pro
            260                 265                 270

Arg Glu Ser Leu Ser Asn Leu Asn Gln Pro Tyr Tyr Pro Thr Glu Ala
            275                 280                 285

Arg Gln Leu Arg Leu Leu Gly Asp Pro Ser Arg Ser Asp Ser Pro Arg
            290                 295                 300

Ser Glu Pro Pro Arg Ser Ser Ile Gln Asp Pro Gln Leu Lys Tyr Leu
305                 310                 315                 320

Thr Ile Leu Ser Asn Ile Arg Arg Tyr Gly Ser Ala Ser Asp Arg Leu
                325                 330                 335

Ala Ser Glu Asn Glu Tyr His Pro Ala Thr Pro Ser Glu Lys Asp Gln
            340                 345                 350

Phe Ala Val Pro Tyr Ser Asp Asn Lys Asn Tyr Pro Ser Thr Leu Ser
            355                 360                 365

Gly Ser Glu His Pro Ser Ala Ser Ala Ala Asn Gly Ser Val Tyr Arg
            370                 375                 380

Ser Glu Phe Tyr Asn Ser Ala Ser Gln Lys Glu Gly Glu Ala Ser Gln
385                 390                 395                 400

Gln His Glu Ile Pro Ala Gly Thr Tyr His His Pro Glu Ala Ser Thr
                405                 410                 415

Val Ser Asn Thr Thr Lys Ser Met Gln Pro Asp Met Gln Ala Val Ser
            420                 425                 430

Val Ala Gln Ser His Thr Glu Thr Ala Gly Tyr Pro Thr Pro Ala His
            435                 440                 445

Gly Glu Ala Ser Gln Pro Pro Ala Gly Ala Ile Gly Tyr Thr His Gln
            450                 455                 460

Pro Gln Ser Val Ala Gly Asn Tyr Ser Thr His Ser Gln Pro Gly Asn
465                 470                 475                 480

Val Glu Glu Ser Thr Gln Ser Tyr Ala Gly Thr Asp Ser Tyr Ser Gln
                485                 490                 495

Gln Gln Tyr Tyr Ala Ala Met Gly Pro Thr Thr Gln Leu His Ala Gly
            500                 505                 510

Gly Tyr Ile Gln Lys Pro His Glu Ile Gly Tyr Ser Gln Gln Pro His
            515                 520                 525

Asp Ala Ala Thr Gly Tyr Ser Gln Gln Pro His Asp Ala Ala Thr Gly
530                 535                 540

Tyr Ser Gln Gln Pro His Asp Ala Ala Thr Gly Tyr Ser Gln Gln Pro
545                 550                 555                 560

His Ala Ala Ser Thr Gly Tyr Ser Gln Gln Thr Tyr Ala Ala Ala Thr
                565                 570                 575

Gly Tyr Thr Gln Gln Pro His Ala Ala Ala Gly Tyr Thr Gln Gln
            580                 585                 590

Pro His Ala Ala Ala Thr Gly Tyr Ser Gln Gln Pro His Ala Ala Ala
            595                 600                 605

Thr Ala His Ala Gln Gln Pro Tyr Ala Ala Thr Ala His Ala Gln
            610                 615                 620

Gln Leu His Ala Val Ala Thr Gly Tyr Ala Leu Gln Leu His Ala Ala
625                 630                 635                 640

Ala Thr Gly Tyr Ala Gln Gln Pro His Ala Ala Thr Gly Tyr Ala
                645                 650                 655

Leu Gln Pro His Ala Gln Ala Val Glu Tyr Thr Met Gln Pro His Ala
            660                 665                 670

Gln Ala Val Gly Tyr Met Pro Gln Tyr His Ala His Ala Val Val Tyr
            675                 680                 685
```

Ser Gln Gln Gly Val Thr Gln Gly Ser Val Pro Arg Ala Pro Gly Thr
    690             695             700

Thr Asp Cys Asn Ala Ala Asn Gln Ala Tyr Ser Ala Thr Gly Asp Trp
705             710             715             720

Asn Ala Val His Gln Ser Tyr Tyr Pro Gln Thr Ala Asp Ala Thr Thr
            725             730             735

Thr Tyr Tyr Gln Thr Ser
        740

<210> SEQ ID NO 64
<211> LENGTH: 195
<212> TYPE: PRT
<213> ORGANISM: Arabidopsis thaliana

<400> SEQUENCE: 64

Met Ala Gly Val Ala Phe Gly Ser Phe Asp Asp Ser Phe Ser Leu Ala
1               5                   10                  15

Ser Leu Arg Ala Tyr Leu Ala Glu Phe Ile Ser Thr Leu Leu Phe Val
            20                  25                  30

Phe Ala Gly Val Gly Ser Ala Ile Ala Tyr Ala Lys Leu Thr Ser Asp
        35                  40                  45

Ala Ala Leu Asp Thr Pro Gly Leu Val Ala Ile Ala Val Cys His Gly
    50                  55                  60

Phe Ala Leu Phe Val Ala Val Ala Ile Gly Ala Asn Ile Ser Gly Gly
65                  70                  75                  80

His Val Asn Pro Ala Val Thr Phe Gly Leu Ala Val Gly Gly Gln Ile
                85                  90                  95

Thr Val Ile Thr Gly Val Phe Tyr Trp Ile Ala Gln Leu Leu Gly Ser
            100                 105                 110

Thr Ala Ala Cys Phe Leu Leu Lys Tyr Val Thr Gly Gly Leu Ala Val
        115                 120                 125

Pro Thr His Ser Val Ala Ala Gly Leu Gly Ser Ile Glu Gly Val Val
    130                 135                 140

Met Glu Ile Ile Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Leu Ala
                165                 170                 175

Ile Gly Leu Ile Val Gly Ala Asn Ile Leu Ala Ala Gly Pro Phe Ser
            180                 185                 190

Gly Gly Ser
        195

<210> SEQ ID NO 65
<211> LENGTH: 248
<212> TYPE: PRT
<213> ORGANISM: Gossypium hirsutum

<400> SEQUENCE: 65

Met Ala Gly Ile Ala Phe Gly Arg Phe Asp Asp Ser Phe Ser Leu Gly
1               5                   10                  15

Thr Val Lys Ala Tyr Leu Ala Glu Phe Ile Ser Thr Leu Val Phe Val
            20                  25                  30

Phe Ala Gly Val Gly Ser Ala Ile Ala Tyr Asn Lys Leu Thr Thr Asp
        35                  40                  45

Ala Ala Leu Asp Pro Asp Gly Leu Val Ala Ile Ala Val Cys His Gly
    50                  55                  60

```
Phe Ala Leu Phe Val Ala Val Ala Ile Gly Ala Asn Ile Ser Gly Gly
 65                  70                  75                  80

His Val Asn Pro Ala Val Thr Phe Gly Leu Ala Leu Gly Gly Gln Ile
                 85                  90                  95

Thr Ile Leu Thr Gly Ile Phe Tyr Trp Ile Ala Gln Leu Leu Gly Ser
            100                 105                 110

Ile Val Ala Cys Phe Leu Leu Lys Ala Val Thr Gly Gly Leu Thr Val
        115                 120                 125

Pro Ile His Gly Leu Gly Ala Gly Val Gly Ala Ile Gln Gly Val Val
130                 135                 140

Met Glu Ile Ile Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Ile Ala
                165                 170                 175

Ile Gly Phe Ile Val Gly Ala Asn Ile Leu Ala Ala Gly Pro Phe Ser
            180                 185                 190

Gly Gly Ser Met Asn Pro Ala Arg Ser Phe Gly Pro Ala Val Ala Ser
        195                 200                 205

Gly Asp Phe Asn Gly Ile Trp Ile Tyr Trp Val Gly Pro Leu Ile Gly
210                 215                 220

Gly Gly Leu Ser Gly Leu Ile Tyr Gly Asn Val Phe Met Asn Ser Asp
225                 230                 235                 240

His Ala Pro Leu Ser Asn Asp Phe
                245

<210> SEQ ID NO 66
<211> LENGTH: 250
<212> TYPE: PRT
<213> ORGANISM: Arabidopsis thaliana

<400> SEQUENCE: 66

Met Ala Gly Val Ala Phe Gly Ser Phe Asp Asp Ser Phe Ser Leu Ala
1               5                   10                  15

Ser Leu Arg Ala Tyr Leu Ala Glu Phe Ile Ser Thr Leu Leu Phe Val
            20                  25                  30

Phe Ala Gly Val Gly Ser Ala Ile Ala Tyr Ala Lys Leu Thr Ser Asp
        35                  40                  45

Ala Ala Leu Asp Thr Pro Gly Leu Val Ala Ile Ala Val Cys His Gly
    50                  55                  60

Phe Ala Leu Phe Val Ala Val Ala Ile Gly Ala Asn Ile Ser Gly Gly
65                  70                  75                  80

His Val Asn Pro Ala Val Thr Phe Gly Leu Ala Val Gly Gly Gln Ile
                85                  90                  95

Thr Val Ile Thr Gly Val Phe Tyr Trp Ile Ala Gln Leu Leu Gly Ser
            100                 105                 110

Thr Ala Ala Cys Phe Leu Leu Lys Tyr Val Thr Gly Gly Leu Ala Val
        115                 120                 125

Pro Thr His Ser Val Ala Ala Gly Leu Gly Ser Ile Glu Gly Val Val
130                 135                 140

Met Glu Ile Ile Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Leu Ala
                165                 170                 175

Ile Gly Leu Ile Val Gly Ala Asn Ile Leu Ala Ala Gly Pro Phe Ser
            180                 185                 190
```

```
Gly Gly Ser Met Asn Pro Ala Arg Ser Phe Gly Pro Ala Val Ala Ala
            195                 200                 205

Gly Asp Phe Ser Gly His Trp Val Tyr Trp Val Pro Leu Ile Gly
    210                 215                 220

Gly Glu Leu Ala Gly Leu Ile Tyr Gly Asn Val Phe Met Gly Ser Ser
225                 230                 235                 240

Glu His Val Pro Leu Ala Ser Ala Asp Phe
                245                 250

<210> SEQ ID NO 67
<211> LENGTH: 250
<212> TYPE: PRT
<213> ORGANISM: Arabidopsis thaliana

<400> SEQUENCE: 67

Met Ala Gly Val Ala Phe Gly Ser Phe Asp Asp Ser Phe Ser Leu Ala
1               5                   10                  15

Ser Leu Arg Ala Tyr Leu Ala Glu Phe Ile Ser Thr Leu Leu Phe Val
                20                  25                  30

Phe Ala Gly Val Gly Ser Ala Ile Ala Tyr Ala Lys Leu Thr Ser Asp
            35                  40                  45

Ala Ala Leu Asp Thr Pro Gly Leu Val Ala Ile Ala Val Cys His Gly
        50                  55                  60

Phe Ala Leu Phe Val Ala Val Ala Ile Gly Ala Asn Ile Ser Gly Gly
65                  70                  75                  80

His Val Asn Pro Ala Val Thr Phe Gly Leu Ala Val Gly Gly Gln Ile
                85                  90                  95

Thr Val Ile Thr Gly Val Phe Tyr Trp Ile Ala Gln Leu Leu Gly Ser
                100                 105                 110

Thr Ala Ala Cys Phe Leu Leu Lys Tyr Val Thr Gly Gly Leu Ala Val
            115                 120                 125

Pro Thr His Ser Val Ala Ala Gly Leu Gly Ser Ile Glu Gly Val Val
        130                 135                 140

Met Glu Ile Ile Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Leu Ala
                165                 170                 175

Ile Gly Leu Ile Val Gly Ala Asn Ile Leu Ala Ala Gly Pro Phe Ser
            180                 185                 190

Gly Gly Ser Met Asn Pro Ala Arg Ser Phe Gly Pro Ala Val Ala Ala
        195                 200                 205

Gly Asp Phe Ser Gly His Trp Val Tyr Trp Val Pro Leu Ile Gly
    210                 215                 220

Gly Gly Leu Ala Gly Leu Ile Tyr Gly Asn Val Phe Met Gly Ser Ser
225                 230                 235                 240

Glu His Val Pro Leu Ala Ser Ala Asp Phe
                245                 250

<210> SEQ ID NO 68
<211> LENGTH: 250
<212> TYPE: PRT
<213> ORGANISM: Arabidopsis thaliana

<400> SEQUENCE: 68

Met Val Lys Ile Glu Ile Gly Ser Val Gly Asp Ser Phe Ser Val Ala
1               5                   10                  15

Ser Leu Lys Ala Tyr Leu Ser Glu Phe Ile Ala Thr Leu Leu Phe Val
```

```
                20                  25                  30
Phe Ala Gly Val Gly Ser Ala Leu Ala Phe Ala Lys Leu Thr Ser Asp
                35                  40                  45
Ala Ala Leu Asp Pro Ala Gly Leu Val Ala Val Ala Val His Ala
    50                  55                  60
Phe Ala Leu Phe Val Gly Val Ser Ile Ala Ala Asn Ile Ser Gly Gly
65                  70                  75                  80
His Leu Asn Pro Ala Val Thr Leu Gly Leu Ala Val Gly Gly Asn Ile
                85                  90                  95
Thr Val Ile Thr Gly Phe Phe Tyr Trp Ile Ala Gln Cys Leu Gly Ser
                100                 105                 110
Ile Val Ala Cys Leu Leu Val Phe Val Thr Asn Gly Glu Ser Val
                115                 120                 125
Pro Thr His Gly Val Ala Ala Gly Leu Gly Ala Ile Glu Gly Val Val
                130                 135                 140
Met Glu Ile Val Val Thr Phe Ala Leu Val Tyr Thr Val Tyr Ala Thr
145                 150                 155                 160
Ala Ala Asp Pro Lys Lys Gly Ser Leu Gly Thr Ile Ala Pro Ile Ala
                165                 170                 175
Ile Gly Phe Ile Val Gly Ala Asn Ile Leu Ala Ala Gly Pro Phe Ser
                180                 185                 190
Gly Gly Ser Met Asn Pro Ala Arg Ser Phe Gly Pro Ala Val Val Ser
                195                 200                 205
Gly Asp Phe Ser Gln Ile Trp Ile Tyr Trp Val Gly Pro Leu Val Gly
                210                 215                 220
Gly Ala Leu Ala Gly Leu Ile Tyr Gly Asp Val Phe Ile Gly Ser Tyr
225                 230                 235                 240
Ala Pro Ala Pro Thr Thr Glu Ser Tyr Pro
                245                 250

<210> SEQ ID NO 69
<211> LENGTH: 248
<212> TYPE: PRT
<213> ORGANISM: Nicotiana glauca

<400> SEQUENCE: 69

Met Pro Gly Ile Ala Phe Gly Arg Ile Asp Asp Ser Phe Ser Val Gly
1                   5                   10                  15
Ser Leu Lys Ala Tyr Leu Ala Glu Phe Ile Ser Thr Leu Leu Phe Val
                20                  25                  30
Phe Ala Gly Val Gly Ser Ala Ile Ala Tyr Asn Lys Leu Thr Ala Asn
                35                  40                  45
Ala Ala Leu Asp Pro Ala Gly Leu Val Ala Val Ala Val Cys His Gly
    50                  55                  60
Phe Ala Leu Phe Val Ala Val Ala Val Gly Ala Asn Ile Ser Gly Gly
65                  70                  75                  80
His Val Asn Pro Ala Val Thr Phe Gly Leu Ala Leu Gly Gly Gln Ile
                85                  90                  95
Thr Leu Leu Thr Gly Leu Phe Tyr Ile Ile Ala Gln Leu Leu Gly Ser
                100                 105                 110
Ile Val Ala Cys Leu Leu Leu Lys Val Val Thr Gly Gly Leu Ala Val
                115                 120                 125
Pro Thr His Asn Val Ala Ala Gly Val Gly Ala Leu Glu Gly Val Val
                130                 135                 140
Met Glu Ile Ile Ile Thr Phe Ala Leu Val Tyr Thr Val Tyr Ala Thr
```

```
                    145                 150                 155                 160
Ala Ala Asp Pro Lys Lys Gly Ser Leu Gly Thr Ile Ala Pro Ile Ala
                165                 170                 175
Ile Gly Phe Ile Val Gly Ala Asn Ile Leu Ala Ala Gly Pro Phe Ser
            180                 185                 190
Gly Gly Ser Met Asn Pro Ala Arg Ser Phe Gly Pro Ala Val Ala Ser
        195                 200                 205
Gly Asp Phe Thr Asn Asn Trp Ile Tyr Trp Ala Gly Pro Leu Val Gly
    210                 215                 220
Gly Gly Leu Ala Gly Leu Thr Tyr Ser Asn Val Phe Met Gln His Glu
225                 230                 235                 240
His Ala Pro Leu Ser Ser Asp Phe
                245

<210> SEQ ID NO 70
<211> LENGTH: 248
<212> TYPE: PRT
<213> ORGANISM: Raphanus sativus

<400> SEQUENCE: 70

Met Ala Gly Val Ala Phe Gly Ser Phe Asp Asp Ser Phe Ser Leu Ala
1               5                   10                  15
Ser Leu Arg Ala Tyr Leu Ala Glu Phe Ile Ser Thr Leu Leu Phe Val
            20                  25                  30
Phe Ala Gly Val Gly Ser Ala Ile Ala Tyr Ala Lys Leu Thr Ser Asp
        35                  40                  45
Ala Ala Leu Asp Thr Pro Gly Leu Val Ala Ile Ala Val Cys His Gly
    50                  55                  60
Phe Ala Leu Phe Val Ala Val Ala Ile Gly Ala Asn Ile Ser Gly Gly
65                  70                  75                  80
His Val Asn Pro Ala Val Thr Phe Gly Leu Ala Val Gly Gly Gln Ile
                85                  90                  95
Thr Leu Ile Thr Gly Val Phe Tyr Trp Val Ala Gln Leu Leu Gly Ser
            100                 105                 110
Thr Ala Ala Cys Phe Leu Leu Lys Tyr Val Thr Gly Gly Leu Ala Val
        115                 120                 125
Pro Thr His Ser Val Ala Ala Gly Val Gly Ala Ile Glu Gly Val Val
    130                 135                 140
Met Glu Ile Ile Ile Thr Phe Ser Leu Val Tyr Thr Val Tyr Pro Thr
145                 150                 155                 160
Ala Ala Asp Pro Lys Lys Gly Ser Leu Gly Thr Ile Ala Pro Leu Ala
                165                 170                 175
Ile Gly Leu Ile Val Gly Ala Asn Ile Leu Ala Ala Gly Pro Phe Ser
            180                 185                 190
Gly Gly Ser Met Asn Pro Ala Arg Ser Phe Gly Pro Ala Val Ala Ala
        195                 200                 205
Gly Asp Phe Ser Gly His Trp Val Tyr Trp Val Gly Pro Leu Ile Gly
    210                 215                 220
Gly Gly Leu Ala Gly Val Thr Tyr Gly Asn Val Phe Met Thr Ser Glu
225                 230                 235                 240
His Val Pro Leu Ala Ser Glu Phe
                245

<210> SEQ ID NO 71
<211> LENGTH: 248
<212> TYPE: PRT
```

<213> ORGANISM: Helianthus annuus

<400> SEQUENCE: 71

Met Pro Gly Ile Ala Phe Gly Ser Phe Asp Asp Ser Phe Ser Leu Ser
1               5                   10                  15

Ser Ile Lys Ser Tyr Val Ala Glu Phe Ile Ser Thr Leu Leu Phe Val
            20                  25                  30

Phe Ala Gly Val Gly Ser Ala Ile Ala Phe Ala Lys Leu Thr Ala Asp
        35                  40                  45

Ala Asp Leu Asp Pro Ala Gly Leu Val Ala Ile Ala Val Cys His Gly
    50                  55                  60

Leu Ala Leu Phe Val Ala Val Ser Ile Ala Ala Asn Ile Ser Gly Gly
65                  70                  75                  80

His Val Asn Pro Ala Val Thr Phe Gly Leu Ala Val Gly Gly Gln Ile
                85                  90                  95

Thr Ile Leu Thr Gly Ile Phe Tyr Trp Ile Ala Gln Cys Ile Gly Ser
            100                 105                 110

Ile Ala Ala Cys Tyr Leu Leu Ser Phe Val Thr Gly Gly Leu Ala Val
        115                 120                 125

Pro Thr His Ala Val Ala Ala Gly Val Gly Ala Ile Gln Gly Val Val
    130                 135                 140

Met Glu Ile Ile Ile Thr Phe Ala Leu Val Tyr Asn Val Tyr Ala Thr
145                 150                 155                 160

Ala Val Asp Pro Lys Lys Gly Asp Leu Gly Thr Ile Ala Pro Leu Ala
                165                 170                 175

Ile Gly Leu Ile Val Gly Ala Asn Ile Leu Ala Ala Gly Pro Phe Ser
            180                 185                 190

Gly Gly Ser Met Asn Pro Ala Arg Ser Phe Gly Pro Ala Val Ala Ala
        195                 200                 205

Gly Asp Phe Ser Gly His Trp Ile Tyr Trp Val Gly Pro Leu Val Gly
    210                 215                 220

Gly Gly Leu Ala Gly Ala Ile Tyr Ser Asn Val Phe Ile Ser Asn Glu
225                 230                 235                 240

His Ala Pro Leu Ser Ser Glu Phe
                245

<210> SEQ ID NO 72
<211> LENGTH: 248
<212> TYPE: PRT
<213> ORGANISM: Oryza sativa

<400> SEQUENCE: 72

Met Val Lys Leu Ala Phe Gly Ser Leu Gly Asp Ser Phe Ser Ala Thr
1               5                   10                  15

Ser Val Lys Ala Tyr Val Ala Glu Phe Ile Ala Thr Leu Leu Phe Val
            20                  25                  30

Phe Ala Gly Val Gly Ser Ala Ile Ala Tyr Gly Gln Leu Thr Asn Gly
        35                  40                  45

Gly Ala Leu Asp Pro Ala Gly Leu Val Ala Ile Ala His Ala
    50                  55                  60

Leu Ala Leu Phe Val Gly Val Ser Val Ala Ala Asn Ile Ser Gly Gly
65                  70                  75                  80

His Leu Asn Pro Ala Val Thr Phe Gly Leu Ala Val Gly Gly His Ile
                85                  90                  95

Thr Ile Leu Thr Gly Leu Phe Tyr Trp Ile Ala Gln Leu Leu Gly Ala
            100                 105                 110

```
Ser Ile Ala Cys Leu Leu Lys Phe Val Thr His Gly Lys Ala Ile
        115                 120                 125

Pro Thr His Gly Val Ala Gly Ile Ser Glu Leu Glu Gly Val Val Met
    130                 135                 140

Glu Ile Val Ile Thr Phe Ala Leu Val Tyr Thr Val Tyr Ala Thr Ala
145                 150                 155                 160

Ala Asp Pro Lys Lys Gly Ser Leu Gly Thr Ile Ala Pro Ile Ala Ile
                165                 170                 175

Gly Phe Ile Val Gly Ala Asn Ile Leu Ala Ala Gly Pro Phe Ser Gly
                180                 185                 190

Gly Ser Met Asn Pro Ala Arg Ser Phe Gly Pro Ala Val Ala Ala Gly
            195                 200                 205

Asn Phe Ala Gly Asn Trp Val Tyr Trp Val Gly Pro Leu Ile Gly Gly
        210                 215                 220

Gly Leu Ala Gly Leu Val Tyr Gly Asp Val Phe Ile Gly Ser Tyr Gln
225                 230                 235                 240

Pro Val Ala Asp Gln Asp Tyr Ala
                245

<210> SEQ ID NO 73
<211> LENGTH: 248
<212> TYPE: PRT
<213> ORGANISM: Zea mays

<400> SEQUENCE: 73

Met Val Lys Leu Ala Phe Gly Ser Phe Arg Asp Ser Leu Ser Ala Ala
1               5                   10                  15

Ser Leu Lys Ala Tyr Val Ala Glu Phe Ile Ala Thr Leu Leu Phe Val
                20                  25                  30

Phe Ala Gly Val Gly Ser Ala Ile Ala Tyr Ser Gln Leu Thr Lys Gly
            35                  40                  45

Gly Ala Leu Asp Pro Ala Gly Leu Val Ala Ile Ala Ile Ala His Ala
        50                  55                  60

Phe Ala Leu Phe Val Gly Val Ser Met Ala Ala Asn Ile Ser Gly Gly
65                  70                  75                  80

His Leu Asn Pro Ala Val Thr Phe Gly Leu Ala Val Gly Gly His Ile
                85                  90                  95

Thr Ile Leu Thr Gly Ile Leu Tyr Trp Val Ala Gln Leu Leu Gly Ala
            100                 105                 110

Ser Val Ala Cys Phe Leu Leu Gln Tyr Val Thr His Gly Gln Ala Ile
        115                 120                 125

Pro Thr His Gly Val Ser Gly Ile Ser Glu Ile Glu Gly Val Val Met
    130                 135                 140

Glu Ile Val Ile Thr Phe Ala Leu Val Tyr Thr Val Tyr Ala Thr Ala
145                 150                 155                 160

Ala Asp Pro Lys Lys Gly Ser Leu Gly Thr Ile Ala Pro Met Ala Ile
                165                 170                 175

Gly Phe Ile Val Gly Ala Asn Ile Leu Ala Ala Gly Pro Phe Ser Gly
                180                 185                 190

Gly Ser Met Asn Pro Ala Arg Ser Phe Gly Pro Ala Val Ala Ala Gly
            195                 200                 205

Asn Phe Ala Gly Asn Trp Val Tyr Trp Val Gly Pro Leu Val Gly Gly
        210                 215                 220

Gly Leu Ala Gly Leu Val Tyr Gly Asp Val Phe Ile Ala Ser Tyr Gln
225                 230                 235                 240
```

```
Pro Val Gly Gln Gln Glu Tyr Pro
            245

<210> SEQ ID NO 74
<211> LENGTH: 249
<212> TYPE: PRT
<213> ORGANISM: Hordeum vulgare

<400> SEQUENCE: 74

Met Val Lys Leu Ala Phe Gly Ser Phe Gly Asp Ser Phe Ser Ala Thr
1               5                   10                  15

Ser Ile Arg Ser Tyr Val Ala Glu Phe Ile Ala Thr Leu Leu Phe Val
            20                  25                  30

Phe Ala Gly Val Gly Ser Ala Ile Ser Tyr Gly Gln Leu Thr Gln Gly
        35                  40                  45

Gly Ala Leu Asp Pro Ala Gly Leu Val Ala Ile Ala Ile Ala His Ala
    50                  55                  60

Phe Ala Leu Phe Val Gly Val Ala Met Ala Ala Asn Ile Ser Gly Gly
65                  70                  75                  80

His Leu Asn Pro Ala Val Thr Phe Gly Leu Ala Val Gly Gly His Val
                85                  90                  95

Thr Ile Leu Thr Gly Leu Phe Tyr Trp Val Ala Gln Leu Leu Gly Ala
            100                 105                 110

Ser Val Ala Cys Leu Leu Leu Gln Phe Val Thr His Ala Gln Ala Met
        115                 120                 125

Pro Thr His Ala Val Ser Gly Ile Ser Glu Val Glu Gly Val Val Met
    130                 135                 140

Glu Ile Val Ile Thr Phe Ala Leu Val Tyr Thr Val Tyr Ala Thr Ala
145                 150                 155                 160

Ala Asp Pro Lys Lys Gly Ser Leu Gly Thr Ile Ala Pro Met Ala Ile
                165                 170                 175

Gly Phe Ile Val Gly Ala Asn Ile Leu Ala Ala Gly Pro Phe Ser Gly
            180                 185                 190

Gly Ser Met Asn Pro Ala Arg Ser Phe Gly Pro Ala Val Ala Ala Gly
        195                 200                 205

Asn Phe Ser Gly His Trp Val Tyr Trp Val Gly Pro Leu Ile Gly Gly
    210                 215                 220

Gly Leu Ala Gly Leu Val Tyr Gly Asp Val Phe Ile Ala Ser Tyr Gln
225                 230                 235                 240

Pro Val Gly His Gln Gln Glu Tyr Pro
                245

<210> SEQ ID NO 75
<211> LENGTH: 228
<212> TYPE: PRT
<213> ORGANISM: Antirrhinum majus

<400> SEQUENCE: 75

Phe Gly Ser Ile Gly Asp Ser Phe Ser Val Ala Ser Ile Lys Ala Tyr
1               5                   10                  15

Val Ala Glu Phe Ile Ala Thr Leu Leu Phe Val Phe Ala Gly Val Gly
            20                  25                  30

Ser Ala Ile Ala Tyr Asn Lys Leu Thr Ser Asp Ala Ala Leu Asp Pro
        35                  40                  45

Ala Gly Leu Val Ala Val Ala Val Ala His Ala Phe Ala Leu Phe Val
    50                  55                  60
```

```
Gly Val Ser Met Ala Ala Asn Val Ser Gly Gly His Leu Asn Pro Ala
 65                  70                  75                  80

Val Thr Leu Gly Leu Ala Val Gly Gly Asn Ile Thr Ile Leu Thr Gly
                 85                  90                  95

Leu Phe Tyr Trp Ile Ala Gln Cys Leu Gly Ser Thr Val Ala Cys Leu
            100                 105                 110

Leu Leu Lys Phe Val Thr Asn Gly Leu Ser Val Pro Thr His Gly Val
        115                 120                 125

Ala Ala Gly Met Asp Ala Ile Gln Gly Val Val Met Glu Ile Ile Ile
    130                 135                 140

Thr Phe Ala Leu Val Tyr Thr Val Tyr Ala Thr Ala Ala Asp Pro Lys
145                 150                 155                 160

Lys Gly Ser Leu Gly Val Ile Ala Pro Ile Ala Ile Gly Phe Ile Val
                165                 170                 175

Gly Ala Asn Ile Leu Ala Ala Gly Pro Phe Ser Gly Gly Ser Met Asn
            180                 185                 190

Pro Ala Arg Ser Phe Gly Pro Ala Val Ala Ser Gly Asp Phe Ser Gln
        195                 200                 205

Asn Trp Ile Tyr Trp Ala Gly Pro Leu Ile Gly Gly Ala Leu Ala Gly
    210                 215                 220

Phe Ile Tyr Gly
225

<210> SEQ ID NO 76
<211> LENGTH: 248
<212> TYPE: PRT
<213> ORGANISM: Zea mays

<400> SEQUENCE: 76

Met Val Lys Leu Ala Phe Gly Ser Phe Arg Asp Ser Leu Ser Ala Ala
 1               5                  10                  15

Ser Leu Lys Ala Tyr Val Ala Glu Phe Ile Ala Thr Leu Leu Phe Val
             20                  25                  30

Phe Ala Gly Val Gly Ser Ala Ile Ala Tyr Ser Gln Leu Thr Lys Gly
         35                  40                  45

Gly Ala Leu Asp Pro Ala Gly Leu Val Ala Ile Ala Ile Ala His Ala
     50                  55                  60

Phe Ala Leu Phe Val Gly Val Ser Met Ala Ala Asn Ile Ser Gly Gly
 65                  70                  75                  80

His Leu Asn Pro Ala Val Thr Phe Gly Leu Ala Val Gly Gly His Ile
                 85                  90                  95

Thr Ile Leu Thr Gly Ile Leu Tyr Trp Val Ala Gln Leu Leu Gly Ala
            100                 105                 110

Ser Val Ala Cys Phe Leu Leu Gln Tyr Val Thr His Gly Gln Ala Ile
        115                 120                 125

Pro Thr His Gly Val Ser Gly Ile Ser Glu Ile Glu Gly Val Val Met
    130                 135                 140

Glu Ile Val Ile Thr Phe Ala Leu Val Tyr Thr Val Tyr Ala Thr Ala
145                 150                 155                 160

Ala Asp Pro Lys Lys Gly Ser Leu Gly Thr Ile Ala Pro Met Ala Ile
                165                 170                 175

Gly Phe Ile Val Gly Ala Asn Ile Leu Ala Ala Gly Pro Phe Ser Gly
            180                 185                 190

Gly Ser Met Asn Pro Ala Arg Ser Phe Gly Pro Ala Val Ala Ala Gly
        195                 200                 205
```

```
Asn Phe Ala Gly Asn Trp Val Tyr Trp Val Gly Pro Leu Val Gly Gly
    210                 215                 220
Gly Leu Ala Gly Pro Val Tyr Gly Asp Val Phe Ile Ala Ser Tyr Gln
225                 230                 235                 240
Pro Val Gly Gln Gln Glu Tyr Pro
                245
```

<210> SEQ ID NO 77
<211> LENGTH: 248
<212> TYPE: PRT
<213> ORGANISM: Helianthus annuus

<400> SEQUENCE: 77

```
Met Pro Gly Ile Ala Phe Gly Ser Phe Asp Asp Ser Phe Ser Ser Ser
1               5                   10                  15
Ser Ile Lys Ala Tyr Ile Ala Glu Phe Ile Ser Thr Leu Leu Phe Val
                20                  25                  30
Phe Ala Gly Val Gly Ser Ala Ile Ala Tyr Ala Lys Leu Thr Ala Asp
            35                  40                  45
Ala Ala Leu Asp Pro Pro Gly Leu Val Ala Val Ala Val Cys His Gly
    50                  55                  60
Phe Ala Leu Phe Val Ala Val Cys Ile Ala Ala Asn Ile Cys Gly Gly
65                  70                  75                  80
His Val Asn Pro Ala Val Thr Leu Gly Leu Ala Val Gly Gly Gln Ile
                85                  90                  95
Thr Phe Leu Thr Gly Leu Phe Tyr Trp Ile Ala Gln Leu Leu Gly Ser
            100                 105                 110
Thr Val Ala Cys Phe Leu Leu Ser Phe Val Thr Gly Gly Leu Ala Val
        115                 120                 125
Pro Thr His Gly Val Ala Glu Gly Val Gly Thr Ile Gln Gly Val Val
    130                 135                 140
Phe Glu Ile Ile Ile Thr Phe Ala Met Val Tyr Thr Val Tyr Ala Thr
145                 150                 155                 160
Ala Cys Asp Pro Lys Lys Gly Ala Leu Gly Thr Ile Ala Pro Ile Ala
                165                 170                 175
Ile Gly Phe Ile Val Gly Ala Asn Ile Leu Ala Ala Gly Pro Phe Ser
            180                 185                 190
Gly Gly Ser Met Asn Pro Ala Arg Ser Phe Gly Pro Ala Val Ala Ser
        195                 200                 205
Phe Asp Phe Ser Gly His Trp Ile Tyr Trp Val Gly Pro Leu Val Gly
    210                 215                 220
Gly Gly Leu Ala Gly Leu Ile Tyr Pro Asn Val Phe Ile Ser Asn Glu
225                 230                 235                 240
His Ile Pro Leu Thr Asn Glu Tyr
                245
```

<210> SEQ ID NO 78
<211> LENGTH: 248
<212> TYPE: PRT
<213> ORGANISM: Helianthus annuus

<400> SEQUENCE: 78

```
Met Pro Gly Ile Ala Phe Gly Ser Phe Asp Asp Ser Phe Ser Ser Ser
1               5                   10                  15
Ser Ile Lys Ala Tyr Ile Ala Glu Phe Ile Ser Thr Leu Leu Phe Val
                20                  25                  30
Phe Ala Gly Val Gly Ser Ala Ile Ala Tyr Ala Lys Leu Thr Ala Asp
```

```
                35                  40                  45
Ala Ala Leu Asp Pro Ser Gly Leu Val Ala Ile Ala Val Cys His Gly
 50                  55                  60

Leu Ala Leu Phe Val Ala Val Ser Ile Ala Ala Asn Ile Ser Gly Gly
 65                  70                  75                  80

His Val Asn Pro Ala Val Thr Phe Gly Leu Ala Val Gly Gly Gln Ile
                 85                  90                  95

Thr Ile Leu Thr Gly Leu Phe Tyr Trp Ile Ala Gln Leu Leu Gly Ser
                100                 105                 110

Val Ala Ala Cys Phe Leu Leu Ser Phe Val Thr Gly Gly Leu Ala Val
                115                 120                 125

Pro Thr His Gly Val Ala Ala Gly Val Gly Val Leu Gln Gly Val Val
            130                 135                 140

Phe Glu Ile Ile Ile Thr Phe Ala Leu Val Tyr Thr Val Tyr Ala Thr
145                 150                 155                 160

Ala Cys Asp Pro Lys Lys Gly Ala Leu Gly Thr Ile Ser Pro Ile Ala
                165                 170                 175

Ile Gly Phe Ile Val Gly Ala Asn Ile Leu Ala Ala Gly Pro Phe Ser
                180                 185                 190

Gly Gly Ser Met Asn Pro Ala Arg Ser Phe Gly Pro Thr Val Ala Ala
                195                 200                 205

Phe Asp Phe Ser Gly His Trp Phe Tyr Trp Val Gly Pro Leu Ile Gly
            210                 215                 220

Gly Gly Leu Ala Gly Ala Ile Tyr Pro Asn Val Phe Ile Ser Asn Glu
225                 230                 235                 240

His Ile Pro Leu Thr Asn Asp Tyr
                245

<210> SEQ ID NO 79
<211> LENGTH: 248
<212> TYPE: PRT
<213> ORGANISM: Vernicia fordii

<400> SEQUENCE: 79

Met Ala Arg Ile Ala Phe Gly Arg Phe Asp Asp Ser Phe Ser Leu Gly
 1               5                  10                  15

Ser Phe Lys Ala Tyr Leu Ala Glu Phe Ile Ser Thr Leu Leu Tyr Val
                20                  25                  30

Phe Ala Gly Val Gly Ser Ala Ile Ala Tyr Asn Lys Leu Thr Ala Asn
                35                  40                  45

Ala Ala Leu Asp Pro Ala Gly Leu Val Ala Ile Ala Ile Cys His Gly
 50                  55                  60

Phe Ala Leu Phe Val Ala Val Ala Val Gly Ala Asn Ile Ser Gly Gly
 65                  70                  75                  80

His Val Asn Pro Ala Val Ala Phe Gly Leu Ala Leu Gly Gly Gln Ile
                 85                  90                  95

Thr Ile Leu Thr Gly Ile Phe Tyr Trp Ile Ala Gln Leu Leu Gly Ser
                100                 105                 110

Ile Val Ala Cys Phe Leu Leu Lys Leu Val Thr Gly Gly Leu Ala Ile
                115                 120                 125

Pro Thr His Ser Val Ala Gly Arg Val Gly Ala Ile Glu Gly Val Val
            130                 135                 140

Met Glu Ile Ile Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Ile Ala
```

```
                        165                 170                 175
Ile Gly Phe Ile Val Gly Ala Asn Ile Leu Ala Ala Gly Pro Phe Ser
            180                 185                 190
Gly Gly Ser Met Tyr Pro Ala Arg Ser Phe Gly Pro Ala Val Val Ser
            195                 200                 205
Gly Asp Phe His Asp Asn Trp Ile Tyr Trp Val Gly Pro Leu Ile Gly
            210                 215                 220
Gly Gly Leu Ala Gly Leu Ile Tyr Gly Asn Leu Tyr Ile Ser Gly Asp
225                 230                 235                 240
His Thr Pro Leu Ser Asn Asp Phe
                245

<210> SEQ ID NO 80
<211> LENGTH: 248
<212> TYPE: PRT
<213> ORGANISM: Daucus carota

<400> SEQUENCE: 80

Met Val Lys Leu Ala Ile Gly Ser Val Gly Asp Ser Phe Ser Ala Val
1               5                   10                  15
Ser Leu Lys Ser Tyr Leu Ala Glu Phe Ile Ala Thr Leu Leu Phe Val
            20                  25                  30
Phe Ala Gly Val Gly Ser Ala Ile Ala Tyr Gly His Leu Thr Ala Asp
            35                  40                  45
Ala Ala Leu Asp Pro Ala Gly Leu Val Ala Ile Ala Ile Ala His Ala
        50                  55                  60
Phe Ala Leu Phe Val Gly Val Ser Met Ala Ala Asn Ile Ser Gly Gly
65                  70                  75                  80
His Leu Asn Pro Ala Val Thr Leu Gly Leu Ala Ile Gly Gly Asn Ile
                85                  90                  95
Thr Ile Ile Thr Gly Leu Phe Tyr Trp Ile Ala Gln Cys Leu Gly Ser
            100                 105                 110
Thr Val Ala Cys Phe Leu Leu Lys Phe Val Thr Ala Gly Lys Ala Ile
            115                 120                 125
Pro Thr His Gly Val Gly Ala Gly Leu Gly Ala Ala Glu Gly Val Val
        130                 135                 140
Phe Glu Ile Val Ile Thr Phe Ala Leu Val Tyr Thr Val Tyr Ala Thr
145                 150                 155                 160
Ala Ala Asp Pro Lys Lys Gly Ser Leu Gly Thr Ile Ala Pro Ile Ala
                165                 170                 175
Ile Gly Phe Ile Val Gly Ala Asn Ile Leu Ala Ala Gly Pro Phe Ser
            180                 185                 190
Gly Gly Ser Met Asn Pro Ala Arg Ser Phe Gly Pro Ala Val Ala Ser
            195                 200                 205
Phe Asp Phe Ser Gly His Trp Ile Tyr Trp Val Gly Pro Leu Ile Gly
        210                 215                 220
Gly Gly Leu Ala Gly Leu Val Tyr Gly Asp Val Phe Ile Gly Ser Tyr
225                 230                 235                 240
Ala Pro Ile Ala Glu Asp Tyr Ala
                245

<210> SEQ ID NO 81
<211> LENGTH: 250
<212> TYPE: PRT
<213> ORGANISM: Antirrhinum majus

<400> SEQUENCE: 81
```

-continued

Met Val Lys Ile Ala Phe Gly Ser Ile Gly Asp Ser Phe Ser Val Ala
1               5                   10                  15

Ser Ile Lys Ala Tyr Val Ala Glu Phe Ile Ala Thr Leu Leu Phe Val
                20                  25                  30

Phe Ala Gly Val Gly Ser Ala Ile Ala Tyr Asn Lys Leu Thr Ser Asp
            35                  40                  45

Ala Ala Leu Asp Pro Ala Gly Leu Val Ala Val Ala His Ala
        50                  55                  60

Phe Ala Leu Phe Val Gly Val Ser Met Ala Ala Asn Val Ser Gly Gly
65                  70                  75                  80

His Leu Asn Pro Ala Val Thr Leu Gly Leu Ala Val Gly Gly Asn Ile
                85                  90                  95

Thr Ile Leu Thr Gly Leu Phe Tyr Trp Ile Ala Gln Cys Leu Gly Ser
                100                 105                 110

Thr Val Ala Cys Leu Leu Leu Lys Phe Val Thr Asn Gly Leu Ser Val
                115                 120                 125

Pro Thr His Gly Val Ala Ala Gly Met Asp Ala Ile Gln Gly Val Val
            130                 135                 140

Met Glu Ile Ile Ile Thr Phe Ala Leu Val Tyr Thr Val Tyr Ala Thr
145                 150                 155                 160

Ala Ala Asp Pro Lys Lys Gly Ser Leu Gly Val Ile Ala Pro Ile Ala
                165                 170                 175

Ile Gly Phe Ile Val Gly Ala Asn Ile Leu Ala Ala Gly Pro Phe Ser
            180                 185                 190

Gly Gly Ser Met Asn Pro Ala Arg Ser Phe Gly Pro Ala Val Ala Ser
        195                 200                 205

Gly Asp Phe Ser Gln Asn Trp Ile Tyr Trp Ala Gly Pro Leu Ile Gly
    210                 215                 220

Gly Ala Leu Ala Gly Phe Ile Tyr Gly Asp Val Phe Ile Thr Ala His
225                 230                 235                 240

Ala Pro Leu Pro Thr Ser Glu Asp Tyr Ala
                245                 250

<210> SEQ ID NO 82
<211> LENGTH: 250
<212> TYPE: PRT
<213> ORGANISM: Nicotiana tabacum

<400> SEQUENCE: 82

Met Val Arg Ile Ala Phe Gly Ser Ile Gly Asp Ser Phe Ser Val Gly
1               5                   10                  15

Ser Leu Lys Ala Tyr Val Ala Glu Phe Ile Ala Thr Leu Leu Phe Val
                20                  25                  30

Phe Ala Gly Val Gly Ser Ala Ile Ala Tyr Asn Lys Leu Thr Ala Asp
            35                  40                  45

Ala Ala Leu Asp Pro Ala Gly Leu Val Ala Val Ala Val Ala His Ala
        50                  55                  60

Phe Ala Leu Phe Val Gly Val Ser Ile Ala Ala Asn Ile Ser Gly Gly
65                  70                  75                  80

His Leu Asn Pro Ala Val Thr Leu Gly Leu Ala Val Gly Gly Asn Ile
                85                  90                  95

Thr Ile Leu Thr Gly Phe Phe Tyr Trp Ile Ala Gln Leu Leu Gly Ser
                100                 105                 110

Thr Val Ala Cys Leu Leu Leu Lys Tyr Val Thr Asn Gly Leu Ala Val
                115                 120                 125

```
Pro Thr His Gly Val Ala Ala Gly Leu Asn Gly Leu Gln Gly Val Val
        130                 135                 140

Met Glu Ile Ile Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Ile Ala
                165                 170                 175

Ile Gly Phe Ile Val Gly Ala Asn Ile Leu Ala Ala Gly Pro Phe Ser
                180                 185                 190

Gly Gly Ser Met Asn Pro Ala Arg Ser Phe Gly Pro Ala Val Val Ala
            195                 200                 205

Gly Asp Phe Ser Gln Asn Trp Ile Tyr Trp Ala Gly Pro Leu Ile Gly
        210                 215                 220

Gly Gly Leu Ala Gly Phe Ile Tyr Gly Asp Val Phe Ile Gly Cys His
225                 230                 235                 240

Thr Pro Leu Pro Thr Ser Glu Asp Tyr Ala
                245                 250

<210> SEQ ID NO 83
<211> LENGTH: 250
<212> TYPE: PRT
<213> ORGANISM: Helianthus annuus

<400> SEQUENCE: 83

Met Val Lys Leu Ala Ile Gly Ser Ile Gly Asp Ser Leu Ser Ala Gly
1               5                   10                  15

Ser Ile Lys Ser Tyr Leu Ala Glu Phe Ile Ala Thr Leu Leu Phe Val
                20                  25                  30

Phe Ala Gly Val Gly Ser Ala Ile Ala Tyr Gly Lys Leu Thr Thr Asp
            35                  40                  45

Ala Ala Leu Asp Pro Ala Gly Leu Val Ala Ile Ala Ile Ala His Ala
        50                  55                  60

Phe Ala Leu Phe Val Gly Val Ser Met Ala Ala Asn Ile Ser Gly Gly
65                  70                  75                  80

His Leu Asn Pro Ala Val Thr Phe Gly Leu Ala Ile Gly Gly Asn Ile
                85                  90                  95

Thr Ile Ile Thr Gly Leu Phe Tyr Trp Ile Ala Gln Cys Leu Gly Ser
                100                 105                 110

Ile Val Ala Cys Phe Leu Leu Gln Phe Val Thr Gly Gly Leu Ala Val
            115                 120                 125

Pro Thr His Gly Val Ala Asp Gly Met Asn Gly Val Gln Gly Val Val
        130                 135                 140

Met Glu Ile Ile Ile Thr Phe Ala Leu Val Tyr Thr Val Tyr Ala Thr
145                 150                 155                 160

Ala Val Asp Pro Lys Lys Gly Ser Leu Gly Thr Ile Ala Pro Met Ala
                165                 170                 175

Ile Gly Phe Ile Val Gly Ala Asn Ile Leu Ala Ala Gly Pro Phe Ser
                180                 185                 190

Gly Gly Ser Met Asn Pro Ala Arg Ser Phe Gly Pro Ala Val Val Ser
            195                 200                 205

Gly Asp Phe Ser Gln Asn Trp Ile Tyr Trp Val Gly Pro Leu Ile Gly
        210                 215                 220

Gly Gly Leu Ala Gly Phe Ile Phe Gly Asp Val Phe Ile Gly Ser Tyr
225                 230                 235                 240

Glu Thr Leu Pro Asp Ser Gly Asp Tyr Ala
                245                 250
```

<210> SEQ ID NO 84
<211> LENGTH: 250
<212> TYPE: PRT
<213> ORGANISM: Solanum tuberosum

<400> SEQUENCE: 84

Met Val Arg Ile Ala Phe Gly Ser Ile Gly Asp Ser Leu Ser Val Gly
1               5                   10                  15

Ser Leu Lys Ala Tyr Leu Ala Glu Phe Ile Ala Thr Leu Leu Phe Val
            20                  25                  30

Phe Ala Gly Val Gly Ser Ala Ile Ala Tyr Asn Lys Leu Thr Ser Asp
        35                  40                  45

Ala Ala Leu Asp Pro Ala Gly Leu Val Ala Ile Ala Val Ala His Ala
    50                  55                  60

Phe Ala Leu Phe Val Gly Val Ser Met Ala Ala Asn Ile Ser Gly Gly
65                  70                  75                  80

His Leu Asn Pro Ala Val Thr Leu Gly Leu Ala Val Gly Gly Asn Ile
                85                  90                  95

Thr Thr Leu Thr Gly Leu Phe Tyr Trp Val Ala Gln Leu Leu Gly Ser
            100                 105                 110

Thr Val Ala Cys Leu Leu Lys Tyr Val Thr Asn Gly Leu Ala Val
        115                 120                 125

Pro Thr His Gly Val Ala Ala Gly Met Asn Gly Ala Glu Gly Val Val
    130                 135                 140

Met Glu Ile Val Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Ile Ala
                165                 170                 175

Ile Gly Phe Ile Val Gly Ala Asn Ile Leu Ala Ala Gly Pro Phe Ser
            180                 185                 190

Gly Gly Ser Met Asn Pro Ala Arg Ser Phe Gly Pro Ala Val Val Ala
        195                 200                 205

Gly Asp Phe Ser Gln Asn Trp Ile Tyr Trp Val Gly Pro Leu Ile Gly
    210                 215                 220

Gly Gly Leu Ala Gly Phe Ile Tyr Gly Asp Val Phe Ile Gly Ser His
225                 230                 235                 240

Thr Pro Leu Pro Thr Ser Glu Asp Tyr Ala
                245                 250

<210> SEQ ID NO 85
<211> LENGTH: 250
<212> TYPE: PRT
<213> ORGANISM: Nicotiana tabacum

<400> SEQUENCE: 85

Met Val Leu Ile Ala Phe Gly Ser Ile Gly Asp Ser Phe Ser Val Gly
1               5                   10                  15

Ser Leu Lys Ala Tyr Val Ala Glu Phe Ile Ala Thr Leu Leu Phe Val
            20                  25                  30

Phe Ala Gly Val Gly Ser Ala Ile Ala Tyr Asn Lys Leu Thr Ala Asp
        35                  40                  45

Ala Ala Leu Asp Pro Ala Gly Leu Val Ala Val Ala Val Ala His Ala
    50                  55                  60

Phe Ala Leu Phe Val Gly Val Ser Ile Ala Ala Asn Ile Ser Gly Gly
65                  70                  75                  80

His Leu Asn Pro Ala Val Thr Leu Gly Leu Ala Val Gly Gly Asn Ile
                85                  90                  95

Thr Ile Leu Thr Gly Phe Phe Tyr Trp Ile Ala Gln Leu Leu Gly Ser
            100                 105                 110

Thr Val Ala Cys Leu Leu Lys Tyr Val Thr Asn Gly Leu Ala Val
        115                 120                 125

Pro Thr His Gly Val Ala Ala Gly Leu Asn Gly Phe Gln Gly Val Val
        130                 135                 140

Met Glu Ile Ile Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Ile Ala
                165                 170                 175

Ile Gly Phe Ile Val Gly Ala Asn Ile Leu Ala Ala Gly Pro Phe Ser
            180                 185                 190

Gly Gly Ser Met Asn Pro Ala Arg Ser Phe Gly Pro Ala Val Val Ala
        195                 200                 205

Gly Asp Phe Ser Gln Asn Trp Ile Tyr Trp Ala Gly Pro Leu Ile Gly
        210                 215                 220

Gly Gly Leu Ala Gly Phe Ile Tyr Gly Asp Val Phe Ile Gly Cys His
225                 230                 235                 240

Thr Pro Leu Pro Thr Ser Glu Asp Tyr Ala
                245                 250

<210> SEQ ID NO 86
<211> LENGTH: 250
<212> TYPE: PRT
<213> ORGANISM: Lycopersicon esculentum

<400> SEQUENCE: 86

Met Val Arg Ile Ala Phe Gly Ser Ile Gly Asp Ser Leu Ser Val Gly
1               5                   10                  15

Ser Leu Lys Ala Tyr Leu Ala Glu Phe Ile Ala Thr Leu Leu Phe Val
            20                  25                  30

Phe Ala Gly Val Gly Ser Ala Ile Ala Phe Asn Lys Leu Thr Ser Gly
        35                  40                  45

Ala Ala Leu Asp Pro Ala Gly Leu Val Ala Ile Ala Val Ala His Ala
    50                  55                  60

Phe Ala Leu Phe Val Gly Val Ser Met Ala Ala Asn Ile Ser Gly Gly
65                  70                  75                  80

His Leu Asn Pro Ala Val Thr Leu Gly Leu Ala Val Gly Gly Asn Ile
                85                  90                  95

Thr Ile Leu Thr Gly Leu Phe Tyr Trp Val Ala Gln Leu Leu Gly Ser
            100                 105                 110

Thr Val Ala Cys Leu Leu Lys Tyr Val Thr Asn Gly Leu Ala Val
        115                 120                 125

Pro Thr His Gly Val Ala Ala Gly Met Ser Gly Ala Glu Gly Val Val
        130                 135                 140

Met Glu Ile Val Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Ile Ala
                165                 170                 175

Ile Gly Phe Ile Val Gly Ala Asn Ile Leu Ala Ala Gly Pro Phe Ser
            180                 185                 190

Gly Gly Ser Met Asn Pro Ala Arg Ser Phe Gly Pro Ala Val Val Ala
        195                 200                 205

Gly Asp Phe Ser Gln Asn Trp Ile Tyr Trp Val Gly Pro Leu Ile Gly
             210                 215                 220

Gly Gly Leu Ala Gly Phe Ile Tyr Gly Asp Val Phe Ile Gly Cys His
225                 230                 235                 240

Thr Pro Leu Pro Thr Ser Glu Asp Tyr Ala
                245                 250

<210> SEQ ID NO 87
<211> LENGTH: 234
<212> TYPE: PRT
<213> ORGANISM: Arabidopsis thaliana

<400> SEQUENCE: 87

Met Val Ser Pro Glu Asn Ala Asn Trp Ile Cys Asp Leu Ile Asp Ala
1               5                   10                  15

Asp Tyr Gly Ser Phe Thr Ile Gln Gly Pro Gly Phe Ser Trp Pro Val
                20                  25                  30

Gln Gln Pro Ile Gly Val Ser Ser Asn Ser Ser Ala Gly Val Asp Gly
            35                  40                  45

Ser Ala Gly Asn Ser Glu Ala Ser Lys Glu Pro Gly Ser Lys Lys Arg
50                  55                  60

Gly Arg Cys Glu Ser Ser Ala Thr Ser Ser Lys Ala Cys Arg Glu
65                  70                  75                  80

Lys Gln Arg Arg Asp Arg Leu Asn Asp Lys Phe Met Glu Leu Gly Ala
                85                  90                  95

Ile Leu Glu Pro Gly Asn Pro Pro Lys Thr Asp Lys Ala Ala Ile Leu
            100                 105                 110

Val Asp Ala Val Arg Met Val Thr Gln Leu Arg Gly Glu Ala Gln Lys
        115                 120                 125

Leu Lys Asp Ser Asn Ser Ser Leu Gln Asp Lys Ile Lys Glu Leu Lys
130                 135                 140

Thr Glu Lys Asn Glu Leu Arg Asp Glu Lys Gln Arg Leu Lys Thr Glu
145                 150                 155                 160

Lys Glu Lys Leu Glu Gln Gln Leu Lys Ala Met Asn Ala Pro Gln Pro
                165                 170                 175

Ser Phe Phe Pro Ala Pro Pro Met Met Pro Thr Ala Phe Ala Ser Ala
            180                 185                 190

Gln Gly Gln Ala Pro Gly Asn Lys Met Val Pro Ile Ile Ser Tyr Pro
        195                 200                 205

Gly Val Ala Met Trp Gln Phe Met Pro Pro Ala Ser Val Asp Thr Ser
    210                 215                 220

Gln Asp His Val Leu Arg Pro Pro Val Ala
225                 230

<210> SEQ ID NO 88
<211> LENGTH: 234
<212> TYPE: PRT
<213> ORGANISM: Arabidopsis thaliana

<400> SEQUENCE: 88

Met Val Ser Pro Glu Asn Ala Asn Trp Ile Cys Asp Leu Ile Asp Ala
1               5                   10                  15

Asp Tyr Gly Ser Phe Thr Ile Gln Gly Pro Gly Phe Ser Trp Pro Val
                20                  25                  30

Gln Gln Pro Ile Gly Val Ser Ser Asn Ser Ser Ala Gly Val Asp Gly
            35                  40                  45

Ser Ala Gly Asn Ser Glu Ala Ser Lys Glu Pro Gly Ser Lys Lys Arg

```
            50                  55                  60
Gly Arg Cys Glu Ser Ser Ala Thr Ser Ser Lys Ala Cys Arg Glu
 65                  70                  75                  80

Lys Gln Arg Arg Asp Arg Leu Asn Asp Lys Phe Met Glu Leu Gly Ala
                 85                  90                  95

Ile Leu Glu Pro Gly Asn Pro Pro Lys Thr Asp Lys Ala Ala Ile Leu
                100                 105                 110

Val Asp Ala Val Arg Met Val Thr Gln Leu Arg Gly Glu Ala Gln Lys
                115                 120                 125

Leu Lys Asp Ser Asn Ser Ser Leu Gln Asp Lys Ile Lys Glu Leu Lys
            130                 135                 140

Thr Glu Lys Asn Glu Leu Arg Asp Glu Lys Gln Arg Leu Lys Thr Glu
145                 150                 155                 160

Lys Glu Lys Leu Glu Gln Gln Leu Lys Ala Ile Asn Ala Pro Gln Pro
                165                 170                 175

Ser Phe Phe Pro Ala Pro Pro Met Met Pro Thr Ala Phe Ala Ser Ala
                180                 185                 190

Gln Gly Gln Ala Pro Gly Asn Lys Met Val Pro Ile Ile Ser Tyr Pro
            195                 200                 205

Gly Val Ala Met Trp Gln Phe Met Pro Pro Ala Ser Val Asp Thr Ser
            210                 215                 220

Gln Asp His Val Leu Arg Pro Pro Val Ala
225                 230
```

```
<210> SEQ ID NO 89
<211> LENGTH: 216
<212> TYPE: PRT
<213> ORGANISM: Oryza sativa

<400> SEQUENCE: 89

Cys Gly Ala Phe Pro Trp Asp Ala Ser Pro Ser Cys Ser Asn Pro Ser
 1               5                  10                  15

Val Glu Val Ser Ser Tyr Val Asn Thr Thr Ser Tyr Val Leu Lys Glu
                20                  25                  30

Pro Gly Ser Asn Lys Arg Val Arg Ser Gly Ser Cys Gly Arg Pro Thr
            35                  40                  45

Ser Lys Ala Ser Arg Glu Lys Ile Arg Arg Asp Lys Met Asn Asp Arg
 50                  55                  60

Phe Leu Glu Leu Gly Thr Thr Leu Glu Pro Gly Lys Pro Val Lys Ser
 65                  70                  75                  80

Asp Lys Ala Ala Ile Leu Ser Asp Ala Thr Arg Met Val Ile Gln Leu
                 85                  90                  95

Arg Ala Glu Ala Lys Gln Leu Lys Asp Thr Asn Glu Ser Leu Glu Asp
                100                 105                 110

Lys Ile Lys Glu Leu Lys Ala Glu Lys Asp Glu Leu Arg Asp Glu Lys
            115                 120                 125

Gln Lys Leu Lys Val Glu Lys Glu Thr Leu Glu Gln Gln Val Lys Ile
        130                 135                 140

Leu Thr Ala Thr Pro Ala Tyr Met Pro His Pro Thr Leu Met Pro Ala
145                 150                 155                 160

Pro Tyr Pro Gln Ala Pro Leu Ala Pro Phe His His Ala Gln Gly Gln
                165                 170                 175

Ala Ala Gly Gln Lys Leu Met Met Pro Phe Val Gly Tyr Pro Gly Tyr
            180                 185                 190

Pro Met Trp Gln Phe Met Pro Pro Ser Glu Val Asp Thr Ser Lys Asp
```

```
                195                 200                 205
Ser Glu Ala Cys Pro Val Ala
    210                 215

<210> SEQ ID NO 90
<211> LENGTH: 226
<212> TYPE: PRT
<213> ORGANISM: Arabidopsis thaliana

<400> SEQUENCE: 90

Met Val Ser Pro Glu Asn Thr Asn Trp Leu Ser Asp Tyr Pro Leu Ile
1               5                   10                  15

Glu Gly Ala Phe Ser Asp Gln Asn Pro Thr Phe Pro Trp Gln Ile Asp
            20                  25                  30

Gly Ser Ala Thr Val Ser Val Glu Val Asp Gly Phe Leu Cys Asp Ala
        35                  40                  45

Asp Val Ile Lys Glu Pro Ser Ser Arg Lys Arg Ile Lys Thr Glu Ser
    50                  55                  60

Cys Thr Gly Ser Asn Ser Lys Ala Cys Arg Glu Lys Gln Arg Arg Asp
65                  70                  75                  80

Arg Leu Asn Asp Lys Phe Thr Glu Leu Ser Val Leu Glu Pro Gly
                85                  90                  95

Arg Thr Pro Lys Thr Asp Lys Val Ala Ile Ile Asn Asp Ala Ile Arg
            100                 105                 110

Met Val Asn Gln Ala Arg Asp Glu Ala Gln Lys Leu Lys Asp Leu Asn
        115                 120                 125

Ser Ser Leu Gln Glu Lys Ile Lys Glu Leu Lys Asp Glu Lys Asn Glu
    130                 135                 140

Leu Arg Asp Glu Lys Gln Lys Leu Lys Val Glu Lys Gly Arg Ile Asp
145                 150                 155                 160

Gln Gln Leu Lys Ala Ile Lys Thr Gln Pro Gln Pro Gln Pro Cys Phe
                165                 170                 175

Leu Pro Asn Pro Gln Thr Leu Ser Gln Ala Gln Ala Pro Gly Ser Lys
            180                 185                 190

Leu Val Pro Phe Thr Thr Tyr Pro Gly Phe Ala Met Trp Gln Phe Met
        195                 200                 205

Pro Pro Ala Ala Val Asp Thr Ser Gln Asp His Val Leu Arg Pro Pro
    210                 215                 220

Val Ala
225

<210> SEQ ID NO 91
<211> LENGTH: 256
<212> TYPE: PRT
<213> ORGANISM: Oryza sativa

<400> SEQUENCE: 91

Met Ala Ser Pro Glu Gly Ser Thr Trp Val Phe Asp Cys Pro Leu Met
1               5                   10                  15

Asp Asp Leu Ala Ala Ala Ala Gly Phe Asp Ala Ala Pro Ala Gly Gly
            20                  25                  30

Phe Tyr Trp Thr Thr Pro Ala Pro Gln Ala Ala Leu Gln Pro Pro
            35                  40                  45

Pro Pro Gln Gln Gln Pro Val Ala Pro Ala Thr Ala Ala Pro Asn Ala
    50                  55                  60

Cys Ala Glu Ile Asn Gly Ser Val Asp Cys Glu His Gly Lys Glu Gln
65                  70                  75                  80
```

```
Pro Thr Asn Lys Arg Pro Arg Ser Glu Ser Gly Thr Arg Pro Ser Ser
                85                  90                  95
Lys Ala Cys Arg Glu Lys Val Arg Arg Asp Lys Leu Asn Glu Arg Phe
            100                 105                 110
Leu Glu Leu Gly Ala Val Leu Glu Pro Gly Lys Thr Pro Lys Met Asp
        115                 120                 125
Lys Ser Ser Ile Leu Asn Asp Ala Ile Arg Val Met Ala Glu Leu Arg
130                 135                 140
Ser Glu Ala Gln Lys Leu Lys Glu Ser Asn Glu Ser Leu Gln Glu Lys
145                 150                 155                 160
Ile Lys Glu Leu Lys Ala Glu Lys Asn Glu Leu Arg Asp Glu Lys Gln
                165                 170                 175
Lys Leu Lys Ala Glu Lys Glu Ser Leu Glu Gln Gln Ile Lys Phe Leu
            180                 185                 190
Asn Ala Arg Pro Ser Phe Val Pro His Pro Val Ile Pro Ala Ser
        195                 200                 205
Ala Phe Thr Ala Pro Gln Gly Gln Ala Gly Gln Lys Leu Met Met
    210                 215                 220
Pro Val Ile Gly Tyr Pro Gly Phe Pro Met Trp Gln Phe Met Pro Pro
225                 230                 235                 240
Ser Asp Val Asp Thr Thr Asp Thr Lys Ser Cys Pro Pro Val Ala
                245                 250                 255

<210> SEQ ID NO 92
<211> LENGTH: 253
<212> TYPE: PRT
<213> ORGANISM: Oryza sativa

<400> SEQUENCE: 92

Met Ser Gly Thr Pro Ala Asp Gly Gly Gly Gly Gly Gly Gly Gly
1               5                   10                  15
Gly Gly Ser Gly Asp Asp Trp Phe Leu Asp Cys Gly Ile Leu Glu Asp
            20                  25                  30
Leu Pro Ala Ala Ala Cys Gly Ala Phe Pro Trp Asp Ala Ser Pro Ser
        35                  40                  45
Cys Ser Asn Pro Ser Val Glu Val Ser Ser Tyr Val Asn Thr Thr Ser
    50                  55                  60
Tyr Val Leu Lys Glu Pro Gly Ser Asn Lys Arg Val Arg Ser Gly Ser
65                  70                  75                  80
Cys Gly Arg Pro Thr Ser Lys Ala Ser Arg Glu Lys Ile Arg Arg Asp
                85                  90                  95
Lys Met Asn Asp Arg Phe Leu Glu Leu Gly Thr Thr Leu Glu Pro Gly
            100                 105                 110
Lys Pro Val Lys Ser Asp Lys Ala Ala Ile Leu Ser Asp Ala Thr Arg
        115                 120                 125
Met Val Ile Gln Leu Arg Ala Glu Ala Lys Gln Leu Lys Asp Thr Asn
    130                 135                 140
Glu Ser Leu Glu Asp Lys Ile Lys Glu Leu Lys Ala Glu Lys Asp Glu
145                 150                 155                 160
Leu Arg Asp Glu Lys Gln Lys Leu Lys Val Glu Lys Glu Thr Leu Glu
                165                 170                 175
Gln Gln Val Lys Ile Leu Thr Ala Thr Pro Ala Tyr Met Pro His Pro
            180                 185                 190
Thr Leu Met Pro Ala Pro Tyr Pro Gln Ala Pro Leu Ala Pro Phe His
        195                 200                 205
```

```
His Ala Gln Gly Gln Ala Ala Gly Gln Lys Leu Met Met Pro Phe Val
    210                 215                 220

Gly Tyr Pro Gly Tyr Pro Met Trp Gln Phe Met Pro Pro Ser Glu Val
225                 230                 235                 240

Asp Thr Ser Lys Asp Ser Glu Ala Cys Pro Pro Val Ala
            245                 250
```

```
<210> SEQ ID NO 93
<211> LENGTH: 1037
<212> TYPE: DNA
<213> ORGANISM: Sorghum bicolor

<400> SEQUENCE: 93
acggtaacag agcaatttca gatcagtaga tgcgaacaaa aaccttgctc actcttctct      60
catttcatag cggaaagtaa ccaaagcgga cagtaacatc atcgaacacg ggggtaccaa     120
cacctaatcc aaaggttcaa cggacactaa cacatgggta actcagaatc caacggaacg     180
gtaacacgat actatagata gatagatagc taggataact tggccgaagc cagggtgggc     240
ccacacaatc agttctcgca ctcgcgcgcc tttcccattc gcgccgccgc cgccgccgct     300
gcaagcgcca gctcgccgtc gtccgagcca aacaccccaa cgccgccatg ggcgtatgc      360 acagccgcgg gaagggtatc tcgtcgtcgg cgctgccgta caagaggacg ccgccgacct     420
ggctcaagac cgccgcctcc gacgtggagg agatgatcac taaggcggcg aagaagggtc     480
agatgccgtc gcagatcggc gtcctgctcc gtgaccagca cggtatcccc cttgtcaaga     540
gcgtcacggg cagcaagatc ctccgcatcc tcaaggccca tgggctggcg ccagaaatcc     600
cggaggacct ctacttcctc atcaagaagg cggtggcgat aaggaagcac cttgagagga     660
acaggaagga caaagactcc aaattcaggc tcattcttgt tgagagcagg atccaccgcc     720
ttgcccgcta ctacaagcgc acaaagaagc ttccacccac ctggaagtat gagtcaacca     780
ccgcaagcac tctggtggcc taagtgagga gctcaacatt aggtgcttga agctgggcta     840
ttcttggaat cattttatg taccgtttta tgagtttgga gtgaactaga gatcttgaat     900
gtcctgtgga ggatgccata aaccttttg gttacataga actgcctgtt gttaactttt     960
gctactcggc atccagattt tgtcagctat aatatgatca tttacattac atggtttgcc    1020
cctaccttcc tgcagtc                                                   1037
```

```
<210> SEQ ID NO 94
<211> LENGTH: 1346
<212> TYPE: DNA
<213> ORGANISM: Sorghum bicolor

<400> SEQUENCE: 94
aagagaagag cagcagcagc aacagccgcg ccatccgctt gcttccttcc ttcctcttct      60
ctccctccta ccccaccgcc ggcgtcgcct cttcgcgttg cgcgccctcg cgtcgcaccc     120
gtgggtagca gccgcgtacc taccaacctg cgtgctgccg ggggagctct gcacgtctcc     180
tgtcgcctcg cctctcggca tggacgccgg gggagagaag ttcagcgacg cggcggcggc     240
ggagggcggt gagggcggcg gcgacctcta cgccgtcctc gggctcaaga aggagtgctc     300
cgacgccgac ctcaaggtcg cttaccggaa gctcgccaag aaatggcacc cggacaaatg     360
ctcctcctcc agcagcgtga acacatgga ggaagccaag gagaagttcc aagagatcca      420
gggcgcctat tccgtactct ctgacgccaa taaacggctc ctctacgatg ttggagtata     480
cgacgatgag gacgacgagg atagcatgca ggggatgggt gacttcattg gtgagatggc     540
```

```
ccagatgatg agccaggtgc ggccgacgag gcaggaaagc tttgaggagc tgcagcagct      600
ttttgtggac atgttccagt ctgatattga ttcaggattc tgcaacgggt ctgctaagga      660
tcaagttcag gggcaagcca aaagtagaac atgctcgacc tcaccttcat catcaccgtc      720
cccacctcct cctcctacta tagtaaagga ggcagaggtg tcatcatgta atggcttcaa      780
taagcggggt tcatcagcaa tggactcagg gaagcctcca aggcctgttg aaggcggtgc      840
tggtcaggct ggattttgtt ttggggtgag cgatacgaag caaacgccga agccgagagg      900
tccgaacacc agccggagga ggaacggccg gaaacagaag ctgtcatcca agcacgatgt      960
ttcatctgaa gatgaaacgg ccggttccta gcaccagcag ctacggtagc agtttgacct     1020
gtggctttgg tgatatcatt cgttggtcct tggcggtgcc gagggcccta gtagccagca     1080
gcggcaggga ggcacagcat gtcgcttctg ctagctgctg tgatctgaag aggcgtttag     1140
ctcatcatat gccttacctt aggcctgtga gggacttcca ttgaaactcg tcgaggatac     1200 tgcattttc tttctccatc tgtgtcggtt gtgttgtaca atacattgag tgacttctaa      1260
tcgattcttt tttttttacca ttaattaaca tctggtatat ccgattgatc gatccctagc    1320
cactgattac atgcatgagt tctttg                                          1346

<210> SEQ ID NO 95
<211> LENGTH: 1623
<212> TYPE: DNA
<213> ORGANISM: Sorghum bicolor

<400> SEQUENCE: 95
gcacgaggcc ctcttccgcc tcctctctct ctctctctct ctctcggctc tcgctctcag       60
acgactgctg ggcagccgcc gccctaggcc aggtgctgag gctttccctg gtctcttcgc      120
cgtcgacgag cacccaccag taggtacttg attggacgag ccatggacag cctgtggcat      180 ctggggacg agctccgtgg gcaaccgaag gtggtggagg accgccagtg gtcgctcatg       240
acgtccaagc tggcggagat caccaggtcc aaggggcgaga ggatgaacga cctcgactac     300
gccaggatga caccgtcccc tgacgccaag cagtgggaca agacgtcctt ccagcatcat      360
gaccagagca ggatggacca catcaatctc ggcctcatga acctggatct caagatgaac     420
gatctcaaga tgaacgaggc ccccaccgcc atgaagctcc ccttccacaa catgccctat      480
aacatgaacc caatgtaccc caaggggagc aatgccaatg tcaatgtcaa tgcgttcaag     540
atgaatgttg gggtgaacaa gtactccaat agtcctaacg ggaaagacgc caatgggaaa     600
aacaatggcg gcagcaacaa caatggagga acagcaatg ggagcgcaaa cggcaattct      660
gcagttgaca agcgcttcaa gacattgcca acaagtgaga tgctaccgag gaatgaagtc     720
cttggtggat acatctttgt ctgcaacaac gataccatgc aggaggatct caagaggcag     780 cttttttggat tgccagcaag atatcgtgat tcagtccgag caattactcc tggcctgcct     840
cttttcctct ataactacac aacccaccag cttcatgggg tatttgaggc tgccagcttt     900
ggtgggtcta atatcgatcc cactgcatgg gaggataaga agtgtaaagg tgaatctaga     960
ttcccagctc aggtgaggat ccgcattagg aagctttgca agccgttgga agaggattcc    1020
ttcaggccag ttttgcacca ttatgatggc ccaaagtttc gccttgagct ctctatcgcg    1080
gagaccttgt cgctgctaga cctatgtgag aaggaaggta tctgagctgt tgggaggtg     1140 gttgccttgt gagcttctag taaatatcaa tcatccttgt atgttttgtg gatggtggtt    1200
ggttggcaat gttgtttatt ttagcgaaag ctgctgctgg ttttgttttc cctaccctgg    1260
atgaaagcaa ggacctggta cttggaaggc cccctcaaac aagctgtgag cctgtcagtg    1320
```

| | |
|---|---:|
| tactgcgttg tgtctgtcgt cgtcaagaac caaaccaatc ttggaccgac tgagagttgg | 1380 |
| agtgtgtatg ttttgctgtc tatctacatg tgttagtaga gtgggtatac ctgggcagaa | 1440 |
| tgggtcctca aaagatgggg ggcctatctg tatactatgt gtaatggtta agatgcatgc | 1500 |
| ggccctaagt aagggctggt gatgtcgatg ctggtgctcc tggtgtgtat tttgtactct | 1560 |
| gttgtacctt gaacctcctt tgcatttgcc ttaatgctgc tgcttttttgc actgtcaaaa | 1620 |
| aaa | 1623 |

<210> SEQ ID NO 96
<211> LENGTH: 1726
<212> TYPE: DNA
<213> ORGANISM: Sorghum bicolor

<400> SEQUENCE: 96

| | |
|---|---:|
| aaaaattccc tgcactttat ttcatttaca tcggtggttg tatcttgcac acggttcatt | 60 |
| taccatacat acatccaaac tttcctcatc aattttttcgt cgtcaggtac ttctaataaa | 120 |
| taccaaaaac ctcgggggca gctcctcttc actgccatga ttttggaagt cgccgcagta | 180 |
| gaaactcaaa gtattgtgca cctgttcaag ccaagagacg agaagatcct cctcgcagaa | 240 |
| ggccacaagc ggccaagaag cccaggcctc tcttcctcga aggcgtactc tggttctctg | 300 |
| gtcggactat ccattgtatt tgcacctcta tcagcacttg ttgcctcatc agagcccatg | 360 |
| tcccacccct ctcctcctcc tgttgatcaa aatatctcgc tgcgcttttg cgagtccttt | 420 |
| tccctccaag gaacagaaac acccggcgct tttaccccac ccgcacccgc tttcccctcc | 480 |
| cggccaagaa caggagcaac aacaaggctc ctcctcgaga cattccattc atccatggcg | 540 |
| aagctcgtga acaagctggt cgattcgttc gaggagcaag acaccccgga cgtcggctgc | 600 |
| gtgcgcgccg tgctggccga gctcgtcctc accttcctct tcgtcttcac cggcgtctcc | 660 |
| gccgccatgg ccgccgggtc cggcgtgaag cccggcgagg ctatgccgat ggcgacgctg | 720 |
| gcggcggtgg caatcgcgca cgcgctggca gccggcgtac tggtgacggc cgggttccac | 780 |
| gtctccggcg gccacctcaa ccccgccgtg acggtggggc tcatggtgcg cggccacatc | 840 |
| accaagctcc gggcggtgct ctacgtcgcc gcgcaggtgc tggcgtcctc cctcgcctgc | 900 |
| atcctgctcc gctacctcag cggcggcatg gtgaccccgg tgcacgcccct tggcgcgggc | 960 |
| atcagcccga tgcagggcct ggtgatggag gtgatcctca ccttctccct gctcttcgtc | 1020 |
| acctacgcca tgatcctgga cccacggagc caggtccgca ccatcggccc gctgctgacc | 1080 |
| ggcctcatcg ttggtgccaa cagcctcgcc ggtgcaact tcagcggcgc gtccatgaac | 1140 |
| ccggcacggt ccttcgggcc agccctggcc agcggggtct ggacaaacca ctggatctac | 1200 |
| tggatcggcc cgctgcttgg cgggcccctg gccgggttca tctacgagtc tttgttcatt | 1260 |
| gtgaacaaga cgcacgagcc gctgctcaat ggagacatct gacgaaccat cggcctgccc | 1320 |
| tgtggctgtg ggcagggcag tcagcatggt tggttcatgc ttgtttctgt aaaatagttc | 1380 |
| attgtctaca agcatgatgg atacatatat tggtcaaggt aattagagag ggttgctgta | 1440 |
| aaatagttac cctggtatag gattgttgga tgtagaaatt gttgatgggc tttgtatttt | 1500 |
| tttccccctt ttcatgccaa ggaattcttt ttttttttaga gggcggggtt ctgtcaagga | 1560 |
| tttgttaagg ctattagtag ttagccatgt agtagaaaac tagagaatgg tatacgtggg | 1620 |
| agtgggacct gaagtttttt caggtacact gtagtactat tgtaatttg tcttgaagat | 1680 |
| ggaattggat gtacagagta aaacttctc tttcaagcag taaaaaa | 1726 |

<210> SEQ ID NO 97

```
<211> LENGTH: 1097
<212> TYPE: DNA
<213> ORGANISM: Sorghum bicolor

<400> SEQUENCE: 97
gcatcagcct gataagctat agccagccat cttctctgaa ttccaactca gtccaagggc      60
tggaagcttg aagtaccgtc agagaaaaag aaaaaaagat ggtgaagctt gcatttggaa     120
gcttgggcga ctctttcagc gccgcgtccc tcaagtccta tgtggccgag ttcattgcca     180
cgctcctctt cgtgttcgcc ggcgtcgggt ccgccattgc ctactcgcaa ttgaccaagg     240
gtggcgctct ggaccccgcc ggcctggtgg ccatcgccat cgcccatgcg ttcgcgctct     300
tcgtcggcgt ctccatggcc gccaacgtct ccggcggcca cctgaacccc gccgtcacct     360
tcggcctcgc cgtcggcggc cacatcacca tcctcaccgg catcttctac tgggtcgccc     420
aggtgctcgg cgcgtccgtg gcgtgccttc tcctgaagta cgtcacccac ggacaggcta     480
tcccgacaca cggcgtgtcc gggatcagcg agatcgaggg cgtggtgatg agatcgtga      540
tcaccttcgc gctcgtgtac accgtgtacg ccaccgcggc cgaccccaag aagggtccc      600
tgggcaccat cgcgcccatc gccatcggct tcatcgtcgg cgccaacatc ctggcggccg     660
gaccctttcag cggcggctcc atgaacccgg cccgctcctt cggccccgcc gtggccgctg     720
gcaacttcgc cggcaactgg gtctactggg tcggcccct catcggcggc ggcctggccg      780
ggctcgtcta cggcgacgtg ttcatcgcct cctaccagcc cgtcggccag caggatcagt     840
acccatgaag aaagtcgatc cggacccaaa tgcaatgcaa cccgtcgtgt tgatttcacc     900
gtcctcgtcg attcgccgtc gtgtcatcgc ttcgcgcttg tgattatgtt tggtcttgtt     960
tgcattaccc cttctggttt aattttcacc aacggtgtca acatgctgta agcgagagaa    1020
ccgttcgatc tatacctgta taaatgtaat gtacggttca gtatttccaa gtacagtata    1080
tgttccggac ggatttc                                                   1097

<210> SEQ ID NO 98
<211> LENGTH: 1160
<212> TYPE: DNA
<213> ORGANISM: Sorghum bicolor

<400> SEQUENCE: 98
gcacgaggcg gcgtcggagc ccacgaccgc ttccgcccca gtccccaccg ccctcgaccc      60
cgattccccc aatccctgcc gcgaccgctg aaccctagcc tactccggcc atctgccgct    120
ggccccggcg atccccgcc atggcctccc ccgaggaac cacgtgggtc ttcgactgtc      180
ccctcatgga cgacctcgcg gtggccgccg acttcgcggc agcccccgcg ggggattttt    240
tctgggcagc gccgccgtcg ctacagccgc aggtggtgca ggcgccggtc cagtctgtcg    300
ttgccgcgtc ggctcccaac ccatgtgtgg aaatcagtag ctctgtggac tgtggtcagg    360
gaaaagaaca gccaacaaat aaacgtccta ggtcagaaag taccgcagaa ccaagcacaa    420
aagcatccag ggagaaaatt agaagggata agctgaacga gagattcctg gaattgggtg    480
ccatttggga gccagggaaa actcctaaaa tggacaagtc agctatatta atgatgctga    540
ttcgtgtagt aggtgaattg cgtagcgaag caaaagagct caaggattca aatgagagcc    600
tacaagagaa gattaaagag ctaaaggctg agaagaatga gctgcgagac gagaagcaaa    660
ggctgaaggc cgagaaggag agcctggagc agcagatcaa gttcctgaat gcccgcccaa    720
gtctggtacc acaccaccca gtgatctcag cctctgcctt cactgctccc caggggccgg    780
cagtcgccgg gcacaagctg atgatgcctg tgcttggcta ccctggattc ccgatgtggc    840
```

```
agttcatgcc gccttctgat gttgacacct ctgatgaccc caagtcttgc ccacctgtgg      900
cgtaagcaag tgaagaggcg atgctgccct ccattgattc aagtctagat cgtgatcagt      960
ctgcagtgtt gttggtgtag ttgactccac tctccagaat ggaagggaag gttatatgtg     1020
tcggatggtg acatggggtg atctgatgac cctttgtat attatatggt aaatgaataa      1080
attccgtgac cagttgcaaa tgaggattag cagactagct catgtctatt cctgccttt       1140 tgtcgtataa accacgttgt                                                 1160
```

<210> SEQ ID NO 99
<211> LENGTH: 151
<212> TYPE: PRT
<213> ORGANISM: Sorghum bicolor

<400> SEQUENCE: 99

```
Met Gly Arg Met His Ser Arg Gly Lys Gly Ile Ser Ser Ser Ala Leu
1               5                   10                  15

Pro Tyr Lys Arg Thr Pro Pro Thr Trp Leu Lys Thr Ala Ala Ser Asp
            20                  25                  30

Val Glu Glu Met Ile Thr Lys Ala Ala Lys Lys Gly Gln Met Pro Ser
        35                  40                  45

Gln Ile Gly Val Leu Leu Arg Asp Gln His Gly Ile Pro Leu Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr Phe Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Arg Thr Lys Lys Leu Pro Pro Thr Trp Lys Tyr Glu Ser Thr
    130                 135                 140

Thr Ala Ser Thr Leu Val Ala
145                 150
```

<210> SEQ ID NO 100
<211> LENGTH: 258
<212> TYPE: PRT
<213> ORGANISM: Sorghum bicolor

<400> SEQUENCE: 100

```
Met Asp Ala Gly Gly Glu Lys Phe Ser Asp Ala Ala Ala Ala Glu Gly
1               5                   10                  15

Gly Glu Gly Gly Gly Asp Leu Tyr Ala Val Leu Gly Leu Lys Lys Glu
            20                  25                  30

Cys Ser Asp Ala Asp Leu Lys Val Ala Tyr Arg Lys Leu Ala Lys Lys
        35                  40                  45

Trp His Pro Asp Lys Cys Ser Ser Ser Ser Val Lys His Met Glu
    50                  55                  60

Glu Ala Lys Glu Lys Phe Gln Glu Ile Gln Gly Ala Tyr Ser Val Leu
65                  70                  75                  80

Ser Asp Ala Asn Lys Arg Leu Leu Tyr Asp Val Gly Val Tyr Asp Asp
                85                  90                  95

Glu Asp Asp Glu Asp Ser Met Gln Gly Met Gly Asp Phe Ile Gly Glu
            100                 105                 110

Met Ala Gln Met Met Ser Gln Val Arg Pro Thr Arg Gln Glu Ser Phe
```

-continued

```
            115                 120                 125
Glu Glu Leu Gln Gln Leu Phe Val Asp Met Phe Gln Ser Asp Ile Asp
130                 135                 140

Ser Gly Phe Cys Asn Gly Ser Ala Lys Asp Gln Val Gln Gly Gln Ala
145                 150                 155                 160

Lys Ser Arg Thr Cys Ser Thr Ser Pro Ser Ser Pro Ser Pro Pro
                165                 170                 175

Pro Pro Pro Thr Ile Val Lys Glu Ala Glu Val Ser Ser Cys Asn Gly
            180                 185                 190

Phe Asn Lys Arg Gly Ser Ser Ala Met Asp Ser Gly Lys Pro Pro Arg
        195                 200                 205

Pro Val Glu Gly Gly Ala Gly Gln Ala Gly Phe Cys Phe Gly Val Ser
    210                 215                 220

Asp Thr Lys Gln Thr Pro Lys Pro Arg Gly Pro Asn Thr Ser Arg Arg
225                 230                 235                 240

Arg Asn Gly Arg Lys Gln Lys Leu Ser Ser Lys His Asp Val Ser Ser
                245                 250                 255

Glu Asp

<210> SEQ ID NO 101
<211> LENGTH: 320
<212> TYPE: PRT
<213> ORGANISM: Sorghum bicolor

<400> SEQUENCE: 101

Met Asp Ser Leu Trp His Leu Gly Asp Glu Leu Arg Gly Gln Pro Lys
1               5                   10                  15

Val Val Glu Asp Arg Gln Trp Ser Leu Met Thr Ser Lys Leu Ala Glu
            20                  25                  30

Ile Thr Arg Ser Lys Gly Glu Arg Met Asn Asp Leu Asp Tyr Ala Arg
        35                  40                  45

Met Asn Thr Val Pro Asp Ala Lys Gln Trp Asp Lys Thr Ser Phe Gln
50                  55                  60

His His Asp Gln Ser Arg Met Asp His Ile Asn Leu Gly Leu Met Asn
65                  70                  75                  80

Leu Asp Leu Lys Met Asn Asp Leu Lys Met Asn Glu Ala Pro Thr Ala
                85                  90                  95

Met Lys Leu Pro Phe His Asn Met Pro Tyr Asn Met Asn Pro Met Tyr
            100                 105                 110

Pro Lys Gly Ser Asn Ala Asn Val Asn Ala Phe Lys Met Asn
        115                 120                 125

Val Gly Val Asn Lys Tyr Ser Asn Ser Pro Asn Gly Lys Asp Ala Asn
130                 135                 140

Gly Lys Asn Asn Gly Gly Ser Asn Asn Gly Gly Asn Ser Asn Gly
145                 150                 155                 160

Ser Ala Asn Gly Asn Ser Ala Val Asp Lys Arg Phe Lys Thr Leu Pro
                165                 170                 175

Thr Ser Glu Met Leu Pro Arg Asn Glu Val Leu Gly Gly Tyr Ile Phe
            180                 185                 190

Val Cys Asn Asn Asp Thr Met Gln Glu Asp Leu Lys Arg Gln Leu Phe
        195                 200                 205

Gly Leu Pro Ala Arg Tyr Arg Asp Ser Val Arg Ala Ile Thr Pro Gly
    210                 215                 220

Leu Pro Leu Phe Leu Tyr Asn Tyr Thr Thr His Gln Leu His Gly Val
225                 230                 235                 240
```

```
Phe Glu Ala Ala Ser Phe Gly Gly Ser Asn Ile Asp Pro Thr Ala Trp
                245                 250                 255

Glu Asp Lys Lys Cys Lys Gly Glu Ser Arg Phe Pro Ala Gln Val Arg
            260                 265                 270

Ile Arg Ile Arg Lys Leu Cys Lys Pro Leu Glu Glu Asp Ser Phe Arg
        275                 280                 285

Pro Val Leu His His Tyr Asp Gly Pro Lys Phe Arg Leu Glu Leu Ser
    290                 295                 300

Ile Ala Glu Thr Leu Ser Leu Leu Asp Leu Cys Glu Lys Glu Gly Ile
305                 310                 315                 320

<210> SEQ ID NO 102
<211> LENGTH: 381
<212> TYPE: PRT
<213> ORGANISM: Sorghum bicolor

<400> SEQUENCE: 102

Met Ile Leu Glu Val Ala Ala Val Glu Thr Gln Ser Ile Val His Leu
1               5                   10                  15

Phe Lys Pro Arg Asp Glu Lys Ile Leu Leu Ala Glu Gly His Lys Arg
            20                  25                  30

Pro Arg Ser Pro Gly Leu Ser Ser Lys Ala Tyr Ser Gly Ser Leu
        35                  40                  45

Val Gly Leu Ser Ile Val Phe Ala Pro Leu Ser Ala Leu Val Ala Ser
    50                  55                  60

Ser Glu Pro Met Ser His Pro Pro Pro Val Asp Gln Asn Ile
65                  70                  75                  80

Ser Leu Arg Phe Cys Glu Ser Phe Ser Leu Gln Gly Thr Glu Thr Pro
                85                  90                  95

Gly Ala Phe Thr Pro Pro Ala Pro Ala Phe Pro Ser Arg Pro Arg Thr
            100                 105                 110

Gly Ala Thr Thr Arg Leu Leu Leu Glu Thr Phe His Ser Ser Met Ala
        115                 120                 125

Lys Leu Val Asn Lys Leu Val Asp Ser Phe Glu Glu Gln Asp Thr Pro
    130                 135                 140

Asp Val Gly Cys Val Arg Ala Val Leu Ala Glu Leu Val Leu Thr Phe
145                 150                 155                 160

Leu Phe Val Phe Thr Gly Val Ser Ala Ala Met Ala Ala Gly Ser Gly
                165                 170                 175

Val Lys Pro Gly Glu Ala Met Pro Met Ala Thr Leu Ala Ala Val Ala
            180                 185                 190

Ile Ala His Ala Leu Ala Ala Gly Val Leu Val Thr Ala Gly Phe His
        195                 200                 205

Val Ser Gly Gly His Leu Asn Pro Ala Val Thr Val Gly Leu Met Val
    210                 215                 220

Arg Gly His Ile Thr Lys Leu Arg Ala Val Leu Tyr Val Ala Ala Gln
225                 230                 235                 240

Val Leu Ala Ser Ser Leu Ala Cys Ile Leu Leu Arg Tyr Leu Ser Gly
                245                 250                 255

Gly Met Val Thr Pro Val His Ala Leu Gly Ala Gly Ile Ser Pro Met
            260                 265                 270

Gln Gly Leu Val Met Glu Val Ile Leu Thr Phe Ser Leu Leu Phe Val
        275                 280                 285

Thr Tyr Ala Met Ile Leu Asp Pro Arg Ser Gln Val Arg Thr Ile Gly
    290                 295                 300
```

Pro Leu Leu Thr Gly Leu Ile Val Gly Ala Asn Ser Leu Ala Gly Gly
305                 310                 315                 320

Asn Phe Ser Gly Ala Ser Met Asn Pro Ala Arg Ser Phe Gly Pro Ala
            325                 330                 335

Leu Ala Ser Gly Val Trp Thr Asn His Trp Ile Tyr Trp Ile Gly Pro
            340                 345                 350

Leu Leu Gly Gly Pro Leu Ala Gly Phe Ile Tyr Glu Ser Leu Phe Ile
            355                 360                 365

Val Asn Lys Thr His Glu Pro Leu Leu Asn Gly Asp Ile
370                 375                 380

<210> SEQ ID NO 103
<211> LENGTH: 249
<212> TYPE: PRT
<213> ORGANISM: Sorghum bicolor

<400> SEQUENCE: 103

Met Val Lys Leu Ala Phe Gly Ser Leu Gly Asp Ser Phe Ser Ala Ala
1               5                   10                  15

Ser Leu Lys Ser Tyr Val Ala Glu Phe Ile Ala Thr Leu Leu Phe Val
            20                  25                  30

Phe Ala Gly Val Gly Ser Ala Ile Ala Tyr Ser Gln Leu Thr Lys Gly
            35                  40                  45

Gly Ala Leu Asp Pro Ala Gly Leu Val Ala Ile Ala Ile Ala His Ala
        50                  55                  60

Phe Ala Leu Phe Val Gly Val Ser Met Ala Ala Asn Val Ser Gly Gly
65                  70                  75                  80

His Leu Asn Pro Ala Val Thr Phe Gly Leu Ala Val Gly Gly His Ile
                85                  90                  95

Thr Ile Leu Thr Gly Ile Phe Tyr Trp Val Ala Gln Val Leu Gly Ala
            100                 105                 110

Ser Val Ala Cys Leu Leu Leu Lys Tyr Val Thr His Gly Gln Ala Ile
            115                 120                 125

Pro Thr His Gly Val Ser Gly Ile Ser Glu Ile Glu Gly Val Val Met
        130                 135                 140

Glu Ile Val Ile Thr Phe Ala Leu Val Tyr Thr Val Tyr Ala Thr Ala
145                 150                 155                 160

Ala Asp Pro Lys Lys Gly Ser Leu Gly Thr Ile Ala Pro Ile Ala Ile
                165                 170                 175

Gly Phe Ile Val Gly Ala Asn Ile Leu Ala Ala Gly Pro Phe Ser Gly
            180                 185                 190

Gly Ser Met Asn Pro Ala Arg Ser Phe Gly Pro Ala Val Ala Ala Gly
            195                 200                 205

Asn Phe Ala Gly Asn Trp Val Tyr Trp Val Gly Pro Leu Ile Gly Gly
        210                 215                 220

Gly Leu Ala Gly Leu Val Tyr Gly Asp Val Phe Ile Ala Ser Tyr Gln
225                 230                 235                 240

Pro Val Gly Gln Gln Asp Gln Tyr Pro
                245

<210> SEQ ID NO 104
<211> LENGTH: 254
<212> TYPE: PRT
<213> ORGANISM: Sorghum bicolor

<400> SEQUENCE: 104

```
Met Ala Ser Pro Glu Gly Thr Thr Trp Val Phe Asp Cys Pro Leu Met
1               5                   10                  15

Asp Asp Leu Ala Val Ala Ala Asp Phe Ala Ala Pro Ala Gly Gly
            20                  25                  30

Phe Phe Trp Ala Ala Pro Pro Ser Leu Gln Pro Gln Val Val Gln Ala
            35                  40                  45

Pro Val Gln Ser Val Val Ala Ala Ser Ala Pro Asn Pro Cys Val Glu
        50                  55                  60

Ile Ser Ser Ser Val Asp Cys Gly Gln Gly Lys Glu Gln Pro Thr Asn
65                  70                  75                  80

Lys Arg Pro Arg Ser Glu Ser Thr Ala Glu Pro Ser Thr Lys Ala Ser
                85                  90                  95

Arg Glu Lys Ile Arg Arg Asp Lys Leu Asn Glu Arg Phe Leu Glu Leu
                100                 105                 110

Gly Ala Ile Leu Glu Pro Gly Lys Thr Pro Lys Met Asp Lys Ser Ala
            115                 120                 125

Ile Leu Asn Asp Ala Ile Arg Val Val Gly Glu Leu Arg Ser Glu Ala
        130                 135                 140

Lys Glu Leu Lys Asp Ser Asn Glu Ser Leu Gln Glu Lys Ile Lys Glu
145                 150                 155                 160

Leu Lys Ala Glu Lys Asn Glu Leu Arg Asp Glu Lys Gln Arg Leu Lys
                165                 170                 175

Ala Glu Lys Glu Ser Leu Glu Gln Gln Ile Lys Phe Leu Asn Ala Arg
                180                 185                 190

Pro Ser Leu Val Pro His His Pro Val Ile Ser Ala Ser Ala Phe Thr
            195                 200                 205

Ala Pro Gln Gly Pro Ala Val Ala Gly His Lys Leu Met Met Pro Val
        210                 215                 220

Leu Gly Tyr Pro Gly Phe Pro Met Trp Gln Phe Met Pro Pro Ser Asp
225                 230                 235                 240

Val Asp Thr Ser Asp Asp Pro Lys Ser Cys Pro Pro Val Ala
            245                 250

<210> SEQ ID NO 105
<211> LENGTH: 151
<212> TYPE: PRT
<213> ORGANISM: Zea mays

<400> SEQUENCE: 105

Met Gly Arg Met His Ser Arg Gly Lys Gly Ile Ser Ser Ala Leu
1               5                   10                  15

Pro Tyr Lys Arg Thr Pro Pro Thr Trp Leu Lys Thr Ala Ala Ser Asp
            20                  25                  30

Val Glu Glu Met Ile Thr Lys Ala Ala Lys Lys Gly Gln Met Pro Ser
        35                  40                  45

Gln Ile Gly Val Leu Leu Arg Asp Gln His Gly Ile Pro Leu Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr Phe Leu Ile Lys Lys Ala Val
                85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
            115                 120                 125
```

Tyr Lys Arg Thr Lys Lys Leu Pro Pro Thr Trp Lys Tyr Glu Ser Thr
            130                 135                 140

Thr Ala Ser Thr Leu Val Ala
145                 150

<210> SEQ ID NO 106
<211> LENGTH: 171
<212> TYPE: PRT
<213> ORGANISM: Saccharum officinarum

<400> SEQUENCE: 106

Arg Arg Arg Arg Arg Lys Arg Gln Leu Ala Val Ala Arg Ala Lys
1               5                   10                  15

His Pro Asn Ala Ala Met Gly Arg Met His Ser Arg Gly Lys Gly Ile
            20                  25                  30

Ser Ser Ser Ala Leu Pro Tyr Lys Arg Thr Pro Thr Trp Leu Lys
        35                  40                  45

Thr Ala Ala Ser Asp Val Glu Glu Met Ile Thr Lys Ala Ala Lys Lys
50                  55                  60

Gly Gln Met Pro Ser Gln Ile Gly Val Leu Leu Arg Asp Gln His Gly
65                  70                  75                  80

Ile Pro Leu Val Lys Ser Val Thr Gly Ser Lys Ile Leu Arg Ile Leu
                85                  90                  95

Lys Ala His Gly Leu Ala Pro Glu Ile Pro Glu Asp Leu Tyr Phe Leu
            100                 105                 110

Ile Lys Lys Ala Val Ala Ile Arg Lys His Leu Glu Arg Asn Arg Lys
        115                 120                 125

Asp Lys Asp Ser Lys Phe Arg Leu Ile Leu Val Glu Ser Arg Ile His
    130                 135                 140

Arg Leu Ala Arg Tyr Tyr Lys Arg Thr Lys Lys Leu Pro Pro Thr Trp
145                 150                 155                 160

Lys Tyr Glu Ser Thr Thr Ala Ser Thr Leu Val
                165                 170

<210> SEQ ID NO 107
<211> LENGTH: 172
<212> TYPE: PRT
<213> ORGANISM: Sorghum bicolor

<400> SEQUENCE: 107

Arg Arg Arg Arg Arg Cys Lys Arg Gln Leu Ala Val Val Arg Ala
1               5                   10                  15

Lys His Pro Asn Ala Ala Met Gly Arg Met His Ser Arg Gly Lys Gly
            20                  25                  30

Ile Ser Ser Ser Ala Leu Pro Tyr Lys Arg Thr Pro Thr Trp Leu
        35                  40                  45

Lys Thr Ala Ala Ser Asp Val Glu Glu Met Ile Thr Lys Ala Ala Lys
50                  55                  60

Lys Gly Gln Met Pro Ser Gln Ile Gly Val Leu Leu Arg Asp Gln His
65                  70                  75                  80

Gly Ile Pro Leu Val Lys Ser Val Thr Gly Ser Lys Ile Leu Arg Ile
                85                  90                  95

Leu Lys Ala His Gly Leu Ala Pro Glu Ile Pro Glu Asp Leu Tyr Phe
            100                 105                 110

Leu Ile Lys Lys Ala Val Ala Ile Arg Lys His Leu Glu Arg Asn Arg
        115                 120                 125

Lys Asp Lys Asp Ser Lys Phe Arg Leu Ile Leu Val Glu Ser Arg Ile

```
                130                 135                 140
His Arg Leu Ala Arg Tyr Tyr Lys Arg Thr Lys Lys Leu Pro Pro Thr
145                 150                 155                 160

Trp Lys Tyr Glu Ser Thr Thr Ala Ser Thr Leu Val
                165                 170

<210> SEQ ID NO 108
<211> LENGTH: 151
<212> TYPE: PRT
<213> ORGANISM: Saccharum officinarum

<400> SEQUENCE: 108

Met Gly Arg Met His Ser Arg Gly Lys Gly Ile Ser Ser Ser Ala Leu
1               5                   10                  15

Pro Tyr Lys Arg Thr Pro Pro Thr Trp Leu Lys Thr Ala Ala Thr Glu
                20                  25                  30

Val Glu Glu Met Ile Thr Lys Ala Ala Lys Lys Gly Gln Met Pro Ser
            35                  40                  45

Gln Ile Gly Val Leu Leu Arg Asp Gln His Gly Ile Pro Leu Val Lys
        50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr Phe Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Arg Thr Lys Lys Leu Pro Pro Thr Trp Lys Tyr Glu Ser Thr
    130                 135                 140

Thr Ala Ser Thr Leu Val Ala
145                 150

<210> SEQ ID NO 109
<211> LENGTH: 187
<212> TYPE: PRT
<213> ORGANISM: Sorghum bicolor

<400> SEQUENCE: 109

Met Pro His Ala Pro Pro Leu Ala Leu Ala Pro Pro Pro Pro Pro Gln
1               5                   10                  15

Leu Leu Gln Gln Gln Ala Pro Ala Arg Arg Arg Leu Gly Arg His
                20                  25                  30

Gln Ser Ala Ala Met Gly Arg Met His Ser Arg Gly Lys Gly Ile Ser
            35                  40                  45

Ser Ser Ala Leu Pro Tyr Lys Arg Thr Pro Pro Thr Trp Leu Lys Thr
        50                  55                  60

Ala Ala Thr Glu Val Glu Glu Met Ile Thr Lys Ala Ala Lys Lys Gly
65                  70                  75                  80

Gln Met Pro Ser Gln Ile Gly Val Leu Leu Arg Asp Gln His Gly Ile
                85                  90                  95

Pro Leu Val Lys Ser Val Thr Gly Ser Lys Ile Leu Arg Ile Leu Lys
            100                 105                 110

Ala His Gly Leu Ala Pro Glu Ile Pro Glu Asp Leu Tyr Phe Leu Ile
        115                 120                 125

Lys Lys Ala Val Ala Ile Arg Lys His Leu Glu Arg Asn Arg Lys Asp
    130                 135                 140
```

-continued

Lys Asp Ser Lys Phe Arg Leu Ile Leu Val Glu Ser Arg Ile His Arg
145                 150                 155                 160

Leu Ala Arg Tyr Tyr Lys Arg Thr Lys Lys Leu Pro Pro Thr Trp Lys
                165                 170                 175

Tyr Glu Ser Thr Thr Ala Ser Thr Leu Val Ala
            180                 185

<210> SEQ ID NO 110
<211> LENGTH: 184
<212> TYPE: PRT
<213> ORGANISM: Oryza sativa
<220> FEATURE:
<221> NAME/KEY: misc_feature
<222> LOCATION: (1)..(2)
<223> OTHER INFORMATION: Xaa can be any naturally occurring amino acid

<400> SEQUENCE: 110

Xaa Xaa Glu Lys Thr Pro Ser Tyr Arg Arg Ser Arg Pro Ser Arg Pro
1               5                   10                  15

Arg Ala Pro Pro Pro Pro Ala Val Ala Gly Ala Lys Pro Leu Asp
            20                  25                  30

Ala Ala Met Gly Arg Met His Ser Arg Gly Lys Gly Ile Ser Ser Ser
        35                  40                  45

Ala Leu Pro Tyr Lys Arg Thr Pro Pro Ser Trp Leu Lys Thr Ala Ala
    50                  55                  60

Ser Asp Val Glu Glu Met Ile Met Lys Ala Ala Lys Lys Gly Gln Met
65                  70                  75                  80

Pro Ser Gln Ile Gly Val Val Leu Arg Asp Gln His Gly Ile Pro Leu
                85                  90                  95

Val Lys Ser Val Thr Gly Ser Lys Ile Leu Arg Ile Leu Lys Ala His
            100                 105                 110

Gly Leu Ala Pro Glu Ile Pro Glu Asp Leu Tyr Phe Leu Ile Lys Lys
        115                 120                 125

Ala Val Ala Ile Arg Lys His Leu Glu Arg Asn Arg Lys Asp Lys Asp
    130                 135                 140

Ser Lys Phe Arg Leu Ile Leu Val Glu Ser Arg Ile His Arg Leu Ala
145                 150                 155                 160

Arg Tyr Tyr Lys Arg Thr Lys Lys Leu Pro Pro Thr Trp Lys Tyr Glu
                165                 170                 175

Ser Thr Thr Ala Ser Thr Leu Val
            180

<210> SEQ ID NO 111
<211> LENGTH: 151
<212> TYPE: PRT
<213> ORGANISM: Zea mays

<400> SEQUENCE: 111

Met Gly Arg Met His Ser Arg Gly Lys Gly Ile Ser Ser Ser Ala Leu
1               5                   10                  15

Pro Tyr Lys Arg Thr Pro Pro Ile Trp Leu Lys Thr Ala Thr Ala Glu
            20                  25                  30

Val Glu Glu Met Ile Thr Lys Ala Ala Lys Lys Gly Gln Met Pro Ser
        35                  40                  45

Gln Ile Gly Val Leu Leu Arg Asp Gln His Gly Ile Pro Leu Val Lys
    50                  55                  60

Ser Val Thr Gly Ser Lys Ile Leu Arg Ile Leu Lys Ala His Gly Leu
65                  70                  75                  80

```
Ala Pro Glu Ile Pro Glu Asp Leu Tyr Phe Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Arg Thr Lys Lys Leu Pro Pro Thr Trp Lys Tyr Glu Ser Thr
    130                 135                 140

Thr Ala Ser Thr Leu Val Ala
145                 150

<210> SEQ ID NO 112
<211> LENGTH: 183
<212> TYPE: PRT
<213> ORGANISM: Hordeum vulgare
<220> FEATURE:
<221> NAME/KEY: misc_feature
<222> LOCATION: (1)..(2)
<223> OTHER INFORMATION: Xaa can be any naturally occurring amino acid

<400> SEQUENCE: 112

Xaa Xaa Pro Leu Phe Tyr Pro Leu Thr Thr Arg Ala Ser Leu Ala Leu
1               5                   10                  15

Pro Ala Ala Ala Ala Ala Ala Pro Leu Ala Ala Ala Ala Ala Ala Ala
            20                  25                  30

Ala Met Gly Arg Met His Ser Arg Gly Lys Gly Ile Ser Ser Ser Ala
        35                  40                  45

Leu Pro Tyr Lys Arg Thr Pro Pro Ser Trp Val Lys Thr Ala Val Ala
    50                  55                  60

Asp Val Asp Glu Leu Ile Thr Lys Ala Lys Lys Gly Gln Met Pro
65                  70                  75                  80

Ser Gln Ile Gly Val Leu Leu Arg Asp Gln His Gly Ile Pro Leu Val
                85                  90                  95

Lys Ser Val Thr Gly Ser Lys Ile Leu Arg Ile Leu Lys Ala His Gly
            100                 105                 110

Leu Ala Pro Glu Ile Pro Glu Asp Leu Tyr Phe Leu Ile Lys Lys Ala
        115                 120                 125

Val Ala Ile Arg Lys His Leu Glu Arg Asn Arg Lys Asp Lys Asp Ser
    130                 135                 140

Lys Phe Arg Leu Ile Leu Val Glu Ser Arg Ile His Arg Leu Ala Arg
145                 150                 155                 160

Tyr Tyr Lys Arg Thr Lys Lys Leu Pro Pro Thr Trp Lys Tyr Glu Ser
                165                 170                 175

Thr Thr Ala Ser Thr Leu Val
            180

<210> SEQ ID NO 113
<211> LENGTH: 178
<212> TYPE: PRT
<213> ORGANISM: Oryza sativa

<400> SEQUENCE: 113

Ser Ser Arg Arg Arg Arg Leu Leu Arg Arg Ala Val Ala Asn Arg Arg
1               5                   10                  15

Arg Arg Ser Pro Ser Pro Asn Ser Pro Leu Pro Pro Trp Gly Arg Met
            20                  25                  30

His Ser Arg Gly Lys Gly Ile Ser Ser Ser Ala Ile Pro Tyr Lys Arg
        35                  40                  45
```

```
Thr Pro Pro Ser Trp Val Lys Thr Ala Ala Asp Val Glu Glu Met
         50                  55                  60

Ile Met Lys Ala Ala Lys Lys Gly Gln Met Pro Ser Gln Ile Gly Val
 65                  70                  75                  80

Val Leu Arg Asp Gln His Gly Ile Pro Leu Val Lys Ser Val Thr Gly
                 85                  90                  95

Ser Lys Ile Leu Arg Ile Leu Lys Ala His Gly Leu Ala Pro Glu Ile
                100                 105                 110

Pro Glu Asp Leu Tyr Phe Leu Ile Lys Lys Ala Val Ala Ile Arg Lys
                115                 120                 125

His Leu Glu Arg Asn Arg Lys Asp Lys Asp Ser Lys Phe Arg Leu Ile
130                 135                 140

Leu Val Glu Ser Arg Ile His Arg Leu Ala Arg Tyr Tyr Lys Arg Thr
145                 150                 155                 160

Lys Lys Leu Pro Pro Thr Trp Lys Tyr Glu Ser Thr Thr Ala Ser Thr
                165                 170                 175

Leu Val

<210> SEQ ID NO 114
<211> LENGTH: 170
<212> TYPE: PRT
<213> ORGANISM: Triticum aestivum

<400> SEQUENCE: 114

Ala Leu Phe Tyr Pro Leu Thr Thr Arg Ala Ser Leu Ala Leu Pro Ala
 1               5                  10                  15

Ala Ala Ala Ala Thr Pro Leu Ala Ala Ala Ala Ala Ala Ala Met Gly
                 20                  25                  30

Arg Met His Ser Arg Gly Lys Gly Ile Ser Ser Ser Ala Leu Pro Tyr
                 35                  40                  45

Lys Arg Thr Pro Pro Ser Trp Val Lys Thr Ala Val Ala Asp Val Asp
 50                  55                  60

Glu Leu Ile Thr Lys Ala Ala Lys Lys Gly Gln Met Pro Ser Gln Ile
 65                  70                  75                  80

Gly Val Leu Leu Arg Asp Gln His Gly Ile Pro Leu Val Lys Ser Val
                 85                  90                  95

Thr Gly Ser Lys Ile Leu Arg Ile Leu Lys Ala His Gly Leu Ala Pro
                100                 105                 110

Glu Ile Pro Glu Asp Leu Tyr Phe Leu Ile Lys Lys Ala Val Ala Ile
                115                 120                 125

Arg Lys His Leu Glu Arg Asn Arg Lys Asp Lys Asp Ser Lys Phe Arg
130                 135                 140

Leu Ile Leu Val Glu Ser Arg Ile His Arg Leu Ala Arg Tyr Tyr Lys
145                 150                 155                 160

Arg Thr Lys Lys Leu Pro Pro Thr Trp Lys
                165                 170

<210> SEQ ID NO 115
<211> LENGTH: 177
<212> TYPE: PRT
<213> ORGANISM: Triticum aestivum
<220> FEATURE:
<221> NAME/KEY: misc_feature
<222> LOCATION: (1)..(2)
<223> OTHER INFORMATION: Xaa can be any naturally occurring amino acid

<400> SEQUENCE: 115
```

```
Xaa Xaa Ala Gly Asn Ser Ala Arg Gly Ser Ser Pro Ser Arg Pro Ser
1               5                   10                  15

Arg Arg Cys Cys Cys Arg Gln Pro Pro Pro Ser Pro Glu Leu Asn
            20                  25                  30

Pro Ser Pro Asp Ala Met Gly Arg Met His Ser Arg Gly Lys Gly Ile
        35                  40                  45

Ser Ser Ser Ala Leu Pro Tyr Lys Arg Thr Pro Pro Ser Trp Val Lys
    50                  55                  60

Thr Ala Val Ala Asp Val Asp Glu Leu Ile Thr Lys Ala Ala Lys Lys
65                  70                  75                  80

Gly Gln Met Pro Ser Gln Ile Gly Val Leu Leu Arg Asp Gln His Gly
                85                  90                  95

Ile Pro Leu Val Lys Ser Val Thr Gly Ser Lys Ile Leu Arg Ile Leu
            100                 105                 110

Lys Ala His Gly Leu Ala Pro Glu Ile Pro Glu Asp Leu Tyr Phe Leu
            115                 120                 125

Ile Lys Lys Ala Val Ala Ile Arg Lys His Leu Glu Arg Asn Arg Lys
            130                 135                 140

Asp Lys Asp Ser Lys Phe Arg Leu Ile Leu Val Glu Ser Arg Ile His
145                 150                 155                 160

Arg Leu Ala Arg Tyr Tyr Lys Arg Thr Lys Leu Pro Pro Thr Trp
                165                 170                 175

Lys
```

```
<210> SEQ ID NO 116
<211> LENGTH: 171
<212> TYPE: PRT
<213> ORGANISM: Hordeum vulgare

<400> SEQUENCE: 116

Arg Arg Arg Ser Cys Pro Ser Ser Pro Ser Arg Arg Cys Cys Cys Arg
1               5                   10                  15

Gln Pro Pro Pro Ser Ser Pro Glu Leu Asn Pro Ser Pro Asp Ala Met
            20                  25                  30

Gly Arg Met His Ser Arg Gly Lys Gly Ile Ser Ser Ser Ala Leu Pro
        35                  40                  45

Tyr Lys Arg Thr Pro Pro Ser Trp Val Lys Thr Ala Val Ala Asp Val
    50                  55                  60

Asp Glu Leu Ile Thr Lys Ala Ala Lys Lys Gly Gln Met Pro Ser Gln
65                  70                  75                  80

Ile Gly Val Leu Leu Arg Asp Gln His Gly Ile Pro Leu Val Lys Ser
                85                  90                  95

Val Thr Gly Ser Lys Ile Leu Arg Ile Leu Lys Ala His Gly Leu Ala
            100                 105                 110

Pro Glu Ile Pro Glu Asp Leu Tyr Phe Leu Ile Lys Lys Ala Val Ala
            115                 120                 125

Ile Arg Lys His Leu Glu Arg Asn Arg Lys Asp Lys Asp Ser Lys Phe
            130                 135                 140

Arg Leu Ile Leu Val Glu Ser Arg Ile His Arg Leu Ala Arg Tyr Tyr
145                 150                 155                 160

Lys Arg Thr Lys Lys Leu Pro Pro Thr Trp Lys
                165                 170
```

```
<210> SEQ ID NO 117
<211> LENGTH: 116
<212> TYPE: PRT
```

-continued

<213> ORGANISM: Triticum aestivum

<400> SEQUENCE: 117

Met Ile Thr Lys Ala Ala Lys Lys Gly Gln Met Pro Ser Gln Ile Gly
1               5                   10                  15

Val Leu Leu Arg Asp Gln His Gly Ile Pro Leu Val Lys Ser Val Thr
            20                  25                  30

Gly Ser Lys Ile Leu Arg Ile Leu Lys Ala His Gly Leu Ala Pro Glu
        35                  40                  45

Ile Pro Glu Asp Leu Tyr Phe Leu Ile Lys Lys Ala Val Ala Ile Arg
    50                  55                  60

Lys His Leu Glu Arg Asn Arg Lys Asp Lys Asp Ser Lys Phe Arg Leu
65                  70                  75                  80

Ile Leu Val Glu Ser Arg Ile His Arg Leu Ala Arg Tyr Tyr Lys Arg
                85                  90                  95

Thr Lys Lys Leu Pro Pro Thr Trp Lys Tyr Glu Ser Thr Thr Ala Ser
            100                 105                 110

Thr Leu Val Ala
        115

<210> SEQ ID NO 118
<211> LENGTH: 116
<212> TYPE: PRT
<213> ORGANISM: Zea mays

<400> SEQUENCE: 118

Met Ile Thr Lys Ala Ala Lys Lys Gly Gln Met Pro Ser Gln Ile Gly
1               5                   10                  15

Val Leu Leu Arg Asp Gln His Gly Ile Pro Leu Val Lys Ser Val Thr
            20                  25                  30

Gly Ser Lys Ile Leu Arg Ile Leu Lys Ala His Gly Leu Ala Pro Glu
        35                  40                  45

Ile Pro Glu Asp Leu Tyr Phe Leu Ile Lys Lys Ala Val Ala Ile Arg
    50                  55                  60

Lys His Leu Glu Arg Asn Arg Lys Asp Lys Asp Ser Lys Phe Arg Leu
65                  70                  75                  80

Ile Leu Val Glu Ser Arg Ile His Arg Leu Ala Arg Tyr Tyr Lys Arg
                85                  90                  95

Thr Lys Lys Leu Pro Pro Thr Trp Lys Tyr Glu Ser Thr Thr Ala Ser
            100                 105                 110

Thr Leu Val Ala
        115

<210> SEQ ID NO 119
<211> LENGTH: 122
<212> TYPE: PRT
<213> ORGANISM: Saccharum officinarum

<400> SEQUENCE: 119

Met Ile Thr Asn Ala Ala Lys Lys Gly Gln Met Pro Ser Gln Ile Gly
1               5                   10                  15

Val Leu Val Arg Asp Gln His Gly Ile Pro Leu Val Lys Ser Val Thr
            20                  25                  30

Gly Ser Met Ile Leu Arg Ile Leu Lys Ala His Gly Leu Ser Leu Glu
        35                  40                  45

Ile Pro Glu Asp Leu Tyr Phe Leu Ile Lys Lys Ala Val Trp Ile Arg
    50                  55                  60

```
Lys His Leu Glu Arg Asn Arg Lys Asp Lys Asp Phe Lys Phe Thr Leu
 65                  70                  75                  80

Ile Leu Val Glu Ser Arg Ile His Arg Leu Ala Arg Tyr Tyr Lys Arg
                 85                  90                  95

Thr Lys Lys Leu Pro Pro Thr Cys Lys Tyr Glu Thr Thr Gly Ser
            100                 105                 110

Thr Leu Val Ala Ile Val Val Ser Ser Thr
        115                 120

<210> SEQ ID NO 120
<211> LENGTH: 210
<212> TYPE: PRT
<213> ORGANISM: Triticum aestivum
<220> FEATURE:
<221> NAME/KEY: misc_feature
<222> LOCATION: (38)..(38)
<223> OTHER INFORMATION: Xaa can be any naturally occurring amino acid

<400> SEQUENCE: 120

Met Pro Ser Gln Ile Gly Val Leu Leu Arg Asp Gln His Gly Ile Pro
  1               5                  10                  15

Leu Val Lys Ser Val Thr Gly Ser Lys Ile Leu Arg Ile Leu Lys Ala
                 20                  25                  30

His Gly Leu Ala Pro Xaa Ile Pro Glu Asp Leu Tyr Phe Leu Ile Lys
             35                  40                  45

Lys Ala Val Ala Ile Arg Lys His Leu Glu Arg Asn Arg Arg Asp Lys
 50                  55                  60

Asp Ser Lys Phe Arg Leu Ile Leu Val Glu Ser Arg Ile His Arg Leu
 65                  70                  75                  80

Ala Arg Tyr Tyr Lys Arg Thr Lys Lys Leu Pro Pro Thr Trp Lys Trp
                 85                  90                  95

Glu Val Lys Ala Val Leu Asp Asp Tyr Pro Lys Leu Cys Leu Thr Lys
            100                 105                 110

Gly Arg Lys Val Leu Glu Ile Arg Pro Ser Ile Glu Trp Asn Lys Gly
            115                 120                 125

His Ala Leu Lys Phe Leu Leu Lys Ser Leu Gly Tyr Ala Gly Arg Ser
130                 135                 140

Asp Val Phe Pro Ile Tyr Ile Gly Asp Asp Arg Thr Asp Glu Asp Ala
145                 150                 155                 160

Phe Lys Val Leu Gln Asn Met Gly Gln Gly Ile Gly Ile Leu Val Thr
                165                 170                 175

Lys Phe Pro Lys Asp Thr Ser Ala Ser Tyr Ser Leu Arg Glu Pro Ala
            180                 185                 190

Glu Val Lys Glu Phe Met Arg Lys Leu Val Lys Ser Asn Gly Ile Lys
            195                 200                 205

Lys Gly
    210

<210> SEQ ID NO 121
<211> LENGTH: 92
<212> TYPE: PRT
<213> ORGANISM: Zea mays

<400> SEQUENCE: 121

Met Pro Leu Val Lys Ser Val Thr Gly Ser Lys Ile Leu Arg Ile Leu
  1               5                  10                  15

Lys Ala His Gly Leu Ala Pro Glu Ile Pro Glu Asp Leu Tyr Phe Leu
                 20                  25                  30
```

```
Ile Lys Lys Ala Val Ala Ile Arg Lys His Leu Glu Arg Asn Arg Lys
             35                  40                  45

Asp Lys Asp Ser Lys Phe Arg Leu Ile Leu Val Glu Ser Arg Ile His
 50                  55                  60

Arg Leu Ala Arg Tyr Tyr Lys Arg Thr Lys Lys Leu Pro Pro Thr Trp
 65                  70                  75                  80

Lys Tyr Glu Ser Thr Thr Ala Ser Thr Leu Val Ala
             85                  90

<210> SEQ ID NO 122
<211> LENGTH: 96
<212> TYPE: PRT
<213> ORGANISM: Triticum aestivum
<220> FEATURE:
<221> NAME/KEY: misc_feature
<222> LOCATION: (86)..(86)
<223> OTHER INFORMATION: Xaa can be any naturally occurring amino acid

<400> SEQUENCE: 122

Met Gly Arg Met His Ser Arg Gly Lys Gly Ile Ser Ser Ser Ala Leu
 1               5                  10                  15

Pro Tyr Lys Arg Thr Pro Pro Thr Trp Leu Lys Thr Ala Ala Ser Asp
             20                  25                  30

Val Glu Glu Met Ile Thr Lys Ala Ala Lys Lys Gly Gln Met Pro Ser
         35                  40                  45

Gln Ile Gly Val Leu Leu Arg Asp Gln His Gly Ile Pro Leu Val Lys
 50                  55                  60

Ser Val Thr Gly Ser Lys Ile Leu Arg Ile Leu Lys Ala His Gly Trp
 65                  70                  75                  80

His Gln Lys Ser Arg Xaa Leu Tyr Phe Ser Ser Arg Arg Arg Trp Arg
             85                  90                  95

<210> SEQ ID NO 123
<211> LENGTH: 327
<212> TYPE: PRT
<213> ORGANISM: Sorghum bicolor
<220> FEATURE:
<221> NAME/KEY: misc_feature
<222> LOCATION: (1)..(2)
<223> OTHER INFORMATION: Xaa can be any naturally occurring amino acid

<400> SEQUENCE: 123

Xaa Xaa Arg Glu Glu Gln Gln Gln Gln Pro Arg His Pro Leu Ala
 1               5                  10                  15

Ser Phe Leu Pro Leu Leu Ser Leu Leu Pro His Arg Arg Arg Arg Leu
             20                  25                  30

Phe Ala Leu Arg Ala Leu Ala Ser His Pro Trp Val Ala Ala Ala Tyr
         35                  40                  45

Leu Pro Thr Cys Val Leu Pro Gly Glu Leu Cys Thr Ser Pro Val Ala
 50                  55                  60

Ser Pro Leu Gly Met Asp Ala Gly Gly Glu Lys Phe Ser Asp Ala Ala
 65                  70                  75                  80

Ala Ala Glu Gly Gly Glu Gly Gly Gly Asp Leu Tyr Ala Val Leu Gly
             85                  90                  95

Leu Lys Lys Glu Cys Ser Asp Ala Asp Leu Lys Val Ala Tyr Arg Lys
             100                 105                 110

Leu Ala Lys Lys Trp His Pro Asp Lys Cys Ser Ser Ser Ser Ser Val
         115                 120                 125

Lys His Met Glu Glu Ala Lys Glu Lys Phe Gln Glu Ile Gln Gly Ala
 130                 135                 140
```

```
Tyr Ser Val Leu Ser Asp Ala Asn Lys Arg Leu Leu Tyr Asp Val Gly
145                 150                 155                 160

Val Tyr Asp Asp Glu Asp Asp Glu Asp Ser Met Gln Gly Met Gly Asp
                165                 170                 175

Phe Ile Gly Glu Met Ala Gln Met Met Ser Gln Val Arg Pro Thr Arg
            180                 185                 190

Gln Glu Ser Phe Glu Glu Leu Gln Gln Leu Phe Val Asp Met Phe Gln
        195                 200                 205

Ser Asp Ile Asp Ser Gly Phe Cys Asn Gly Ser Ala Lys Asp Gln Val
    210                 215                 220

Gln Gly Gln Ala Lys Ser Arg Thr Cys Ser Thr Ser Pro Ser Ser Ser
225                 230                 235                 240

Pro Ser Pro Pro Pro Pro Thr Ile Val Lys Glu Ala Glu Val Ser
                245                 250                 255

Ser Cys Asn Gly Phe Asn Lys Arg Gly Ser Ala Met Asp Ser Gly
    260                 265                 270

Lys Pro Pro Arg Pro Val Glu Gly Gly Ala Gly Gln Ala Gly Phe Cys
        275                 280                 285

Phe Gly Val Ser Asp Thr Lys Gln Thr Pro Lys Pro Arg Gly Pro Asn
290                 295                 300

Thr Ser Arg Arg Arg Asn Gly Arg Lys Gln Lys Leu Ser Ser Lys His
305                 310                 315                 320

Asp Val Ser Ser Glu Asp Glu
                325

<210> SEQ ID NO 124
<211> LENGTH: 265
<212> TYPE: PRT
<213> ORGANISM: Saccharum officinarum

<400> SEQUENCE: 124

Met Asp Ala Gly Gly Glu Lys Cys Gly Asp Ala Ala Ala Ala Glu Gly
1               5                   10                  15

Gly Glu Gly Gly Gly Asp Leu Tyr Ala Val Leu Gly Leu Lys Lys Glu
                20                  25                  30

Cys Ser Asp Ala Asp Leu Lys Val Ala Tyr Arg Lys Leu Ala Lys Lys
            35                  40                  45

Trp His Pro Asp Lys Cys Ser Ser Ser Ser Val Lys His Met Glu
        50                  55                  60

Glu Ala Lys Glu Lys Phe Gln Glu Ile Gln Ala Tyr Ser Val Leu
65                  70                  75                  80

Ser Asp Ala Asn Lys Arg Leu Leu Tyr Asp Val Gly Val Tyr Asp Asp
                85                  90                  95

Glu Asp Asp Glu Asp Ser Met Gln Gly Met Gly Asp Phe Ile Gly Glu
            100                 105                 110

Met Ala Gln Met Met Ser Gln Val Arg Pro Thr Arg Gln Glu Ser Phe
        115                 120                 125

Glu Glu Leu Gln Gln Leu Phe Val Asp Met Phe Gln Ser Asp Ile Asp
    130                 135                 140

Ser Gly Phe Cys Asn Gly Thr Ala Lys Gly His Gln Val Gln Gly Gln
145                 150                 155                 160

Ala Lys Ser Arg Thr Cys Ser Thr Ser Pro Ser Ser Pro Ser Pro
                165                 170                 175

Pro Pro Pro Thr Ile Val Lys Glu Ala Glu Val Pro Ser Cys Asn Gly
            180                 185                 190
```

```
Phe Asn Lys Arg Gly Ser Ser Ala Met Asp Ser Gly Lys Pro Pro Arg
                195                 200                 205

Pro Val Glu Gly Gly Ala Gly Gln Arg Gln Ala Gly Phe Cys Phe Gly
    210                 215                 220

Val Ser Asp Thr Lys Gln Ala Ala Lys Pro Arg Gly Pro Asn Thr Ser
225                 230                 235                 240

Arg Arg Arg Asn Gly Arg Lys Gln Lys Leu Ser Ser Lys His Asp Val
                245                 250                 255

Ser Ser Glu Asp Glu Thr Ala Gly Ser
                260                 265

<210> SEQ ID NO 125
<211> LENGTH: 320
<212> TYPE: PRT
<213> ORGANISM: Sorghum bicolor

<400> SEQUENCE: 125

Met Asp Ser Leu Trp His Leu Gly Asp Glu Leu Arg Gly Gln Pro Lys
1               5                   10                  15

Val Val Glu Asp Arg Gln Trp Ser Leu Met Thr Ser Lys Leu Ala Glu
                20                  25                  30

Ile Thr Arg Ser Lys Gly Glu Arg Met Asn Asp Leu Asp Tyr Ala Arg
            35                  40                  45

Met Asn Thr Val Pro Asp Ala Lys Gln Trp Asp Lys Thr Ser Phe Gln
50                  55                  60

His His Asp Gln Ser Arg Met Asp His Ile Asn Leu Gly Leu Met Asn
65                  70                  75                  80

Leu Asp Leu Lys Met Asn Asp Leu Lys Met Asn Glu Ala Pro Thr Ala
                85                  90                  95

Met Lys Leu Pro Phe His Asn Met Pro Tyr Asn Met Asn Pro Met Tyr
            100                 105                 110

Pro Lys Gly Ser Asn Ala Asn Val Asn Val Asn Ala Phe Lys Met Asn
        115                 120                 125

Val Gly Val Asn Lys Tyr Ser Asn Ser Pro Asn Gly Lys Asp Ala Asn
    130                 135                 140

Gly Lys Asn Asn Gly Gly Ser Asn Asn Gly Gly Asn Ser Asn Gly
145                 150                 155                 160

Ser Ala Asn Gly Asn Ser Ala Val Asp Lys Arg Phe Lys Thr Leu Pro
                165                 170                 175

Thr Ser Glu Met Leu Pro Arg Asn Glu Val Leu Gly Gly Tyr Ile Phe
            180                 185                 190

Val Cys Asn Asn Asp Thr Met Gln Glu Asp Leu Lys Arg Gln Leu Phe
        195                 200                 205

Gly Leu Pro Ala Arg Tyr Arg Asp Ser Val Arg Ala Ile Thr Pro Gly
    210                 215                 220

Leu Pro Leu Phe Leu Tyr Asn Tyr Thr Thr His Gln Leu His Gly Val
225                 230                 235                 240

Phe Glu Ala Ala Ser Phe Gly Gly Ser Asn Ile Asp Pro Thr Ala Trp
                245                 250                 255

Glu Asp Lys Lys Cys Lys Gly Glu Ser Arg Phe Pro Ala Gln Val Arg
            260                 265                 270

Ile Arg Ile Arg Lys Leu Cys Lys Pro Leu Glu Glu Asp Ser Phe Arg
        275                 280                 285

Pro Val Leu His His Tyr Asp Gly Pro Lys Phe Arg Leu Glu Leu Ser
    290                 295                 300
```

```
Ile Ala Glu Thr Leu Ser Leu Leu Asp Leu Cys Glu Lys Glu Gly Ile
305                 310                 315                 320

<210> SEQ ID NO 126
<211> LENGTH: 265
<212> TYPE: PRT
<213> ORGANISM: Saccharum officinarum

<400> SEQUENCE: 126

Met Asn Thr Asp Pro Asp Ala Lys Gln Trp Asp Lys Thr Ser Tyr Gln
1               5                   10                  15

His His Asn Glu Ser Arg Met Asp His Ile Asn Leu Gly Leu Met Asn
            20                  25                  30

Leu Asp Leu Lys Met Asn Glu Ala Ala Thr Ala Met Lys Leu Pro Phe
        35                  40                  45

His Asn Met Pro Tyr Asn Met Asn Pro Met Tyr Pro Lys Gly Ser Asn
    50                  55                  60

Val Asn Val Asn Ala Phe Lys Met Asn Val Gly Val Asn Lys Tyr Ser
65                  70                  75                  80

Asn Ser Pro Asn Gly Lys Asp Ala Asn Gly Lys Asn Asn Gly Gly Ser
                85                  90                  95

Asn Asn Asn Gly Gly Asn Ser Asn Gly Ser Ala Asn Ser Asn Ser Ala
            100                 105                 110

Val Asp Lys Arg Phe Lys Thr Leu Pro Thr Ser Glu Met Leu Pro Arg
        115                 120                 125

Asn Glu Val Leu Gly Gly Tyr Ile Phe Val Cys Asn Asn Asp Thr Met
    130                 135                 140

Gln Glu Asp Leu Lys Arg Gln Leu Phe Gly Leu Pro Ala Arg Tyr Arg
145                 150                 155                 160

Asp Ser Val Arg Ala Ile Thr Pro Gly Leu Pro Leu Phe Leu Tyr Asn
                165                 170                 175

Tyr Thr Thr His Gln Leu His Gly Val Phe Glu Ala Ala Ser Phe Gly
            180                 185                 190

Gly Ser Asn Ile Asp Pro Thr Ala Trp Glu Asp Lys Lys Cys Lys Gly
        195                 200                 205

Glu Ser Arg Phe Pro Ala Gln Val Arg Ile Arg Ile Arg Lys Leu Cys
    210                 215                 220

Lys Pro Leu Glu Glu Asp Ser Phe Arg Pro Val Leu His His Tyr Asp
225                 230                 235                 240

Gly Pro Lys Phe Arg Leu Glu Leu Ser Ile Ala Glu Thr Leu Ser Leu
                245                 250                 255

Leu Asp Leu Cys Glu Lys Glu Gly Ile
            260                 265

<210> SEQ ID NO 127
<211> LENGTH: 200
<212> TYPE: PRT
<213> ORGANISM: Saccharum officinarum
<220> FEATURE:
<221> NAME/KEY: misc_feature
<222> LOCATION: (1)..(2)
<223> OTHER INFORMATION: Xaa can be any naturally occurring amino acid

<400> SEQUENCE: 127

Xaa Xaa Gln Pro Lys Val Val Glu Asp Arg Gln Trp Ser Leu Met Thr
1               5                   10                  15

Ser Lys Leu Ala Glu Ile Thr Arg Ser Lys Gly Glu Arg Met Asn Asp
            20                  25                  30
```

```
Leu Asp Tyr Ala Arg Met Asn Thr Val Pro Asp Ala Lys Gln Trp Asp
             35                  40                  45

Lys Thr Ser Tyr Gln His His Asp Glu Ser Arg Met Asp His Ile Asn
 50                  55                  60

Leu Gly Leu Met Asn Leu Asp Leu Lys Met Asn Asp Leu Lys Met Asn
 65                  70                  75                  80

Glu Ala Ala Thr Ala Met Lys Leu Pro Phe His Asn Met Pro Tyr Asn
                 85                  90                  95

Met Asn Pro Met Tyr Pro Lys Gly Ser Asn Val Asn Val Asn Ala Phe
            100                 105                 110

Lys Met Asn Val Gly Val Asn Lys Tyr Ser Ser Ser Pro Asn Gly Lys
            115                 120                 125

Asp Ala Asn Gly Lys Asn Asn Gly Gly Ser Asn Asn Gly Gly Asn
        130                 135                 140

Ser Asn Gly Ser Ala Asn Ser Asn Ser Ala Val Asp Lys Arg Phe Lys
145                 150                 155                 160

Thr Leu Pro Thr Ser Glu Met Leu Pro Arg Asn Glu Val Leu Gly Gly
                165                 170                 175

Tyr Ile Phe Val Cys Asn Asn Asp Thr Met Gln Glu Asp Leu Lys Arg
            180                 185                 190

Gln Leu Phe Gly Leu Pro Ala Arg
            195                 200

<210> SEQ ID NO 128
<211> LENGTH: 381
<212> TYPE: PRT
<213> ORGANISM: Sorghum bicolor

<400> SEQUENCE: 128

Met Ile Leu Glu Val Ala Ala Val Glu Thr Gln Ser Ile Val His Leu
 1               5                  10                  15

Phe Lys Pro Arg Asp Glu Lys Ile Leu Leu Ala Glu Gly His Lys Arg
            20                  25                  30

Pro Arg Ser Pro Gly Leu Ser Ser Lys Ala Tyr Ser Gly Ser Leu
         35                  40                  45

Val Gly Leu Ser Ile Val Phe Ala Pro Leu Ser Ala Leu Val Ala Ser
 50                  55                  60

Ser Glu Pro Met Ser His Pro Pro Pro Pro Val Asp Gln Asn Ile
 65                  70                  75                  80

Ser Leu Arg Phe Cys Glu Ser Phe Ser Leu Gln Gly Thr Glu Thr Pro
                 85                  90                  95

Gly Ala Phe Thr Pro Pro Ala Pro Ala Phe Pro Ser Arg Pro Arg Thr
            100                 105                 110

Gly Ala Thr Thr Arg Leu Leu Leu Glu Thr Phe His Ser Ser Met Ala
            115                 120                 125

Lys Leu Val Asn Lys Leu Val Asp Ser Phe Glu Glu Gln Asp Thr Pro
        130                 135                 140

Asp Val Gly Cys Val Arg Ala Val Leu Ala Glu Leu Val Leu Thr Phe
145                 150                 155                 160

Leu Phe Val Phe Thr Gly Val Ser Ala Ala Met Ala Ala Gly Ser Gly
                165                 170                 175

Val Lys Pro Gly Glu Ala Met Pro Met Ala Thr Leu Ala Ala Val Ala
            180                 185                 190

Ile Ala His Ala Leu Ala Ala Gly Val Leu Val Thr Ala Gly Phe His
            195                 200                 205
```

Val Ser Gly Gly His Leu Asn Pro Ala Val Thr Val Gly Leu Met Val
210                 215                 220

Arg Gly His Ile Thr Lys Leu Arg Ala Val Leu Tyr Val Ala Ala Gln
225                 230                 235                 240

Val Leu Ala Ser Ser Leu Ala Cys Ile Leu Leu Arg Tyr Leu Ser Gly
            245                 250                 255

Gly Met Val Thr Pro Val His Ala Leu Gly Ala Gly Ile Ser Pro Met
            260                 265                 270

Gln Gly Leu Val Met Glu Val Ile Leu Thr Phe Ser Leu Leu Phe Val
        275                 280                 285

Thr Tyr Ala Met Ile Leu Asp Pro Arg Ser Gln Val Arg Thr Ile Gly
290                 295                 300

Pro Leu Leu Thr Gly Leu Ile Val Gly Ala Asn Ser Leu Ala Gly Gly
305                 310                 315                 320

Asn Phe Ser Gly Ala Ser Met Asn Pro Ala Arg Ser Phe Gly Pro Ala
            325                 330                 335

Leu Ala Ser Gly Val Trp Thr Asn His Trp Ile Tyr Trp Ile Gly Pro
            340                 345                 350

Leu Leu Gly Gly Pro Leu Ala Gly Phe Ile Tyr Glu Ser Leu Phe Ile
        355                 360                 365

Val Asn Lys Thr His Glu Pro Leu Leu Asn Gly Asp Ile
370                 375                 380

<210> SEQ ID NO 129
<211> LENGTH: 308
<212> TYPE: PRT
<213> ORGANISM: Saccharum officinarum

<400> SEQUENCE: 129

Pro Thr Arg Pro Pro Pro Val Val Gln Asn Ile Ser Leu Arg Phe
1               5                   10                  15

Ser Glu Ser Phe Ser Leu Gln Gly Thr Gly Thr Gly Ala Phe Thr
            20                  25                  30

Pro Pro Pro Ala Phe Pro Ser Pro Gly Arg Leu Leu Leu Ala Ile
        35                  40                  45

Val His Ser Phe Met Ala Lys Leu Val Asn Lys Leu Val Asp Ser Phe
50                  55                  60

Asp His Asp Glu Thr Thr Pro Asp Val Gly Cys Val Arg Ala Val Leu
65                  70                  75                  80

Ala Glu Leu Val Leu Thr Phe Leu Phe Val Phe Thr Gly Val Ser Ala
            85                  90                  95

Ala Met Ala Ala Gly Ser Gly Gly Lys Pro Gly Glu Ala Met Pro Met
        100                 105                 110

Ala Thr Leu Ala Ala Val Ala Ile Ala His Ala Leu Ala Ala Gly Val
        115                 120                 125

Leu Val Thr Ala Gly Phe His Val Ser Gly Gly His Leu Asn Pro Ala
    130                 135                 140

Val Thr Val Gly Leu Met Val Cys Gly His Ile Thr Lys Leu Arg Ala
145                 150                 155                 160

Val Leu Tyr Ile Ala Ala Gln Leu Leu Ala Ser Ser Leu Ala Cys Ile
                165                 170                 175

Leu Leu Arg Tyr Leu Ser Gly Gly Met Val Thr Pro Val His Ala Leu
            180                 185                 190

Gly Ala Gly Ile Ser Pro Met Gln Gly Leu Val Met Glu Val Ile Leu
        195                 200                 205

Thr Phe Ser Leu Leu Phe Val Thr Tyr Ala Met Ile Leu Asp Pro Arg
        210                 215                 220

Ser Gln Val Arg Thr Ile Gly Pro Leu Leu Thr Gly Leu Ile Val Gly
225                 230                 235                 240

Ala Asn Ser Leu Ala Gly Gly Asn Phe Thr Gly Ala Ser Met Asn Pro
                245                 250                 255

Ala Arg Ser Phe Gly Pro Ala Leu Ala Thr Gly Val Trp Thr Asn His
            260                 265                 270

Trp Val Tyr Trp Ile Gly Pro Leu Leu Gly Gly Pro Leu Ala Gly Phe
        275                 280                 285

Val Tyr Glu Ser Leu Phe Ile Val Asn Lys Thr His Glu Pro Leu Leu
290                 295                 300

Asn Gly Asp Ile
305

<210> SEQ ID NO 130
<211> LENGTH: 257
<212> TYPE: PRT
<213> ORGANISM: Zea mays

<400> SEQUENCE: 130

Met Ala Lys Leu Val Asn Lys Leu Val Asp Ser Phe Asp His His Glu
1               5                   10                  15

Ala Pro Ala Pro Asp Val Gly Cys Val Arg Ala Val Leu Ala Glu Leu
            20                  25                  30

Val Leu Thr Phe Leu Phe Val Thr Gly Val Ser Ala Ser Met Ala
        35                  40                  45

Ala Gly Ala Gly Gly Lys Pro Gly Glu Ala Met Pro Met Ala Thr Leu
    50                  55                  60

Ala Ala Val Ala Ile Ala His Ala Leu Ala Ala Gly Val Leu Val Thr
65                  70                  75                  80

Ala Gly Phe His Val Ser Gly Gly His Leu Asn Pro Ala Val Thr Val
                85                  90                  95

Gly Ile Leu Val Arg Gly His Ile Thr Lys Leu Arg Ala Leu Leu Tyr
            100                 105                 110

Val Ala Ala Gln Leu Leu Ala Ser Ser Leu Ala Cys Ile Leu Leu Arg
        115                 120                 125

Tyr Leu Ser Gly Gly Met Val Thr Pro Val His Ala Leu Gly Ala Gly
    130                 135                 140

Ile Ser Pro Met Gln Gly Leu Val Met Glu Val Ile Leu Thr Phe Ser
145                 150                 155                 160

Leu Leu Phe Val Thr Tyr Ala Met Ile Leu Asp Pro Arg Ser Gln Val
                165                 170                 175

Arg Thr Ile Gly Pro Leu Leu Thr Gly Leu Ile Val Gly Ala Asn Ser
            180                 185                 190

Leu Ala Gly Gly Asn Phe Thr Gly Ala Ser Met Asn Pro Ala Arg Ser
        195                 200                 205

Phe Gly Pro Ala Met Ala Thr Gly Val Trp Thr Asn His Trp Val Tyr
    210                 215                 220

Trp Ile Gly Pro Leu Leu Gly Gly Ser Leu Ala Gly Phe Val Tyr Glu
225                 230                 235                 240

Ser Leu Phe Met Val Tyr Lys Thr His Glu Pro Leu Leu Asn Gly Asp
                245                 250                 255

Ile

<210> SEQ ID NO 131
<211> LENGTH: 255
<212> TYPE: PRT
<213> ORGANISM: Zea mays

<400> SEQUENCE: 131

```
Met Ala Lys Leu Met Asn Lys Leu Val Asp Ser Phe Glu His Asp Glu
1               5                   10                  15

Ile Leu Asp Val Gly Cys Val Arg Ala Val Leu Ala Glu Leu Val Leu
                20                  25                  30

Thr Phe Leu Phe Val Phe Thr Gly Val Ser Ala Ala Met Ala Ala Gly
            35                  40                  45

Ser Asp Gly Lys Pro Gly Asp Ala Met Pro Met Ala Thr Leu Ala Ala
        50                  55                  60

Val Ala Ile Ala His Ala Leu Ala Ala Gly Val Leu Val Thr Ala Gly
65                  70                  75                  80

Phe His Val Ser Gly Gly His Leu Asn Pro Ala Val Thr Val Gly Leu
                85                  90                  95

Met Val Arg Gly His Ile Thr Lys Leu Arg Ala Val Leu Tyr Val Ala
                100                 105                 110

Ala Gln Leu Leu Ala Ser Ser Ala Ala Cys Val Leu Leu Arg Phe Leu
            115                 120                 125

Ser Gly Gly Met Val Thr Pro Val His Ala Leu Gly Arg Gly Ile Ser
        130                 135                 140

Pro Met Gln Gly Leu Val Met Glu Val Ile Leu Thr Phe Ser Leu Leu
145                 150                 155                 160

Phe Val Thr Tyr Ala Met Ile Leu Asp Pro Arg Ser Gln Val Arg Ala
                165                 170                 175

Ile Gly Pro Leu Leu Thr Gly Leu Ile Val Gly Ala Asn Ser Leu Ala
                180                 185                 190

Gly Gly Asn Phe Thr Gly Ala Ser Met Asn Pro Ala Arg Ser Phe Gly
            195                 200                 205

Pro Ala Leu Ala Thr Gly Asp Trp Thr Asn His Trp Val Tyr Trp Ile
210                 215                 220

Gly Pro Leu Leu Gly Gly Pro Leu Ala Gly Phe Val Tyr Glu Ser Leu
225                 230                 235                 240

Phe Leu Val Gln Lys Met His Glu Pro Leu Leu Asn Gly Glu Val
                245                 250                 255
```

<210> SEQ ID NO 132
<211> LENGTH: 254
<212> TYPE: PRT
<213> ORGANISM: Sorghum bicolor

<400> SEQUENCE: 132

```
Met Ala Ser Pro Glu Gly Thr Thr Trp Val Phe Asp Cys Pro Leu Met
1               5                   10                  15

Asp Asp Leu Ala Val Ala Ala Asp Phe Ala Ala Ala Pro Ala Gly Gly
                20                  25                  30

Phe Phe Trp Ala Ala Pro Pro Ser Leu Gln Pro Gln Val Val Gln Ala
            35                  40                  45

Pro Val Gln Ser Val Val Ala Ser Ala Pro Asn Pro Cys Val Glu
        50                  55                  60

Ile Ser Ser Ser Val Asp Cys Gly Gln Gly Lys Glu Gln Pro Thr Asn
65                  70                  75                  80

Lys Arg Pro Arg Ser Glu Ser Thr Ala Glu Pro Ser Thr Lys Ala Ser
```

```
                    85                  90                  95
Arg Glu Lys Ile Arg Arg Asp Lys Leu Asn Glu Arg Phe Leu Glu Leu
                100                 105                 110

Gly Ala Ile Leu Glu Pro Gly Lys Thr Pro Lys Met Asp Lys Ser Ala
                115                 120                 125

Ile Leu Asn Asp Ala Ile Arg Val Val Gly Glu Leu Arg Ser Glu Ala
            130                 135                 140

Lys Glu Leu Lys Asp Ser Asn Glu Ser Leu Gln Glu Lys Ile Lys Glu
145                 150                 155                 160

Leu Lys Ala Glu Lys Asn Glu Leu Arg Asp Glu Lys Gln Arg Leu Lys
                165                 170                 175

Ala Glu Lys Glu Ser Leu Glu Gln Gln Ile Lys Phe Leu Asn Ala Arg
                180                 185                 190

Pro Ser Leu Val Pro His His Pro Val Ile Ser Ala Ser Ala Phe Thr
                195                 200                 205

Ala Pro Gln Gly Pro Ala Val Ala Gly His Lys Leu Met Met Pro Val
            210                 215                 220

Leu Gly Tyr Pro Gly Phe Pro Met Trp Gln Phe Met Pro Pro Ser Asp
225                 230                 235                 240

Val Asp Thr Ser Asp Asp Pro Lys Ser Cys Pro Pro Val Ala
                245                 250

<210> SEQ ID NO 133
<211> LENGTH: 252
<212> TYPE: PRT
<213> ORGANISM: Zea mays

<400> SEQUENCE: 133

Met Ala Ser Pro Glu Gly Thr Thr Trp Val Phe Asp Cys Pro Leu Met
1               5                   10                  15

Asp Asp Leu Ala Val Ala Ala Asp Phe Ala Ala Ala Pro Ala Gly Gly
                20                  25                  30

Phe Phe Trp Ala Ala Pro Pro Ser Leu Gln Pro Gln Ala Pro Val Gln
            35                  40                  45

Ser Val Val Ala Ala Ser Ala Pro Asn Pro Cys Met Glu Ile Ser Ser
50                  55                  60

Ser Val Asp Cys Gly Gln Glu Lys Glu Gln Pro Thr Asn Lys Arg Pro
65                  70                  75                  80

Arg Ser Glu Ser Thr Thr Glu Ser Ser Thr Lys Ala Ser Arg Glu Lys
                85                  90                  95

Ile Arg Arg Asp Lys Leu Asn Glu Arg Phe Leu Glu Leu Gly Ala Ile
                100                 105                 110

Leu Glu Pro Gly Lys Thr Pro Lys Met Asp Lys Thr Ala Ile Leu Ser
            115                 120                 125

Asp Ala Ile Arg Val Val Gly Glu Leu Arg Ser Glu Ala Lys Lys Leu
130                 135                 140

Lys Asp Ser Asn Glu Asn Leu Gln Glu Lys Ile Lys Glu Leu Lys Ala
145                 150                 155                 160

Glu Lys Asn Glu Leu Arg Asp Glu Lys Gln Arg Leu Lys Ala Glu Lys
                165                 170                 175

Glu Ser Leu Glu Gln Gln Ile Lys Phe Leu Asn Ala Arg Pro Ser Leu
                180                 185                 190

Val Pro His His Pro Val Ile Pro Ala Ser Ala Phe Pro Ala Pro Gln
            195                 200                 205

Gly Pro Ala Ala Ala Ala Arg His Lys Leu Met Met Pro Val Ile Gly
```

```
                210                 215                 220
Tyr Pro Gly Phe Pro Met Trp Gln Phe Met Pro Pro Ser Asp Val Asp
225                 230                 235                 240

Thr Ser Asp Asp Pro Arg Ser Cys Pro Pro Val Ala
                245                 250

<210> SEQ ID NO 134
<211> LENGTH: 159
<212> TYPE: PRT
<213> ORGANISM: Saccharum officinarum

<400> SEQUENCE: 134

Met Ala Ser Pro Glu Gly Thr Thr Trp Val Phe Asp Cys Pro Leu Met
1               5                   10                  15

Asp Asp Leu Ala Val Ala Ala Asp Phe Ala Ala Pro Ala Gly Gly
            20                  25                  30

Phe Phe Trp Ala Ala Pro Pro Ser Leu Gln Pro Gln Val Val Gln Ala
        35                  40                  45

Pro Val Gln Ser Val Val Ala Ala Ser Ala Pro Asn Pro Pro Cys Val
    50                  55                  60

Glu Ile Ser Ser Ser Val Asp Cys Gly Gln Gly Lys Glu Gln Pro Thr
65                  70                  75                  80

Asn Lys Arg Pro Arg Ser Glu Ser Thr Ala Glu Pro Ser Thr Lys Ala
                85                  90                  95

Ser Arg Glu Lys Ile Arg Arg Asp Lys Leu Asn Lys Arg Phe Leu Glu
            100                 105                 110

Trp Gly Ala Ile Val Glu Pro Gly Glu Thr Pro Lys Met Asp Lys Ser
        115                 120                 125

Ala Ile Leu Asn Asp Ala Ile Arg Ala Val Ser Glu Leu Arg Ser Glu
    130                 135                 140

Thr Lys Lys Leu Lys Asp Ser Asn Glu Ser Leu Gln Gly Glu Asp
145                 150                 155

<210> SEQ ID NO 135
<211> LENGTH: 151
<212> TYPE: PRT
<213> ORGANISM: Brassica napus

<400> SEQUENCE: 135

Met Gly Arg Met His Ser Arg Gly Lys Gly Ile Ser Ala Ser Ala Leu
1               5                   10                  15

Pro Tyr Lys Arg Ser Pro Pro Thr Trp Leu Lys Thr Thr Ala Leu Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140
```

```
Thr Ala Ser Thr Leu Val Ala
145                 150

<210> SEQ ID NO 136
<211> LENGTH: 151
<212> TYPE: PRT
<213> ORGANISM: Brassica napus

<400> SEQUENCE: 136

Met Gly Arg Met His Ser Arg Gly Lys Gly Ile Ser Ala Ser Ala Leu
1               5                   10                  15

Pro Tyr Lys Arg Ser Pro Thr Trp Leu Lys Thr Thr Ala Leu Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 137
<211> LENGTH: 151
<212> TYPE: PRT
<213> ORGANISM: Solanum tuberosum

<400> SEQUENCE: 137

Met Gly Arg Met His Ser Arg Gly Lys Gly Ile Ser Ala Ser Ala Leu
1               5                   10                  15

Pro Tyr Lys Arg Thr Pro Ser Trp Leu Lys Thr Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150
```

```
<210> SEQ ID NO 138
<211> LENGTH: 151
<212> TYPE: PRT
<213> ORGANISM: Gossypium sp.

<400> SEQUENCE: 138

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ser Gln Asp
            20                  25                  30

Val Glu Glu Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 139
<211> LENGTH: 151
<212> TYPE: PRT
<213> ORGANISM: Gossypium sp.

<400> SEQUENCE: 139

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ser Gln Asp
            20                  25                  30

Val Glu Glu Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 140
<211> LENGTH: 151
<212> TYPE: PRT
```

<213> ORGANISM: Lycopersicon esculentum

<400> SEQUENCE: 140

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 141
<211> LENGTH: 151
<212> TYPE: PRT
<213> ORGANISM: Lycopersicon esculentum

<400> SEQUENCE: 141

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 142
<211> LENGTH: 151
<212> TYPE: PRT
<213> ORGANISM: Lycopersicon esculentum

<400> SEQUENCE: 142

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
            85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 143
<211> LENGTH: 151
<212> TYPE: PRT
<213> ORGANISM: Lycopersicon esculentum

<400> SEQUENCE: 143

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
            85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 144
<211> LENGTH: 151
<212> TYPE: PRT
<213> ORGANISM: Solanum tuberosum

<400> SEQUENCE: 144

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp

```
                    20                  25                  30

Val Glu Asp Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
        50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 145
<211> LENGTH: 151
<212> TYPE: PRT
<213> ORGANISM: Solanum tuberosum

<400> SEQUENCE: 145

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 146
<211> LENGTH: 151
<212> TYPE: PRT
<213> ORGANISM: Solanum tuberosum

<400> SEQUENCE: 146

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45
```

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 147
<211> LENGTH: 151
<212> TYPE: PRT
<213> ORGANISM: Solanum tuberosum

<400> SEQUENCE: 147

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 148
<211> LENGTH: 151
<212> TYPE: PRT
<213> ORGANISM: Capsicum annuum

<400> SEQUENCE: 148

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 149
<211> LENGTH: 151
<212> TYPE: PRT
<213> ORGANISM: Arabidopsis thaliana

<400> SEQUENCE: 149

Met Gly Arg Met His Ser Arg Gly Lys Gly Ile Ser Ala Ser Ala Leu
1               5                   10                  15

Pro Tyr Lys Arg Ser Ser Pro Ser Trp Leu Lys Thr Thr Ser Gln Asp
                20                  25                  30

Val Asp Glu Ser Ile Cys Lys Phe Ala Lys Lys Gly Leu Thr Pro Ser
            35                  40                  45

Gln Ile Gly Val Ile Leu Arg Asp Ser His Gly Ile Pro Gln Val Lys
        50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 150
<211> LENGTH: 151
<212> TYPE: PRT
<213> ORGANISM: Brassica napus

<400> SEQUENCE: 150

Met Gly Arg Leu His Ser Lys Gly Lys Gly Ile Ser Ala Ser Ala Leu
1               5                   10                  15

Pro Tyr Lys Arg Ser Pro Pro Ser Trp Leu Lys Thr Thr Ser Gln Asp
                20                  25                  30

Val Asp Glu Ser Ile Cys Lys Phe Ala Lys Lys Gly Leu Thr Pro Ser
            35                  40                  45

Gln Ile Gly Val Ile Leu Arg Asp Ser His Gly Ile Pro Gln Val Lys
        50                  55                  60

Ser Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val

```
            85                  90                  95
Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 151
<211> LENGTH: 151
<212> TYPE: PRT
<213> ORGANISM: Brassica napus

<400> SEQUENCE: 151

Met Gly Arg Leu His Ser Lys Gly Lys Gly Ile Ser Ala Ser Ala Leu
1               5                   10                  15

Pro Tyr Lys Arg Ser Pro Ser Trp Leu Lys Thr Thr Ser Glu Asp
            20                  25                  30

Val Asp Glu Ser Ile Cys Lys Phe Ala Lys Lys Gly Leu Thr Pro Ser
            35                  40                  45

Gln Ile Gly Val Ile Leu Arg Asp Ser His Gly Ile Pro Gln Val Lys
        50                  55                  60

Ser Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
            85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 152
<211> LENGTH: 151
<212> TYPE: PRT
<213> ORGANISM: Brassica napus

<400> SEQUENCE: 152

Met Gly Arg Leu His Ser Lys Gly Lys Gly Ile Ser Ala Ser Ala Leu
1               5                   10                  15

Pro Tyr Lys Arg Ser Pro Ser Trp Leu Lys Thr Thr Ser Gln Asp
            20                  25                  30

Val Asp Glu Ser Ile Cys Lys Phe Ala Lys Lys Gly Leu Thr Pro Ser
            35                  40                  45

Gln Ile Gly Val Ile Leu Arg Asp Ser His Gly Ile Pro Gln Val Lys
        50                  55                  60

Ser Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
            85                  90                  95

Ala Ile Arg Lys His Leu Glu Arg Asn Arg Lys Asp Lys Asp Ser Lys
            100                 105                 110
```

```
Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
        130                 135                 140

Thr Ala Ser Thr Leu Val Ala
145                 150

<210> SEQ ID NO 153
<211> LENGTH: 151
<212> TYPE: PRT
<213> ORGANISM: Gossypium Sp.

<400> SEQUENCE: 153

Met Gly Arg Met His Ser Arg Gly Lys Gly Ile Ser Ala Ser Ala Leu
1               5                   10                  15

Pro Tyr Arg Arg Thr Pro Pro Ser Trp Leu Lys Ile Ser Ser Gln Asp
            20                  25                  30

Val Glu Glu Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 154
<211> LENGTH: 151
<212> TYPE: PRT
<213> ORGANISM: Gossypium Sp.

<400> SEQUENCE: 154

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ser Gln Asp
            20                  25                  30

Val Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125
```

Tyr Lys Lys Thr Lys Lys Leu Pro Pro Val Trp Lys Tyr Glu Ser Thr
130                 135                 140

Thr Ala Ser Thr Leu Val Ala
145                 150

<210> SEQ ID NO 155
<211> LENGTH: 151
<212> TYPE: PRT
<213> ORGANISM: Gossypium Sp.

<400> SEQUENCE: 155

Met Gly Arg Met His Ser Arg Gly Lys Gly Ile Ser Ala Ser Ala Leu
1               5                   10                  15

Pro Tyr Lys Arg Thr Pro Ser Trp Leu Lys Ile Ser Ser Gln Asp
            20                  25                  30

Val Glu Glu Asn Ile Cys Lys Phe Ala Lys Lys Gly Leu Thr Pro Ser
                35                  40                  45

Gln Ile Gly Val Ile Leu Arg Asp Ser His Gly Ile Ala Gln Val Arg
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
130                 135                 140

Thr Ala Ser Thr Leu Val Ala
145                 150

<210> SEQ ID NO 156
<211> LENGTH: 151
<212> TYPE: PRT
<213> ORGANISM: Arabidopsis thaliana

<400> SEQUENCE: 156

Met Gly Arg Met His Ser Arg Gly Lys Gly Ile Ser Ala Ser Ala Leu
1               5                   10                  15

Pro Tyr Lys Arg Ser Ser Pro Ser Trp Leu Lys Thr Thr Pro Gln Asp
            20                  25                  30

Val Asp Glu Ser Ile Cys Lys Phe Ala Lys Lys Gly Leu Thr Pro Ser
                35                  40                  45

Gln Ile Gly Val Ile Leu Arg Asp Ser His Gly Ile Pro Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
                100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
130                 135                 140

Thr Ala Ser Thr Leu Val Ala

<210> SEQ ID NO 157
<211> LENGTH: 151
<212> TYPE: PRT
<213> ORGANISM: Glycine max

<400> SEQUENCE: 157

Met Gly Arg Met His Ser Arg Gly Lys Gly Ile Ser Ser Ala Leu
1               5                   10                  15

Pro Tyr Lys Arg Thr Pro Ser Trp Leu Lys Ile Ser Ser Gln Asp
                20                  25                  30

Val Glu Glu Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Asn
        50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ser Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 158
<211> LENGTH: 215
<212> TYPE: PRT
<213> ORGANISM: Capsicum annuum
<220> FEATURE:
<221> NAME/KEY: misc_feature
<222> LOCATION: (1)..(3)
<223> OTHER INFORMATION: Xaa can be any naturally occurring amino acid

<400> SEQUENCE: 158

Xaa Xaa Xaa Glu Arg Glu Arg Glu Arg Glu Arg Glu Arg Glu
1               5                   10                  15

Arg Glu Arg Glu Arg Glu Arg Glu Arg Glu Arg Glu Arg Glu Arg Glu
                20                  25                  30

Arg Glu Arg Glu Arg Glu Arg Glu Arg Glu Arg Gly Gln Pro Asn Ser
            35                  40                  45

Ser Leu Ser Pro Pro Ser Pro Leu Thr Thr Asn Thr Gln Pro Ala
        50                  55                  60

Ile Met Gly Arg Met His Ser Arg Gly Lys Gly Ile Ser Ala Ser Ala
65                  70                  75                  80

Leu Pro Tyr Lys Arg Thr Pro Ser Trp Leu Lys Ile Ser Ala Pro
                85                  90                  95

Asp Val Glu Asp Asn Ile Cys Lys Phe Ala Lys Lys Gly Leu Ala Pro
            100                 105                 110

Ser Gln Ile Gly Val Ile Leu Arg Asp Ser His Gly Ile Ala Gln Val
        115                 120                 125

Lys Ser Val Thr Gly Ser Lys Ile Leu Arg Ile Leu Lys Ala His Gly
    130                 135                 140

Leu Ala Pro Glu Ile Pro Glu Asp Leu Tyr His Leu Ile Lys Lys Ala

```
                145                 150                 155                 160
Val Ala Ile Arg Lys His Leu Glu Arg Asn Arg Lys Asp Lys Asp Ser
                165                 170                 175

Lys Phe Arg Leu Ile Leu Val Glu Ser Arg Ile His Arg Leu Ala Arg
                180                 185                 190

Tyr Tyr Lys Lys Thr Lys Lys Leu Pro Pro Val Trp Lys Tyr Glu Ser
                195                 200                 205

Thr Thr Ala Ser Thr Leu Val
                210                 215

<210> SEQ ID NO 159
<211> LENGTH: 151
<212> TYPE: PRT
<213> ORGANISM: Populus Sp.

<400> SEQUENCE: 159

Met Gly Arg Met His Ser His Gly Lys Gly Ile Ser Ala Ser Ala Leu
1               5                   10                  15

Pro Tyr Lys Arg Thr Pro Pro Ser Trp Leu Lys Ile Ser Ala Gln Asp
                20                  25                  30

Val Glu Asp Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Arg
        50                  55                  60

Ser Val Thr Gly Asn Gln Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Ser
    130                 135                 140

Thr Ala Ser Thr Leu Val Ala
145                 150

<210> SEQ ID NO 160
<211> LENGTH: 151
<212> TYPE: PRT
<213> ORGANISM: Medicago truncatula

<400> SEQUENCE: 160

Met Gly Arg Met His Ser Gly Gly Lys Gly Ile Ser Ser Ser Ala Leu
1               5                   10                  15

Pro Tyr Lys Arg Ser Ala Pro Gly Trp Leu Lys Thr Ser Thr Gln Asp
                20                  25                  30

Val Glu Glu Thr Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
        50                  55                  60

Phe Ile Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ser Ile Arg Lys His Leu Glu Arg Asn Arg Lys Asp Lys Asp Ser Lys
            100                 105                 110
```

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 161
<211> LENGTH: 151
<212> TYPE: PRT
<213> ORGANISM: Populus Sp.

<400> SEQUENCE: 161

Met Gly Arg Met His Ser Arg Gly Lys Gly Ile Ser Ala Ser Ala Leu
1               5                   10                  15

Pro Tyr Lys Arg Thr Pro Ser Trp Leu Lys Ile Ser Ala Gln Asp
            20                  25                  30

Val Asp Asp Ser Ile Cys Lys Phe Ala Lys Lys Gly Leu Thr Pro Ser
            35                  40                  45

Gln Ile Gly Val Ile Leu Arg Asp Ser His Gly Ile Ala Gln Val Arg
    50                  55                  60

Ser Val Thr Gly Asn Gln Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Ala Pro Val Trp Lys Tyr Glu Ser Ser
    130                 135                 140

Thr Ala Ser Thr Leu Val Ala
145                 150

<210> SEQ ID NO 162
<211> LENGTH: 151
<212> TYPE: PRT
<213> ORGANISM: Medicago truncatula

<400> SEQUENCE: 162

Met Gly Arg Met His Ser Gly Gly Lys Gly Ile Ser Ser Ser Ala Leu
1               5                   10                  15

Pro Tyr Lys Arg Thr Pro Ala Ser Trp Leu Lys Ile Ser Thr Gln Asp
            20                  25                  30

Val Asp Glu Thr Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
    50                  55                  60

Ala Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ser Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Thr
            130                 135                 140

Thr Ala Ser Thr Leu Val Ala
145                 150

<210> SEQ ID NO 163
<211> LENGTH: 151
<212> TYPE: PRT
<213> ORGANISM: Populus Sp.

<400> SEQUENCE: 163

Met Gly Arg Met His Ser Lys Gly Lys Gly Ile Ser Ala Ser Ala Leu
1               5                   10                  15

Pro Tyr Lys Arg Thr Pro Ser Trp Leu Lys Ile Ser Pro Gln Asp
            20                  25                  30

Val Asp Asp Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
50                  55                  60

Ala Val Thr Gly Asn Gln Ile Leu Arg Ile Leu Lys Ala His Gly Leu
65                  70                  75                  80

Ala Pro Glu Ile Pro Glu Asp Leu Tyr His Leu Ile Lys Lys Ala Val
            85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
            115                 120                 125

Tyr Lys Lys Thr Lys Lys Leu Pro Pro Val Trp Lys Tyr Glu Ser Ser
            130                 135                 140

Thr Ala Ser Thr Leu Val Ala
145                 150

<210> SEQ ID NO 164
<211> LENGTH: 148
<212> TYPE: PRT
<213> ORGANISM: Medicago truncatula

<400> SEQUENCE: 164

Met His Ser Lys Gly Lys Gly Ile Ser Ser Ala Leu Pro Tyr Lys
1               5                   10                  15

Arg Thr Ser Pro Ser Trp Leu Lys Ile Ser Pro Glu Val Asp Glu
            20                  25                  30

Thr Ile Cys Lys Phe Ala Lys Lys Gly Leu Thr Pro Ser Gln Ile Gly
            35                  40                  45

Val Ile Leu Arg Asp Ser His Gly Ile Ala Gln Val Lys Ser Val Thr
            50                  55                  60

Gly Ser Lys Ile Leu Arg Ile Leu Lys Ala His Gly Leu Ala Pro Glu
65                  70                  75                  80

Ile Pro Glu Asp Leu Tyr His Leu Ile Lys Lys Ala Val Ser Ile Arg
            85                  90                  95

Lys His Leu Glu Arg Asn Arg Lys Asp Lys Asp Ser Lys Phe Arg Leu
            100                 105                 110

Ile Leu Val Glu Ser Arg Ile His Arg Leu Ala Arg Tyr Tyr Lys Lys
            115                 120                 125

Thr Lys Lys Leu Pro Pro Val Trp Lys Tyr Glu Ser Thr Thr Ala Ser
            130                 135                 140

Thr Leu Val Ala

<210> SEQ ID NO 165
<211> LENGTH: 151
<212> TYPE: PRT
<213> ORGANISM: Hordeum vulgare

<400> SEQUENCE: 165

Met Gly Arg Met His Ser Asn Gly Lys Gly Met Ser Ser Ser Val Ile
1               5                   10                  15

Pro Tyr Lys Arg Glu Ala Pro Ala Trp Val Lys Thr Ala Ala Pro Asp
            20                  25                  30

Val Glu Glu Met Ile Val Arg Ala Ala Lys Lys Gly Gln Leu Pro Ser
        35                  40                  45

Gln Ile Gly Ala Leu Leu Arg Asp Gly His Gly Ile Pro Leu Ser Lys
    50                  55                  60

Ala Val Thr Gly Ala Lys Ile Val Arg Leu Leu Lys Ala Arg Gly Leu
65                  70                  75                  80

Ala Pro Glu Met Pro Glu Asp Leu Tyr Phe Leu Ile Lys Lys Ala Val
                85                  90                  95

Ala Ile Arg Lys His Leu Glu Arg Asn Arg Ser Asp Val Asp Ala Lys
            100                 105                 110

Phe Arg Leu Ile Leu Val Glu Ser Arg Val His Arg Leu Thr Arg Tyr
        115                 120                 125

Tyr Arg Leu Thr Lys Lys Met Pro Ala Ala Trp Lys Tyr Glu Ser Thr
    130                 135                 140

Thr Ala Ser Thr Leu Val Ala
145                 150

<210> SEQ ID NO 166
<211> LENGTH: 185
<212> TYPE: PRT
<213> ORGANISM: Triticum aestivum
<220> FEATURE:
<221> NAME/KEY: misc_feature
<222> LOCATION: (1)..(2)
<223> OTHER INFORMATION: Xaa can be any naturally occurring amino acid

<400> SEQUENCE: 166

Xaa Xaa Gly Thr Ser Ile Phe Arg Phe Pro Ser Pro Pro Pro Gln
1               5                   10                  15

Gln Leu Leu Pro Ile Ser Leu Leu Ala Ala Ala Leu Arg Ser Pro Leu
            20                  25                  30

Ala Ala Met Gly Arg Met His Ser Asn Gly Lys Gly Met Ser Ser Ser
        35                  40                  45

Val Ile Pro Tyr Lys Arg Glu Ala Pro Ala Trp Val Lys Thr Ser Ala
    50                  55                  60

Pro Asp Val Glu Glu Ile Ile Val Arg Ala Ala Lys Lys Gly Gln Leu
65                  70                  75                  80

Pro Ser Gln Ile Gly Ala Leu Leu Arg Asp Gly Tyr Gly Ile Pro Leu
                85                  90                  95

Ser Lys Ala Val Thr Gly Ala Lys Ile Val Arg Leu Leu Lys Ala Arg
            100                 105                 110

Gly Leu Ala Pro Glu Met Pro Glu Asp Leu Tyr Phe Leu Ile Lys Lys
        115                 120                 125

Ala Val Ala Ile Arg Lys His Leu Glu Arg Asn Arg Ser Asp Val Asp
    130                 135                 140

Ala Lys Phe Arg Leu Ile Leu Val Glu Ser Arg Val His Arg Leu Thr

```
              145                 150                 155                 160
Arg Tyr Tyr Arg Leu Thr Lys Lys Met Pro Ala Ala Trp Lys Tyr Glu
                165                 170                 175

Ser Thr Thr Ala Ser Thr Leu Val Ala
            180                 185

<210> SEQ ID NO 167
<211> LENGTH: 151
<212> TYPE: PRT
<213> ORGANISM: Oryza sativa

<400> SEQUENCE: 167

Met Gly Arg Leu His Ser Lys Gly Lys Gly Ile Ala Ser Ser Thr Leu
1               5                   10                  15

Pro Tyr Ser Arg Thr Pro Pro Ala Trp Leu Lys Thr Thr Pro Asp Gln
            20                  25                  30

Val Val Asp His Ile Cys Lys Leu Ala Lys Lys Gly Ala Thr Pro Ser
        35                  40                  45

Gln Ile Gly Val Val Leu Arg Asp Ser His Gly Val Ala Gln Val Lys
    50                  55                  60

Ile Val Thr Gly Asn Lys Ile Leu Arg Ile Leu Lys Ser Asn Gly Leu
65                  70                  75                  80

Ala Pro Glu Leu Pro Glu Asp Leu Tyr Phe Leu Ile Lys Lys Ala Val
                85                  90                  95

Ala Val Arg Lys His Leu Glu Arg Asn Arg Lys Asp Lys Asp Ser Lys
            100                 105                 110

Phe Arg Leu Ile Leu Ile Glu Ser Arg Ile His Arg Leu Ser Arg Tyr
        115                 120                 125

Tyr Lys Thr Val Gly Val Leu Pro Pro Thr Trp Arg Tyr Glu Ser Ala
    130                 135                 140

Thr Ala Ser Thr Leu Val Ala
145                 150

<210> SEQ ID NO 168
<211> LENGTH: 151
<212> TYPE: PRT
<213> ORGANISM: Oryza sativa

<400> SEQUENCE: 168

Met Gly Arg Met His Ser Ser Gly Lys Gly Met Ser Cys Ser Val Leu
1               5                   10                  15

Pro Tyr Arg Arg Ala Ala Pro Ala Trp Val Lys Thr Ser Ala Ser Glu
            20                  25                  30

Val Glu Glu Met Ile Val Arg Val Ala Lys Lys Gly Gln Leu Pro Ser
        35                  40                  45

Gln Ile Gly Ala Ile Leu Arg Asp Ala His Ala Val Pro Leu Ala Gln
    50                  55                  60

Gly Val Thr Gly Gly Lys Ile Leu Arg Val Leu Lys Ser Arg Gly Leu
65                  70                  75                  80

Ala Pro Glu Val Pro Glu Asp Leu Tyr Phe Leu Ile Lys Lys Ala Val
                85                  90                  95

Ala Met Arg Lys His Leu Glu Arg Asn Arg Lys Asp Lys Asp Thr Lys
            100                 105                 110

Phe Arg Leu Ile Leu Val Glu Ser Arg Val His Arg Leu Thr Arg Tyr
        115                 120                 125

Tyr Arg Leu Ala Lys Lys Ile Pro Ala Phe Phe Lys Tyr Asp Ser Thr
    130                 135                 140
```

Thr Ala Ser Thr Leu Val Ala
145                 150

<210> SEQ ID NO 169
<211> LENGTH: 151
<212> TYPE: PRT
<213> ORGANISM: Triticum aestivum

<400> SEQUENCE: 169

Met Gly Arg Leu His Ser Lys Gly Lys Gly Ile Ser Ala Ser Ala Leu
1               5                   10                  15

Pro Tyr Ser Arg Ser Ser Pro Ala Trp Leu Lys Thr Thr Pro Glu Gln
            20                  25                  30

Val Val Glu Gln Ile Ser Lys Leu Ala Arg Lys Gly Ala Thr Pro Ser
        35                  40                  45

Gln Ile Gly Val Ile Leu Arg Asp Ser His Gly Ile Ala Gln Val Lys
    50                  55                  60

His Val Thr Gly Asn Arg Ile Leu Arg Ile Leu Lys Ser Ser Gly Leu
65                  70                  75                  80

Ala Pro Glu Leu Pro Glu Asp Leu Tyr Met Leu Ile Lys Lys Ala Val
                85                  90                  95

Ala Val Arg Lys His Leu Glu Arg Asn Arg Lys Asp Lys Asp Ser Lys
            100                 105                 110

Phe Arg Leu Ile Leu Ile Glu Ser Arg Ile His Arg Leu Ala Arg Tyr
        115                 120                 125

Tyr Lys Thr Val Gly Val Leu Pro Pro Thr Trp Lys Tyr Glu Ser Ala
    130                 135                 140

Thr Ala Ser Thr Ile Val Ala
145                 150

<210> SEQ ID NO 170
<211> LENGTH: 151
<212> TYPE: PRT
<213> ORGANISM: Hordeum vulgare

<400> SEQUENCE: 170

Met Gly Arg Leu His Ser Lys Gly Lys Gly Ile Ser Ala Ser Ala Leu
1               5                   10                  15

Pro Tyr Ser Arg Ser Ser Pro Ala Trp Leu Lys Thr Thr Pro Glu Gln
            20                  25                  30

Val Val Glu Gln Ile Ser Lys Leu Ala Arg Lys Gly Ala Thr Pro Ser
        35                  40                  45

Gln Ile Gly Val Ile Leu Arg Asp Ser His Gly Ile Ala Gln Val Lys
    50                  55                  60

His Val Thr Gly Asn Arg Ile Leu Arg Ile Leu Lys Ser Ser Gly Leu
65                  70                  75                  80

Ala Pro Glu Leu Pro Glu Asp Leu Tyr Met Leu Ile Lys Lys Ala Val
                85                  90                  95

Ala Val Arg Lys His Leu Glu Arg Asn Arg Lys Asp Lys Asp Ser Lys
            100                 105                 110

Phe Arg Leu Ile Leu Ile Glu Ser Arg Ile His Arg Leu Ala Arg Tyr
        115                 120                 125

Tyr Lys Thr Val Gly Val Leu Pro Pro Thr Trp Lys Tyr Glu Ser Ala
    130                 135                 140

Thr Ala Ser Thr Ile Val Ala
145                 150

<210> SEQ ID NO 171
<211> LENGTH: 151
<212> TYPE: PRT
<213> ORGANISM: Arabidopsis thaliana

<400> SEQUENCE: 171

Met Gly Arg Leu His Ser Lys Gly Lys Gly Ile Ser Ala Ser Ala Leu
1               5                   10                  15

Pro Tyr Ser Arg Ser Ser Pro Ala Trp Leu Lys Thr Thr Pro Glu Gln
            20                  25                  30

Val Val Glu Gln Ile Ser Lys Leu Ala Arg Lys Gly Ala Thr Pro Ser
        35                  40                  45

Gln Ile Gly Val Ile Leu Arg Asp Ser His Gly Ile Ala Gln Val Lys
    50                  55                  60

His Val Thr Gly Asn Arg Ile Leu Arg Ile Leu Lys Ser Ser Gly Leu
65                  70                  75                  80

Ala Pro Glu Leu Pro Glu Asp Leu Tyr Met Leu Ile Lys Lys Ala Val
                85                  90                  95

Ala Val Arg Lys His Leu Glu Arg Asn Arg Lys Asp Lys Asp Ser Lys
            100                 105                 110

Phe Arg Leu Ile Leu Ile Glu Ser Arg Ile His Arg Leu Ala Arg Tyr
        115                 120                 125

Tyr Lys Thr Val Gly Val Leu Pro Pro Thr Trp Lys Tyr Glu Ser Ala
    130                 135                 140

Thr Ala Ser Thr Ile Val Ala
145                 150

<210> SEQ ID NO 172
<211> LENGTH: 151
<212> TYPE: PRT
<213> ORGANISM: Hordeum vulgare

<400> SEQUENCE: 172

Met Gly Arg Met His Ser Gly Gly Lys Gly Ile Ala Lys Ser Ser Leu
1               5                   10                  15

Pro Tyr Arg Arg Ser Pro Pro Ser Trp Leu Lys Val Thr Ala Ser Gln
            20                  25                  30

Val Glu Asp His Val Asn Lys Leu Ala Lys Arg Gly Leu Thr Pro Ser
        35                  40                  45

Gln Ile Gly Val Ile Leu Arg Asp Ser Asn Gly Ile Ala Gln Val Lys
    50                  55                  60

Ser Val Thr Gly Asn Lys Ile Leu Arg Ile Leu Lys Lys Ser Gly Leu
65                  70                  75                  80

Ala Pro Ala Ile Pro Glu Asp Leu Tyr Met Leu Ile Lys Lys Ala Val
                85                  90                  95

Ala Val Arg Lys His Leu Glu Arg Asn Lys Lys Asp Lys Asp Ser Lys
            100                 105                 110

Phe Arg Leu Ile Leu Ile Glu Ser Arg Ile His Arg Leu Ala Arg Tyr
        115                 120                 125

Tyr Arg Ala Ser Arg Lys Leu Asp Ala Asn Trp Lys Tyr Glu Ser Ala
    130                 135                 140

Thr Ala Ser Ala Leu Val Ala
145                 150

<210> SEQ ID NO 173
<211> LENGTH: 175
<212> TYPE: PRT

-continued

<213> ORGANISM: Saccharum officinarum

<400> SEQUENCE: 173

| Leu | Ala | Thr | Ala | Ala | Asn | Leu | Ser | Leu | Ala | Leu | Pro | Pro | Ala | Arg | Arg |
|---|---|---|---|---|---|---|---|---|---|---|---|---|---|---|---|
| 1 | | | | 5 | | | | | 10 | | | | | 15 | |

| Arg | Pro | Pro | Leu | Ala | Ala | Thr | Ala | Ala | Met | Gly | Arg | Met | Tyr | Gly | Pro |
|---|---|---|---|---|---|---|---|---|---|---|---|---|---|---|---|
| | | | 20 | | | | | 25 | | | | | 30 | | |

| Gly | Lys | Gly | Met | Ser | Ser | Ser | Val | Leu | Pro | Tyr | Ala | Arg | Val | Ala | Pro |
|---|---|---|---|---|---|---|---|---|---|---|---|---|---|---|---|
| | | 35 | | | | | 40 | | | | | 45 | | | |

| Gly | Trp | Val | Arg | Ser | Thr | Ala | Gly | Glu | Val | Glu | Met | Ile | Val | Arg |
|---|---|---|---|---|---|---|---|---|---|---|---|---|---|---|
| 50 | | | | | 55 | | | | | 60 | | | | |

| Ala | Ala | Lys | Lys | Gly | His | Leu | Pro | Ser | Gln | Ile | Gly | Ala | Leu | Leu | Arg |
|---|---|---|---|---|---|---|---|---|---|---|---|---|---|---|---|
| 65 | | | | | 70 | | | | | 75 | | | | | 80 |

| Asp | Thr | His | Gly | Val | Pro | Leu | Val | His | Gly | Val | Thr | Gly | Gly | Lys | Ile |
|---|---|---|---|---|---|---|---|---|---|---|---|---|---|---|---|
| | | | | 85 | | | | | 90 | | | | | 95 | |

| Leu | Arg | Met | Leu | Lys | Ala | Arg | Gly | Leu | Ala | Pro | Glu | Val | Pro | Glu | Asp |
|---|---|---|---|---|---|---|---|---|---|---|---|---|---|---|---|
| | | | 100 | | | | | 105 | | | | | 110 | | |

| Leu | Tyr | Phe | Leu | Ile | Lys | Lys | Ala | Val | Ala | Ile | Arg | Lys | His | Leu | Asp |
|---|---|---|---|---|---|---|---|---|---|---|---|---|---|---|---|
| | | | 115 | | | | | 120 | | | | | 125 | | |

| Arg | Asn | Arg | Thr | Asp | Val | Asp | Ala | Lys | Phe | Arg | Leu | Ile | Leu | Val | Glu |
|---|---|---|---|---|---|---|---|---|---|---|---|---|---|---|---|
| | 130 | | | | | 135 | | | | | 140 | | | | |

| Ser | Arg | Val | His | Arg | Leu | Ile | Arg | Tyr | Tyr | Arg | Arg | Thr | Lys | Lys | Ile |
|---|---|---|---|---|---|---|---|---|---|---|---|---|---|---|---|
| 145 | | | | | 150 | | | | | 155 | | | | | 160 |

| Ala | Pro | Asn | Leu | Lys | Tyr | Glu | Ser | Thr | Thr | Ala | Ser | Ala | Leu | Val |
|---|---|---|---|---|---|---|---|---|---|---|---|---|---|---|
| | | | | 165 | | | | | 170 | | | | | 175 |

<210> SEQ ID NO 174
<211> LENGTH: 131
<212> TYPE: PRT
<213> ORGANISM: Hordeum vulgare

<400> SEQUENCE: 174

| Ile | Ser | Ala | Ser | Ala | Leu | Pro | Tyr | Lys | Arg | Thr | Pro | Pro | Ser | Trp | Leu |
|---|---|---|---|---|---|---|---|---|---|---|---|---|---|---|---|
| 1 | | | | 5 | | | | | 10 | | | | | 15 | |

| Lys | Ile | Ser | Ser | Gln | Asp | Val | Glu | Asp | Asn | Ile | Cys | Lys | Phe | Ala | Lys |
|---|---|---|---|---|---|---|---|---|---|---|---|---|---|---|---|
| | | | 20 | | | | | 25 | | | | | 30 | | |

| Lys | Gly | Leu | Thr | Pro | Ser | Gln | Ile | Gly | Val | Ile | Leu | Arg | Asp | Ser | His |
|---|---|---|---|---|---|---|---|---|---|---|---|---|---|---|---|
| | | | 35 | | | | | 40 | | | | | 45 | | |

| Gly | Ile | Ala | His | Val | Lys | Ser | Val | Thr | Gly | Ser | Lys | Ile | Leu | Arg | Ile |
|---|---|---|---|---|---|---|---|---|---|---|---|---|---|---|---|
| | 50 | | | | | 55 | | | | | 60 | | | | |

| Leu | Lys | Ala | His | Gly | Leu | Ala | Pro | Glu | Ile | Pro | Glu | Asp | Leu | Tyr | His |
|---|---|---|---|---|---|---|---|---|---|---|---|---|---|---|---|
| 65 | | | | | 70 | | | | | 75 | | | | | 80 |

| Leu | Ile | Lys | Lys | Ala | Val | Ala | Ile | Arg | Lys | His | Leu | Glu | Arg | Asn | Arg |
|---|---|---|---|---|---|---|---|---|---|---|---|---|---|---|---|
| | | | | 85 | | | | | 90 | | | | | 95 | |

| Lys | Asp | Lys | Asp | Ser | Lys | Phe | Arg | Leu | Ile | Leu | Val | Glu | Ser | Arg | Ile |
|---|---|---|---|---|---|---|---|---|---|---|---|---|---|---|---|
| | | | 100 | | | | | 105 | | | | | 110 | | |

| His | Arg | Leu | Ala | Arg | Tyr | Tyr | Lys | Thr | Lys | Lys | Leu | Pro | Pro | Val |
|---|---|---|---|---|---|---|---|---|---|---|---|---|---|---|
| | | 115 | | | | | 120 | | | | | 125 | | |

| Trp | Lys | Tyr |
|---|---|---|
| | 130 | |

<210> SEQ ID NO 175
<211> LENGTH: 151
<212> TYPE: PRT
<213> ORGANISM: Populus Sp.

<400> SEQUENCE: 175

Met Gly Arg Met His Asn Pro His Lys Gly Ile Ala Gly Ser Ala Leu
1               5                   10                  15

Pro Tyr Lys Arg Thr Pro Pro Arg Trp Leu Lys Val Thr Pro Glu Glu
            20                  25                  30

Val Ser Glu Gln Ile Phe Lys Leu Ala Arg Lys Gly Met Thr Pro Ser
        35                  40                  45

Gln Ile Gly Val Val Leu Arg Asp Ser His Gly Ile Ala Gln Val Lys
    50                  55                  60

Ser Val Thr Gly Ala Lys Ile Leu Arg Ile Leu Lys Gly Asn Gly Leu
65                  70                  75                  80

Ala Pro Glu Leu Pro Glu Asp Leu Tyr His Leu Ile Lys Lys Ala Val
            85                  90                  95

Ser Val Arg Lys His Leu Glu Arg Asn Arg Lys Asp Lys Asp Ser Lys
        100                 105                 110

Phe Arg Leu Ile Leu Ile Glu Ser Arg Ile His Arg Leu Val Arg Tyr
    115                 120                 125

Tyr Lys Thr Lys Ser Gln Leu Ser Pro Ser Phe Lys Tyr Glu Ser Ala
    130                 135                 140

Thr Ala Ser Thr Ile Val Ser
145                 150

<210> SEQ ID NO 176
<211> LENGTH: 151
<212> TYPE: PRT
<213> ORGANISM: Hordeum vulgare

<400> SEQUENCE: 176

Met Gly Arg Met His Thr Pro Gly Lys Gly Ile Ser Lys Ser Ala Leu
1               5                   10                  15

Pro Tyr Arg Arg Ser Val Ala Thr Trp Leu Lys Ser Ser Glu Asp
            20                  25                  30

Val Lys Asp His Ile Phe Lys Leu Ala Lys Lys Gly Leu Thr Pro Ser
        35                  40                  45

Lys Ile Gly Val Ile Leu Arg Asp Ser His Gly Val Ala Gln Val Arg
    50                  55                  60

Phe Val Thr Gly Asn Lys Ile Leu Arg Ile Met Lys Ala Met Gly Leu
65                  70                  75                  80

Ala Pro Gly Leu Pro Glu Asp Leu Tyr His Leu Ile Lys Lys Ala Val
            85                  90                  95

Ala Ile Arg Lys His Leu Glu Arg Asn Arg Lys Asp Arg Asp Ser Lys
        100                 105                 110

Phe Arg Leu Ile Leu Val Glu Ser Arg Ile His Arg Leu Ala Arg Tyr
    115                 120                 125

Tyr Lys Arg Lys Ser Lys Ile Ala Pro Asn Trp Arg Tyr Glu Ser Ser
    130                 135                 140

Thr Ala Ser Ala Leu Val Ala
145                 150

<210> SEQ ID NO 177
<211> LENGTH: 164
<212> TYPE: PRT
<213> ORGANISM: Oryza sativa
<220> FEATURE:
<221> NAME/KEY: misc_feature
<222> LOCATION: (1)..(2)
<223> OTHER INFORMATION: Xaa can be any naturally occurring amino acid

<400> SEQUENCE: 177

Xaa Xaa Glu Lys Gly Ile Ser Ser Ala Leu Pro Cys Lys Arg Ile
1               5                   10                  15

Pro Pro Ser Leu Leu Lys Asn Ala Ala Ser Asn Val Glu Glu Met Ile
            20                  25                  30

Met Lys Ala Ala Lys Met Gly Gln Met Ser Ser Gln Ile Gly Val Val
            35                  40                  45

Leu Arg His Gln His Gly Ile Pro Leu Val Lys Ser Ile Ala Ser Ser
        50                  55                  60

Lys Ile Leu His Ile Leu Lys Ala His Gly Leu Ala Pro Lys Ile Leu
65                  70                  75                  80

Glu Asp Leu Tyr Phe Leu Ile Lys Lys Ala Val Ala Ile Arg Lys His
                85                  90                  95

Leu Glu Arg Asn Arg Lys Asp Lys Asp Ser Ser Phe Arg Leu Ile Leu
            100                 105                 110

Val Glu Ser Arg Ile His Arg Leu Val Arg Tyr Tyr Lys Arg Thr Lys
            115                 120                 125

Lys Leu Pro Pro Thr Leu Arg Phe Lys Trp Ile Leu Phe Lys Val Gly
            130                 135                 140

Leu Met Leu Ser Ser Leu Leu Leu Thr Cys Val Leu Ser Asn Leu Arg
145                 150                 155                 160

Asn Gly Leu Leu

<210> SEQ ID NO 178
<211> LENGTH: 118
<212> TYPE: PRT
<213> ORGANISM: Glycine max

<400> SEQUENCE: 178

Glu Glu Asn Ile Cys Lys Phe Ala Lys Lys Gly Leu Thr Pro Ser Gln
1               5                   10                  15

Ile Gly Val Ile Leu Arg Asp Ser His Gly Ile Ala Gln Val Asn Ser
            20                  25                  30

Val Thr Gly Ser Lys Ile Leu Arg Ile Leu Lys Ala His Gly Leu Ala
        35                  40                  45

Pro Glu Ile Pro Glu Asp Leu Tyr His Leu Ile Lys Lys Ala Val Ser
    50                  55                  60

Ile Arg Lys His Leu Glu Arg Asn Arg Lys Asp Lys Asp Ser Lys Phe
65                  70                  75                  80

Arg Leu Ile Leu Val Glu Ser Arg Ile His Arg Leu Ala Arg Tyr Tyr
                85                  90                  95

Lys Lys Thr Lys Lys Leu Pro Pro Val Trp Lys Tyr Glu Ser Thr Thr
            100                 105                 110

Ala Ser Thr Leu Val Ala
        115

<210> SEQ ID NO 179
<211> LENGTH: 135
<212> TYPE: PRT
<213> ORGANISM: Populus Sp.

<400> SEQUENCE: 179

Ser Ala Leu Pro Tyr Lys Arg Thr Pro Pro Ser Trp Leu Lys Thr Ser
1               5                   10                  15

Ala Asn Glu Val Cys Asp His Val Cys Arg Leu Ala Lys Lys Gly Leu
            20                  25                  30

Thr Pro Ser Gln Ile Gly Val Val Leu Arg Asp Ser His Gly Ile Pro
        35                  40                  45

```
Gln Val Lys Ser Val Thr Asn Asn Lys Ile Leu Arg Ile Leu Lys Ala
     50                  55                  60

Asn Gly Phe Ala Pro Glu Leu Pro Glu Asp Leu Tyr His Leu Ile Lys
 65                  70                  75                  80

Lys Ala Ala Ser Ile Arg Lys His Leu Lys Arg Ser Arg Gln Asp Lys
                 85                  90                  95

Asp Ala Lys Phe His Leu Ile Leu Val Glu Ala Arg Ile His Arg Val
            100                 105                 110

Ser Arg Tyr Tyr Lys Glu Ser Lys His Leu Pro Ala Asn Trp Arg Tyr
        115                 120                 125

Glu Ser Pro Thr Ala Ala Thr
130                 135

<210> SEQ ID NO 180
<211> LENGTH: 116
<212> TYPE: PRT
<213> ORGANISM: Nicotiana tabacum

<400> SEQUENCE: 180

Met Gly Arg Met His Ser Arg Gly Lys Gly Ile Ser Ala Ser Ala Leu
 1               5                  10                  15

Pro Tyr Lys Arg Thr Pro Ser Trp Leu Lys Ile Ser Ala Pro Asp
            20                  25                  30

Val Glu Asp Asn Ile Cys Lys Phe Ala Lys Lys Gly Leu Thr Pro Ser
            35                  40                  45

Gln Ile Gly Val Ile Leu Arg Asp Ser His Gly Ile Ala Gln Val Lys
     50                  55                  60

Ser Val Thr Gly Ser Lys Ile Leu Arg Ile Leu Lys Ala His Gly Leu
 65                  70                  75                  80

Ala Pro Glu Ile Pro Glu Asp Leu Tyr His Leu Ile Lys Lys Ala Val
                 85                  90                  95

Ala Ile Arg Lys His Leu Glu Arg Asp Arg Lys Asp Lys Asp Ser Lys
            100                 105                 110

Phe Arg Leu Ile
115

<210> SEQ ID NO 181
<211> LENGTH: 152
<212> TYPE: PRT
<213> ORGANISM: Triticum aestivum
<220> FEATURE:
<221> NAME/KEY: misc_feature
<222> LOCATION: (129)..(130)
<223> OTHER INFORMATION: Xaa can be any naturally occurring amino acid

<400> SEQUENCE: 181

Met Gly Gly Ile Asp Ser Arg Arg Glu Gly Tyr Met Val Val Gly Val
 1               5                  10                  15

Ala Val Gln Glu Asp Ser Ser Glu Val Gly Ser Arg Pro Thr Val Ala
            20                  25                  30

Asp Val Asp Glu Leu Ile Thr Lys Ala Ala Lys Lys Gly Gln Met Pro
            35                  40                  45

Ser Gln Ile Gly Val Leu Leu Arg Asp Gln His Gly Ile Pro Leu Val
     50                  55                  60

Lys Ser Val Thr Gly Ser Lys Ile Leu Arg Ile Ile Lys Ala His Gly
 65                  70                  75                  80

Leu Ala Pro Glu Ile Pro Glu Asp Leu Tyr Phe Leu Ile Lys Lys Ala
                 85                  90                  95
```

```
Val Ala Ile Arg Lys His Leu Glu Arg Asn Arg Lys Asp Lys Asp Ser
            100                 105                 110

Lys Phe Arg Leu Ile Leu Val Glu Ser Arg Ile His Arg Pro Pro Arg
        115                 120                 125

Xaa Xaa Lys Gly Arg Lys Lys Phe Pro Asp Lys Trp Lys Pro Pro Pro
    130                 135                 140

Pro Pro Gly Ser Ile Leu Val Ala
145                 150

<210> SEQ ID NO 182
<211> LENGTH: 128
<212> TYPE: PRT
<213> ORGANISM: Brassica napus

<400> SEQUENCE: 182

Ser Arg Cys Glu Asx Arg Ala Ser Ser Ile Cys Ala Asn Ala Pro Ser
1               5                   10                  15

Leu Gln Val Cys Glu Glu Gly Leu Thr Pro Ser Gln Ile Gly Val Ile
            20                  25                  30

Leu Arg Asp Ser His Gly Ile Pro Gln Val Lys Ser Val Thr Gly Asn
        35                  40                  45

Lys Ile Leu Arg Ile Leu Lys Ala His Gly Leu Ala Pro Glu Ile Pro
    50                  55                  60

Asp Asp Leu Tyr His Leu Ile Lys Lys Ala Val Ala Ile Arg Lys His
65                  70                  75                  80

Leu Glu Arg Asn Arg Lys Asp Lys Asp Ser Lys Phe Arg Leu Ile Leu
                85                  90                  95

Ala Glu Ser Arg Ile His Arg Leu Ala Arg Tyr Tyr Lys Lys Thr Lys
            100                 105                 110

Lys Leu Pro Pro Val Trp Lys Tyr Glu Ser Thr Thr Ala Ser Thr Leu
        115                 120                 125

<210> SEQ ID NO 183
<211> LENGTH: 121
<212> TYPE: PRT
<213> ORGANISM: Triticum aestivum
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid

<400> SEQUENCE: 183

Ala Ala Met Gly Arg Met His Ser Arg Gly Lys Gly Ile Ser Ser Ser
1               5                   10                  15

Ala Leu Pro Tyr Lys Arg Thr Pro Pro Thr Trp Leu Lys Thr Ala Ala
            20                  25                  30

Ser Asp Val Glu Glu Met Ile Thr Lys Ala Ala Lys Lys Gly Gln Met
        35                  40                  45

Pro Ser Gln Ile Gly Val Leu Leu Arg Asp Gln His Gly Ile Pro Leu
    50                  55                  60

Val Lys Ser Val Thr Gly Ser Lys Ile Leu Arg Ile Leu Lys Ala Met
65                  70                  75                  80

Gly Trp Asn Arg Asn Pro Gly Gly Leu Tyr Ser His Gln Glu Ala Val
                85                  90                  95

Ala Ile Arg Asn Thr Leu Glu Glu Gln Glu Gly Gln Arg Ser Lys Ser
```

Xaa Ser Ser Xaa Gln Asn Arg Phe Asn
        115                 120

<210> SEQ ID NO 184
<211> LENGTH: 102
<212> TYPE: PRT
<213> ORGANISM: Populus Sp.

<400> SEQUENCE: 184

Met Gly Arg Met His Ser Lys Gly Lys Gly Ile Ser Ala Ser Ala Leu
1               5                   10                  15

Pro Tyr Lys Arg Thr Ser Pro Ser Trp Leu Lys Ile Ser Pro Gln Asp
            20                  25                  30

Val Asp Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Thr Val Thr Gly Asn Gln Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Cys Tyr Leu Gly Ser Ile
            100

<210> SEQ ID NO 185
<211> LENGTH: 142
<212> TYPE: PRT
<213> ORGANISM: Oryza sativa

<400> SEQUENCE: 185

Glu Asp Gly Ser Asp Val Val Ala Asp Trp Arg Cys Ala Pro Ser Gln
1               5                   10                  15

His Gly Ile Pro Leu Val Lys Ser Ile Ala Ser Ser Lys Ile Leu His
            20                  25                  30

Ile Leu Asn Ala His Gly Leu Ala Pro Lys Ile Leu Glu Asp Leu Tyr
        35                  40                  45

Phe Leu Ile Lys Lys Ala Val Ala Ile Arg Lys His Leu Glu Arg Asn
    50                  55                  60

Arg Lys Asp Lys Asp Ser Ser Phe Arg Leu Ile Leu Val Glu Ser Arg
65                  70                  75                  80

Ile His Arg Leu Val Arg Tyr Tyr Lys Arg Thr Lys Lys Leu Pro Pro
                85                  90                  95

Thr Leu Arg Ser Trp Ile Ile Phe Leu Glu Phe Ser Thr Val Phe Ser
            100                 105                 110

Cys Ser Arg Met Leu Gln Met Asp Thr Leu Gln Ser Arg Leu Asp Val
        115                 120                 125

Glu Phe Leu Val Ala His Met Cys Ser Val Lys Phe Lys Glu
    130                 135                 140

<210> SEQ ID NO 186
<211> LENGTH: 163
<212> TYPE: PRT
<213> ORGANISM: Triticum aestivum

<400> SEQUENCE: 186

Phe Pro Ser Pro Pro Gln Gln Leu Leu Pro Ile Ser Leu Leu Ala
1               5                   10                  15

Ala Ala Leu Arg Ser Pro Leu Ala Ala Met Gly Arg Met His Ser Asn
         20                  25                  30

Gly Lys Gly Met Ser Ser Val Ile Pro Tyr Lys Arg Glu Ala Pro
         35                  40                  45

Thr Trp Val Lys Thr Ser Ala Pro Asp Val Glu Glu Ile Ile Val Arg
 50                  55                  60

Ala Ala Lys Lys Gly Gln Leu Pro Ser Gln Ile Gly Ala Leu Leu Arg
 65                  70                  75                  80

Asp Gly Tyr Gly Ile Pro Leu Ser Lys Ala Val Thr Gly Ala Lys Ile
                 85                  90                  95

Val Arg Leu Leu Lys Ala Arg Gly Leu Ala Pro Glu Met Pro Arg Gly
                100                 105                 110

Pro Leu Leu Pro His Gln Glu Gly Arg Cys Asp Ser Glu Ala Pro Gly
             115                 120                 125

Arg Gly Thr Ser Arg Thr Trp Thr Pro Ser Ser Ala Ser Ser Ser Ser
130                 135                 140

Arg Thr Arg Ser Asn Ala Ser Thr Ala Thr Thr Ala Ser Thr Arg Arg
145                 150                 155                 160

Cys Arg Arg

<210> SEQ ID NO 187
<211> LENGTH: 333
<212> TYPE: PRT
<213> ORGANISM: Oryza sativa
<220> FEATURE:
<221> NAME/KEY: misc_feature
<222> LOCATION: (1)..(2)
<223> OTHER INFORMATION: Xaa can be any naturally occurring amino acid

<400> SEQUENCE: 187

Xaa Xaa Val Glu Thr Ser Asp Leu Arg Glu Arg Glu Arg Glu Gly Lys
 1               5                  10                  15

Gly Arg Arg Arg Arg Gly Thr Lys Arg Thr Arg Ala Arg Ala
             20                  25                  30

Ile Phe Ala Leu Leu Pro Leu Ser Ser Leu Ser Ser Pro Leu Leu Arg
             35                  40                  45

Ser Ser Ala Ser Pro Ala Gly Arg Arg Leu Pro Val Leu Glu Ala Ala
 50                  55                  60

Ala Ala Asp Thr Gly Asp Asp Met Ala Asp Gly Gly Glu Lys Cys
 65                  70                  75                  80

Arg Asp Ala Ala Gly Glu Gly Gly Gly Asp Leu Tyr Ala Val
                 85                  90                  95

Leu Gly Leu Lys Lys Glu Cys Ser Asp Ala Asp Leu Lys Leu Ala Tyr
                100                 105                 110

Arg Lys Leu Ala Met Arg Trp His Pro Asp Lys Cys Ser Ser Ser Ser
             115                 120                 125

Ser Ala Lys His Met Glu Glu Ala Lys Glu Lys Phe Gln Glu Ile Gln
130                 135                 140

Gly Ala Tyr Ser Val Leu Ser Asp Ser Asn Lys Arg Phe Leu Tyr Asp
145                 150                 155                 160

Val Gly Val Tyr Asp Asp Asp Asn Asp Asp Asn Leu Gln Gly
                165                 170                 175

Met Gly Asp Phe Ile Gly Glu Met Ala Gln Met Met Ser Gln Ala Arg
             180                 185                 190

Pro Thr Arg Gln Glu Ser Phe Lys Glu Leu Gln Gln Leu Phe Val Asp
             195                 200                 205

```
Met Phe Gln Ala Asp Leu Asp Ser Gly Phe Cys Asn Gly Pro Ser Lys
    210                 215                 220

Cys Tyr His Thr Gln Ala Gln Ser Gln Thr Arg Thr Ser Ser Thr Ser
225                 230                 235                 240

Pro Ser Met Ser Pro Ser Pro Pro Pro Val Ala Thr Glu Ala Glu
            245                 250                 255

Ser Pro Ser Cys Asn Gly Ile Asn Lys Arg Gly Ser Ser Ala Met Asp
            260                 265                 270

Ser Gly Lys Pro Pro Arg Ala Ser Glu Val Ser Ala Gly Gln Ser Gln
        275                 280                 285

Ser Gly Phe Cys Phe Gly Lys Ser Asp Ala Lys Gln Ala Ala Lys Thr
        290                 295                 300

Arg Ser Gly Asn Thr Ala Ser Arg Arg Arg Asn Gly Arg Lys Gln Lys
305                 310                 315                 320

Val Ser Ser Lys His Asp Val Ser Ser Glu Asp Glu Met
                325                 330

<210> SEQ ID NO 188
<211> LENGTH: 294
<212> TYPE: PRT
<213> ORGANISM: Hordeum vulgare

<400> SEQUENCE: 188

Trp Arg Gly Ala Gln Thr Ala Glu Glu Arg Glu Arg Gly Lys Leu Gln
1               5                   10                  15

Glu Pro Pro Pro Pro Pro Ala His Pro Ala Gly Asp Ala Arg
            20                  25                  30

Gly Met Ala Thr Gly Gly Asp Gly Asp Pro Ala Ala Pro Gly Gly Gly
                35                  40                  45

Asp Leu Tyr Ala Val Leu Gly Leu Ser Lys Glu Cys Ser Asp Ala Asp
    50                  55                  60

Leu Lys Val Ala Tyr Arg Lys Leu Ala Met Arg Trp His Pro Asp Arg
65                  70                  75                  80

Cys Ser Ser Ser Ser Gly Thr Lys His Met Glu Glu Ala Lys Glu Lys
                85                  90                  95

Phe Gln Glu Ile Gln Gly Ala Tyr Ser Val Leu Ser Asp Ala Asn Lys
            100                 105                 110

Arg Phe Leu Tyr Asp Val Gly Val Tyr Gln Glu Glu Asp Ser Asp
        115                 120                 125

Asp Ser Met Gln Gly Met Gly Asp Phe Leu Gly Glu Met Ala His Met
    130                 135                 140

Met Ser Gln Thr Arg Pro Ala Arg Gln Glu Ser Phe Glu Glu Leu Gln
145                 150                 155                 160

Gln Leu Phe Val Asp Met Phe Gln Ser Asp Ile Asp Ser Gly Phe Cys
                165                 170                 175

Asn Gly Pro Ala Lys Gly His His Asp Pro Phe Gln Arg Gln Thr Gln
            180                 185                 190

Thr Phe Ser Thr Ser Pro Ser Ser Pro Pro Ser Pro Pro Pro Pro Leu
        195                 200                 205

Ala Thr Glu Ala Glu Ala Ala Ser Cys Asn Gly Ile Asn Lys Arg Gly
    210                 215                 220

Ser Ser Ala Met Gly Ser Gly Lys Pro Pro Arg Ala Glu Ala Glu Gly
225                 230                 235                 240

Ala Gly Tyr Gly Gln Ser Glu Pro Cys Phe Gly Thr Ser Asp Ala Lys
                245                 250                 255
```

-continued

Gln Ala Pro Arg Ala Arg Gly Gly Asn Thr Ser Arg Arg Asn Gly
            260                 265                 270

Gln Lys Gln Lys Leu Ser Ser Lys His Asp Val Ser Ser Glu Asp Glu
        275                 280                 285

Met Leu Ser Pro Gln Gln
        290

<210> SEQ ID NO 189
<211> LENGTH: 301
<212> TYPE: PRT
<213> ORGANISM: Triticum aestivum

<400> SEQUENCE: 189

Arg Glu Arg Glu Arg Glu Gly Arg Lys Arg Gln Glu Pro Pro Pro
1               5                   10                  15

Ser Ser Pro Leu Ser Ser Ser Ser Pro Ala His Pro Arg Ala Pro
            20                  25                  30

Gln Ala Gly Gly Ala Gly Arg Gly Met Ala Thr Gly Gly Asp Gly Cys
            35                  40                  45

Gly Gly Gly Glu Pro Ala Ala Pro Gly Gly Gly Asp Leu Tyr Ala Val
        50                  55                  60

Leu Gly Leu Ser Lys Glu Cys Ser Asp Ala Asp Leu Lys Leu Ala Tyr
65                  70                  75                  80

Arg Lys Leu Ala Met Arg Trp His Pro Asp Arg Cys Ser Ser Ser Ser
                85                  90                  95

Gly Thr Lys Arg Met Glu Glu Ala Lys Glu Lys Phe Gln Glu Ile Gln
            100                 105                 110

Gly Ala Tyr Ser Val Leu Ser Asp Ala Asn Lys Arg Phe Leu Tyr Asp
            115                 120                 125

Val Gly Val Tyr Gln Glu Glu Glu Asp Ser Asp Ser Met Gln Gly
        130                 135                 140

Met Gly Asp Phe Leu Gly Glu Met Ala His Met Met Ser Gln Thr Arg
145                 150                 155                 160

Pro Ala Arg Gln Glu Ser Phe Glu Glu Leu Gln Gln Leu Phe Val Asp
                165                 170                 175

Met Phe Gln Ser Asp Ile Asp Ser Gly Phe Cys Asn Arg Pro Ala Lys
            180                 185                 190

Gly His His Asp Pro Phe Gln Thr Phe Ser Thr Ser Pro Ser Ser Ser
        195                 200                 205

Pro Ser Pro Pro Pro Val Ala Thr Glu Ala Glu Ala Ala Ser Cys
    210                 215                 220

Asn Gly Ile Asn Lys Arg Gly Ser Ser Ala Met Gly Ser Gly Lys Pro
225                 230                 235                 240

Pro Arg Ala Gly Glu Ala Gly Ala Gly Tyr Gly Gln Pro Glu Phe Cys
                245                 250                 255

Phe Gly Thr Ser Asp Ala Lys Gln Ala Pro Lys Ala Arg Gly Arg Asn
            260                 265                 270

Thr Ser Arg Arg Arg Asn Gly Gln Lys Gln Lys Leu Ser Ser Lys His
        275                 280                 285

Asp Val Ser Ser Glu Asp Glu Met Leu Ser Pro Gln Gln
    290                 295                 300

<210> SEQ ID NO 190
<211> LENGTH: 203
<212> TYPE: PRT
<213> ORGANISM: Zea mays

```
<400> SEQUENCE: 190

Met Glu Glu Ala Lys Glu Lys Phe Gln Glu Ile Gln Gly Ala Tyr Ser
1               5                   10                  15

Val Leu Ser Asp Ala Asn Lys Arg Leu Leu Tyr Asp Val Gly Val Tyr
            20                  25                  30

Asp Asp Glu Asp Glu Glu Ser Met Gln Gly Met Gly Asp Phe Ile
        35                  40                  45

Gly Glu Met Ala Gln Met Met Ser Gln Ala Gln Pro Thr Arg Gln Glu
50                  55                  60

Ser Phe Glu Glu Leu Gln Gln Leu Phe Val Asp Met Phe Gln Ser Asp
65                  70                  75                  80

Ile Asp Ser Gly Phe Cys Asn Arg Thr Ala Lys Ala His Gln Phe Gln
                85                  90                  95

Gly Pro Ala Lys Ser Arg Thr Cys Ser Thr Ser Pro Ser Ser Ser Pro
            100                 105                 110

Ser Pro Pro Pro Thr Thr Ala Lys Asp Ala Glu Val Pro Ser Cys Asn
        115                 120                 125

Gly Phe Asn Lys Arg Gly Ser Ser Ala Leu Asp Ser Gly Lys Pro Pro
130                 135                 140

Lys Pro Val Glu Gly Gly Ala Gly Gln Asn Gln Ala Gly Phe Cys Phe
145                 150                 155                 160

Gly Val Ser Asp Thr Lys Glu Thr Pro Lys Leu Pro Gly Gln Asn Ala
                165                 170                 175

Ser Arg Arg Arg Asn Gly Arg Lys Gln Lys Leu Ser Ser Lys His Asp
            180                 185                 190

Val Ser Ser Glu Asp Glu Thr Ala Ala Gly Ser
            195                 200

<210> SEQ ID NO 191
<211> LENGTH: 164
<212> TYPE: PRT
<213> ORGANISM: Triticum aestivum

<400> SEQUENCE: 191

Met Gln Gly Met Gly Asp Phe Leu Gly Glu Met Ala His Met Met Ser
1               5                   10                  15

Gln Thr Arg Pro Ala Arg Gln Glu Ser Phe Glu Glu Leu Gln Gln Leu
            20                  25                  30

Phe Val Asp Met Phe Gln Ser Asp Ile Asp Ser Gly Phe Cys Asn Gly
        35                  40                  45

Pro Ala Lys Gly His His Asp Pro Phe Gln Thr Phe Ser Thr Phe Pro
50                  55                  60

Ser Ser Ser Pro Ser Pro Pro Pro Leu Ala Thr Glu Ala Glu Ala
65                  70                  75                  80

Ala Ser Cys Asn Gly Ile Asn Lys Arg Gly Ser Ser Ala Met Gly Ser
                85                  90                  95

Gly Lys Pro Pro Arg Thr Gly Glu Ala Gly Ala Gly Tyr Gly Gln Pro
            100                 105                 110

Glu Phe Cys Phe Gly Arg Ser Asp Ala Lys Gln Ala Pro Lys Ala Arg
        115                 120                 125

Gly Gly Asn Thr Ser Arg Arg Arg Asn Gly Gln Lys Gln Lys Pro Ser
130                 135                 140

Ser Lys His Asp Val Ser Ser Glu Asp Glu Met Leu Ser Pro Gln Gln
145                 150                 155                 160

Pro Arg Val Val
```

<210> SEQ ID NO 192
<211> LENGTH: 134
<212> TYPE: PRT
<213> ORGANISM: Zea mays

<400> SEQUENCE: 192

Met Arg Gln Glu Ser Phe Glu Glu Leu Gln Gln Leu Phe Val Asp Met
1               5                   10                  15

Phe Gln Ser Asp Ile Asp Ser Gly Phe Cys Asn Gly Thr Ala Lys Gly
                20                  25                  30

His Gln Val Gln Gly Gln Ala Lys Ser Arg Thr Cys Ser Pro Arg Ser
            35                  40                  45

Pro Pro Thr Thr Ile Val Lys Glu Ala Glu Val Ser Ser Cys Asn Gly
    50                  55                  60

Phe Asn Lys Arg Gly Ser Ser Ala Met Asp Ser Gly Lys Pro Pro Arg
65                  70                  75                  80

Pro Val Glu Cys Gly Ala Gly Gln Ser Gln Ala Gly Phe Cys Phe Gly
                85                  90                  95

Val Ser Asp Thr Pro Lys Pro Arg Gly Pro Asn Ala Asn Arg Lys Arg
                100                 105                 110

Asn Gly Arg Lys Gln Lys Leu Phe Pro Lys His Tyr Val Thr Ser Glu
            115                 120                 125

Asp Asp Thr Ala Gly Ser
            130

<210> SEQ ID NO 193
<211> LENGTH: 143
<212> TYPE: PRT
<213> ORGANISM: Triticum aestivum
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (141)..(142)
<223> OTHER INFORMATION: Xaa can be any naturally occurring amino acid

<400> SEQUENCE: 193

Gly Ala Leu Val Leu Pro Ser Arg Cys Cys Ser Cys Ala Val Leu Ser
1               5                   10                  15

Asp Ala Asn Lys Arg Phe Leu Tyr Asp Val Gly Val Tyr Gln Glu Glu
                20                  25                  30

Glu Asp Ser Asp Asp Ser Met Gln Gly Met Gly Asp Phe Leu Gly Glu
            35                  40                  45

Met Ala His Met Met Ser Gln Ala Arg Pro Ala Arg Gln Glu Ser Phe
    50                  55                  60

Glu Glu Leu Gln Gln Leu Phe Val Asp Met Phe Gln Ser Asp Ile Asp
65                  70                  75                  80

Ser Gly Phe Cys Asn Gly Pro Ala Lys Gly His His Asp Pro Phe Gln
                85                  90                  95

Thr Phe Ser Thr Ser Pro Ser Ser Pro Ser Pro Pro Pro Leu
                100                 105                 110

Ala Thr Glu Ala Glu Ala Ala Ser Cys Asn Gly Ile Asn Lys Arg Gly
            115                 120                 125

Ser Ser Ala Xaa Gly Leu Trp Gly Lys Pro Pro Arg Xaa Xaa Gly
            130                 135                 140

```
<210> SEQ ID NO 194
<211> LENGTH: 322
<212> TYPE: PRT
<213> ORGANISM: Zea mays

<400> SEQUENCE: 194

Met Asp Gly Leu Trp His Leu Gly Asp Glu Leu Arg Gly Gln Pro Lys
1               5                   10                  15

Val Val Glu Asp Arg Gln Trp Ser Leu Met Thr Ser Lys Leu Ala Glu
            20                  25                  30

Ile Thr Arg Ser Arg Gly Glu Arg Thr Asn Asp Leu Asp Tyr Ala Arg
        35                  40                  45

Met Asn Ala Ala Pro Asp Ala Lys Arg Trp Gly Lys Ala Ala Ser Tyr
    50                  55                  60

Gln His His Asp Glu Gly Arg Met Asp His His Val Gly Leu Ser Leu
65                  70                  75                  80

Lys Met Asn Asp Leu Lys Met Asn Glu Ala Ala Ala Ala Val Met
                85                  90                  95

Lys Leu Pro Phe Arg Gly Val Pro Tyr Asn Val Asn Pro Met Tyr Pro
            100                 105                 110

Lys Gly Ser Asn Ala Asn Ala Asn Val Asn Ala Phe Lys Met Asn Val
        115                 120                 125

Gly Val Asn Lys Tyr Ser Ser Ser Ala Asn Gly Lys Asp Ser Gly Gly
    130                 135                 140

Lys Ser Ser Gly Gly Ser Asn Asn Ser Gly Gly Gly Asn Gly
145                 150                 155                 160

Asn Gly Thr Ala Asn Gly Ser Ser Ala Val Asp Lys Arg Phe Lys Thr
                165                 170                 175

Leu Pro Thr Ser Glu Met Leu Pro Lys Asn Glu Val Leu Gly Gly Tyr
            180                 185                 190

Ile Phe Val Cys Asn Asn Asp Thr Met Gln Glu Asp Leu Lys Arg Gln
        195                 200                 205

Leu Phe Gly Leu Pro Ala Arg Tyr Arg Asp Ser Val Arg Ala Ile Thr
    210                 215                 220

Pro Gly Leu Pro Leu Phe Leu Tyr Asn Tyr Thr Thr His Gln Leu His
225                 230                 235                 240

Gly Val Phe Glu Ala Ala Ser Phe Gly Gly Ser Asn Ile Asp Pro Thr
                245                 250                 255

Ala Trp Glu Asp Lys Lys Cys Lys Gly Glu Ser Arg Phe Pro Ala Gln
            260                 265                 270

Val Arg Ile Arg Val Arg Lys Leu Cys Lys Pro Leu Glu Glu Asp Ser
        275                 280                 285

Phe Arg Pro Val Leu His His Tyr Asp Gly Pro Lys Phe Arg Leu Glu
    290                 295                 300

Leu Ser Ile Ala Glu Thr Leu Ser Leu Leu Asp Leu Cys Glu Lys Glu
305                 310                 315                 320

Gly Ile

<210> SEQ ID NO 195
<211> LENGTH: 310
<212> TYPE: PRT
<213> ORGANISM: Triticum aestivum

<400> SEQUENCE: 195

Met Asp Asn Leu Trp His Leu Gly Asp Glu Phe Arg Gly Gln Ser Lys
1               5                   10                  15
```

Val Val Glu Asp Arg Gln Trp Ser Leu Met Thr Ser Lys Leu Ala Glu
            20                  25                  30

Ile Thr Lys Ser Lys Ala Glu Arg Met Asn Asp Phe Glu Tyr Ala Arg
         35                  40                  45

Met Asn Thr Val Pro Asp Val Lys Gln Trp Asp Lys Leu Ser Tyr His
     50                  55                  60

Gln Glu Asp Asn Lys Met Asp His Leu Asn Leu Gly Leu Met Asn Leu
65                  70                  75                  80

Asp Leu Lys Met Asn Asp Leu Lys Met Asn Glu Ala Ala Met Lys Tyr
                85                  90                  95

Pro Phe Arg Asn Met Ala Tyr Asn Met Asn Pro Met Tyr Pro Lys Gly
            100                 105                 110

Asn Asn Gly Asn Val Asn Ser Phe Lys Met Asn Val Gly Val Asn Lys
        115                 120                 125

Tyr Pro Asn Asn Gln Asn Gly Lys Glu Ala Asn Gly Lys His Asn Gly
    130                 135                 140

Gly Asn Asn Asn Gly Gly Asn Ser Asn Asn Ser Val Asp Lys
145                 150                 155                 160

Arg Phe Lys Thr Leu Pro Thr Ser Glu Met Leu Pro Arg Asn Glu Val
                165                 170                 175

Leu Gly Gly Tyr Ile Phe Val Cys Asn Asn Asp Thr Met Gln Glu Asp
            180                 185                 190

Leu Lys Arg Gln Leu Phe Gly Leu Pro Ala Arg Tyr Arg Asp Ser Val
        195                 200                 205

Arg Ala Ile Thr Pro Gly Leu Pro Leu Phe Leu Tyr Asn Tyr Thr Thr
    210                 215                 220

His Gln Leu His Gly Val Phe Glu Ala Ala Ser Phe Gly Gly Ser Asn
225                 230                 235                 240

Ile Asp Pro Thr Ala Trp Glu Asp Lys Lys Cys Lys Gly Glu Ser Arg
                245                 250                 255

Phe Pro Ala Gln Val Arg Ile Arg Ile Arg Arg Leu Cys Lys Ala Leu
            260                 265                 270

Glu Glu Asp Ala Phe Arg Pro Val Leu His His Tyr Asp Gly Pro Lys
        275                 280                 285

Phe Arg Leu Glu Leu Ser Ile Ala Glu Thr Leu Ser Leu Leu Asp Leu
    290                 295                 300

Cys Lys Thr Glu Asp Ala
305                 310

<210> SEQ ID NO 196
<211> LENGTH: 309
<212> TYPE: PRT
<213> ORGANISM: Hordeum vulgare

<400> SEQUENCE: 196

Met Asp Asn Leu Trp His Leu Gly Asp Glu Phe Arg Gly Gln Ser Lys
1               5                   10                  15

Val Val Glu Asp Arg Gln Trp Ser Leu Met Thr Ser Lys Leu Ala Glu
            20                  25                  30

Ile Thr Lys Ser Lys Ala Glu Arg Met Asn Asp Phe Glu Tyr Ala Arg
         35                  40                  45

Met Asn Thr Val Pro Asp Val Lys Gln Trp Asp Lys Leu Ser Tyr His
     50                  55                  60

Gln Glu Asp Asn Lys Met Asp His Leu Asn Leu Gly Leu Met Asn Leu
65                  70                  75                  80

```
Asp Leu Lys Met Asn Asp Leu Lys Met Asn Glu Ala Ala Met Lys Tyr
                85                  90                  95

Pro Phe Arg Asn Met Ala Tyr Asn Met Asn Pro Met Tyr Pro Lys Gly
            100                 105                 110

Asn Asn Gly Asn Val Asn Ser Phe Lys Met Asn Val Gly Val Asn Lys
            115                 120                 125

Tyr Pro Asn Asn Gln Asn Gly Lys Glu Ala Asn Gly Lys His Asn Gly
            130                 135                 140

Gly Asn Asn Asn Gly Gly Asn Ser Asn Asn Ser Val Asp Lys Arg
145                 150                 155                 160

Phe Lys Thr Leu Pro Thr Ser Glu Met Leu Pro Arg Asn Glu Val Leu
            165                 170                 175

Gly Gly Tyr Ile Phe Val Cys Asn Asn Asp Thr Met Gln Glu Asp Leu
            180                 185                 190

Lys Arg Gln Leu Phe Gly Leu Pro Ala Arg Tyr Arg Asp Ser Val Arg
            195                 200                 205

Ala Ile Thr Pro Gly Leu Pro Leu Phe Leu Tyr Asn Tyr Thr Thr His
            210                 215                 220

Gln Leu His Gly Val Phe Glu Ala Ala Ser Phe Gly Gly Ser Asn Ile
225                 230                 235                 240

Asp Pro Thr Ala Trp Glu Asp Lys Lys Cys Lys Gly Glu Ser Arg Phe
            245                 250                 255

Pro Ala Gln Val Arg Ile Arg Ile Arg Arg Leu Cys Lys Ala Leu Glu
            260                 265                 270

Glu Asp Ala Phe Arg Pro Val Leu His His Tyr Asp Gly Pro Lys Phe
            275                 280                 285

Arg Leu Glu Leu Ser Ile Ala Glu Thr Leu Ser Leu Leu Asp Leu Cys
            290                 295                 300

Lys Ser Glu Asp Ala
305

<210> SEQ ID NO 197
<211> LENGTH: 314
<212> TYPE: PRT
<213> ORGANISM: Oryza sativa

<400> SEQUENCE: 197

Met Asp Asn Leu Trp His Leu Gly Asp Glu Phe Arg Gly Gln Ser Lys
1               5                   10                  15

Val Val Glu Asp Arg Gln Trp Ser Leu Met Thr Ser Lys Leu Ala Glu
            20                  25                  30

Ile Asn Lys Ser Lys Ala Glu Arg Thr Asn Glu Leu Asp Tyr Ala Arg
            35                  40                  45

Met Asn Thr Ile Pro Asp Val Lys Gln Trp Asp Lys Val Ser Tyr His
50                  55                  60

Gln Asp Glu Ser Lys Met Asp His Leu Asn Leu Gly Leu Met Asn Leu
65                  70                  75                  80

Asp Leu Lys Met Asn Asp Ile Arg Met Asn Asp Ala Ala Met Lys Asn
                85                  90                  95

Pro Phe Arg Gly Met Ala Tyr Asn Met Asn Gln Leu Tyr Pro Lys Gly
            100                 105                 110

Gly Asn Gly Asn Val Asn Ser Phe Lys Met Asn Val Gly Val Asn Lys
            115                 120                 125

Tyr Leu His Ser Pro Asn Gly Lys Asp Val Asn Gly Lys Asn Ser Gly
            130                 135                 140
```

```
Ala Asn Ser Asn Gly Ser Asn Ser Ser Gly Asn Asn Ser Ser Asn Ser
145                 150                 155                 160

Ala Val Asp Lys Arg Phe Lys Thr Leu Pro Thr Ser Glu Met Leu Pro
            165                 170                 175

Arg Asn Glu Val Leu Gly Gly Tyr Ile Phe Val Cys Asn Asn Asp Thr
        180                 185                 190

Met Gln Glu Asp Leu Lys Arg Gln Leu Phe Gly Leu Pro Ala Arg Tyr
    195                 200                 205

Arg Asp Ser Val Arg Ala Ile Ile Pro Gly Leu Pro Leu Phe Leu Tyr
210                 215                 220

Asn Tyr Thr Thr His Gln Leu His Gly Val Phe Glu Ala Ser Ser Phe
225                 230                 235                 240

Gly Gly Ser Asn Ile Asp Pro Thr Ala Trp Glu Asp Lys Lys Cys Lys
            245                 250                 255

Gly Glu Ser Arg Phe Pro Ala Gln Val Arg Ile Arg Ile Arg Lys Leu
        260                 265                 270

Cys Lys Pro Leu Glu Glu Asp Ala Phe Arg Pro Val Leu His His Tyr
    275                 280                 285

Asp Gly Pro Lys Phe Arg Leu Glu Leu Ser Ile Ala Glu Thr Leu Ser
290                 295                 300

Leu Leu Asp Leu Cys Glu Lys Glu Gly Val
305                 310

<210> SEQ ID NO 198
<211> LENGTH: 356
<212> TYPE: PRT
<213> ORGANISM: Zea mays
<220> FEATURE:
<221> NAME/KEY: misc_feature
<222> LOCATION: (1)..(2)
<223> OTHER INFORMATION: Xaa can be any naturally occurring amino acid

<400> SEQUENCE: 198

Xaa Xaa Ala Thr Cys Leu Leu Ser Phe Leu Pro Ser Ile Pro Pro Cys
1               5                   10                  15

Leu Arg Pro Leu Leu Thr Pro Val Gly Arg Gly Ala Ala Ala Asp Cys
            20                  25                  30

Trp Asp Cys Pro Thr Pro Ser Ala Gln Val Ile Phe Gly Pro Phe Ala
        35                  40                  45

Gly Asp Glu His His Gln Val Cys Gln Val Asp Arg Ala Met Asp Ser
    50                  55                  60

Leu Trp His Leu Gly Asp Glu Leu Arg Gly Gln Pro Lys Val Val Glu
65                  70                  75                  80

Asp Arg Gln Trp Ser Leu Met Thr Ser Lys Leu Ala Glu Ile Thr Arg
                85                  90                  95

Ser Lys Gly Glu Arg Met Asn Thr Val Pro Asp Ala Lys Gln Trp Asp
            100                 105                 110

Lys Thr Ser Tyr Gln Leu His Asp Asp Ser Arg Met Gly His Ile Asn
        115                 120                 125

Leu Gly Leu Met Asn Leu Asp Leu Lys Met Asn Glu Ala Ala Ala Met
    130                 135                 140

Lys Leu Pro Phe Arg Gly Met Pro Tyr Asn Met Asn Gln Met Tyr Leu
145                 150                 155                 160

Lys Gly Ser Asn Ala Asn Ser Asn Val Asn Ala Phe Lys Met Asn Val
                165                 170                 175

Gly Val Asn Lys Tyr Ser Asn Ser Pro Asn Gly Lys Asp Ala Asn Gly
            180                 185                 190
```

```
Lys Asn Asn Gly Gly Ser Gly Gly Asn Asn Asn Gly Ser Ala Asn
        195                 200                 205

Gly Thr Ser Val Ala Asp Lys Arg Phe Lys Thr Leu Pro Thr Ser Glu
    210                 215                 220

Met Leu Pro Arg Asn Glu Val Leu Gly Gly Tyr Ile Phe Val Cys Asn
225                 230                 235                 240

Asn Asp Thr Met Gln Glu Asp Leu Lys Arg Gln Leu Phe Gly Leu Pro
                245                 250                 255

Ala Arg Tyr Arg Asp Ser Val Arg Ala Ile Thr Pro Gly Leu Pro Leu
            260                 265                 270

Phe Leu Tyr Asn Tyr Thr Thr His Gln Leu His Gly Val Phe Glu Ala
        275                 280                 285

Ala Ser Phe Gly Gly Ser Asn Ile Asp Pro Thr Ala Trp Glu Asp Lys
    290                 295                 300

Lys Cys Lys Gly Glu Ser Arg Phe Pro Ala Gln Val Arg Ile Cys Ile
305                 310                 315                 320

Arg Lys Leu Cys Lys Pro Leu Glu Glu Asp Ser Phe Arg Pro Val Leu
                325                 330                 335

His His Tyr Asp Gly Pro Lys Phe Arg Leu Glu Leu Ser Ile Ala Glu
            340                 345                 350

Thr Leu Ser Leu
        355

<210> SEQ ID NO 199
<211> LENGTH: 340
<212> TYPE: PRT
<213> ORGANISM: Triticum aestivum
<220> FEATURE:
<221> NAME/KEY: misc_feature
<222> LOCATION: (338)..(340)
<223> OTHER INFORMATION: Xaa can be any naturally occurring amino acid

<400> SEQUENCE: 199

Val Gly Gly Ala Lys Trp Glu Pro Thr Pro Ser Gln Pro Ser Gly Leu
1               5                   10                  15

Leu Ser Ser Gln Gln Phe Ala Ile Arg Pro Gln Ile Gln Arg Pro
            20                  25                  30

Pro Arg Arg Asn Pro Ala Pro Asn Leu Ala Glu Ser Leu Asn Arg Ala
        35                  40                  45

Met Asp Asn Leu Trp His Leu Gly Asp Glu Phe Arg Gly Gln Ser Lys
    50                  55                  60

Val Val Glu Asp Arg Gln Trp Ser Leu Met Thr Ser Lys Leu Ala Glu
65                  70                  75                  80

Ile Thr Lys Ser Lys Ala Glu Arg Met Asn Asp Phe Glu Tyr Ala Arg
                85                  90                  95

Met Asn Thr Val Pro Asp Val Lys Gln Trp Asp Lys Leu Ser Tyr His
            100                 105                 110

Gln Glu Asp Asn Lys Met Asp His Leu Asn Leu Gly Leu Met Asn Leu
        115                 120                 125

Asp Leu Lys Met Asn Asp Leu Lys Met Asn Glu Ala Ala Met Lys Tyr
    130                 135                 140

Pro Phe Arg Asn Met Ala Tyr Asn Met Asn Pro Met Tyr Pro Lys Gly
145                 150                 155                 160

Asn Asn Gly Asn Val Asn Ser Phe Lys Met Asn Val Gly Val Asn Lys
                165                 170                 175

Tyr Pro Asn Asn Gln Asn Gly Lys Glu Ala Asn Gly Lys His Asn Gly
```

```
                    180                 185                 190
Gly Asn Asn Asn Gly Gly Asn Ser Asn Asn Ser Val Asp Lys
            195                 200                 205
Arg Phe Lys Thr Leu Pro Thr Ser Glu Met Leu Pro Arg Asn Glu Val
            210                 215                 220
Leu Gly Gly Tyr Ile Phe Val Cys Asn Asn Asp Thr Met Gln Glu Asp
225                 230                 235                 240
Leu Lys Arg Gln Leu Phe Gly Leu Pro Ala Arg Tyr Arg Asp Ser Val
            245                 250                 255
Arg Ala Ile Thr Pro Gly Leu Pro Leu Phe Leu Tyr Asn Tyr Thr Thr
            260                 265                 270
His Gln Leu His Gly Val Phe Glu Ala Ala Ser Phe Gly Gly Ser Asn
            275                 280                 285
Ile Asp Pro Thr Ala Trp Glu Asp Lys Lys Cys Lys Gly Glu Ser Arg
            290                 295                 300
Phe Pro Ala Gln Val Arg Ile Arg Ile Arg Leu Cys Lys Ala Leu
305                 310                 315                 320
Glu Glu Asp Ala Phe Arg Pro Val Leu His His Tyr Asp Gly Pro Lys
            325                 330                 335
Phe Xaa Xaa Xaa
            340

<210> SEQ ID NO 200
<211> LENGTH: 314
<212> TYPE: PRT
<213> ORGANISM: Oryza sativa

<400> SEQUENCE: 200

Met Asp Asn Leu Trp His Leu Gly Asp Glu Phe Arg Gly Gln Ser Lys
1               5                   10                  15
Val Val Glu Asp Arg Gln Trp Ser Leu Met Thr Ser Lys Leu Ala Glu
            20                  25                  30
Ile Asn Lys Ser Lys Ala Glu Arg Thr Asn Glu Leu Asp Tyr Ala Arg
        35                  40                  45
Met Asn Thr Ile Pro Asp Val Lys Gln Trp Asp Lys Val Ser Tyr His
    50                  55                  60
Gln Asp Glu Ser Lys Met Asp His Leu Asn Leu Gly Leu Met Asn Leu
65                  70                  75                  80
Asp Leu Lys Met Asn Asp Ile Arg Met Asn Asp Ala Ala Met Lys Asn
                85                  90                  95
Pro Phe Arg Gly Met Ala Tyr Asn Met Asn Gln Leu Tyr Pro Lys Gly
            100                 105                 110
Gly Asn Gly Asn Val Asn Ser Phe Lys Met Asn Val Gly Val Asn Lys
        115                 120                 125
Tyr Leu His Ser Pro Asn Gly Lys Asp Val Asn Gly Lys Asn Ser Gly
    130                 135                 140
Ala Asn Ser Asn Gly Ser Asn Ser Ser Gly Asn Asn Ser Ser Asn Ser
145                 150                 155                 160
Ala Val Asp Lys Arg Phe Lys Thr Leu Pro Thr Ser Glu Met Leu Pro
                165                 170                 175
Arg Asn Glu Val Leu Gly Gly Tyr Ile Phe Val Cys Asn Asn Asp Thr
            180                 185                 190
Met Gln Glu Asp Leu Lys Arg Gln Leu Phe Gly Leu Pro Ala Arg Tyr
        195                 200                 205
Arg Asp Ser Val Arg Ala Ile Ile Pro Gly Leu Pro Leu Phe Leu Tyr
```

```
                210                 215                 220
Asn Tyr Thr Thr His Gln Leu His Gly Val Ser Glu Ala Ser Ser Phe
225                 230                 235                 240

Gly Gly Ser Asn Leu Asp Pro Thr Glu Trp Asp Asp Thr Thr Cys Asn
                245                 250                 255

Gly Glu Ser Arg Phe Pro Ala Gln Val Thr Leu Arg Leu Pro Lys Leu
                260                 265                 270

Cys Lys Pro Leu Glu Asp Ala Ala Ser Thr Pro Val Leu His His Tyr
                275                 280                 285

Asp Gly Pro Gln Ser Arg Leu Asp Leu Ser Ile Ala Asp Asn Leu Ser
                290                 295                 300

Leu Leu His Leu Cys Ala Gln Gln Arg Val
305                 310

<210> SEQ ID NO 201
<211> LENGTH: 184
<212> TYPE: PRT
<213> ORGANISM: Oryza sativa

<400> SEQUENCE: 201

Met Asp Asn Leu Trp His Leu Gly Asp Glu Phe Arg Gly Gln Ser Lys
1               5                   10                  15

Val Val Glu Asp Arg Gln Trp Ser Leu Met Thr Ser Lys Leu Ala Glu
                20                  25                  30

Ile Asn Lys Ser Lys Ala Glu Arg Thr Asn Glu Leu Asp Tyr Ala Arg
            35                  40                  45

Met Asn Thr Ile Pro Asp Val Lys Gln Trp Asp Lys Val Ser Tyr His
50                  55                  60

Gln Asp Glu Ser Lys Met Asp His Leu Asn Leu Gly Leu Met Asn Leu
65                  70                  75                  80

Asp Leu Lys Met Asn Asp Ile Arg Met Asn Asp Ala Ala Met Lys Asn
                85                  90                  95

Pro Phe Arg Gly Met Ala Tyr Asn Met Asn Gln Leu Tyr Pro Lys Gly
            100                 105                 110

Gly Asn Gly Asn Val Asn Ser Phe Lys Met Asn Val Gly Val Asn Lys
        115                 120                 125

Tyr Leu His Ser Pro Asn Gly Lys Asp Val Asn Gly Lys Arg Phe Lys
    130                 135                 140

Thr Leu Pro Thr Ser Glu Met Leu Pro Arg Asn Glu Val Leu Gly Gly
145                 150                 155                 160

Tyr Ile Phe Val Cys Asn Asn Asp Thr Met Gln Glu Asp Leu Lys Arg
                165                 170                 175

Gln Leu Phe Gly Leu Pro Ala Arg
            180

<210> SEQ ID NO 202
<211> LENGTH: 197
<212> TYPE: PRT
<213> ORGANISM: Gossypium Sp.

<400> SEQUENCE: 202

Met Gly Thr Arg Ala Lys Glu Lys Asn Ile Met Glu Pro Arg Val Gly
1               5                   10                  15

Arg Arg Thr Ala Thr Arg Lys Asn Asn Asn Asn Asp Asn Asn
                20                  25                  30

Glu Asn Lys Asp Gly Lys Ser Ala Ala Asp Lys Arg Phe Lys Thr Leu
            35                  40                  45
```

```
Pro Pro Ser Glu Ser Leu Pro Arg Asn Glu Thr Val Gly Gly Tyr Ile
    50                  55                  60

Phe Val Cys Asn Asn Asp Thr Met Glu Glu Asn Leu Arg Arg Gln Leu
 65                  70                  75                  80

Phe Gly Leu Pro Pro Arg Tyr Arg Asp Ser Val Arg Ala Ile Thr Pro
                 85                  90                  95

Gly Leu Pro Leu Phe Leu Tyr Asn Tyr Ser Thr His Gln Leu His Gly
            100                 105                 110

Val Phe Glu Ala Ala Ser Phe Gly Gly Thr Asn Ile Asp Pro Thr Ala
            115                 120                 125

Trp Glu Asp Lys Lys Cys Pro Gly Glu Ser Arg Phe Pro Ala Gln Val
130                 135                 140

Arg Val Ile Thr Arg Lys Ile Cys Glu Pro Leu Glu Glu Asp Ser Phe
145                 150                 155                 160

Arg Pro Ile Leu His His Tyr Asp Gly Pro Lys Phe Arg Leu Glu Leu
                165                 170                 175

Asn Ile Pro Glu Ala Leu Ser Leu Leu Asp Ile Phe Ala Asp Gln Gln
            180                 185                 190

Asp Thr Cys Ile Ser
            195

<210> SEQ ID NO 203
<211> LENGTH: 188
<212> TYPE: PRT
<213> ORGANISM: Solanum tuberosum

<400> SEQUENCE: 203

Lys Phe Gly Lys Gly Phe Phe Glu Asp Glu His Lys Ser Val Lys Lys
 1                5                  10                  15

Asn Asn Lys Ser Val Lys Glu Ser Asn Lys Asp Val Asn Ser Glu Lys
                 20                  25                  30

Gln Asn Gly Val Asp Lys Arg Phe Lys Thr Leu Pro Pro Ala Glu Ser
             35                  40                  45

Leu Pro Arg Asn Glu Thr Val Gly Gly Tyr Ile Phe Val Cys Asn Asn
    50                  55                  60

Asp Thr Met Ala Glu Asn Leu Lys Arg Glu Leu Phe Gly Leu Pro Pro
 65                  70                  75                  80

Arg Tyr Arg Asp Ser Val Arg Gln Ile Thr Pro Gly Leu Pro Leu Phe
                 85                  90                  95

Leu Tyr Asn Tyr Ser Thr His Gln Leu His Gly Val Phe Glu Ala Ala
            100                 105                 110

Ser Phe Gly Gly Ser Asn Ile Asp Pro Ser Ala Trp Glu Asp Lys Lys
            115                 120                 125

Asn Pro Gly Glu Ser Arg Phe Pro Ala Gln Val Leu Val Thr Arg
130                 135                 140

Lys Val Cys Glu Pro Leu Glu Glu Asp Ser Phe Arg Pro Ile Leu His
145                 150                 155                 160

His Tyr Asp Gly Pro Lys Phe Arg Leu Glu Leu Asn Val Pro Glu Ala
                165                 170                 175

Ile Ser Leu Leu Asp Ile Phe Glu Glu Asn Lys Asn
            180                 185

<210> SEQ ID NO 204
<211> LENGTH: 255
<212> TYPE: PRT
<213> ORGANISM: Triticum aestivum
```

<400> SEQUENCE: 204

```
Met Asp Thr Lys His Ala Asp Ser Phe Asp Glu Arg Asp Val Val
1               5                   10                  15

Asp Ala Gly Cys Val Arg Ala Val Leu Gly Glu Leu Val Leu Thr Phe
            20                  25                  30

Leu Phe Val Phe Thr Gly Val Ala Ala Met Ala Ala Gly Val Pro
        35                  40                  45

Glu Leu Gln Gly Ala Ala Met Pro Met Ala Thr Leu Ala Gly Val Ala
50                  55                  60

Leu Ala Gln Ala Leu Ala Ala Gly Val Leu Val Thr Ala Gly Phe His
65                  70                  75                  80

Val Ser Gly Gly His Leu Asn Pro Ala Val Thr Val Ala Leu Leu Ala
                85                  90                  95

Arg Gly His Ile Thr Ala Phe Arg Ala Val Leu Tyr Val Ala Ala Gln
                100                 105                 110

Leu Leu Ala Ser Ser Leu Ala Cys Ile Leu Leu Arg Tyr Leu Ser Gly
            115                 120                 125

Gly Gln Ala Thr Pro Val Pro Val His Thr Leu Gly Ala Gly Ile Gly
130                 135                 140

Pro Met Gln Gly Leu Val Met Glu Val Ile Leu Thr Phe Ser Leu Leu
145                 150                 155                 160

Phe Val Val Tyr Ala Thr Ile Ile Asp Pro Arg Thr Thr Val Pro Gly
                165                 170                 175

Tyr Gly Pro Met Leu Thr Gly Leu Ile Val Gly Ala Asn Thr Ile Ala
            180                 185                 190

Gly Gly Asn Phe Ser Gly Ala Ser Met Asn Pro Ala Arg Ser Phe Gly
        195                 200                 205

Pro Ala Leu Ala Thr Gly Val Trp Thr Asn His Trp Val Tyr Trp Val
210                 215                 220

Gly Pro Leu Val Gly Gly Pro Leu Ala Gly Phe Val Tyr Glu Thr Val
225                 230                 235                 240

Phe Met Val Thr Lys Thr His Glu Pro Leu Leu Gly Trp Asp Phe
                245                 250                 255
```

<210> SEQ ID NO 205
<211> LENGTH: 256
<212> TYPE: PRT
<213> ORGANISM: Triticum aestivum

<400> SEQUENCE: 205

```
Met Asp Thr Lys His Ala Asp Ser Leu Asp Glu Arg Asp Val Val
1               5                   10                  15

Val Asp Ala Gly Cys Val Arg Ala Val Leu Gly Glu Leu Val Leu Thr
            20                  25                  30

Phe Leu Phe Val Phe Thr Gly Val Ala Ala Met Ala Ala Gly Val
        35                  40                  45

Pro Glu Leu Gln Gly Ala Ala Met Pro Met Ala Thr Leu Ala Gly Val
50                  55                  60

Ala Leu Ala Gln Ala Leu Ala Ala Gly Val Leu Val Thr Ala Gly Phe
65                  70                  75                  80

His Val Ser Gly Gly His Leu Asn Pro Ala Val Thr Val Ala Leu Leu
                85                  90                  95

Ala Arg Gly His Ile Thr Ala Phe Arg Ala Val Leu Tyr Val Ala Ala
                100                 105                 110
```

Gln Leu Leu Ala Ser Ser Leu Ala Cys Ile Leu Leu Arg Tyr Leu Ser
            115                 120                 125

Gly Gly Gln Ala Thr Pro Val Pro Val His Thr Leu Gly Thr Gly Ile
130                 135                 140

Gly Pro Met Gln Gly Leu Val Met Glu Ile Ile Leu Thr Phe Ser Leu
145                 150                 155                 160

Leu Phe Val Val Tyr Ala Thr Ile Leu Asp Pro Arg Thr Thr Val Pro
                165                 170                 175

Gly Tyr Gly Pro Met Leu Thr Gly Leu Ile Val Gly Ala Asn Thr Ile
            180                 185                 190

Ala Gly Gly Asn Phe Ser Gly Ala Ser Met Asn Pro Ala Arg Ser Phe
        195                 200                 205

Gly Pro Ala Leu Ala Thr Gly Val Trp Thr Asn His Trp Val Tyr Trp
    210                 215                 220

Val Gly Pro Leu Val Gly Gly Pro Leu Ala Gly Phe Val Tyr Glu Thr
225                 230                 235                 240

Val Phe Met Val Thr Lys Thr His Glu Pro Leu Leu Gly Trp Asp Phe
                245                 250                 255

<210> SEQ ID NO 206
<211> LENGTH: 257
<212> TYPE: PRT
<213> ORGANISM: Hordeum vulgare

<400> SEQUENCE: 206

Met Ala Ala Thr Lys His Ala Asp Ser Phe Asp Glu Arg Glu Val Ala
1               5                   10                  15

Val Val Asp Thr Gly Cys Val Arg Ala Val Leu Gly Glu Leu Val Leu
                20                  25                  30

Thr Phe Leu Phe Val Phe Thr Gly Val Ala Ala Ala Met Ala Ala Gly
            35                  40                  45

Val Pro Glu Leu Pro Gly Ala Ala Met Pro Met Ala Thr Leu Ala Gly
        50                  55                  60

Val Ala Leu Ala Gln Ala Leu Ala Ala Gly Val Leu Val Thr Ala Gly
65                  70                  75                  80

Phe His Val Ser Gly Gly His Leu Asn Pro Ala Val Thr Val Ala Leu
                85                  90                  95

Leu Ala Arg Gly His Ile Thr Ala Phe Arg Ala Val Leu Tyr Val Val
            100                 105                 110

Ala Gln Leu Leu Ala Ser Ser Leu Ala Cys Ile Leu Leu Arg Cys Leu
        115                 120                 125

Thr Gly Gly Gln Pro Thr Pro Val Pro Val His Thr Leu Gly Ala Gly
    130                 135                 140

Ile Gly Pro Met Gln Gly Leu Val Met Glu Ile Ile Leu Thr Phe Ser
145                 150                 155                 160

Leu Leu Phe Val Val Tyr Ala Thr Ile Leu Asp Pro Arg Thr Thr Val
                165                 170                 175

Pro Gly Tyr Gly Pro Met Leu Thr Gly Leu Ile Val Gly Ala Asn Thr
            180                 185                 190

Ile Ala Gly Gly Asn Phe Ser Gly Ala Ser Met Asn Pro Ala Arg Ser
        195                 200                 205

Phe Gly Pro Ala Leu Ala Thr Gly Val Trp Thr Asn His Trp Ile Tyr
    210                 215                 220

Trp Val Gly Pro Leu Val Gly Gly Pro Leu Ala Gly Phe Val Tyr Glu
225                 230                 235                 240

```
Met Val Phe Met Val Lys Lys Thr His Glu Pro Leu Leu Gly Trp Asp
                245                 250                 255
Phe

<210> SEQ ID NO 207
<211> LENGTH: 336
<212> TYPE: PRT
<213> ORGANISM: Triticum aestivum

<400> SEQUENCE: 207

Met Gly Pro Val Phe Leu Leu Gly Leu Ser Gln His Gly Ser Ala Pro
1               5                   10                  15

Gly Leu Phe Arg Ala Leu Phe Leu Pro Arg Ser His Thr Asp Tyr Ser
            20                  25                  30

His His Ile Pro Arg Ser Arg Ala Thr Ser Leu Val Ser Met Asp Thr
        35                  40                  45

Lys His Ala Asp Ser Phe Glu Glu Arg Asp Val Val Val Asp Ala Gly
    50                  55                  60

Cys Val Arg Ala Val Leu Gly Glu Leu Val Leu Thr Phe Leu Phe Val
65                  70                  75                  80

Phe Thr Gly Val Ala Ala Ala Met Ala Ala Gly Val Pro Glu Leu Pro
                85                  90                  95

Gly Ala Ala Met Pro Met Ala Thr Leu Ala Gly Val Ala Leu Ala Gln
            100                 105                 110

Ala Leu Ala Ala Gly Val Leu Val Thr Ala Gly Phe His Val Ser Gly
        115                 120                 125

Gly His Leu Asn Pro Ala Val Thr Val Ala Leu Leu Ala Arg Gly His
    130                 135                 140

Ile Thr Ala Phe Arg Ala Val Leu Tyr Val Ala Ala Gln Leu Leu Ala
145                 150                 155                 160

Ser Ser Leu Ala Cys Ile Leu Leu Arg Tyr Leu Ser Gly Gly Gln Ala
                165                 170                 175

Thr Pro Val Pro Val His Thr Leu Gly Ala Gly Ile Gly Pro Met Gln
            180                 185                 190

Gly Leu Val Met Glu Val Ile Leu Thr Phe Ser Leu Leu Phe Val Val
        195                 200                 205

Tyr Ala Thr Ile Ile Asp Pro Arg Thr Thr Val Pro Gly Tyr Gly Pro
    210                 215                 220

Met Leu Thr Gly Leu Ile Val Gly Ala Asn Thr Ile Ala Gly Gly Asn
225                 230                 235                 240

Phe Ser Gly Ala Ser Met Asn Pro Ala Arg Ser Phe Gly Pro Ala Leu
                245                 250                 255

Ala Met Gly Val Trp Thr Asn His Trp Val Tyr Trp Val Gly Pro Leu
            260                 265                 270

Val Gly Gly Pro Leu Ala Gly Phe Val Tyr Glu Met Val Phe Met Val
        275                 280                 285

Lys Lys Asp Ala Arg Ala Ser Ala Trp Leu Gly Leu Leu Glu Asn Arg
    290                 295                 300

Leu Leu Pro Tyr Leu His Leu His Phe Ala Met Tyr Thr Ser Val Tyr
305                 310                 315                 320

Lys Ala Ile Asp Val Ala Gly Arg Phe Phe Arg Pro Ser Asp Ser Ser
                325                 330                 335

<210> SEQ ID NO 208
<211> LENGTH: 315
<212> TYPE: PRT
```

<213> ORGANISM: Oryza sativa

<400> SEQUENCE: 208

Ile Lys Ser Arg Gly Lys Gln Arg Gln Ala Glu Gln Arg Arg Glu
1               5                   10                  15

Pro His Leu Gly Lys Lys Lys Arg Lys Ile Ile Ser Ser His Phe Leu
            20                  25                  30

Leu Pro Phe Ser Ser Pro Arg Ile Phe Thr Lys Gln Ile Ser Leu Gln
        35                  40                  45

Phe Phe Ser Phe Phe Phe Leu Ile Leu Arg Ile Phe Ser Ile Glu Glu
50                  55                  60

Arg Arg Glu Leu Trp Asp Arg Phe Arg Ala Met Ala Lys Glu Val Asp
65                  70                  75                  80

Pro Cys Asp His Gly Glu Val Val Asp Ala Gly Cys Val Arg Ala Val
                85                  90                  95

Leu Ala Glu Leu Val Leu Thr Phe Val Phe Val Phe Thr Gly Val Ala
            100                 105                 110

Ala Thr Met Ala Ala Gly Val Pro Glu Val Ala Gly Ala Ala Met Pro
        115                 120                 125

Met Ala Ala Leu Ala Gly Val Ala Ile Ala Thr Ala Leu Ala Ala Gly
130                 135                 140

Val Leu Val Thr Ala Gly Phe His Val Ser Gly Gly His Leu Asn Pro
145                 150                 155                 160

Ala Val Thr Val Ala Leu Leu Ala Arg Gly His Ile Thr Ala Phe Arg
                165                 170                 175

Ser Ala Leu Tyr Val Ala Ala Gln Leu Leu Ala Ser Ser Leu Ala Cys
            180                 185                 190

Ile Leu Leu Arg Tyr Leu Thr Gly Gly Met Ala Thr Pro Val His Thr
        195                 200                 205

Leu Gly Ser Gly Ile Gly Pro Met Gln Gly Leu Val Met Glu Ile Ile
210                 215                 220

Leu Thr Phe Ser Leu Leu Phe Val Val Tyr Ala Thr Ile Leu Asp Pro
225                 230                 235                 240

Arg Ser Ser Val Pro Gly Phe Gly Pro Leu Leu Thr Gly Leu Ile Val
                245                 250                 255

Gly Ala Asn Thr Ile Ala Gly Gly Asn Phe Ser Gly Ala Ser Met Asn
            260                 265                 270

Pro Ala Arg Ser Phe Gly Pro Ala Leu Ala Thr Gly Val Trp Thr His
        275                 280                 285

His Trp Ile Tyr Trp Leu Gly Pro Leu Ile Gly Gly Pro Leu Ala Gly
290                 295                 300

Leu Val Tyr Glu Ser Leu Phe Leu Val Lys Arg
305                 310                 315

<210> SEQ ID NO 209
<211> LENGTH: 202
<212> TYPE: PRT
<213> ORGANISM: Saccharum officinarum
<220> FEATURE:
<221> NAME/KEY: misc_feature
<222> LOCATION: (198)..(198)
<223> OTHER INFORMATION: Xaa can be any naturally occurring amino acid

<400> SEQUENCE: 209

Pro Pro Pro Pro Pro Pro Pro Val Val Gln Asn Ile Ser Leu Arg
1               5                   10                  15

Phe Ser Glu Ser Phe Ser Leu Gln Gly Thr Gly Thr Thr Gly Ala Phe

```
                20              25              30
Thr Pro Pro Pro Ala Phe Pro Ser Pro Pro Gly Thr Gly Ala Thr Arg
            35              40              45
Leu Leu Leu Ala Ile Val His Ser Phe Met Ala Lys Leu Val Asn Lys
 50              55              60
Leu Leu Asp Ser Phe Asp His Asp Asp Thr Thr Pro Asp Val Gly Cys
65              70              75              80
Val Arg Ala Val Leu Ala Glu Leu Val Leu Thr Phe Leu Phe Val Phe
                85              90              95
Thr Gly Val Ser Ala Ala Met Ala Ala Gly Ser Gly Gly Lys Pro Gly
            100             105             110
Glu Ala Met Pro Met Ala Thr Leu Ala Ala Val Ala Ile Ala Asn Ala
            115             120             125
Leu Ala Ala Gly Val Leu Val Thr Ala Gly Phe His Val Ser Gly Gly
            130             135             140
His Leu Asn Pro Ala Val Thr Val Gly Leu Met Val Cys Arg His Ile
145             150             155             160
Thr Lys Leu Arg Ala Val Leu Tyr Ile Ala Ala Gln Leu Leu Ala Ser
            165             170             175
Ser Leu Ala Cys Ile Leu Leu Arg Tyr Leu Ser Gly Gly Met Val Thr
            180             185             190
Pro Val His Ala Leu Xaa Ala Gly Ile Lys
            195             200

<210> SEQ ID NO 210
<211> LENGTH: 256
<212> TYPE: PRT
<213> ORGANISM: Oryza sativa

<400> SEQUENCE: 210

Met Ala Ser Pro Glu Gly Ser Thr Trp Val Phe Asp Cys Pro Leu Met
1               5               10              15
Asp Asp Leu Ala Ala Ala Ala Gly Phe Asp Ala Ala Pro Ala Gly Gly
            20              25              30
Phe Tyr Trp Thr Thr Pro Ala Pro Gln Ala Ala Leu Gln Pro Pro
            35              40              45
Pro Pro Gln Gln Gln Pro Val Ala Pro Thr Ala Ala Pro Asn Ala
 50              55              60
Cys Ala Glu Ile Asn Gly Ser Val Asp Cys Glu His Gly Lys Glu Gln
65              70              75              80
Pro Thr Asn Lys Arg Pro Arg Ser Glu Ser Gly Thr Arg Pro Ser Ser
            85              90              95
Lys Ala Cys Arg Glu Lys Val Arg Arg Asp Lys Leu Asn Glu Arg Phe
            100             105             110
Leu Glu Leu Gly Ala Val Leu Glu Pro Gly Lys Thr Pro Lys Met Asp
            115             120             125
Lys Ser Ser Ile Leu Asn Asp Ala Ile Arg Val Met Ala Glu Leu Arg
            130             135             140
Ser Glu Ala Gln Lys Leu Lys Glu Ser Asn Glu Ser Leu Gln Glu Lys
145             150             155             160
Ile Lys Glu Leu Lys Ala Glu Lys Asn Glu Leu Arg Asp Glu Lys Gln
            165             170             175
Lys Leu Lys Ala Glu Lys Glu Ser Leu Glu Gln Gln Ile Lys Phe Leu
            180             185             190
Asn Ala Arg Pro Ser Phe Val Pro His Pro Pro Val Ile Pro Ala Ser
```

-continued

```
                195                 200                 205
Ala Phe Thr Ala Pro Gln Gly Gln Ala Ala Gly Gln Lys Leu Met Met
        210                 215                 220

Pro Val Ile Gly Tyr Pro Gly Phe Pro Met Trp Gln Phe Met Pro Pro
225                 230                 235                 240

Ser Asp Val Asp Thr Thr Asp Thr Lys Ser Cys Pro Pro Val Ala
                245                 250                 255

<210> SEQ ID NO 211
<211> LENGTH: 251
<212> TYPE: PRT
<213> ORGANISM: Triticum aestivum

<400> SEQUENCE: 211

Met Ala Ser Pro Glu Gly Ser Asn Trp Val Phe Asp Cys Pro Leu Met
1               5                   10                  15

Asp Asp Leu Ala Ala Ala Asp Phe Ala Ala Ser Ala Gly Gly Phe
            20                  25                  30

Tyr Trp Thr Pro Pro Met Gln Pro Gln Met His Thr Leu Ala Gln Ala
        35                  40                  45

Val Ser Ala Thr Pro Ala Pro Asn Pro Cys Ala Glu Ile Asn Ser Ser
    50                  55                  60

Val Ser Val Asp Trp Asp His Ala Lys Gly Gln Pro Lys Asn Lys Arg
65                  70                  75                  80

Pro Arg Ser Glu Thr Gly Ala Gln Pro Ser Lys Ala Cys Arg Glu
            85                  90                  95

Lys Val Arg Arg Asp Lys Leu Asn Glu Arg Phe Leu Glu Leu Gly Ala
            100                 105                 110

Val Leu Asp Pro Gly Lys Thr Pro Lys Ile Asp Lys Cys Ala Ile Leu
        115                 120                 125

Asn Asp Ala Ile Arg Ala Val Thr Glu Leu Arg Ser Glu Ala Glu Lys
130                 135                 140

Leu Lys Asp Ser Asn Glu Ser Leu Gln Glu Lys Ile Arg Glu Leu Lys
145                 150                 155                 160

Ala Glu Lys Asn Glu Leu Arg Asp Glu Lys Gln Lys Leu Lys Ala Glu
                165                 170                 175

Lys Glu Ser Leu Glu Gln Gln Ile Lys Phe Met Asn Ala Arg Gln Ser
            180                 185                 190

Leu Val Pro His Pro Ser Val Ile Pro Ala Ala Phe Ala Ala Ala
        195                 200                 205

Gln Gly Gln Ala Ala Gly His Lys Leu Met Met Pro Val Met Ser Tyr
    210                 215                 220

Pro Gly Phe Pro Met Trp Gln Phe Met Pro Pro Ser Asp Val Asp Thr
225                 230                 235                 240

Ser Asp Asp Pro Lys Ser Cys Pro Pro Val Ala
                245                 250

<210> SEQ ID NO 212
<211> LENGTH: 251
<212> TYPE: PRT
<213> ORGANISM: Hordeum vulgare

<400> SEQUENCE: 212

Met Ala Ser Pro Glu Gly Ser Asn Trp Val Phe Asp Cys Pro Leu Met
1               5                   10                  15

Asp Asp Leu Ala Ala Ala Asp Phe Ala Ala Val Pro Ala Gly Gly Phe
            20                  25                  30
```

Tyr Trp Asn Pro Pro Met Pro Pro Gln Met His Thr Leu Ala Gln Ala
            35                  40                  45

Val Ser Ala Thr Pro Ala Pro Asn Pro Cys Ala Glu Ile Asn Ser Ser
 50                  55                  60

Val Ser Val Asp Trp Asp His Ala Lys Gly Gln Pro Lys Asn Lys Arg
 65                  70                  75                  80

Pro Arg Ser Glu Thr Gly Ala Gln Pro Ser Ser Lys Ala Cys Arg Glu
                 85                  90                  95

Lys Val Arg Arg Asp Lys Leu Asn Glu Arg Phe Leu Glu Leu Gly Ala
                100                 105                 110

Val Leu Asp Pro Gly Lys Thr Pro Lys Ile Asp Lys Cys Ala Ile Leu
            115                 120                 125

Asn Asp Ala Ile Arg Ala Val Thr Glu Leu Arg Ser Glu Ala Glu Lys
130                 135                 140

Leu Lys Asp Ser Asn Glu Ser Leu Gln Glu Lys Ile Arg Glu Leu Lys
145                 150                 155                 160

Ala Glu Lys Asn Glu Leu Arg Asp Gly Lys Gln Lys Leu Lys Ala Glu
                165                 170                 175

Lys Glu Ser Leu Glu Gln Gln Ile Lys Phe Met Asn Ala Arg Gln Arg
            180                 185                 190

Leu Val Pro His Pro Ser Val Ile Pro Ala Thr Ala Phe Ala Ala Ala
            195                 200                 205

Gln Gly Gln Ala Ala Gly His Lys Leu Met Met Pro Val Met Ser Tyr
        210                 215                 220

Pro Gly Phe Pro Met Trp Gln Phe Met Pro Pro Ser Asp Val Asp Thr
225                 230                 235                 240

Ser Asp Asp Pro Lys Ser Cys Pro Pro Val Ala
                245                 250

<210> SEQ ID NO 213
<211> LENGTH: 214
<212> TYPE: PRT
<213> ORGANISM: Oryza sativa

<400> SEQUENCE: 213

Met Tyr Leu Leu Leu Tyr Ile Ile Val Thr Tyr Gly Ile Leu Lys Tyr
1               5                   10                  15

Lys Phe Ile Phe Phe Thr Ser Ala Glu Ile Asn Gly Ser Val Asp Cys
            20                  25                  30

Glu His Gly Lys Glu Gln Pro Thr Asn Lys Arg Pro Arg Ser Glu Ser
        35                  40                  45

Gly Thr Arg Pro Ser Ser Lys Ala Cys Arg Glu Lys Val Arg Arg Asp
 50                  55                  60

Lys Leu Asn Glu Arg Phe Leu Glu Leu Gly Ala Val Leu Glu Pro Gly
 65                  70                  75                  80

Lys Thr Pro Lys Met Asp Lys Ser Ser Ile Leu Asn Asp Ala Ile Arg
                 85                  90                  95

Val Met Ala Glu Leu Arg Ser Glu Ala Gln Lys Leu Lys Glu Ser Asn
                100                 105                 110

Glu Ser Leu Gln Glu Lys Ile Lys Glu Leu Lys Ala Glu Lys Asn Glu
            115                 120                 125

Leu Arg Asp Glu Lys Gln Lys Leu Lys Ala Glu Lys Glu Ser Leu Glu
        130                 135                 140

Gln Gln Ile Lys Phe Leu Asn Ala Arg Pro Ser Phe Val Pro His Pro
145                 150                 155                 160

```
Pro Val Ile Pro Ala Ser Ala Phe Thr Ala Pro Gln Gly Gln Ala Ala
            165                 170                 175

Gly Gln Lys Leu Met Met Pro Val Ile Gly Tyr Pro Gly Phe Pro Met
        180                 185                 190

Trp Gln Phe Met Pro Pro Ser Asp Val Asp Thr Thr Asp Asp Thr Lys
    195                 200                 205

Ser Cys Pro Pro Val Ala
        210

<210> SEQ ID NO 214
<211> LENGTH: 882
<212> TYPE: PRT
<213> ORGANISM: Oryza sativa

<400> SEQUENCE: 214

Met Val Lys Leu Ala Phe Gly Ser Cys Gly Asp Ser Phe Ser Ala Ser
1               5                   10                  15

Ser Ile Lys Ala Tyr Val Ala Glu Phe Ile Ala Thr Leu Leu Phe Val
            20                  25                  30

Phe Ala Gly Val Gly Ser Ala Ile Ala Tyr Gly Gln Leu Thr Lys Gly
        35                  40                  45

Gly Ala Leu Asp Pro Ala Gly Leu Val Ala Ile Ala Ile Ala His Ala
    50                  55                  60

Phe Ala Leu Phe Val Gly Val Ser Met Ala Ala Asn Ile Ser Gly Gly
65                  70                  75                  80

His Leu Asn Pro Val Val Thr Phe Gly Leu Ala Val Gly Gly His Ile
                85                  90                  95

Thr Ile Leu Thr Gly Ile Phe Tyr Trp Val Ala Gln Leu Leu Gly Ala
            100                 105                 110

Ser Val Ala Cys Leu Leu Cys Ser Ser Pro Pro Thr Asp Arg Leu Ala
        115                 120                 125

Ile Pro Thr His Ala Ile Ala Gly Ile Ser Glu Ile Glu Gly Met Val
    130                 135                 140

Met Glu Ile Val Ile Thr Phe Ala Leu Val Tyr Thr Gly Tyr Ala Thr
145                 150                 155                 160

Ala Ala Asp Pro Lys Lys Gly Ser Leu Gly Thr Val Ala Pro Met Asp
                165                 170                 175

Ile Gly Phe Ile Val Gly Ala Asn Ile Leu Ala Ala Gly Pro Phe Ser
            180                 185                 190

Gly Ser Ser Met Asn Pro Ala Arg Ser Phe Gly Pro Ala Val Ala Ala
        195                 200                 205

Gly Asn Phe Ala Gly Asn Trp Val Tyr Trp Val Gly Pro Leu Ile Gly
    210                 215                 220

Gly Gly Leu Ala Gly Leu Val Tyr Asp Asp Val Phe Ile Ala Ser Tyr
225                 230                 235                 240

Gln Pro Val Met Ile Gly Phe Thr Val Ile Leu Cys Asp Arg Ser Asp
                245                 250                 255

Gln Ala Val Tyr Ala Gly Gln Thr Ser Gly Asp Arg Ala Val Thr Pro
            260                 265                 270

Cys Leu Gly Arg Val Phe Ala Val Met Asp Arg Glu Ser Ala Trp Cys
        275                 280                 285

Arg Met Gln Ser Tyr Ile Met Ala Glu Asn Tyr Asp Ile Trp Arg Lys
    290                 295                 300

Val Ser His Pro Tyr Val Ile Pro Glu Ala Ile Asn Thr Ala Ala Glu
305                 310                 315                 320
```

```
Lys Thr Ala Phe Glu Gln Asn Cys Lys Ala Arg Asn Ile Leu Leu Ser
                325                 330                 335

Gly Ile Ser Arg Ser Asp Tyr Asp Arg Val Ala His Leu Gln Thr Ala
                340                 345                 350

His Glu Ile Trp Ile Ala Leu Ser Asn Phe His Gln Gly Thr Asn Asn
                355                 360                 365

Ile Lys Glu Leu Arg Arg Asp Leu Phe Lys Lys Glu Tyr Ile Lys Phe
                370                 375                 380

Glu Met Lys Pro Gly Glu Ala Leu Asp Asp Tyr Leu Ser Arg Phe Asn
385                 390                 395                 400

Lys Ile Leu Ser Asp Leu Arg Ser Val Asp Ser Ser Tyr Asp Ala Asn
                405                 410                 415

Tyr Pro Gln Ser Glu Ile Ser Arg His Phe Leu Asn Gly Leu Asp Met
                420                 425                 430

Ser Ile Trp Glu Met Lys Val Thr Ser Ile Gln Glu Ser Val Asn Met
                435                 440                 445

Ser Thr Leu Thr Leu Asp Ser Leu Tyr Thr Lys Leu Lys Thr His Glu
                450                 455                 460

Met Asn Ile Leu Ala Arg Lys Val Asp Ser Lys Ser Ser Ala Leu Val
465                 470                 475                 480

Ser Ser Ser Thr Ser Leu Asp Val Gly Ala Ser Ser Ser Lys Ser Ser
                485                 490                 495

Val Leu Ala Leu Phe Asn Ala Met Ser Asp Asp Gln Leu Glu Gln Phe
                500                 505                 510

Glu Glu Glu Asp Leu Val Leu Leu Ser Asn Lys Phe Ser Arg Ala Met
                515                 520                 525

Lys Asn Val Arg Asn Arg Lys Gly Glu Pro Asn Arg Cys Phe Glu
                530                 535                 540

Cys Gly Ala Leu Asp His Leu Arg Ser His Cys Pro Lys Leu Gly Arg
545                 550                 555                 560

Gly Lys Lys Glu Asp Asp Gly Arg Val Lys Glu Asp Val Asn Lys
                565                 570                 575

Lys Lys Asn Met Lys Glu Lys Glu Lys Lys His Cys Met Gln Trp
                580                 585                 590

Leu Ile Gln Glu Leu Ile Lys Val Phe Asp Glu Ser Glu Asp Glu Asp
                595                 600                 605

Glu Gly Lys Gly Lys Gln Val Val Asp Leu Ala Phe Ile Ala Arg Asn
                610                 615                 620

Ala Ser Ser Asp Val Asp Glu Ser Asp Asp Asn Glu Glu Lys Leu
625                 630                 635                 640

Ser Tyr Asp Gln Leu Glu Tyr Ala Ala Tyr Lys Phe Ala Lys Lys Leu
                645                 650                 655

Gln Thr Cys Ser Ile Val Leu Asp Glu Lys Asp His Thr Ile Glu Ile
                660                 665                 670

Leu Asn Ala Glu Ile Ala Arg Leu Lys Ser Leu Ile Pro Asn Asp Asp
                675                 680                 685

Asn Cys Gln Ser Cys Glu Val Leu Phe Ser Glu Ile Asn Ala Leu Arg
                690                 695                 700

Asp Val Asn Ser Val Asn Cys Lys Lys Leu Glu Phe Glu Ile Glu Lys
705                 710                 715                 720

Ser Lys Lys Leu Glu Ser Ser Phe Ala Leu Gly Phe Ala Leu His Ala
                725                 730                 735

Arg Val Val Asp Glu Leu Ile Leu Thr Lys Asn Val Leu Lys Lys Ile
```

```
                      740               745               750
Gln Ser Cys Phe Leu Cys Lys Phe Phe Gly Gln Cys Phe Met Cys Asn
            755               760               765
Lys Ala Lys Gln Asn Asn Gly Val Leu Ile Ser Gln Asp Cys Ser Lys
        770               775               780
Cys Val Leu Asn Glu Leu Lys Leu Lys Asp Ala Leu Glu Arg Val Lys
785               790               795               800
His Met Glu Glu Ile Ile Lys Gln Asp Glu Val Phe Ser Cys Ser Thr
                805               810               815
Cys Arg Lys Gln Lys Gly Leu Leu Asp Ala Cys Lys Asn Cys Ala Ile
            820               825               830
Leu Thr Gln Glu Val Ser Tyr Leu Lys Ser Ser Leu Gln Arg Phe Ser
        835               840               845
Asp Gly Lys Lys Asn Leu Asn Met Ile Leu Asp Gln Ser Asn Val Ser
    850               855               860
Thr His Asn Arg Gly Leu Gly Phe Asp Ser Tyr Ser Lys Asp Leu Asp
865               870               875               880
Val Ala

<210> SEQ ID NO 215
<211> LENGTH: 249
<212> TYPE: PRT
<213> ORGANISM: Glycine max

<400> SEQUENCE: 215

Met Val Lys Ile Ala Leu Gly Thr Leu Asp Asp Ser Phe Ser Ala Ala
1               5                   10                  15
Ser Leu Lys Ala Tyr Phe Ala Glu Phe His Ala Thr Leu Ile Phe Val
            20                  25                  30
Phe Ala Gly Val Gly Ser Ala Ile Ala Tyr Asn Glu Leu Thr Lys Asp
        35                  40                  45
Ala Ala Leu Asp Pro Thr Gly Leu Val Ala Val Ala His Ala
    50                  55                  60
Phe Ala Leu Phe Val Gly Val Ser Val Ala Ala Asn Ile Ser Gly Gly
65                  70                  75                  80
His Leu Asn Pro Ala Val Thr Phe Gly Leu Ala Ile Gly Gly Asn Ile
                85                  90                  95
Thr Leu Ile Thr Gly Phe Leu Tyr Trp Ile Ala Gln Leu Leu Gly Ser
            100                 105                 110
Ile Val Ala Cys Leu Leu Leu Asn Leu Ile Thr Ala Lys Ser Ile Pro
        115                 120                 125
Ser His Ser Pro Ala Asn Gly Val Asn Asp Leu Gln Ala Val Val Phe
    130                 135                 140
Glu Ile Val Ile Thr Phe Gly Leu Val Tyr Thr Val Tyr Ala Thr Ala
145                 150                 155                 160
Val Asp Pro Lys Lys Gly Ser Leu Gly Ile Ile Ala Pro Ile Ala Ile
                165                 170                 175
Gly Phe Val Val Gly Ala Asn Ile Leu Ala Ala Gly Pro Phe Ser Gly
            180                 185                 190
Gly Ser Met Asn Pro Ala Arg Ser Phe Gly Pro Ala Val Val Ser Gly
        195                 200                 205
Asp Leu Ala Ala Asn Trp Ile Tyr Trp Val Gly Pro Leu Ile Gly Gly
    210                 215                 220
Gly Leu Ala Gly Leu Ile Tyr Gly Asp Val Phe Ile Gly Ser Tyr Ala
225                 230                 235                 240
```

```
Pro Val Pro Ala Ser Glu Thr Tyr Pro
                245

<210> SEQ ID NO 216
<211> LENGTH: 248
<212> TYPE: PRT
<213> ORGANISM: Triticum aestivum

<400> SEQUENCE: 216

Met Pro Ala Ser Ile Ala Phe Gly Arg Phe Asp Asp Ser Phe Ser Leu
1               5                   10                  15

Ala Ser Phe Lys Ala Tyr Ile Ala Glu Phe Ile Ser Thr Leu Ile Phe
                20                  25                  30

Val Phe Ala Gly Val Gly Ser Ala Ile Ala Tyr Ser Lys Val Ser Gly
            35                  40                  45

Gly Ala Pro Leu Asp Pro Ser Gly Leu Ile Ala Val Ala Ile Cys His
        50                  55                  60

Gly Phe Gly Leu Phe Val Ala Val Ala Val Gly Ala Asn Ile Ser Gly
65                  70                  75                  80

Gly His Val Asn Pro Ala Val Thr Phe Gly Leu Ala Leu Gly Gly Gln
                85                  90                  95

Ile Thr Ile Leu Thr Gly Ile Phe Tyr Trp Val Ala Gln Leu Leu Gly
                100                 105                 110

Ala Ile Val Gly Ala Phe Leu Val Gln Phe Cys Thr Gly Val Ala Thr
            115                 120                 125

Pro Thr His Gly Leu Ser Gly Val Gly Ala Phe Glu Gly Val Val Met
        130                 135                 140

Glu Ile Ile Val Thr Phe Gly Leu Val Tyr Thr Val Tyr Ala Thr Ala
145                 150                 155                 160

Ala Asp Pro Lys Lys Gly Ser Leu Gly Thr Ile Ala Pro Ile Ala Ile
                165                 170                 175

Gly Phe Ile Val Gly Ala Asn Ile Leu Val Ala Gly Pro Phe Ser Gly
            180                 185                 190

Gly Ser Met Asn Pro Ala Arg Ser Phe Gly Pro Ala Val Ala Ser Gly
        195                 200                 205

Asp Phe Thr Asn Ile Trp Ile Tyr Trp Ala Gly Pro Leu Ile Gly Gly
        210                 215                 220

Gly Leu Ala Gly Val Val Tyr Arg Tyr Leu Tyr Met Cys Asp Asp His
225                 230                 235                 240

Thr Ala Val Ala Gly Asn Asp Tyr
                245

<210> SEQ ID NO 217
<211> LENGTH: 248
<212> TYPE: PRT
<213> ORGANISM: Triticum aestivum

<400> SEQUENCE: 217

Met Pro Gly Ser Ile Ala Phe Gly Arg Phe Asp Asp Ser Phe Ser Leu
1               5                   10                  15

Ala Ser Phe Lys Ala Tyr Ile Ala Glu Phe Ile Ser Thr Leu Ile Phe
                20                  25                  30

Val Phe Ala Gly Val Gly Ser Ala Ile Ala Tyr Thr Lys Val Ser Gly
            35                  40                  45

Gly Ala Pro Leu Asp Pro Ser Gly Leu Ile Ala Val Ala Ile Cys His
        50                  55                  60
```

```
Gly Phe Gly Leu Phe Val Ala Val Ala Ile Gly Ala Asn Ile Ser Gly
 65                  70                  75                  80

Gly His Val Asn Pro Ala Val Thr Phe Gly Leu Ala Leu Gly Gly Gln
                 85                  90                  95

Ile Thr Ile Leu Thr Gly Ile Phe Tyr Trp Val Ala Gln Leu Leu Gly
            100                 105                 110

Ala Ile Val Gly Ala Phe Leu Val Gln Phe Cys Thr Gly Val Ala Thr
        115                 120                 125

Pro Thr His Gly Leu Ser Gly Val Gly Ala Phe Glu Gly Val Val Met
130                 135                 140

Glu Ile Ile Val Thr Phe Gly Leu Val Tyr Thr Val Tyr Ala Thr Ala
145                 150                 155                 160

Ala Asp Pro Lys Lys Gly Ser Leu Gly Thr Ile Ala Pro Ile Ala Ile
                165                 170                 175

Gly Phe Ile Val Gly Ala Asn Ile Leu Val Ala Gly Pro Phe Ser Gly
            180                 185                 190

Gly Ser Met Asn Pro Ala Arg Ser Phe Gly Pro Ala Val Ala Ser Gly
        195                 200                 205

Asp Phe Thr Asn Ile Trp Ile Tyr Trp Ala Gly Pro Leu Ile Gly Gly
210                 215                 220

Gly Leu Ala Gly Val Val Tyr Arg Tyr Val Tyr Met Cys Asp Asp His
225                 230                 235                 240

Ser Ser Val Ala Gly Asn Asp Tyr
                245

<210> SEQ ID NO 218
<211> LENGTH: 207
<212> TYPE: PRT
<213> ORGANISM: Solanum tuberosum

<400> SEQUENCE: 218

Met Val Lys Ile Ala Phe Gly Ser Ile Gly Asp Ser Leu Ser Val Gly
1               5                   10                  15

Ser Leu Lys Ala Tyr Leu Ala Glu Phe Ile Ala Thr Leu Leu Phe Val
            20                  25                  30

Phe Ala Gly Val Gly Ser Ala Ile Ala Tyr Asn Lys Leu Thr Ser Asp
        35                  40                  45

Ala Ala Leu Asp Pro Ala Gly Leu Val Ala Ile Ala Val Ala His Ala
    50                  55                  60

Phe Ala Leu Phe Val Gly Val Ser Met Ala Ala Asn Ile Ser Gly Gly
 65                 70                  75                  80

His Leu Asn Pro Ala Val Thr Leu Gly Leu Ala Val Gly Gly Asn Ile
                85                  90                  95

Thr Ile Leu Thr Gly Leu Phe Tyr Trp Val Ala Gln Leu Leu Gly Ser
            100                 105                 110

Thr Val Ala Cys Leu Leu Leu Lys Tyr Val Thr Asn Gly Leu Ala Val
        115                 120                 125

Pro Thr His Gly Val Ala Gly Met Asn Gly Ala Glu Gly Val Val
130                 135                 140

Met Glu Ile Val Ile Thr Phe Ala Leu Val Tyr Thr Val Tyr Ala Thr
145                 150                 155                 160

Ala Ala Val Val Ala Gly Asp Phe Ser Gln Asn Trp Ile Tyr Trp Val
                165                 170                 175

Gly Pro Leu Ile Gly Gly Leu Ala Gly Phe Ile Tyr Gly Asp Val
            180                 185                 190
```

```
Phe Ile Gly Ser His Thr Pro Leu Pro Thr Ser Glu Asp Tyr Ala
            195                 200                 205
```

<210> SEQ ID NO 219
<211> LENGTH: 224
<212> TYPE: PRT
<213> ORGANISM: Saccharum officinarum
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid

<400> SEQUENCE: 219

```
Phe Gln Pro Arg Arg Ala Lys Arg Glu Ser Lys Met Val Lys Leu Ala
1               5                   10                  15

Phe Gly Ser Val Gly Asp Ser Phe Ser Ala Thr Ser Ile Lys Ala Tyr
            20                  25                  30

Val Ser Glu Phe Ile Ala Thr Leu Leu Phe Val Phe Ala Gly Val Gly
        35                  40                  45

Ser Ala Ile Ala Tyr Gly Gln Leu Thr Asn Asp Gly Ala Leu Asp Pro
    50                  55                  60

Ala Gly Leu Val Ala Ile Ala Ile Ala His Ala Leu Ala Leu Phe Val
65                  70                  75                  80

Gly Val Ser Ile Ala Ala Asn Ile Ser Gly Gly His Leu Asn Pro Ala
                85                  90                  95

Val Thr Phe Gly Leu Ala Val Gly Gly His Ile Thr Ile Leu Thr Gly
            100                 105                 110

Leu Phe Tyr Trp Val Ala Gln Leu Leu Gly Ala Ser Val Ala Cys Leu
        115                 120                 125

Leu Leu Lys Phe Val Thr His Gly Lys Ala Ile Pro Thr His Gly Val
130                 135                 140

Ser Gly Ile Ser Glu Leu Glu Gly Val Val Phe Glu Ile Val Ile Thr
145                 150                 155                 160

Phe Ala Leu Val Tyr Thr Val Tyr Ala Thr Ala Xaa Arg Pro Gln Glu
                165                 170                 175

Gly Leu Pro Arg His His Arg Ala His Arg His Arg Leu His Arg Arg
            180                 185                 190

Arg Gln His Pro Arg Arg Gly Ala Leu Gln Pro Arg Leu His Glu Pro
        195                 200                 205

Gly Pro Ser Phe Gly Pro Xaa Val Ala Arg Gly Asn Phe Ala Gly Asn
    210                 215                 220
```

<210> SEQ ID NO 220
<211> LENGTH: 128
<212> TYPE: PRT
<213> ORGANISM: Populus Sp.

<400> SEQUENCE: 220

```
Met Ile Thr Trp Phe Gln Gln Ala Val Pro Ile His Ser Val Ala Ala
1               5                   10                  15

Gly Val Gly Ala Ile Glu Gly Val Val Met Glu Ile Ile Ile Thr Phe
            20                  25                  30

Ala Leu Val Tyr Thr Val Tyr Ala Thr Ala Ala Asp Pro Lys Lys Gly
        35                  40                  45

Ser Leu Gly Thr Ile Ala Pro Ile Ala Ile Gly Phe Ile Val Gly Ala
    50                  55                  60
```

```
Asn Ile Leu Ala Ala Gly Pro Phe Ser Gly Gly Ser Met Asn Pro Ala
 65                  70                  75                  80

Arg Ser Phe Gly Pro Ala Val Ala Ser Gly Asp Phe His Asp Asn Trp
                 85                  90                  95

Ile Tyr Trp Ala Gly Pro Leu Val Gly Gly Ile Ala Gly Leu Ile
            100                 105                 110

Tyr Gly Asn Val Phe Ile Thr Asp His Thr Pro Leu Ser Gly Asp Phe
            115                 120                 125
```

<210> SEQ ID NO 221
<211> LENGTH: 114
<212> TYPE: PRT
<213> ORGANISM: Solanum tuberosum

<400> SEQUENCE: 221

```
Met Ser Gly Ala Glu Gly Val Val Met Glu Ile Val Ile Thr Phe Ala
 1               5                  10                  15

Leu Val Tyr Thr Val Tyr Ala Thr Ala Ala Asp Pro Lys Lys Gly Ser
             20                  25                  30

Leu Gly Thr Ile Ala Pro Met Ala Ile Gly Phe Ile Val Gly Ala Asn
             35                  40                  45

Ile Leu Ala Ala Gly Pro Phe Ser Gly Gly Ser Met Asn Pro Ala Arg
 50                  55                  60

Ser Phe Gly Pro Ala Val Val Ala Gly Asp Phe Phe Gln Asn Trp Ile
 65                  70                  75                  80

Tyr Trp Val Gly Pro Leu Ile Gly Gly Gly Leu Ala Gly Phe Ile Tyr
             85                  90                  95

Gly Asp Val Phe Ile Gly Ser Pro Pro Pro Leu Pro Thr Ser Glu Asp
            100                 105                 110

Tyr Ala
```

<210> SEQ ID NO 222
<211> LENGTH: 128
<212> TYPE: PRT
<213> ORGANISM: Glycine max
<220> FEATURE:
<221> NAME/KEY: misc_feature
<222> LOCATION: (13)..(15)
<223> OTHER INFORMATION: Xaa can be any naturally occurring amino acid

<400> SEQUENCE: 222

```
Met Ser Gln Glu Ala Phe Gln Leu Gln Ser Thr Val Xaa Xaa Xaa Gly
 1               5                  10                  15

Val Gly Ala Val Glu Gly Val Val Thr Glu Ile Ile Ile Thr Phe Gly
             20                  25                  30

Leu Val Tyr Thr Val Tyr Ala Thr Ala Ala Asp Pro Lys Lys Gly Ser
             35                  40                  45

Leu Gly Thr Ile Ala Pro Ile Ala Ile Gly Phe Ile Val Gly Ala Asn
             50                  55                  60

Ile Leu Ala Ala Gly Pro Phe Ser Gly Gly Ser Met Asn Pro Ala Arg
 65                  70                  75                  80

Ser Phe Gly Pro Ala Val Val Ser Gly Asp Phe His Asp Asn Trp Ile
                 85                  90                  95

Tyr Trp Val Gly Pro Leu Ile Gly Gly Gly Leu Ala Gly Leu Ile Tyr
            100                 105                 110

Gly Asn Val Phe Ile Arg Ser Asp His Ala Pro Leu Ser Ser Glu Phe
            115                 120                 125
```

```
<210> SEQ ID NO 223
<211> LENGTH: 104
<212> TYPE: PRT
<213> ORGANISM: Solanum tuberosum

<400> SEQUENCE: 223

Met Glu Ile Ile Ile Thr Phe Gly Leu Val Tyr Thr Val Phe Ala Thr
1               5                   10                  15

Ala Ala Asp Pro Lys Lys Gly Ser Leu Gly Thr Ile Ala Pro Ile Ala
            20                  25                  30

Ile Gly Phe Ile Val Gly Ala Asn Ile Leu Ala Ala Gly Pro Phe Ser
        35                  40                  45

Gly Gly Ser Met Asn Pro Ala Arg Ser Phe Gly Pro Ala Met Ala Thr
    50                  55                  60

Gly Asn Phe Glu Gly Phe Trp Ile Tyr Trp Ile Gly Pro Leu Val Gly
65                  70                  75                  80

Gly Ser Leu Ala Gly Leu Ile Tyr Thr Asn Val Phe Met Gln Gln Glu
                85                  90                  95

His Ala Pro Leu Ser Asn Glu Phe
            100

<210> SEQ ID NO 224
<211> LENGTH: 149
<212> TYPE: PRT
<213> ORGANISM: Zea mays

<400> SEQUENCE: 224

Met Val Lys Leu Ala Phe Gly Ser Phe Arg Asp Ser Leu Ser Ala Ala
1               5                   10                  15

Ser Leu Lys Ala Tyr Val Ala Glu Phe Ile Ala Thr Leu Leu Phe Val
            20                  25                  30

Phe Ala Gly Val Gly Ser Ala Ile Ala Tyr Ser Gln Leu Thr Lys Gly
        35                  40                  45

Gly Ala Leu Asp Pro Ala Gly Leu Val Ala Ile Ala Ile Ala His Ala
    50                  55                  60

Phe Ala Leu Phe Val Gly Val Ser Met Ala Ala Asn Ile Ser Gly Gly
65                  70                  75                  80

His Leu Asn Pro Ala Val Thr Phe Gly Pro Phe Asp Gly Ala Ser Met
                85                  90                  95

Asn Pro Ala Arg Ser Phe Gly Pro Ala Val Ala Ala Gly Asn Phe Ala
            100                 105                 110

Gly Asn Trp Val Tyr Trp Val Gly Pro Leu Val Gly Gly Gly Leu Ala
        115                 120                 125

Gly Leu Val Tyr Gly Asp Val Phe Ile Ala Ser Tyr Gln Pro Val Gly
    130                 135                 140

Gln Gln Glu Tyr Pro
145

<210> SEQ ID NO 225
<211> LENGTH: 149
<212> TYPE: PRT
<213> ORGANISM: Zea mays

<400> SEQUENCE: 225

Met Val Lys Leu Ala Phe Gly Ser Phe Arg Asp Ser Leu Ser Ala Ala
1               5                   10                  15

Ser Leu Lys Ala Tyr Val Ala Glu Phe Ile Ala Thr Leu Leu Phe Val
            20                  25                  30
```

```
Phe Ala Gly Val Gly Ser Ala Ile Ala Tyr Ser Gln Leu Thr Lys Gly
             35                  40                  45

Gly Ala Leu Asp Pro Ala Gly Leu Val Ala Ile Ala Ile Ala His Ala
 50                  55                  60

Phe Ala Leu Phe Val Gly Val Ser Met Ala Ala Asn Ile Ser Gly Gly
 65                  70                  75                  80

His Leu Asn Pro Ala Val Thr Phe Gly Pro Phe Asp Gly Ala Ser Met
             85                  90                  95

Asn Pro Ala Arg Ser Phe Gly Pro Ala Val Ala Gly Asn Phe Ala
            100                 105                 110

Gly Asn Trp Val Tyr Trp Val Gly Pro Leu Val Gly Gly Leu Ala
            115                 120                 125

Gly Leu Val Tyr Gly Asp Val Phe Ile Ala Ser Tyr Gln Pro Val Gly
            130                 135                 140

Gln Gln Glu Tyr Pro
145

<210> SEQ ID NO 226
<211> LENGTH: 105
<212> TYPE: PRT
<213> ORGANISM: Oryza sativa

<400> SEQUENCE: 226

Met Glu Ile Ile Val Thr Phe Gly Leu Val Tyr Thr Val Tyr Ala Thr
  1               5                  10                  15

Ala Ala Asp Pro Lys Lys Gly Ser Leu Gly Thr Ile Ala Pro Ile Ala
             20                  25                  30

Ile Gly Phe Ile Val Gly Ala Asn Ile Leu Val Ala Gly Pro Phe Ser
             35                  40                  45

Gly Gly Ser Met Asn Pro Ala Arg Ser Phe Gly Pro Ala Val Ala Ser
             50                  55                  60

Gly Asp Tyr Thr Asn Ile Trp Ile Tyr Trp Val Gly Pro Leu Val Gly
 65                  70                  75                  80

Gly Gly Leu Ala Gly Leu Val Tyr Arg Tyr Val Tyr Met Cys Gly Asp
             85                  90                  95

His Ala Pro Val Ala Ser Ser Glu Phe
            100                 105

<210> SEQ ID NO 227
<211> LENGTH: 126
<212> TYPE: PRT
<213> ORGANISM: Triticum aestivum

<400> SEQUENCE: 227

Ser Arg Cys Glu Leu Tyr Cys Pro Glu Arg Ser Ile Cys Asn Glu Ser
  1               5                  10                  15

Cys Leu Glu Asn Thr Met Met Glu Ile Ile Ile Thr Phe Gly Leu Val
             20                  25                  30

Tyr Thr Val Phe Ala Thr Ala Ala Asp Pro Lys Lys Gly Ser Leu Gly
             35                  40                  45

Thr Ile Ala Pro Ile Ala Ile Gly Leu Ile Val Gly Ala Asn Ile Leu
             50                  55                  60

Ala Ala Gly Pro Phe Ser Gly Gly Ser Met Asn Pro Ala Arg Ser Phe
 65                  70                  75                  80

Gly Pro Ala Met Val Ser Gly Asn Phe Glu Gly Phe Trp Ile Tyr Trp
             85                  90                  95
```

```
Ile Gly Pro Leu Val Gly Gly Ser Leu Ala Gly Leu Ile Tyr Thr Asn
            100                 105                 110

Val Phe Met Thr Gln Glu His Ala Pro Leu Ser Asn Glu Phe
            115                 120                 125
```

<210> SEQ ID NO 228
<211> LENGTH: 140
<212> TYPE: PRT
<213> ORGANISM: Capsicum annuum

<400> SEQUENCE: 228

```
Met Ala Gly Ile Ala Phe Gly Arg Val Asp Asp Ser Phe Ser Ala Gly
1               5                   10                  15

Ser Leu Lys Ala Tyr Leu Ala Glu Phe Ile Ser Thr Leu Leu Phe Val
            20                  25                  30

Phe Ala Gly Val Gly Ser Ala Ile Ala Tyr Asn Lys Leu Thr Val Asn
        35                  40                  45

Ala Ala Leu Asp Pro Ala Gly Leu Val Ala Ile Ala Val Cys His Gly
    50                  55                  60

Phe Gly Leu Phe Val Ala Val Ser Ile Ala Ala Asn Ile Ser Gly Gly
65                  70                  75                  80

His Val Asn Pro Ala Val Thr Phe Gly Leu Ala Leu Gly Gly Gln Ile
                85                  90                  95

Thr Leu Leu Thr Gly Leu Phe Leu His His Cys Ser Thr Phe Gly Leu
            100                 105                 110

His Cys Ser Leu His Pro Pro Gln Ile Arg His Arg Arg Ile Gly Tyr
        115                 120                 125

Ser Asn Ser Trp Ser Gly Ser Trp Cys Gly Cys His
    130                 135                 140
```

<210> SEQ ID NO 229
<211> LENGTH: 101
<212> TYPE: PRT
<213> ORGANISM: Hordeum vulgare

<400> SEQUENCE: 229

```
Met Thr Phe Gly Leu Val Tyr Thr Val Tyr Ala Thr Ala Val Asp Pro
1               5                   10                  15

Lys Lys Gly Ser Leu Gly Thr Ile Ala Pro Ile Ala Ile Gly Phe Ile
            20                  25                  30

Val Gly Ala Asn Ile Leu Val Gly Gly Ala Phe Ser Gly Ala Ser Met
        35                  40                  45

Asn Pro Ala Val Ser Phe Gly Pro Ala Leu Val Ser Trp Glu Trp Gly
    50                  55                  60

Tyr Gln Trp Val Tyr Trp Val Gly Pro Leu Ile Gly Gly Gly Leu Ala
65                  70                  75                  80

Gly Val Ile Tyr Glu Leu Leu Phe Ile Ser Arg Thr His Glu Gln Leu
                85                  90                  95

Pro Thr Thr Asp Tyr
            100
```

<210> SEQ ID NO 230
<211> LENGTH: 154
<212> TYPE: PRT
<213> ORGANISM: Gossypium Sp.

<400> SEQUENCE: 230

```
Met Val Met Pro Phe Gly Leu Val Tyr Pro Val Tyr Ala Pro Ala Val
1               5                   10                  15
```

```
Asp Pro Lys Lys Gly Ser Leu Gly Thr Ile Ala Pro Leu Ala Ile Gly
            20                  25                  30

Phe Ile Val Gly Ala Asn Ile Leu Ala Gly Gly Ala Phe Asp Gly Ala
            35                  40                  45

Ser Met Asn Pro Ala Val Ser Phe Gly Pro Pro Leu Val Ser Trp Thr
        50                  55                  60

Trp Asp Asn Pro Trp Ile Tyr Trp Val Gly Pro Leu Ile Gly Gly Gly
65                  70                  75                  80

Leu Ala Gly Phe Phe Arg Ser Ser Phe Ser Ser Ala Thr Pro Arg Ser
                85                  90                  95

Ser Ser Gln Pro Pro Ile Ile Lys Pro Asn Gln Gly Leu Ile Asp Leu
            100                 105                 110

Phe Val Pro Leu Lys Pro Asp Phe Phe Arg Phe His Leu Ser Phe Leu
            115                 120                 125

Phe Leu Ser Leu Phe Val Phe Asn Leu Gly Pro Val Asp Phe Val
            130                 135                 140

Tyr Phe Phe Phe Ile Pro His Pro Phe Ser
145                 150
```

<210> SEQ ID NO 231
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 231
tacgactcac tatagggcga                                                 20

<210> SEQ ID NO 232
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 232
gctatgacca tgattacgcc                                                 20

<210> SEQ ID NO 233
<211> LENGTH: 3207
<212> TYPE: DNA
<213> ORGANISM: Artificial sequence
<220> FEATURE:
<223> OTHER INFORMATION: pKG(NOSter) plasmid

<400> SEQUENCE: 233
taaattatcg cgcgcggtgt catctatgtt actagatcgg gaattcaatg cggccgccac       60
cgcggtggcc agcttttgtt cccttttagtg agggttaatt gcgcgcttgg cgtaatcatg     120
gtcatagctg tttcctgtgt gaaattgtta tccgctcaca attccacaca acatacgagc     180
cggaagcata aagtgtaaag cctggggtgc ctaatgagtg agctaactca cattaattgc     240
gttgcgctca ctgcccgctt tccagtcggg aaacctgtcg tgccagctgc attaatgaat     300
cggccaacgc gcggggagag gcggtttgcg tattgggcgc tcttccgctt cctcgctcac     360
tgactcgctg cgctcggtcg ttcggctgcg gcgagcggta tcagctcact caaaggcggt     420
aatacggtta tccacagaat cagggggataa gcaggaaag aacatgtgag caaaaggcca     480
gcaaaaggcc aggaaccgta aaaaggccgc gttgctggcg ttttccata ggctccgccc     540

```
ccctgacgag catcacaaaa atcgacgctc aagtcagagg tggcgaaacc cgacaggact    600
ataaagatac caggcgtttc ccctggaag ctccctcgtg cgctctcctg ttccgaccct     660
gccgcttacc ggatacctgt ccgcctttct cccttcggga agcgtggcgc tttctcatag    720
ctcacgctgt aggtatctca gttcggtgta ggtcgttcgc tccaagctgg gctgtgtgca    780 cgaaccccccc gttcagcccg accgctgcgc cttatccggt aactatcgtc ttgagtccaa   840
cccggtaaga cacgacttat cgccactggc agcagccact ggtaacagga ttagcagagc    900
gaggtatgta ggcggtgcta cagagttctt gaagtggtgg cctaactacg gctacactag    960
aaggacagta tttggtatct gcgctctgct gaagccagtt accttcggaa aaagagttgg    1020
tagctcttga tccggcaaac aaaccaccgc tggtagcggt ggtttttttg tttgcaagca    1080
gcagattacg cgcagaaaaa aaggatctca agaagatcct ttgatctttt ctacggggtc    1140
tgacgctcag tggaacgaaa actcacgtta agggattttg gtcatgagat tatcaaaaag    1200
gatcttcacc tagatccttt taaattaaaa atgaagtttt aaatcaatct aaagtatata    1260
tgagtaaact tggtctgaca gttaccaatg cttaatcagt gaggcaccta tctcagcgat    1320
ctgtctattt cgttcatcca tagttgcctg actccccgtc gtgtagataa ctacgatacg    1380
ggagggctta ccatctggcc ccagtgctgc aatgataccg cgagacccac gctcaccggc    1440
tccagattta tcagcaataa accagccagc cggaagggcc gagcgcagaa gtggtcctgc    1500
aactttatcc gcctccatcc agtctattaa ttgttgccgg gaagctagag taagtagttc    1560
gccagttaat agtttgcgca acgttgttgc cattgctaca ggcatcgtgg tgtcacgctc    1620
gtcgtttggt atggcttcat tcagctccgg ttcccaacga tcaaggcgag ttacatgatc    1680
ccccatgttg tgcaaaaaag cggttagctc cttcggtcct ccgatcgttg tcagaagtaa    1740
gttggccgca gtgttatcac tcatggttat ggcagcactg cataattctc ttactgtcat    1800
gccatccgta agatgctttt ctgtgactgg tgagtactca accaagtcat tctgagaata    1860
gtgtatgcgg cgaccgagtt gctcttgccc ggcgtcaata cgggataata ccgcgccaca    1920
tagcagaact ttaaaagtgc tcatcattgg aaaacgttct cggggcgaaa actctcaag    1980 gatcttaccg ctgttgagat ccagttcgat gtaacccact cgtgcaccca actgatcttc    2040
agcatctttt actttcacca gcgtttctgg gtgagcaaaa acaggaaggc aaaatgccgc    2100
aaaaaaggga ataagggcga cacgaaatg ttgaatactc atactcttcc tttttcaata    2160
ttattgaagc atttatcagg gttattgtct catgagcgga tacatatttg aatgtattta    2220
gaaaaataaa caaatagggg ttccgcgcac atttccccga aaagtgccac ctaaattgta    2280
agcgttaata ttttgttaaa attcgcgtta aattttttgtt aaatcagctc attttttaac    2340
caataggccg aaatcggcaa aatcccttat aaatcaaaag aatagaccga gatagggttg    2400
agtgttgttc cagtttggaa caagagtcca ctattaaaga acgtggactc caacgtcaaa    2460
gggcgaaaaa ccgtctatca gggcgatggc ccactacgtg aaccatcacc ctaatcaagt    2520
tttttggggt cgaggtgccg taaagcacta atcggaacc ctaaagggag ccccgattt     2580 agagcttgac ggggaaagcc ggcgaacgtg cgagaaagg aagggaagaa agcgaaagga    2640
gcgggcgcta gggcgctggc aagtgtagcg gtcacgctgc gcgtaaccac cacacccgcc    2700
gcgcttaatg cgccgctaca gggcgcgtcc cattcgccat tcaggctgcg caactgttgg    2760
gaagggcgat cggtgcgggc ctcttcgcta ttacgccagc tggcgaaagg gggatgtgct    2820
gcaaggcgat taagttgggt aacgccaggg ttttcccagt cacgacgttg taaaacgacg    2880
gccagtgagc gcgcgtaata cgactcacta tagggcgaat tgggtaccgc ggccgctatt    2940
```

| | |
|---|---|
| gataagctta atatgtcgac gatttctcta gaatacgagc tcgaatttcc ccgatcgttc | 3000 |
| aaacatttgg caataaagtt tcttaagatt gaatcctgtt gccggtcttg cgatgattat | 3060 |
| catataattt ctgttgaatt acgttaagca tgtaataatt aacatgtaat gcatgacgtt | 3120 |
| atttatgaga tgggttttta tgattagagt cccgcaatta tacatttaat acgcgataga | 3180 |
| aaacaaaata tagcgcgcaa actagga | 3207 |

<210> SEQ ID NO 234
<211> LENGTH: 3868
<212> TYPE: DNA
<213> ORGANISM: Artificial sequence
<220> FEATURE:
<223> OTHER INFORMATION: pKG(35S+NOSter) plasmid

<400> SEQUENCE: 234

| | |
|---|---|
| gtaggtatct cagttcggtg taggtcgttc gctccaagct gggctgtgtg cacgaacccc | 60 |
| ccgttcagcc cgaccgctgc gccttatccg gtaactatcg tcttgagtcc aacccggtaa | 120 |
| gacacgactt atcgccactg gcagcagcca ctggtaacag gattagcaga gcgaggtatg | 180 |
| taggcggtgc tacagagttc ttgaagtggt ggcctaacta cggctacact agaaggacag | 240 |
| tatttggtat ctgcgctctg ctgaagccag ttaccttcgg aaaaagagtt ggtagctctt | 300 |
| gatccggcaa acaaaccacc gctggtagcg tggttttttt gtttgcaag cagcagatta | 360 |
| cgcgcagaaa aaaggatctc aagaagatc ctttgatctt ttctacgggg tctgacgctc | 420 |
| agtggaacga aaactcacgt taagggattt tggtcatgag attatcaaaa aggatcttca | 480 |
| cctagatcct tttaaattaa aaatgaagtt ttaaatcaat ctaaagtata tatgagtaaa | 540 |
| cttggtctga cagttaccaa tgcttaatca gtgaggcacc tatctcagcg atctgtctat | 600 |
| ttcgttcatc catagttgcc tgactccccg tcgtgtagat aactacgata cgggagggct | 660 |
| taccatctgg ccccagtgct gcaatgatac cgcgagaccc acgctcaccg gctccagatt | 720 |
| tatcagcaat aaaccagcca gccggaaggg ccgagcgcag aagtggtcct gcaactttat | 780 |
| ccgcctccat ccagtctatt aattgttgcc gggaagctag agtaagtagt tcgccagtta | 840 |
| atagtttgcg caacgttgtt gccattgcta caggcatcgt ggtgtcacgc tcgtcgtttg | 900 |
| gtatggcttc attcagctcc ggttcccaac gatcaaggcg agttacatga tcccccatgt | 960 |
| tgtgcaaaaa agcggttagc tccttcggtc ctccgatcgt tgtcagaagt aagttggccg | 1020 |
| cagtgttatc actcatggtt atggcagcac tgcataattc tcttactgtc atgccatccg | 1080 |
| taagatgctt ttctgtgact ggtgagtact caaccaagtc attctgagaa tagtgtatgc | 1140 |
| ggcgaccgag ttgctcttgc ccggcgtcaa tacgggataa taccgcgcca catagcagaa | 1200 |
| ctttaaaagt gctcatcatt ggaaaacgtt cttcggggcg aaaactctca aggatcttac | 1260 |
| cgctgttgag atccagttcg atgtaaccca ctcgtgcacc caactgatct tcagcatctt | 1320 |
| ttactttcac cagcgtttct gggtgagcaa aaacaggaag gcaaaatgcc gcaaaaaagg | 1380 |
| gaataagggc gacacggaaa tgttgaatac tcatactctt ccttttcaa tattattgaa | 1440 |
| gcatttatca gggttattgt ctcatgagcg gatacatatt tgaatgtatt tagaaaaata | 1500 |
| aacaaatagg ggttccgcgc acatttcccc gaaaagtgcc acctaaattg taagcgttaa | 1560 |
| tattttgtta aaattcgcgt taaatttttg ttaaatcagc tcattttta accaataggc | 1620 |
| cgaaatcggc aaaatccctt ataaatcaaa agaatagacc gagatagggt tgagtgttgt | 1680 |
| tccagtttgg aacaagagtc cactattaaa gaacgtggac tccaacgtca aagggcgaaa | 1740 |
| aaccgtctat cagggcgatg gcccactacg tgaaccatca ccctaatcaa gttttttggg | 1800 |

```
gtcgaggtgc cgtaaagcac taaatcggaa ccctaaaggg agcccccgat ttagagcttg    1860
acggggaaag ccggcgaacg tggcgagaaa ggaaggaag aaagcgaaag gagcgggcgc    1920
tagggcgctg gcaagtgtag cggtcacgct gcgcgtaacc accacaccg ccgcgcttaa     1980 tgcgccgcta cagggcgcgt cccattcgcc attcaggctg cgcaactgtt gggaagggcg    2040
atcggtgcgg gcctcttcgc tattacgcca gctggcgaaa gggggatgtg ctgcaaggcg    2100
attaagttgg gtaacgccag gttttccca gtcacgacgt tgtaaaacga cggccagtga    2160
gcgcgcgtaa tacgactcac tatagggcga attgggtacc gcggccgcta ttgataagct    2220
tgcatgcctg caggtcaatt ctcatgtttg acagcttatc atcggtgcga tgccccccat    2280
cgtaggtgaa ggtggaaatt aatgatccat cttgagacca caggcccaca acagctacca    2340
gtttcctcaa gggtccacca aaacgtaag cgcttacgta catggtcgat aagaaaaggc     2400
aatttgtaga tgttaacatc caacgtcgct ttcagggatc ccccctcaga agaccagagg    2460
gctattgaga cttttcaaca aagggtaata tcgggaaacc tcctcggatt ccattgccca    2520
gctatctgtc acttcatcga aaggacagta gaaaggaag gtggctccta caaatgccat    2580
cattgcgata aggaaaggc tatcgttcaa gatgcctcta ccgacagtgg tcccaaagat    2640
ggacccccac ccacgaggaa catcgtggaa aagaagacg ttccaaccac gtcttcaaag    2700
caagtggatt gatgtgatat ctccactgac gtaaggatg acgcacaatc ccactatcct    2760
tcgcaagacc cttcctctat ataaggaagt tcatttcatt tggagaggac aggcttcttg    2820
agatccttca acaattacca acaacaacaa acaacaaaca acattacaat tactatttac    2880
aattacagtc gacgatttct ctagaatacg agctcgaatt tccccgatcg ttcaaacatt    2940
tggcaataaa gtttcttaag attgaatcct gttgccggtc ttgcgatgat tatcatataa    3000
tttctgttga attacgttaa gcatgtaata attaacatgt aatgcatgac gttatttatg    3060
agatgggttt ttatgattag agtcccgcaa ttatacattt aatacgcgat agaaaacaaa    3120
atatagcgcg caaactagga taaattatcg cgcgcggtgt catctatgtt actagatcgg    3180
gaattcaatg cggccgccac cgcggtggcc agcttttgtt cccttagtg agggttaatt    3240 gcgcgcttgg cgtaatcatg gtcatagctg tttcctgtgt gaaattgtta tccgctcaca    3300
attccacaca acatacgagc cggaagcata agtgtaaag cctggggtgc ctaatgagtg     3360
agctaactca cattaattgc gttgcgctca ctgcccgctt tccagtcggg aaacctgtcg    3420
tgccagctgc attaatgaat cggccaacgc gcggggagag cggtttgcg tattgggcgc     3480 tcttccgctt cctcgctcac tgactcgctg cgctcggtcg ttcggctgcg gcgagcggta    3540
tcagctcact caaaggcggt aatacggtta tccacagaat caggggataa cgcaggaaag    3600
aacatgtgag caaaaggcca gcaaaaggcc aggaaccgta aaaaggccgc gttgctggcg    3660 ttttccata ggctccgccc cctgacgag catcacaaaa atcgacgctc aagtcagagg      3720
tggcgaaacc cgacaggact ataaagatac caggcgtttc ccctggaag ctccctcgtg     3780 cgctctcctg ttccgaccct gccgcttacc ggatacctgt ccgcctttct cccttcggga    3840
agcgtggcgc tttctcatag ctcacgct                                       3868
```

<210> SEQ ID NO 235
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 235

```
tcagccaccc aaaccatgac                                                  20
```

<210> SEQ ID NO 236
<211> LENGTH: 151
<212> TYPE: PRT
<213> ORGANISM: Lycopersicon esculentum

<400> SEQUENCE: 236

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 237
<211> LENGTH: 219
<212> TYPE: PRT
<213> ORGANISM: Lycopersicon esculentum

<400> SEQUENCE: 237

Met Glu Asp Lys Ser Asn Asp Tyr Tyr Ala Val Leu Gly Leu Lys Lys
1               5                   10                  15

Glu Cys Thr Asp Thr Glu Leu Arg Asn Ala Tyr Lys Lys Leu Ala Leu
            20                  25                  30

Lys Trp His Pro Asp Arg Cys Ser Ala Ser Gly Asn Leu Lys Phe Val
        35                  40                  45

Asp Glu Ala Lys Lys Gln Phe Gln Ala Ile Gln Glu Ala Tyr Ser Val
    50                  55                  60

Leu Ser Asp Ala Asn Lys Lys Phe Leu Tyr Asp Val Gly Val Tyr Asp
65                  70                  75                  80

Ser Gly Asp Asp Asp Glu Asn Gly Met Gly Asp Phe Leu Asn Glu
                85                  90                  95

Met Ala Ala Met Met Ser Gln Asn Lys Ser Asn Glu Asn Gln Gly Glu
            100                 105                 110

Glu Thr Phe Glu Glu Leu Gln Asp Met Phe Asn Glu Met Phe Asn Ser
        115                 120                 125

Asp Asn Gly Thr Phe Ser Ser Ser Ser Ser Ser Ser Ser Ser Ser Trp
    130                 135                 140

Thr Gly Thr Pro Ser Met Cys Ser Thr Thr Ser Thr Ser Ser Ser
145                 150                 155                 160

Glu Thr Phe Leu Thr Phe Pro Asn Lys Arg Ser Ser Gly Glu Met Lys
                165                 170                 175

```
Ser Gly Ser Ser Val Arg Gly Asp Ser Cys Gln Phe Gln Gly Phe Cys
            180                 185                 190

Val Gly Ala Gly Gly Thr Ser Gly Lys Cys Asn Glu Arg Glu Arg Ser
            195                 200                 205

Trp Arg Lys Asn Ser Lys Ser Gly Arg Lys His
            210                 215

<210> SEQ ID NO 238
<211> LENGTH: 298
<212> TYPE: PRT
<213> ORGANISM: Lycopersicon esculentum

<400> SEQUENCE: 238

Met Glu Asn Met Gln Ser Tyr Trp Gln Phe Gly Asp Glu Leu Arg Gly
1               5                   10                  15

Gln Ser Lys Ala Ser Glu Asp His Lys Trp Ser Thr Ala Ala Ile Lys
            20                  25                  30

Leu Ser Glu Gln Met Lys Tyr Lys Gly Glu Arg Arg Asn Asn Leu Asp
            35                  40                  45

Leu Ser Lys Ser Ser Ala Glu Ile Arg Pro Arg Gly Asn His Met Phe
        50                  55                  60

Gln Glu Asp Asn Lys Trp Glu Ser Leu Asn Phe Asn Met Leu Asn Leu
65                  70                  75                  80

Glu Ser Lys Met Thr Glu Asn Met Ser Lys Asn Arg Ile Met Asp Ser
                85                  90                  95

Ile Phe Asn Ala Asn Pro Val Tyr Leu Lys Pro Asn Phe Asn Ser Leu
            100                 105                 110

Gly Asn Ser Ser Leu Ser Lys Phe Asn Ala Ser Asn Tyr Thr Lys Glu
            115                 120                 125

Pro Ser Lys Asn Asn Asn Asn Val Glu Ser Thr Asn Gly Asn Asn
        130                 135                 140

Ser Val Asp Lys Arg Phe Lys Thr Leu Pro Ala Ala Glu Thr Leu Pro
145                 150                 155                 160

Lys Asn Glu Val Leu Gly Gly Tyr Ile Phe Val Cys Asn Asn Asp Thr
                165                 170                 175

Met Gln Glu Asp Leu Lys Arg Leu Leu Phe Gly Leu Pro Pro Arg Tyr
            180                 185                 190

Arg Asp Ser Val Arg Ala Ile Thr Pro Gly Leu Pro Leu Phe Leu Tyr
            195                 200                 205

Asn Tyr Thr Thr His Gln Leu His Gly Ile Phe Glu Ala Ser Ser Phe
        210                 215                 220

Gly Gly Ser Asn Ile Asp Pro Thr Ala Trp Glu Asp Lys Lys Cys Lys
225                 230                 235                 240

Gly Glu Ser Arg Phe Pro Ala Gln Val Arg Ile Arg Val Arg Lys Val
                245                 250                 255

Cys Asn Pro Leu Glu Glu Asp Ala Phe Arg Pro Val Leu His His Tyr
            260                 265                 270

Asp Gly Pro Lys Phe Arg Leu Glu Leu Ser Ile Pro Thr Leu Asp
            275                 280                 285

Leu Leu Asp Leu Cys Glu Lys Ala Gly Val
            290                 295

<210> SEQ ID NO 239
<211> LENGTH: 249
<212> TYPE: PRT
<213> ORGANISM: Lycopersicon esculentum
```

<400> SEQUENCE: 239

```
Met Ala Gly Gly Val Ala Ile Gly Ser Phe Ser Asp Ser Phe Ser Val
1               5                   10                  15

Val Ser Leu Lys Ser Tyr Leu Ala Glu Phe Ile Ser Thr Leu Ile Phe
            20                  25                  30

Val Phe Ala Gly Val Gly Ser Ala Ile Ala Tyr Gly Lys Leu Thr Thr
        35                  40                  45

Asn Ala Ala Leu Asp Pro Ala Gly Leu Val Ala Ile Ala Val Cys His
    50                  55                  60

Gly Phe Ala Leu Phe Val Ala Val Ser Ile Ser Ala Asn Ile Ser Gly
65                  70                  75                  80

Gly His Val Asn Pro Ala Val Thr Cys Gly Leu Thr Phe Gly Gly His
                85                  90                  95

Ile Thr Phe Ile Thr Gly Ser Phe Tyr Met Leu Ala Gln Leu Thr Gly
            100                 105                 110

Ala Ala Val Ala Cys Phe Leu Leu Lys Phe Val Thr Gly Gly Cys Ala
        115                 120                 125

Ile Pro Thr His Gly Val Gly Ala Gly Val Ser Ile Leu Glu Gly Leu
130                 135                 140

Val Met Glu Ile Ile Ile Thr Phe Gly Leu Val Tyr Thr Val Phe Ala
145                 150                 155                 160

Thr Ala Ala Asp Pro Lys Lys Gly Ser Leu Gly Thr Ile Ala Pro Ile
                165                 170                 175

Ala Ile Gly Leu Ile Val Gly Ala Asn Ile Leu Ala Ala Gly Pro Phe
            180                 185                 190

Ser Gly Gly Ser Met Asn Pro Ala Arg Ser Phe Gly Pro Ala Met Val
        195                 200                 205

Ser Gly Asn Phe Glu Gly Phe Trp Ile Tyr Trp Ile Gly Pro Leu Val
210                 215                 220

Gly Gly Ser Leu Ala Gly Leu Ile Tyr Thr Asn Val Phe Met Thr Gln
225                 230                 235                 240

Glu His Ala Pro Leu Ser Asn Glu Phe
                245
```

<210> SEQ ID NO 240
<211> LENGTH: 244
<212> TYPE: PRT
<213> ORGANISM: Lycopersicon esculentum

<400> SEQUENCE: 240

```
Met Glu Val Asp Ser Ser Gly Asn Pro Asn Trp Leu Phe Asp Tyr Glu
1               5                   10                  15

Leu Met Thr Asp Ile Thr Ser Ala Ala Ser Val Thr Val Ala Glu Phe
            20                  25                  30

Gln Ser Pro Ala Thr Ile Asp Phe Ser Trp Pro Ala Gln Thr Ile Tyr
        35                  40                  45

Ala Ser Ser Asn Leu Ile Thr Glu Thr Asp Tyr Thr Phe Ala Asp Ser
    50                  55                  60

Glu Val Ser Lys Glu Ala Ser Ser Arg Lys Arg Leu Lys Ser Glu Cys
65                  70                  75                  80

Cys Ser Ser Pro Arg Ser Lys Ala Cys Arg Glu Lys Leu Arg Arg Asp
                85                  90                  95

Arg Leu Asn Glu Arg Phe Leu Ala Leu Ser Ser Val Leu Asp Pro Gly
            100                 105                 110
```

```
Arg Pro Pro Lys Thr Glu Lys Val Ala Ile Leu Ser Asp Ala Gln Arg
        115                 120                 125

Met Leu Ile Glu Leu Arg Thr Glu Thr Gln Lys Leu Lys Glu Ser Asn
    130                 135                 140

Glu Glu Leu Gln Glu Lys Ile Lys Glu Leu Lys Ala Glu Lys Asn Glu
145                 150                 155                 160

Leu Arg Asp Glu Lys Gln Arg Leu Lys Glu Lys Asp Asn Leu Glu
                165                 170                 175

Gln Gln Val Lys Ser Leu Ala Ser Lys Ala Gly Phe Leu Ser His Pro
                180                 185                 190

Ser Ala Met Gly Ala Ala Phe Thr Ala Gln Gly Gln Val Ala Ala Ser
            195                 200                 205

Asn Lys Leu Met Pro Phe Ile Gly Tyr Pro Ser Val Ala Met Trp Arg
            210                 215                 220

Phe Met Gln Pro Ala Val Val Asp Thr Ser Gln Asp His Val Leu Arg
225                 230                 235                 240

Pro Pro Val Ala

<210> SEQ ID NO 241
<211> LENGTH: 362
<212> TYPE: PRT
<213> ORGANISM: Sorghum bicolor

<400> SEQUENCE: 241

Met Glu Gly Tyr Asp Arg Glu Phe Trp Gln Phe Ser Asp Thr Leu Arg
1               5                   10                  15

Leu Gln Thr Ala Ala Phe Ser Gly Leu Ser Leu Gly Asp Ser Ile Trp
                20                  25                  30

Ser Pro Ala Thr Gly Gly Ala Ala Ala Asp Arg Arg Asn Asn Ser
            35                  40                  45

Asn Asp Leu Phe Ala Ala Ser Ala Ser Pro Ala Asp Thr Thr Ala Ala
        50                  55                  60

Lys Asn Asn Gly Gly Val Gly Leu Arg Leu Asn Leu Asn Asp Gly Gly
65                  70                  75                  80

Pro Gly Leu Ile Gly Ser Gly Lys Leu Ala Phe Gly Gly Ser Lys Ala
                85                  90                  95

Asp Arg Tyr Asn Asn Leu Pro Ala Thr Thr Glu Lys Ala Ala Ser Ala
            100                 105                 110

Tyr Asn Asn Asn Ile Asn Val Asn Ala Gly Tyr Ala Lys Asn Asn
            115                 120                 125

Asn Asn Ala Leu Ala Phe Asn Lys Met Gly Ile Tyr Gly Tyr Asn Thr
        130                 135                 140

Asn Asn Ser Asn Ile Ser Asn Ser Ser Gly Glu Val Lys Ser
145                 150                 155                 160

Tyr Phe Asn Lys Ser Ala Gly Arg Ala Ala Ser Asn Asn Ser His Gly
                165                 170                 175

His Gly His Ala Gly Gly Lys Lys Gly Gly Glu Tyr Gly Asn Lys Lys
            180                 185                 190

Lys His Gly Lys Asn Glu Gly Asn Asn Gly Gly Gly Ala Gly Ala
        195                 200                 205

Thr Asp Lys Arg Phe Lys Thr Leu Pro Ala Ser Glu Ala Leu Pro Arg
210                 215                 220

Gly Gln Ala Ile Gly Gly Tyr Ile Phe Val Cys Asn Asn Asp Thr Met
225                 230                 235                 240

Asp Glu Asn Leu Arg Arg Glu Leu Phe Gly Leu Pro Ser Arg Tyr Arg
```

-continued

```
                245                 250                 255
Asp Ser Val Arg Ala Ile Arg Pro Gly Leu Pro Leu Phe Leu Tyr Asn
            260                 265                 270

Tyr Ser Thr His Gln Leu His Gly Ile Phe Glu Ala Val Ser Phe Gly
            275                 280                 285

Gly Thr Asn Ile Asp Pro Thr Ala Trp Glu Asp Lys Lys Cys Pro Gly
            290                 295                 300

Glu Ser Arg Phe Pro Ala Gln Val Arg Val Ala Thr Arg Lys Ile Tyr
305                 310                 315                 320

Asp Pro Leu Glu Glu Asp Ala Phe Arg Pro Ile Leu His His Tyr Asp
            325                 330                 335

Gly Pro Lys Phe Arg Leu Glu Leu Ser Val Thr Glu Ala Leu Ala Leu
            340                 345                 350

Leu Asp Ile Phe Ala Asp Lys Asp Asp Ala
            355                 360

<210> SEQ ID NO 242
<211> LENGTH: 249
<212> TYPE: PRT
<213> ORGANISM: Hordeum vulgare

<400> SEQUENCE: 242

Met Val Lys Leu Ala Phe Gly Ser Phe Gly Asp Ser Phe Ser Ala Thr
1               5                   10                  15

Ser Ile Arg Ser Tyr Val Ala Glu Phe Ile Ala Thr Leu Leu Phe Val
            20                  25                  30

Phe Ala Gly Val Gly Ser Ala Ile Ser Tyr Gly Gln Leu Thr Gln Gly
        35                  40                  45

Gly Ala Leu Asp Pro Ala Gly Leu Val Ala Ile Ala Ile Ala His Ala
    50                  55                  60

Phe Ala Leu Phe Val Gly Val Ala Met Ala Ala Asn Ile Ser Gly Gly
65                  70                  75                  80

His Leu Asn Pro Ala Val Thr Phe Gly Leu Ala Val Gly Gly His Val
            85                  90                  95

Thr Ile Leu Thr Gly Leu Phe Tyr Trp Val Ala Gln Leu Leu Gly Ala
            100                 105                 110

Ser Val Ala Cys Leu Leu Leu Gln Phe Val Thr His Ala Gln Ala Met
        115                 120                 125

Pro Thr His Ala Val Ser Gly Ile Ser Glu Val Glu Gly Val Val Met
    130                 135                 140

Glu Ile Val Ile Thr Phe Ala Leu Val Tyr Thr Val Tyr Ala Thr Ala
145                 150                 155                 160

Ala Asp Pro Lys Lys Gly Ser Leu Gly Thr Ile Ala Pro Met Ala Ile
            165                 170                 175

Gly Phe Ile Val Gly Ala Asn Ile Leu Ala Ala Gly Pro Phe Ser Gly
            180                 185                 190

Gly Ser Met Asn Pro Ala Arg Ser Phe Gly Pro Ala Val Ala Ala Gly
        195                 200                 205
```

```
Asn Phe Ser Gly His Trp Val Tyr Trp Val Gly Pro Leu Ile Gly Gly
    210                 215                 220

Gly Leu Ala Gly Leu Val Tyr Gly Asp Val Phe Ile Ala Ser Tyr Gln
225                 230                 235                 240

Pro Val Gly His Gln Gln Glu Tyr Pro
                245

<210> SEQ ID NO 243
<211> LENGTH: 250
<212> TYPE: PRT
<213> ORGANISM: Hordeum vulgare

<400> SEQUENCE: 243

Met Val Lys Leu Ala Phe Gly Ser Val Gly Asp Ser Phe Ser Val Thr
1               5                   10                  15

Ser Ile Lys Ala Tyr Val Ala Glu Phe Ile Ala Thr Leu Leu Phe Val
                20                  25                  30

Phe Ala Gly Val Gly Ser Ala Ile Ala Phe Gly Gln Leu Thr Asn Gly
            35                  40                  45

Gly Ala Leu Asp Pro Ala Gly Leu Val Ala Ile Ala Val Ala His Ala
        50                  55                  60

Leu Ala Leu Phe Val Gly Val Ser Val Ala Ala Asn Thr Ser Gly Gly
65                  70                  75                  80

His Leu Asn Pro Ala Val Thr Phe Gly Leu Ala Val Gly Gly His Ile
                85                  90                  95

Thr Val Leu Thr Gly Leu Phe Tyr Trp Val Ala Gln Leu Leu Gly Ala
            100                 105                 110

Ser Val Ala Cys Leu Leu Leu Arg Phe Val Thr His Gly Lys Ala Ile
        115                 120                 125

Pro Thr His Gly Val Ser Gly Gly Thr Thr Glu Leu Glu Gly Val Val
    130                 135                 140

Phe Glu Ile Val Ile Thr Phe Ala Leu Val Tyr Thr Val Tyr Ala Thr
145                 150                 155                 160

Ala Ala Asp Pro Lys Lys Gly Ser Leu Gly Thr Ile Ala Pro Ile Ala
                165                 170                 175

Ile Gly Phe Ile Val Gly Ala Asn Ile Leu Ala Ala Gly Pro Phe Ser
            180                 185                 190

Gly Gly Ser Met Asn Pro Ala Arg Ser Phe Gly Pro Ala Val Ala Ala
        195                 200                 205

Ala Asp Phe Ala Gly Asn Trp Val Tyr Trp Val Gly Pro Leu Ile Gly
    210                 215                 220

Gly Gly Leu Ala Gly Leu Val Tyr Gly Asp Val Phe Ile Gly Gly Ser
225                 230                 235                 240

Tyr Gln Gln Val Ala Asp Gln Asp Tyr Ala
                245                 250

<210> SEQ ID NO 244
<211> LENGTH: 249
<212> TYPE: PRT
<213> ORGANISM: Zea mays

<400> SEQUENCE: 244

Met Val Lys Leu Ala Phe Gly Ser Val Gly Asp Ser Phe Ser Ala Thr
1               5                   10                  15

Ser Ile Lys Ala Tyr Val Ala Glu Phe Ile Ala Thr Leu Leu Phe Val
                20                  25                  30

Phe Ala Gly Val Gly Ser Ala Ile Ala Tyr Gly Gln Leu Thr Asn Gly
```

-continued

```
                35                  40                  45
Gly Ala Leu Asp Pro Ala Gly Leu Val Ala Ile Ala Ile Ala His Ala
 50                  55                  60
Leu Ala Leu Phe Val Gly Val Ser Val Ala Ala Asn Ile Ser Gly Gly
 65                  70                  75                  80
His Leu Asn Pro Ala Val Thr Phe Gly Leu Ala Val Gly Gly His Ile
                 85                  90                  95
Thr Ile Leu Thr Gly Val Phe Tyr Trp Val Ala Gln Leu Leu Gly Ala
            100                 105                 110
Thr Val Ala Cys Leu Leu Leu Gly Phe Val Thr His Gly Lys Ala Ile
            115                 120                 125
Pro Thr His Ala Val Ala Gly Ile Ser Glu Leu Glu Gly Val Val Phe
            130                 135                 140
Glu Val Val Ile Thr Phe Ala Leu Val Tyr Thr Val Tyr Ala Thr Ala
145                 150                 155                 160
Ala Asp Pro Lys Lys Gly Ser Leu Gly Thr Ile Ala Pro Ile Ala Ile
                165                 170                 175
Gly Phe Ile Val Gly Ala Asn Ile Leu Ala Ala Gly Pro Phe Ser Gly
            180                 185                 190
Gly Ser Met Asn Pro Ala Arg Ser Phe Gly Pro Ala Val Ala Ala Gly
            195                 200                 205
Asp Phe Ala Gly Asn Trp Val Tyr Trp Val Gly Pro Leu Val Gly Gly
            210                 215                 220
Gly Leu Ala Gly Leu Val Tyr Gly Asp Val Phe Ile Gly Gly Ser Tyr
225                 230                 235                 240
Gln Gln Val Ala Asp Gln Asp Tyr Ala
                245

<210> SEQ ID NO 245
<211> LENGTH: 249
<212> TYPE: PRT
<213> ORGANISM: Zea mays

<400> SEQUENCE: 245

Met Val Lys Leu Ala Phe Gly Ser Val Gly Asp Ser Phe Ser Ala Thr
  1               5                  10                  15
Ser Ile Lys Ala Tyr Val Ala Glu Phe Ile Ala Thr Leu Leu Phe Val
                 20                  25                  30
Phe Ala Gly Val Gly Ser Ala Ile Ala Tyr Gly Gln Leu Thr Asn Gly
             35                  40                  45
Gly Ala Leu Asp Pro Ala Gly Leu Val Ala Ile Ala Ile Ala His Ala
 50                  55                  60
Leu Ala Leu Phe Val Gly Val Ser Val Ala Ala Asn Ile Ser Gly Gly
 65                  70                  75                  80
His Leu Asn Pro Ala Val Thr Phe Gly Leu Ala Val Gly Gly His Ile
                 85                  90                  95
Thr Ile Leu Thr Gly Val Phe Tyr Trp Val Ala Gln Leu Leu Gly Ala
            100                 105                 110
Thr Val Ala Cys Leu Leu Leu Gly Phe Val Thr His Gly Lys Ala Ile
            115                 120                 125
Pro Thr His Ala Val Ala Gly Ile Ser Glu Leu Glu Gly Val Val Phe
            130                 135                 140
Glu Val Val Ile Thr Phe Ala Leu Val Tyr Thr Val Tyr Ala Thr Ala
145                 150                 155                 160
Ala Asp Pro Lys Lys Gly Ser Leu Gly Thr Ile Ala Pro Ile Ala Ile
```

```
                165                 170                 175
Gly Phe Ile Val Gly Ala Asn Ile Leu Ala Ala Gly Pro Phe Ser Gly
            180                 185                 190

Gly Ser Met Asn Pro Ala Arg Ser Phe Gly Pro Ala Val Ala Ala Gly
        195                 200                 205

Asp Phe Ala Gly Asn Trp Val Tyr Trp Val Gly Pro Leu Val Gly Gly
    210                 215                 220

Gly Leu Ala Gly Leu Val Tyr Gly Asp Val Phe Ile Gly Gly Ser Tyr
225                 230                 235                 240

Gln Gln Val Ala Asp Gln Asp Tyr Ala
                245

<210> SEQ ID NO 246
<211> LENGTH: 248
<212> TYPE: PRT
<213> ORGANISM: Zea mays

<400> SEQUENCE: 246

Met Val Lys Leu Ala Phe Gly Ser Phe Arg Asp Ser Leu Ser Ala Ala
1               5                   10                  15

Ser Leu Lys Ala Tyr Val Ala Glu Phe Ile Ala Thr Leu Leu Phe Val
            20                  25                  30

Phe Ala Gly Val Gly Ser Ala Ile Ala Tyr Ser Gln Leu Thr Lys Gly
        35                  40                  45

Gly Ala Leu Asp Pro Ala Gly Leu Val Ala Ile Ala Ile Ala His Ala
    50                  55                  60

Phe Ala Leu Phe Val Gly Val Ser Met Ala Ala Asn Ile Ser Gly Gly
65                  70                  75                  80

His Leu Asn Pro Ala Val Thr Phe Gly Leu Ala Val Gly Gly His Ile
                85                  90                  95

Thr Ile Leu Thr Gly Ile Leu Tyr Trp Val Ala Gln Leu Leu Gly Ala
            100                 105                 110

Ser Val Ala Cys Phe Leu Leu Gln Tyr Val Thr His Gly Gln Ala Ile
        115                 120                 125

Pro Thr His Gly Val Ser Gly Ile Ser Glu Ile Glu Gly Val Val Met
    130                 135                 140

Glu Ile Val Ile Thr Phe Ala Leu Val Tyr Thr Val Tyr Ala Thr Ala
145                 150                 155                 160

Ala Asp Pro Lys Lys Gly Ser Leu Gly Thr Ile Ala Pro Met Ala Ile
                165                 170                 175

Gly Phe Ile Val Gly Ala Asn Ile Leu Ala Ala Gly Pro Phe Ser Gly
            180                 185                 190

Gly Ser Met Asn Pro Ala Arg Ser Phe Gly Pro Ala Val Ala Ala Gly
        195                 200                 205

Asn Phe Ala Gly Asn Trp Val Tyr Trp Val Gly Pro Leu Val Gly Gly
    210                 215                 220

Gly Leu Ala Gly Leu Val Tyr Gly Asp Val Phe Ile Ala Ser Tyr Gln
225                 230                 235                 240

Pro Val Gly Gln Gln Glu Tyr Pro
                245

<210> SEQ ID NO 247
<211> LENGTH: 1603
<212> TYPE: DNA
<213> ORGANISM: Sorghum bicolor

<400> SEQUENCE: 247
```

-continued

```
tactggacct ccacacttgc acttggttgg agcttcttct cctttttttt tttccattgc      60
tcctctgctt cgcgtcgcct cgcgtctctt ctctccctcc cccggcaggc taacagacac     120
agcagagcgc aggaacacag agcgagagag atcaatcgag gccatggagg gctacgaccg     180
cgagttctgg cagttcagcg acacgctgcg cctgcagacg gccgccttct ccggcctatc     240
cctcggcgac tccatctggt cccccgccac cggcggcgcc gccgccgccg accggcgcaa     300
caacagcaac gacctcttcg ccgcatccgc gtcgcccgcc gacaccaccg ccgccaagaa     360
caacggcggc gtcggcctca gactcaatct caacgatggc gggccaggcc tcatcggctc     420
cgggaagctc gccttcggcg gcagcaaggc cgaccgctac aacaacctcc ccgccaccac     480
cgagaaggcc gcgtccgcgt acaacaacaa catcaacgtc aacgccgct acgcaagaa      540
caacaacaac aacgccctgg cgttcaacaa gatggggatc tacggctaca acacgaacaa     600
cagcaacatc agcaacaaca gcagcagcgg ggaggtgaag agctacttca caagtccgc      660
cgggagggcg gcgagcaaca acagccacgg gcacgggcac gccggcggca agaagggagg     720
ggagtacggc aataagaaga agcacggcaa gaacgagggc aacaacggcg gtggcggagc     780
gggggccacg gacaagcggt tcaagacgct gccggcgtcg gaggcgctgc cgcggggggca    840
ggccatcggc gggtacatct tcgtctgcaa caacgacacc atggacgaga acctcaggag     900
ggagctcttc gggctgccgt ccaggtacag ggactcggtg cgtgccatcc gccctgggct     960
gccctcttc ctctacaact actccaccca ccaactccac ggcatcttcg aggccgtgag     1020
ctttggcggg accaacatcg acccgacggc gtgggaggac aagaagtgcc ccggcgagtc    1080
gcgcttccct gcacaggtgc gggtggcaac gcggaagatc tacgaccccc tggaggagga    1140
cgccttccgc cccatcctcc accactacga cgggcccaag ttccggctcg agctctccgt    1200
caccgaggcc ctcgcactcc tcgacatctt cgccgacaag gacgacgcct gatcctagat    1260
cctcctcatc ggatcgtcag ggactcgagg cttggaactt ggatgaatga acaataatgg    1320
atggacatgt atcccgtcct acgagacggg agtatacaca ccagcacggt ggagtactag    1380
tatattaatt aataattaat ataatatatc cacctttgtt tgatgttatg gctatgtat    1440
gaggcacgcg tccaattgtt ttgtttttat aacacttgtg cgatgattgc agagaactag    1500
ccctcgtttt tgtaagatat actcccacta agatatctgt attgttcggg tctaactgac    1560
atgtataaac atctgtgaaa taataagttc ttgtgcgaaa aaa                      1603
```

<210> SEQ ID NO 248
<211> LENGTH: 976
<212> TYPE: DNA
<213> ORGANISM: Hordeum vulgare

<400> SEQUENCE: 248

```
cacgaggctg tgatcagatc agacttcgaa ctctttagcc tgaagaagtc acagagaaaa      60
cagtcgagtg caactgcaag atggtgaagc ttgcgtttgg aagcttcggc gactcgttca     120
gcgccacgtc catcaggtcc tatgtcgcgg agttcatcgc caccctcctc ttcgtgttcg     180
ccggcgtcgg gtccgccatt tcctacgggc aactgacgca gggtggcgca ctggacccgg     240
ctggccttgt ggcgatcgcc atcgccatg ccttcgccct cttcgtcggc gtggcgatgg      300
ctgccaacat ctccggcggc cacctgaacc ccgccgtcac gttcggcctc gccgtcggcg     360
gccacgtcac catcctcacc gggctcttct actgggtcgc ccagtgctc ggcgcctccg      420
tggcatgcct cctcctgcag tttgtcaccc acgcccaggc tatgccgacg cacgccgtgt     480
ccggcatcag cgaggtcgag ggcgtggtga tggagatcgt gatcaccttc gcgctggtgt     540
```

```
acacggtgta cgcgacggcg gccgacccca agaagggctc cctcggcacc atcgcgccca    600
tggcgatcgg cttcatcgtc ggcgccaaca tcctcgccgc cgggcccttc agcggcggct    660
ccatgaaccc ggcgcgctcc ttcgggccgg ccgtggcggc cggcaacttc tccgccact     720 gggtgtactg ggtcgggcca ctcattggtg gcggcctcgc cgggctcgtc tacggcgacg    780
tgttcatcgc ctcctaccag ccggtcggcc accagcagga atacccatga agcgcacgga    840
tccgaaccta gcttctttgg ctcgttgctt gtttccccctt gtgtgatgaa tttcccttct   900
cgattctaat ccacctcaaa aatgtaaaag tgtaagagaa ccactcgatc ttacatgaac    960
ggttcagcgt ttttcg                                                    976

<210> SEQ ID NO 249
<211> LENGTH: 1281
<212> TYPE: DNA
<213> ORGANISM: Zea mays

<400> SEQUENCE: 249
aaatgttttg tgacgattat ccccgcaccg tccagagtac tctaacccac aagttgaggc     60
cgccctgcag cccatcagac gaggacgcgc gcgtgtataa aagctgactg gactcccagc    120
gtctgtcagc gaaccgaagc agcagccaat tcgctcgagt tcagatcgag cgcgcgccaa    180
gcaagtcttc cggccggccg cgaagagcgc aatcaagcaa gacaagatgg tgaagctcgc    240
cttcggaagc gtcggcgact ccttcagcgc cacctccatc aaggcctacg tggccgagtt    300
catcgccacc ctcctcttcg tcttcgccgg cgtcggttcc gccatcgcct acgggcaact    360
gacgaatggc ggcgcgctgg acccggcggg cctggtggcg atcgcgatcg cgcacgcgct    420
ggcgctgttc gtgggcgtgt ccgtcgcggc gaacatctcg ggcggccacc tgaacccggc    480
cgtgacgttc gggctggccg tgggcggcca catcaccatc ctgacgggcg tcttctactg    540
ggtggcccag ctgctgggcg ccaccgtggc gtgcctgctc ctcgggttcg tcacccacgg    600
caaggccatc ccgacgcacg ccgtcgcggg catcagcgag ctggaaggcg tcgtgttcga    660
ggtcgtcatc accttcgcgc tcgtctacac cgtgtacgcc accgccgccg accccaagaa    720
gggctcgctc ggcaccatcg cgcccatcgc catcggcttc atcgtcggcg ccaacatcct    780
cgccgcgggg ccccttcagcg gcggctccat gaaccccgcc cgtccttcg gccccgccgt    840 cgccgcgggc gacttcgccg gaaactgggt ctactgggtc ggcccgctcg tcggcggcgg    900
cctcgctggc ctcgtctacg gcgacgtctt cattggcggc tcctaccagc aggtcgcgga    960
ccaggactac gcctaattta ttcaccactc catctccgct ctggatgaat ggattcaaaa   1020
ccgtcgtcgt ttgcttttgc tcctcgccac gttcaattaa tggttgtgta tgcatgtatg   1080
tgccaatatg atgtgccttt gccctggtcc attcatttcc ctttcttttt tcggggtgaa   1140
atagatgtaa agatctcgtc ttgcctgccg tactcgcgct gtgttgggaa aaattggttt   1200
tcgttccaag tttgtttacg catggatttc ttkrctcctt tatggttttg attcacgtct   1260
gccccgtaag tctatttctc a                                             1281

<210> SEQ ID NO 250
<211> LENGTH: 1281
<212> TYPE: DNA
<213> ORGANISM: Zea mays

<400> SEQUENCE: 250
aaatgttttg tgacgattat ccccgcaccg tccagagtac tctaacccac aagttgaggc     60
cgccctgcag cccatcagac gaggacgcgc gcgtgtataa aagctgactg gactcccagc    120
```

```
gtctgtcagc gaagccgaag cagcagccaa ttcgctcgag ttcagatcga gcgcgcgcca      180
agcaagtctt ccggccggcc gcgaagagcg caatcaagca agacaagatg gtgaagctcg      240
ccttcggaag cgtcggcgac tccttcagcg ccacctccat caaggcctac gtggccgagt      300
tcatcgccac cctcctcttc gtcttcgccg gcgtcggttc cgccatcgcc tacgggcaac      360
tgacgaatgg cggcgcgctg gacccggcgg gcctggtggc gatcgcgatc gcgcacgcgc      420
tggcgctgtt cgtgggcgtg tccgtcgcgg cgaacatctc gggcggccac ctgaacccgg      480
ccgtgacgtt cgggctggcc gtgggcggcc acatcaccat cctgacgggc gtcttctact      540
gggtggccca gctgctgggc gccaccgtgg cgtgcctgct cctcgggttc gtcacccacg      600
gcaaggccat cccgacgcac gccgtcgcgg gcatcagcga gctggaaggc gtcgtgttcg      660
aggtcgtcat caccttcgcg ctcgtctaca ccgtgtacgc caccgccgcc gaccccaaga      720
agggctcgct cggcaccatc gcgcccatcg ccatcggctt catcgtcggc gccaacatcc      780
tcgccgcggg gcccttcagc ggcggctcca tgaaccccgc ccgctccttc ggccccgccg      840
tcgccgcggg cgacttcgcc ggaaactggg tctactgggt cggcccgctc gtcggcggcg      900
gcctcgctgg cctcgtctac ggcgacgtct cattggcgg ctcctaccag caggtcgcgg      960
accaggacta cgcctaattt attcaccact ccatctccgc tctggatgaa tggattcaaa     1020
accgtcgtcg tttgcttttg ctcctcgcca cgttcaatta atggttgtgt atgcatgtat     1080
gtgccaatat gatgtgcctt tgccctggtc cattcatttc cctttctttt tcggggtga     1140 aatagatgta aagatctcgt cttgcctgcc gtactcgcgc tgtgttggga aaaattggtt     1200
ttcgttccaa gtttgtttac gcatggattt cttggctcct ttatggtttt gattcacgtc     1260
tgccccgtaa gtctatttct c                                               1281

<210> SEQ ID NO 251
<211> LENGTH: 1081
<212> TYPE: DNA
<213> ORGANISM: Zea mays

<400> SEQUENCE: 251
gaattccatt gtcttgggag cctcagagcg ccagccaagt cttgcggtcg cgaagagcaa       60
cgcaacaaga tggtgaagct cgcattcgga agcgtcggcg actcccttcag cgtcacctcc     120 atcaaggcct acgtggcgga gttcatcgcc accctcctct tcgtcttcgc cggcgtgggt     180
tccgccatcg ccttcgggca actgacgaat ggcggcgcgc tggaccctgc gggtctggtg     240
gcgatcgcgg tggcgcacgc gctggccctc ttcgtgggcg tctccgtggc cgcgaacacc     300
tccggcggcc acctgaaccc cgccgtgacg ttcggcctgg ccgtgggcgg ccacatcacc     360
gtcctcaccg gcctcttcta ctgggtggcc cagctgctgg gcgcgtccgt ggcgtgcctg     420
ctcctcaggt tcgtgaccca cggcaaggcc atcccgaccc acggcgtctc cggcggcacc     480
accgagctgg agggcgtcgt gttcgagatc gtcatcacct tcgcgctcgt gtacaccgtg     540
tacgccaccg ccgccgaccc caagaagggc tccctcggca ccatcgcgcc catcgccatc     600
ggcttcatcg tcgcgccaa catcctcgcc gcggggcccc tcagcggcgg ctccatgaac     660 cccgccgct ccttcggccc cgccgtcgcc gcggccgact cgccggcaa ctgggtctac     720 tgggtcggcc cgctcatcgg cggcggactc gctggcctcg tctacggcga cgtcttcatc     780
ggcggctcct accagcaggt cgccgaccag gactacgcct aagtagtgct ccgttcgtct     840
ggattcagct catccaacgc aggcggccgt ttcgatcggc gtcgtcattt gctttgctct     900
tcatttcatc acgttatgta acgtgccaat gatgtgtgtc gtcctggtct gttccattcc     960
```

-continued

```
gtccttgtat tcatttccct tcttttttcg gggtaaaatc gatgtaaaga tctcatccga    1020
tctgccgttt tcgatcgcct tggagtggaa aaaaaacagg tgattttcgt tttatgcatg    1080
g                                                                   1081

<210> SEQ ID NO 252
<211> LENGTH: 1054
<212> TYPE: DNA
<213> ORGANISM: Zea mays

<400> SEQUENCE: 252
gcacgaggcc atcttctctg aattccagtc caagggccgg aataccgtca gagggagtgg      60
bgagaggggg ggaaaaaaga tggtgaagct cgcatttgga agctttcgcg actctttgag     120
cgccgcgtcg ctcaaggcct atgtggccga gttcattgcc acgctgctct tcgtgttcgc     180
cggcgtcggg tccgccattg cctactcgca attgacgaag ggcggcgctc tggaccccgc     240
cggcctggtg gccatcgcca tcgcccatgc gttcgcgctc ttcgtcggcg tctccatggc     300
cgccaacatc tccggcggcc acctgaaccc cgccgtcacc ttcggcctcg ccgtcggcgg     360
ccacatcacc atcctcaccg gcatcctcta ctgggttgcc cagcttctcg gcgcttccgt     420
ggcgtgcttt ctcctgcagt acgtcaccca cggacaggct atcccgacgc acggcgtctc     480
cgggatcagc gagatcgagg gcgtggtgat ggagatcgtg atcaccttcg cgctggtgta     540
caccgtgtac gccaccgcgg ccgacccgaa gaagggtcc ctgggcacca tcgcgcccat     600
ggccatcggc ttcatcgtcg gcgccaacat cctggccgcc ggccccttca gcggcggctc     660
catgaacccg gcccgctcct tcggccccgc cgtggcggcc ggtaacttcg ccggcaactg     720
ggtgtactgg gtcggccccc tcgtcggcgg tggcctggcg gggctcgtct acggcgacgt     780
gttcatcgcc tcctaccagc cggtcggcca gcaggagtac ccatgaaagt ccggatgagc     840
tagcccgatc gatccgtctg tgttgatttc accatcgtcg tcgtcgtgtc atctggcgct     900
tcgtgctgtg atcatgtttt gtcctgtttg catttcccaa cgtctggttt tcatttccat     960
tcaccaacgg tgccaagatg ccgtaagcaa gcgagagaag tgttcggtct gtatctgtat    1020
aaatgcaatg cacagttcgg cgttacgatg aacg                                1054
```